US012440578B2

(12) United States Patent
Popma et al.

(10) Patent No.: US 12,440,578 B2
(45) Date of Patent: Oct. 14, 2025

(54) NUCLEIC ACID CONSTRUCTS COMPRISING GENE EDITING MULTI-SITES AND USES THEREOF

(71) Applicant: IO BIOSCIENCES, INC., Chalfont, PA (US)

(72) Inventors: Sicco Hans Popma, Chalfont, PA (US); Di Zhang, Chalfont, PA (US)

(73) Assignee: IO BIOSCIENCES, INC., Chalfont, PA (US)

( * ) Notice: Subject to any disclaimer, the term of this patent is extended or adjusted under 35 U.S.C. 154(b) by 641 days.

(21) Appl. No.: 16/486,804

(22) PCT Filed: Feb. 22, 2018

(86) PCT No.: PCT/US2018/019297

§ 371 (c)(1),
(2) Date: Aug. 16, 2019

(87) PCT Pub. No.: WO2018/156818

PCT Pub. Date: Aug. 30, 2018

(65) Prior Publication Data

US 2019/0381192 A1 Dec. 19, 2019

Related U.S. Application Data

(60) Provisional application No. 62/573,353, filed on Oct. 17, 2017, provisional application No. 62/551,383, filed on Aug. 29, 2017, provisional application No. 62/538,328, filed on Jul. 28, 2017, provisional application No. 62/461,991, filed on Feb. 22, 2017.

(51) Int. Cl.

| | |
|---|---|
| ***A61K 35/12*** | (2015.01) |
| ***A61K 35/17*** | (2025.01) |
| ***A61K 35/28*** | (2015.01) |
| ***A61K 38/00*** | (2006.01) |
| ***A61K 40/15*** | (2025.01) |
| ***A61K 40/31*** | (2025.01) |
| ***A61K 40/42*** | (2025.01) |
| ***A61K 48/00*** | (2006.01) |
| ***C07K 14/00*** | (2006.01) |
| ***C07K 16/28*** | (2006.01) |
| ***C12N 15/00*** | (2006.01) |
| ***C12N 15/09*** | (2006.01) |
| ***C12N 15/10*** | (2006.01) |
| ***C12N 15/62*** | (2006.01) |
| ***C12N 15/63*** | (2006.01) |
| ***C12N 15/66*** | (2006.01) |
| ***C12N 15/85*** | (2006.01) |
| ***C12N 15/90*** | (2006.01) |

(52) U.S. Cl.

CPC ............ *A61K 48/005* (2013.01); *A61K 40/15* (2025.01); *A61K 40/31* (2025.01); *A61K 40/4211* (2025.01); *C07K 16/2803* (2013.01); *C12N 15/102* (2013.01); *C12N 15/85* (2013.01); *C12N 15/907* (2013.01); *A61K 2239/31* (2023.05); *A61K 2239/48* (2023.05); *C07K 2317/622* (2013.01); *C07K 2319/03* (2013.01); *C07K 2319/33* (2013.01); *C12N 2310/20* (2017.05)

(58) Field of Classification Search

None
See application file for complete search history.

(56) References Cited

U.S. PATENT DOCUMENTS

| | | | |
|---|---|---|---|
| 5,122,464 | A | 6/1992 | Wilson et al. |
| 5,350,674 | A | 9/1994 | Boenisch et al. |
| 5,354,844 | A | 10/1994 | Beug et al. |
| 5,459,127 | A | 10/1995 | Felgner et al. |
| 5,580,859 | A | 12/1996 | Felgner et al. |
| 5,585,362 | A | 12/1996 | Wilson et al. |
| 5,589,466 | A | 12/1996 | Felgner et al. |
| 5,693,622 | A | 12/1997 | Wolff et al. |
| 5,770,359 | A | 6/1998 | Wilson et al. |
| 5,843,780 | A | 12/1998 | Thomson |
| 5,885,827 | A | 3/1999 | Wabl et al. |
| 6,200,806 | B1 | 3/2001 | Thomson |
| 7,029,913 | B2 | 4/2006 | Thomson |
| 7,153,684 | B1 | 12/2006 | Hogan |

(Continued)

FOREIGN PATENT DOCUMENTS

| | | | |
|---|---|---|---|
| CN | 110651046 | A | 1/2020 |
| CN | 116218890 | A | 6/2023 |

(Continued)

OTHER PUBLICATIONS

Guignard et al. Gene Organization and Promoter Function for CC Chemokine Receptor 5 (CCR5) (J Immunolo, 1998, 160:985-992) (Year: 1998).*

(Continued)

*Primary Examiner* — Arthur S Leonard

(74) *Attorney, Agent, or Firm* — WILSON SONSINI GOODRICH & ROSATI

(57) ABSTRACT

Disclosed herein is a polynucleotide construct comprising one or more primary endonuclease recognition sequences upstream and downstream of a multiple gene editing site that comprises a plurality of secondary endonuclease recognition sequences. The primary endonuclease recognition sequences facilitate insertion of the multiple gene editing site into a host cell genome. The secondary endonuclease recognition sequences facilitate insertion of one or more exogenous donor genes into the host cell.

18 Claims, 40 Drawing Sheets

Specification includes a Sequence Listing.

(56) References Cited

U.S. PATENT DOCUMENTS

| | | | |
|---|---|---|---|
| 8,802,921 B2 | 8/2014 | Ainley et al. |
| 9,034,652 B2 | 5/2015 | Belisle et al. |
| 10,828,330 B2 | 11/2020 | Popma et al. |
| 2004/0040047 A1 | 2/2004 | Spencer et al. |
| 2009/0047263 A1 | 2/2009 | Yamanaka et al. |
| 2009/0068742 A1 | 3/2009 | Yamanaka |
| 2009/0191159 A1 | 7/2009 | Sakurada et al. |
| 2009/0227032 A1 | 9/2009 | Yamanaka et al. |
| 2009/0246875 A1 | 10/2009 | Yamanaka et al. |
| 2009/0304646 A1 | 12/2009 | Sakurada et al. |
| 2012/0003630 A1 | 1/2012 | Collins et al. |
| 2014/0090113 A1 | 3/2014 | Cogan et al. |
| 2014/0179006 A1 | 6/2014 | Zhang |
| 2014/0234972 A1 | 8/2014 | Zhang |
| 2015/0259684 A1 | 9/2015 | Church et al. |
| 2016/0024474 A1 | 1/2016 | Conway et al. |
| 2016/0024529 A1 | 1/2016 | Carstens |
| 2016/0145645 A1 | 5/2016 | Bahr et al. |
| 2017/0175128 A1 | 6/2017 | Welstead et al. |
| 2017/0218381 A1 | 8/2017 | Breuner et al. |
| 2017/0321248 A1 | 11/2017 | Paul et al. |
| 2019/0160098 A1 | 5/2019 | Novina |
| 2021/0093668 A1 | 4/2021 | Popma et al. |
| 2021/0332356 A1 | 10/2021 | Popma et al. |
| 2024/0026350 A1 | 1/2024 | Popma et al. |

FOREIGN PATENT DOCUMENTS

| | | |
|---|---|---|
| WO | WO-9208796 A1 | 5/1992 |
| WO | WO-9428143 A1 | 12/1994 |
| WO | WO-9502684 A1 | 1/1995 |
| WO | WO-9518863 A1 | 7/1995 |
| WO | WO-9521931 A1 | 8/1995 |
| WO | WO-9617823 A1 | 6/1996 |
| WO | WO-9625508 A1 | 8/1996 |
| WO | WO-9920741 A1 | 4/1999 |
| WO | WO-0132901 A1 | 5/2001 |
| WO | WO-0151616 A2 | 7/2001 |
| WO | WO-03020920 A1 | 3/2003 |
| WO | WO-03059923 A3 | 10/2003 |
| WO | WO-2004050884 A2 | 6/2004 |
| WO | WO-2016073559 A1 | 5/2016 |
| WO | WO-2018005276 A1 | 1/2018 |
| WO | WO-2018149418 A1 | 8/2018 |
| WO | WO-2018156818 A1 | 8/2018 |
| WO | WO-2019050994 A1 | 3/2019 |
| WO | WO-2020010452 A1 | 1/2020 |
| WO | WO-2020047300 A1 | 3/2020 |
| WO | WO-2021016608 A1 | 1/2021 |
| WO | WO-2021207401 A1 | 10/2021 |

OTHER PUBLICATIONS

GenBank AF032132. *Homo sapiens* CC chemokine receptor 5 (CCR5) gene, promoter and 5'UTR (1998, pp. 1-2) (Year: 1998).*
Kotin et al. Characterization of a preferred site on human chromosome 19q for integration of adeno-associated virus DNA by non-homologous recombination (EMBO, 1992, 11:5071-5078) (Year: 1992).*
Muller et al. *Streptococcus thermophilus* CRISPR-Cas9 Systems Enable Specific Editing of the Human Genome (Mol Therapy, 2016, 24:636-644) (Year: 2016).*
Baetge et al. Transgenic mice express the human phenylethanolamine N-methyltransferase gene in adrenal medulla and retina. PNAS USA 85:3648-3652 (1988).
Banfalvi, G., Cell cycle synchronization of animal cells and nuclei by centrifugal elutriation., Nat. Protoc. 3, 663-673 (2008).
Beyrouthy, M., et al., Identification of G1-Regulated Genes in Normally Cycling Human Cells,PLoS One 3, e3943 (2008).
Bird, et al. Single-chain antigen-binding proteins. Science. Oct. 21, 1988;242(4877):423-6.
Boundy et al. Regulation of tyrosine hydroxylase promoter activity by chronic morphine in TH9.0-LacZ transgenic mice. J Neurosci 18:9989-9995 (1998).
Brash et al., Strontium phosphate transfection of human cells in primary culture: stable expression of the simian virus 40 large-T-antigen gene in primary human bronchial epithelial cells, Mol. Cell Biol., 7: 2031-2034 (1987).
Casanova et al., Conditional Mutagenesis of CamKIV. Genesis 31:37-42 (2001).
Chakrabarti. Promoting adipose specificity: the adiponectin promoter. Endocrinol 151:2408-2410 (2010).
Chen et al. A lymphoproliferative abnormality associated with inappropriate expression of the Thy-1 antigen in transgenic mice. Cell 51:7-19 (1987).
Chen et al. Analysis of a 762-bp proximal leptin promoter to drive and control regulation of transgene expression of growth hormone receptor in mice. Biochem. Biophys. Res. Comm. 262:187-192 (1999).
Chevalier, B., et al., (2001), The homing endonuclease I-CreI uses three metals, one of which is shared between the two active sites, Nature Structural Biolology, 8, 312-316).
Chevalier, B. et al., Homing endonucleases: structural and functional insight into the catalysists of intron/intein mobility; 2001, Nucleic Acids Research, 29, 3757-3774.
Chinnalyan, Arul M., et al., (1995), FADD a Novel Death Domain-Containing Protein, Interacts with the Death Domain of Fas and Initiates Apoptosis, Cell, 81, 505-512.
Chu, Van Trung et al., Efficient generation of Rosa26 knock-in mice using CRISPR?Cas9 in C57BL/6 zygotes, BMC Biotechnology (2016), pp. 1-15.
Colberre-Garapin et al. A new dominant hybrid selective marker for higher eukaryotic cells. J Mol Biol 150:1-14 (1981).
Comb, Michael et al. (1988), Proteins bound at adjacent DNA elements act synergistically to regulate human proenkephalin cAMP inducible transcription, The EMBO Journal, vol. 7, No. 12 pp. 3793-3805.
Conese, et al. Gene therapy progress and prospects: episomally maintained self-replicating systems. Gene Ther. Dec. 2004;11(24):1735-41.
Cools, et al., A replication stress-induced synchronization method for *Arabidopsis thaliana* root meristems, The Plant Journal (2010) 64, 705-714.
Coquelle, A. et al., Enrichment of non-synchronized cells in the G1, S and G2 phases of the cell cycle for the study of apoptosis, Biochem. Pharmacol. 72, 1396-1404 (2006).
Corpet et al., Multiple sequence alignment with hierarichal clustering, Nucleic Acids Res., 16:10881-10890 (1988).
Davies, DM and Maher, J., Gated chimeric antigen receptor T-cells: the next logical step in reducing toxicity. Transl Cancer Res 2016;5(S1):S61-S65.
Di Stasi, Antonio et al., Inducible Apoptosis as a Safety Switch for Adoptive Cell Therapy, The New England Journal of Medicine, (2011) 365:1673-1683.
Dolezel, J. et al., Cell cycle synchronization in plant root meristems Methods in Cell Science, 1999, vol. 21, Issue 2-3, pp. 95-107.
Drabek, et al. The expression of bacterial nitroreductase in transgenic mice results in specific cell killing by the prodrug CB1954. Gene Therapy, Feb. 1997, 4(2):93-100.
Duportet, Xavier, et al., A platform for rapid prototyping of synthetic gene networks in mammalian cells, 13440--13451 Nucleic Acids research, 2014, vol. 42, No. 21.
E-CRISP, e-crisp.org/E-CRISP/workdir/Fri_Oct_25_15:30:07_20191572017407/index.html; last visited Oct. 25, 2019.
Franz et al. Analysis of tissue-specific gene delivery by recombinant adenoviruses containing cardiac-specific promoters. Cardiovasc. Res. 35:560-566 (1997).
Gaidukov, Leonid, A mulit-landing pad DNA integration platform for mammalian cell engineering, 4072-4086 Nucleic Acids Research, 2018, vol. 46, No. 8.
Genbank, NM_010020, 2019.
Ghosh et al., Design of liposomes for circumventing the reticuloendothelial cells., Glycobiology 5: 505-10 (1991).
Grindley, Nigel, et al., (2006) , Mechanisms of Site_Specific Recombination, Ann Rev Biochem 16:16.

(56) References Cited

OTHER PUBLICATIONS

Groisberg, Roman, et al., Characteristics and outcomes of patients with advanced sarcoma enrolled in early phase immunotherapy trials, J. ImmunoTherapy of Cancer (2017)5:100.
Grosse, J., et al., Cell separation by countercurrent centrifugal elutriation: recent developments. Prep Biochem Biotechnol. 2012; 42(3):217-33.
Henikoff et al. Amino acid substitution matrices from protein blocks. PNAS USA 89(22):10915-10919 (1992).
Higgins et al.: Clustal: a package for performing multiple sequence alignment on a microcomputer; Elsevier Science Publishers B.V. (Biomedical Division); Gene. 73 (1988) 237-244.
Higgins, et al. Fast and sensitive multiple sequence alignments on a microcomputer. Comput Appl Biosci. Apr. 1989;5(2):151-3.
Holliger et al.: Engineered antibody fragments and the rise of single domains. Nat. Biotechnol. 23(9):1126-36 (2005).
Huang, et al. Parallelization of a Local Similarity Algorithm. Cabios. 1992; 8(2): 155-165.
Hunter et al. Targeting gene expression to specific cardiovascular cell types in transgenic mice. Hypertension 22:608-617 (1993).
Huston et al. Protein engineering of antibody binding sites: recovery of specific activity in an anti-digoxin single-chain Fv analogue produced in *Escherichia coli*. PNAS USA 85(16):5879-5883 (1988).
Inniss, M.C., et al., (2017), A novel Bxb1 integrase RMCE system for high fidelity site-specific integration of mAb expression cassette in CHO cells., Biotechnol Bioeng., 114(8):1837-1846.
Jinek et al. A programmable dual-RNA-guided DNA endonuclease in adaptive bacterial immunity. Science 337(6096):816-821 (2012).
Johnston, S.A., Biolistic transformation: microbes to mice, Nature, 346: 776-777 (1990).
Juan et al., Separation of Live Cells in Different Phases of the Cell Cycle for Gene Expression Analysis, Cytometry 49, 170-175 (2002).
Kaneda et al. Tissue-specific and high-level expression of the human tyrosine hydroxylase gene in transgenic mice. Neuron 6:583-594 (1991).
Kent et al., Ouabain resistance conferred by expression of the cDNA for a murine Na +, K+—ATPase α subunit, Science, 237: 901-903 (1987).
Kita et al. Identification of the promoter region required for human adiponectin gene transcription: Association with CCAAT/enhancer binding protein-beta and tumor necrosis factor-alpha. Biochem Biophys Res Comm 331:484-490 (2005).
Knight et al. Regulation of the human GLUT4 gene promoter: interaction between a transcriptional activator and myocyte enhancer factor 2A. PNAS USA 100:14725-14730 (2003).
Koshimizu, U., et al. (1996), Functional requirement of gp130-mediated signaling for growth and survival of mouse primordial germ cells in vitro and derivation of embryonic germ (EG) cells, Development, 122:1235.
Kumagai-Sano, F. et al., Cell cycle synchronization of tobacco BY-2 cells, Nat Protoc. 2006;1(6):2621-7.
Kuriki et al., Structural and functional analysis of a new upstream promoter of the human FAT/CD36 gene. Biol Pharm Bull 25:1476-1478 (2002).
Linn et al. Conservation of an AE3 CI-/HCO3-exchanger cardiac-specific exon and promoter region and AE3 mRNA expression patterns in murine and human hearts. Circ. Res. 76:584-591 (1995).
Liu et al. CMV enhancer/human PDGF-beta promoter for neuron-specific transgene expression. Gene Therapy 11:52-60 (2004).
Llewellyn, M. et al., Orderly recruitment of motor units under optical control in vivo. Nat. Med. 16(10):1161-1166 (2010).
Los, M. et al., (1995), Requirement of an ICE/CED-3 protease for Fas/APO-1-mediated apoptosis,Nature 375 (6526), 81-3.
Lowy et al., Isolation of transforming DNA: Cloning the hamster aprt gene. Cell 22:817-823 (1980).
Lu, Xiao-Hong et al., Bacterial Artificial Chromosome Transgenic Mice Expressing a Truncated Mutant Parkin Exhibit Age-Dependent Hypokinetic Motor Deficits, Dopaminergic Neuron Deternation, and Accumulation of Proteinase K-Resistant a-Synuclein, 1962, The Journal of Neuroscience, Feb. 18, 2009, 29(7):1962-1976.
Mason et al. Regulation of Leptin Promoter Function by Sp1, C/EBP, and a Novel Factor. Endocrinol 139:1013-1022, (1998).
Matsui, Y., et al., (1992), Derivation of pluripotential embryonic stem cells from murine primordial germ cells in culture, Cell 70:841.
Mayford et al. The 3'-untranslated region of CaMKII alpha is a cis-acting signal for the localization and translation of mRNA in dendrites. PNAS USA 93:13250-13255 (1996).
Merrill, G.F., Cell synchronization, Methods Cell Biol. 1998; 57:229-49.
Miura, M., et al., (1993), Induction of apoptosis in fibroblasts by IL-1β-converting enzyme, a mammalian homolog of the C. elegans cell death gene ced-3, Cell 75, 653-660.
Morrison et al.: Regulatory Mechanisms in Stem Cell Biology. Cell 88(3):287-298 (1997).
Mulligan, R.C. et al., Selection for animal cells that express the *Escherichia coli* gene coding for xanthine-guanine phosphoribosyltransferase, Proc. Natl. Acad. Sci. USA, vol. 78, No. 4, pp. 20172-2076, Apr. 1981.
Muzio, M. et al., FLICE, A Novel FADD-Homologous ICE/CED-3-like Protease, is Recruited to the CD95 (Fas/APO-1) Death-Inducing Signaling Complete, Cell, vol. 85, 817-827, Jun. 14, 1996.
Needleman et al. A general method applicable to the search for similarities in the amino acid sequence of two proteins. J. Mol. Biol. 48:443-453 (1970).
Oberdick et al. A promoter that drives transgene expression in cerebellar Purkinje and retinal bipolar neurons. Science 248:223-226 (1990).
Oh, Myung Sook et al. (2009), Expression of transgenes in midbrain dopamine neurons using the tyrosine hydroxylase promoter, Gene Ther 16:437.
O'Hare et al. Transformation of mouse fibroblasts to methotrexate resistance by a recombinant plasmid expressing a prokaryotic dihydrofolate reductase. PNAS USA 78:1527-1531 (1981).
Oikawa, et al. Intra-operative Guidance with Real-time Information of Open MRI and Manipulators Using Coordinate-Integration Module. Proceedings of SPIE, vol. 5029: 653-660, 2003.
Osbourn, et al. Directed selection of MIP-1 alpha neutralizing CCR5 antibodies from a phage display human antibody library. Nat Biotechnol. Aug. 1998;16(8):778-81.
Parmacek et al. A novel myogenic regulatory circuit controls slow/cardiac troponin C gene transcription in skeletal muscle. Mol Cell Biol 14:1870-1885 (1994).
Pavjani et al. Fat apoptosis through targeted activation of caspase 8: a new mouse model of inducible and reversible lipoatrophy. Nat. Med. 11:797-803 (2005).
Pearson, et al. Improved Tools for Biological Sequence Comparison. Proc. Nat'l Acad. Sci. USA. 85 (1988): 2444-48.
Pearson, W.R. Using the FASTA Program to Search Protein and DNA Sequence Databases. Meth. Mol. Biol. 1994; 24:307-331.
Platt et al. Obesity-linked regulation of the adipsin gene promoter in transgenic mice. PNAS USA 86:7490-7494 (1989).
Radovick et al. Migratory arrest of gonadotropin-releasing hormone neurons in transgenic mice. PNAS USA 88:3402-3406 (1991).
Ran, et al. Double Nicking by RNA-Guided CRISPR Cas9 for Enhanced Genome Editing Specificity. Cell. Aug. 28, 2013. pii: S0092-8674(13)01015-5. doi: 10.1016/j.cell.2013.08.021. [Epub ahead of print].
Robbins, J. et al. (1995), In vivo definition of a cardiac specific promoter and its potential utility in remodeling the heart, Ann. N.Y. Acad. Sci. 752:492-505.
Rosner, M. et al., Merging high-quality biochemical fractionation with a refined flow cytometry approach to monitor nucleocytoplasmic protein expression throughout the unperturbed mammalian cell cycle. Nat Protoc. Mar. 2013; 8(3):602-26.
Ross, S. et al., (1990), A fat-specific enhancer is the primary determinant of gene expression for adipocyte P2 in vivo, Proc. Natl. Acad. Sci. USA 87:9590.
Sadelain, M., et al. (2012), Safe harbours for the integration of new DNA in the human genome, Nat. Rev. Cancer 12:51-58.

(56) References Cited

OTHER PUBLICATIONS

Santerre et al. Expression of prokaryotic genes for hygromycin B and G418 resistance as dominant-selection markers in mouse L cells. Gene 30(1-3):147-156 (1984).
Sartorelli et al. Myocardial activation of the human cardiac alpha-actin promoter by helix-loop-helix proteins. PNAS USA 89:4047-4051 (1992).
Sasaoka et al. Analysis of the human tyrosine hydroxylase promoter-chloramphenicol acetyltransferase chimeric gene expression in transgenic mice. Brain Res Mol Brain Res 16:274-786 (1992).
Sato et al. Dual Promoter Structure of Mouse and Human Fatty Acid Translocase/CD36 Genes and Unique Transcriptional Activation by Peroxisome Proliferator-activated Receptor α and γ Ligands J Biol Chem 277:15703-15711 (2002).
Schorl, C. and Sedivy, J.M., Analysis of cell cycle phases and progression in cultured mammalian cells., Methods 41, 143-150 (2007).
Seo et al. Functional Characterization of the Human Resistin Promoter with Adipocyte Determination- and Differentiation-Dependent Factor 1/Sterol Regulatory Element Binding Protein 1c and CCAAT Enhancer Binding Protein-α Mol Endocrinol 17:1522 (2003).
Shamblott, et al. Derivation of pluripotent stem cells from cultured human primordial germ cells, Proc. Natl. Acad. Sci. USA, vol. 95, pp. 13726-13731 (1998).
Shamblott, et al. Human embryonic germ cell derivatives express a broad range of developmentally distinct markers and proliferate extensively in vitro, Proc. Natl. Acad. Sci., vol. 98 No. 1, pp. 113-118 (2001).
Sharma, Arun Kumar, Synchronization in plant cells—an introduction, Methods in Cell Science, 1999, vol. 21, Issue 2-3, pp. 73-78.
Shi, Shuobo et al., A highly efficient single-step, markerless strategy for multi-copy chromosomal integration of a large biochemical pathways in *Saccharomyces cerevisiae*, Metabolic Engineering, 33 (2019) 19-27.
Smith and Waterman, Comparison of Biosequences. Adv. Appl. Math., 2:482-489 (1981).
Szybalska et al. Genetics of human cell line. IV. DNA-mediated heritable transformation of a biochemical trait. PNAS USA 48:2026-2034 (1962).
Tabor et al. Identification of Conserved cis-Elements and Transcription Factors Required for Sterol-regulated Transcription of Stearoyl-CoA Desaturase 1 and 2 J Biol Chem 274:20603 (1999).
Takahashi, et al. Induction of pluripotent stem cells from adult human fibroblasts by defined factors. Cell. Nov. 30, 2007;131(5):861-72.
Takahashi et al.,, Induction of pluripotent stem cells from fibroblast cultures, Nat Protoc. 2007; 2(12):3081-9.
Thomson et al. Embryonic stem cell lines derived from human blastocysts. Science. Nov. 6, 1998;282(5391):1145-7.
Thomson, et al. Isolation of a primate embryonic stem cell line. Proc Natl Acad Sci U S A. Aug. 15, 1995;92(17):7844-8.
Thomson et al., Pluripotent Cell Lines Derived from Common Marmoset (*Callithrix jacchus*) Blastocysts, (1996) Biol. Reprod. 55:254-259.
Thorpe & Smith, In vitro site-specific integration of bacteriophage DNA catalyzed by a recombinase of the resolvase/invertase family, Proc. Nat. Acad. Sci. 95:5505-5510, 1998.
Tiscornia, Gustavo, A general method for gene knockdown in mice by using lentiviral vectors expressing small interfering RNA, PNAS100:1844-18848 (2003).
Tozzo et al. Amelioration of Insulin Resistance in Streptozotocin Diabetic Mice by Transgenic Overexpression of GLUT4 Driven by an Adipose-Specific Promoter. Endocrinol. 138:1604-1611 (1997).
Ui-Tei et al. Sensitive assay of RNA interference in *Drosophila* and Chinese hamster cultured cells using firefly luciferase gene as target. FEBS Letters 479: 79-82 (2000).
Wei, et al., Experimental tumor therapy in mice using the cyclophosphamide-activating cytochrome P450 2B1 gene, Human Gene Therapy 5(8):969-978, 1994.
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Yu, et al. Induced pluripotent stem cell lines derived from human somatic cells. Science. Dec. 21, 2007;318(5858):1917-20. Epub Nov. 20, 2007.
Zeevi, Vardit et al., Zinc Finger Nuclease and Homing Endonuclease-Mediated Assembly of Multigene Plant Transformation Vectors, Plant Physiology, Jan. 2012, vol. 158, pp. 132-144.
Extended European Search Report for corresponding European Patent Application No. 18756843.1 issued Nov. 2, 2020.
Glaser, et al., "GFP to BFP Conversion: A Versatile Assay for the Quantification of CRISPR/Cas9-mediated Genome Editing" Molecular Therapy-Nucleic Acids, vol. 5, (2016) p. 334.
Howeden, et al., "Site-specific, Rep-mediated integration of the intact [beta]-globin locus in the human erythroleukaemic cell line K562" Gene Therapy, vol. 15, No. 20 (2008) p. 1380, col. 1, paragraph 2; figures 2, 5.
No Author Listed "Homologous Recombination Targeting Vectors" (2016) Retrieved from the Internet : www.biocat.com/genomics/genome-engineering/homologous-recombination-targeting-vectors.
Papapetrou, et al., "Gene Insertion Into Genomic Safe Harbors for Human Gene Therapy" Molecular Therapy, vol. 24, No. 4, (2016) pp. 678-684.
Wang, et al. "Highly efficient homology-driven genome editing in human T cells by combining zinc-finger nuclease mRNA and AAV6 donor delivery", Nucleic Acids Research, vol. 44, No. 3, Nov. 2, 2015 (Nov. 2, 2015), pp. e30-e30, XP055737865, ISSN: 0305-1048, DOI: 10.1093/nar/gkv1121.
Nov. 4, 2019 First Action Interview Pilot Program Pre-Interview Communication U.S. Appl. No. 16/363,963.
Jun. 15, 2020 Office Action U.S. Appl. No. 16/363,963.
Aug. 21, 2020 Notice of Allowance U.S. Appl. No. 16/363,963.
Aug. 9, 2022 Non-Final Office Action U.S. Appl. No. 16/486,804.
Extended European Search Report for European Patent Application No. 19853894.4 issued May 10, 2022.
Genbank Accession No. CP011030, Pseudoalteromonas issachenkonii strain KMM 3549 chromosome I, complete sequence, Jun. 20, 2015 (online). [Retrieved on May 17, 2018]. Retrieved from the internet: ,URL: http://www.ncbi.nlm.nih.gov/nuccore/CP011030/c.
Genbank Accession No. CP013350, Pseudoalteromonas issachenkonii strain KCTC 12958 chromosome I, complete sequence, Dec. 2, 2015 [online]. [Retrieved from the internet: URL: Entire >https://www.ncbi.nlm.nih.gov/nuccore/CPO13350/C Entire document.
Genbank Accession No. CP011421 "Klebsiella pneumoniae strain yzusk-4 genome" Jul. 30, 2015 [online] https://www.ncbi.nlm.nih.gov/nuccore/CP011421.
International Preliminary Report on Patentability dated Aug. 27, 2019 for International Application No. PCT/US2018/019297.
International Preliminary Report on Patentability dated Mar. 2, 2021 for PCT/US19/48882.
International Preliminary Report on Patentability dated Oct. 6, 2022 for International Application No. PCT/US2021/026240.
International Search Report and Written Opinion dated Aug. 10, 2021 for International Application No. PCT/US2021/026240.
International Search Report and Written Opinion dated Jan. 6, 2020 for PCT/US19/48882.
PCT/US2018/019297 International Search Report and Written Opinion dated Jul. 6, 2018.
Thermes, V. et al., "I-Scel meganuclease mediates highly efficient transgenesis in fish", Mechanisms of Development, 2002, vol. 118, pp. 91-98.
Wang et al. Highly efficient homology-driven genome editing in human T cells by combining zinc-finger nuclease mRNA and AAV6 donor delivery, Nucleic Acids Research, Nov. 2, 2015, vol. 44, No. 3, pp. 1-9.
Carlsten, M. et al., "Genetic manipulation of NK cells for cancer immunotherapy: techniques and clinical implications," Frontiers in Immunology, 2015;6:266.
Chu, V.T. et al., "Increasing the efficiency of homology-directed repair for CRISPR-Cas9-induced precise gene editing in mammalian cells," Nature Biotechnology, 2015;33(5):543-548.

(56) References Cited

OTHER PUBLICATIONS

CRISPR RGEN tools, phiC31 attP, Bxb1 attP Cas9 recognition gRNA targets, www.rgenome.net/cas-designer.
Dong, G. et al., "Generation of Natural Killer Cell Lymphoma Models in vitro by Gene Editing," 2016;128(22):2724.
Galetto, R. et al., "Targeted approaches for gene therapy and the emergence of engineered meganucleases," Expert Opin Biol Ther., 2009;9(10):1289-1303.
Zhu, F. et al., "Dice, an efficient system for iterative genomic editing in human pluripotent stem cells," Nucleic Acids Research, 2014;42(5):e34.
Casanova, Emilio et al. A CamKIIalpha iCre BAC allows brain-specific gene inactivation. genesis 31(1): 37-42 (2001).
Christ, Nicole, and Peter Dröge. Genetic manipulation of mouse embryonic stem cells by mutant λ integrase. Genesis 32(3):203-208 (2002).
Christiansen, Bettina et al. A Resolvase-like Protein is Required for the Site-specific Integration of the Temperate Lactococcal Bacteriophage TP901-1. Journal of Bacteriology 178(17):5164-5173 (1996).
Curiel, David T. et al. High-efficiency gene transfer mediated by adenovirus coupled to DNA-polylysine complexes. Human gene therapy 3(2):147-154 (1992).
Gerlitz, M. et al. Partitioning of broad-host-range plasmid RP4 is a complex system involving site-specific recombination. Journal of bacteriology 172(11):6194-6203 (1990).
Ghosh, Pallavi. et al. Control of phage Bxb1 excision by a novel recombination directionality factor. PLoS Biology 4(6):e186, 1-11 (2006).
Gottfried, Pnina et al. Site-specific recombination in *Arabidopsis* plants promoted by the Integrase protein of coliphage HK022. Plant Molecular Biology 57(3):435-444 (2005).
Keravala, Annahita et al. A diversity of serine phage integrases mediate site-specific recombination in mammalian cells. Molecular Genetics and Genomics 276(2):135-146 (2006).
Kholodii, Gennady. The shuffling function of resolvases. Gene 269(1-2):121-130 (2001).
Kim, Amy I. et al. Mycobacteriophage Bxb1 integrates into the Mycobacterium smegmatis groEL1 gene. Molecular microbiology 50(2):463-473 (2003).
Kolot, M. et al. Site promiscuity of coliphage HK022 integrase as a tool for gene therapy. Gene therapy 22(7):521-527 (2015).
Kuhstoss, Stuart, and R. Nagaraja Rao. Analysis of the Integration Function of the *Streptomycete* Bacteriophage phi C31. Journal of Molecular Biology 222(4):897-908 (1991).
Lombardo, A. et al., Gene editing in human stem cells using zinc finger nucleases and integrase-defective lentiviral vector delivery, Nat Biotechnol., vol. 25, 11 (2007):1298-1306.
Machida, Chiyoko. et al. Use of the R-RS site-specific recombination system in plants. Plant Molecular Biology Manual :117-141 (2000).
Matsuura, Manabu. et al. The sre Fene (ORF469) Encodes a Site-specific Recombinase Responsible for Integration of the R4 Phage Genome. Journal of Bacteriology 178(11):3374-3376 (1996).
Moehle et al., Targeted gene addition into a specified location in the human genome using designed zinc finger nucleases. PNAS 104:3055-3060 (2007).
Olivares, Eric C. et al. Phage R4 integrase mediates site-specific integration in human cells. Gene 278(1-2):167-176 (2001).
Rubtsova, Myroslava et al. Expression of active *Streptomyces* phage phiC31 integrase in transgenic wheat plants. Plant cell reports 27(12):1821-1831 (2008).
Russell, John P. et al. Phage Bxb1 Integrase Mediates Highly Efficient Site-specific Recombination in Mammalian Cells. Biotechniques 40(4):460-464 (2006).
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Sauer, Brian, and Nancy Henderson. Targeted insertion of exogenous DNA into the eukaryotic genome by the Cre recombinase. The New Biologist 2(5):441-449 (1990).
Schwikardi, Micha, and Peter Dröge. Site-specific recombination in mammalian cells catalyzed by γδ resolvase mutants: implications for the topology of episomal DNA. FEBS letters 471(2-3):147-150 (2000).
Stoll, Stephanie M. et al. Phage TP901-1 site-specific integrase functions in human cells. Journal of bacteriology 184(13):3657-3663 (2002).
Thomson, James G, and David W. Ow. Site-specific recombination systems for the genetic manipulation of eukaryotic genomes. genesis 44(10):465-476 (2006).
Thomson, James G. et al. ParA resolvase catalyzes site-specific excision of DNA from the *Arabidopsis* genome. Transgenic research 18(2):237-248 (2009). Published Online Aug. 14, 2008.
Thomson, James G. et al. PhiC31 recombination system demonstrates heritable germinal transmission of site-specific excision from the *Arabidopsis* genome. BMC biotechnology 10(1):17, 1-12 (2010).
Thorpe, Helena M. et al. Control of directionality in the site-specific recombination system of the *Streptomyces* phage φ C31. Molecular microbiology 38(2):232-241 (2000).
Urnov, Fyodor D. et al. Highly Efficient Endogenous Human Gene Correction Using Designed Zinc-finger Nucleases. Nature 435(7042):646-651 (2005).
Wilson et al. Hepatocyte-directed gene transfer in vivo leads to transient improvement of hypercholesterolemia in low intensity lipoprotein receptor-deficient rabbits. J Biol Chem 267(2):963-967 (1992).
Bourgeois, Leanne. Development and Application of the Landing Pad platform: A synthetic CRISPR/Cas9 Platform for Multi-copy Gene Integration in *Saccharomyces cerevisiae*. Diss. Concordia University (2018).
Cao, M. et al. GenBank Accession No. NC_001401. Version No. NC_001401.1. Adeno-associated virus—2, complete genome. 1: pp. 3. Record created Aug. 13, 2018. Retrieved Dec. 9, 2024. Retrieved from: https://www.ncbi.nlm.nih.gov/nuccore/NC_001401.
GenBank Accession No. NG050616 retrieved from:https://www.ncbi.nlm.nih.gov/nuccore/NG_050616 on Aug. 20, 2024.
Maity, Tuhin S. et al. Exploring the Sequence-function Relationship in Transcriptional Regulation by the Lac O1 Operator. The FEBS Journal 279(14):2534-2543 (2012).
Matreyek, Kenneth A. et al. A Platform for Functional Assessment of Large Variant Libraries in Mammalian Cells. Nucleic Acids Research 45(11):e102, 1-12 (2017).
Petek, Lisa M. et al. Frequent Endonuclease Cleavage at Off-target Locations in Vivo. Molecular Therapy 18(5):983-986 (2010).
Poen, S.L, and Pornbunlualarp S.S. GenBank Accession No. EF136884 retrieved from:https://www.ncbi.nlm.nih.gov/nuccore/EF136884.1 on Aug. 20, 2024.
Prasher, D C. et al. GenBank Accession No. M62653 retrieved from:https://www.ncbi.nlm.nih.gov/nuccore/M62653 on Aug. 20, 2024.
Quadros, Rolen M. et al. Insertion of Sequences at the Original Provirus Integration Site of mouse ROSA26 Locus using the CRISPR/Cas9 System. FEBS Open Bio 5(1):191-197 (2015).
Samulski, R. J. et al. Targeted Integration of Adeno-associated Virus (AAV) Into Human Chromosome 19. The Embo Journal 10(12):3941-3950 (1991).
Schaeffer, Scott M, and Paul A. Nakata. CRISPR/Cas9-mediated Genome Editing and Gene Replacement in Plants: Transitioning From Lab to Field. Plant Science 240:130-142 (2015).
Silva, George et al. Meganucleases and Other Tools for Targeted Genome Engineering: Perspectives and Challenges for Gene Therapy. Current Gene Therapy 11(1):11-27 (2011).
U.S. Appl. No. 17/021,526 Office Action dated Aug. 1, 2024.
U.S. Appl. No. 17/185,507 Office Action dated Aug. 15, 2024.
Sander, Jeffry D, and J Keith Joung. CRISPR-Cas Systems for editing, Regulating and Targeting Genomes. Nature Biotechnology 32(4):347-355 (2014).
U.S. Appl. No. 17/185,507 Office Action dated Apr. 3, 2025.

(56) References Cited

OTHER PUBLICATIONS

Wang, Jian et al. Whole-genome Sequencing Identifies I-SceI-mediated Transgene Integration Sites in Xenopus Tropicalis Snai2:eGFP Line. G3 12(5):jkac037, 1-8 (2022).

* cited by examiner

Transfection Efficiency Assessment

P1312, NK-92, SF/CA-137, NFE = 60-70%, V = 65%

```
        site #1 RC                                   site #2                          site #3 RC
  1  CCATCGTACG TCGGAATACG GATCTAATCA ACTTTCTGCC GTACTGTGAT ACACGCGACA GGAACTGTGC GAAATCGCCA
     GGTAGCATGC AGCCTTATGC CTAGATTAGT TGAAAGACGG CATGACACTA TGTGCGCTGT CCTTGACACG CTTTAGCGGT

        site #3 RC                                 site #4                            site #5 RC
 81  TAGCGATTTA TCGGAGCGCC ATTACGTACT CAGCTTATTA CCGATACGAT ACGAACAGGT CTAGCAAACT GCTGCCTGAC
     ATCGCTAAAT AGCCTCGCGG TAATGCATGA GTCGAATAAT GGCTATGCTA TGCTTGTCCA GATCGTTTGA CGACGGACTG

      site #5 RC                                 site #6
161  GACGGTTGCG CGTCCGTTAA TACAGCACAA AAGTAATCGG TTGCGCCGCT CGGGGGATCG AGTTTAACTC ACCTACGCTA
     CTGCCAACGC GCAGGCAATT ATGTCGTGTT TTCATTAGCC AACGCGGCGA GCCCCCTAGC TCAAATTGAG TGGATGCGAT

                                          site #7                                 site #8 RC
241  CGCTAACGGG CGATCGTTCG TACGCGAGTT TTATTTACCC CGCGCGAGGT GGGCGAAATT ATAGTCGTCC AAGACCGACG
     GCGATTGCCC GCTAGCAAGC ATGCGCTCAA AATAAATGGG GCGCGCTCCA CCCGCTTTAA TATCAGCAGG TTCTGGCTGC

       site #8 RC                          site #9                                   site #10 RC
321  TACGATACAA CTCTAAATTT GCAGAATAGT ATTCGAGTAC GCGTCGATGG AAGTCATATC ACGCGCCCAT CGACGCGTAC
     ATGCTATGTT GAGATTTAAA CGTCTTATCA TAAGCTCATG CGCAGCTACC TTCAGTATAG TGCGCGGGTA GCTGCGCATG

     site #10 RC                      site #11
401  TCGAATACTG AACTCGCGTT CGACGCGTGC GATCGTACCG TGTACGGACT AGCGTCTGCT TACCTACGCT ACGCTAACGG
     AGCTTATGAC TTGAGCGCAA GCTGCGCACG CTAGCATGGC ACATGCCTGA TCGCAGACGA ATGGATGCGA TGCGATTGCC

                                site #12                                       site #13 RC
481  GCGATCACAG TTTGTGTCAT CCGCATGGCA ATCTACGCGC GAGGATTTTT GTGCTCAAGC CGGATCGACC GGGTCGGTTC
     CGCTAGTGTC AAACACAGTA GGCGTACCGT TAGATGCGCG CTCCTAAAAA CACGAGTTCG GCCTAGCTGG CCCAGCCAAG

      site #13 RC                 site #14                                     site #15 RC
561  ACTAACATCA GACGCAAATT CTTCGATACG GTACGAATAG GCGTTTTGGT CCGCCCCCGG CGTACGCGTC CCATATAAAC
     TGATTGTAGT CTGCGTTTAA GAAGCTATGC CATGCTTATC CGCAAAACCA GGCGGGGGCC GCATGCGCAG GGTATATTTG

                              site #16                                     site #17 RC
641  TGTTGTCTAA TTCAAAGAGT GGCCGCGATA ATCGAAGGAC ATTTGTTACA AGACCTACCG GTTACCGCGA GGATTAATGT
     ACAACAGATT AAGTTTCTCA CCGGCGCTAT TAGCTTCCTG TAAACAATGT TCTGGATGGC CAATGGCGCT CCTAATTACA

                            site #18
721  ATCTTACACG TAAGAGTGGG CGCGAATATC GTAGG
     TAGAATGTGC ATTCTCACCC GCGCTTATAG CATCC
```

FIG. 25

NUCLEIC ACID CONSTRUCTS COMPRISING GENE EDITING MULTI-SITES AND USES THEREOF

CROSS REFERENCE

This application is a national stage application of International Application No. PCT/US2018/019297, filed Feb. 22, 2018, which claims the benefit of U.S. Provisional Application Nos. 62/461,991, filed Feb. 22, 2017, 62/538,328, filed Jul. 28, 2017, 62/551,383, filed Aug. 29, 2017, and 62/573,353, filed Oct. 17, 2017, each of which is incorporated herein by reference in its entirety.

REFERENCE TO A SEQUENCE LISTING

The present application includes a Sequence Listing which has been submitted electronically in ASCII format and is hereby incorporated by reference in its entirety. Said ASCII copy, created on Dec. 19, 2024, is named 53407-701_831_SL.txt and is 35,451 bytes in size.

BACKGROUND OF THE DISCLOSURE

Cell therapies enter a new era with the advent of widely available and constantly improving gene modification techniques. Gene modification of cells allows for genetic properties to be deleted, corrected or added in a transient or permanent fashion. For example, the addition of chimeric antigen receptors to patient's white blood cells has led to personalized cell therapies that specifically kill targeted tumor cells in the field of immune oncology. Several clinical proof of concept studies have now shown promising results for this therapeutic approach. This information can now be used to create cell therapies that adhere to more classic pharmaceutical and biotechnology drug development and commercial models allowing for maximum patient access, give healthcare providers options for treatment, and provide commercial value to the developer. These personalized clinical studies show feasibility of the concept, but face significant scalability and commercial challenges before it can become widely available to all patients in need. There remains a need to provide an avenue to translate the proof of concept studies to a more widely available system, for use in a broader spectrum of patients or against a broader spectrum of conditions.

INCORPORATION BY REFERENCE

All publications, patents, and patent applications mentioned in this specification are herein incorporated by reference to the same extent as if each individual publication, patent, or patent application was specifically and individually indicated to be incorporated by reference. Absent any indication otherwise, publications, patents, and patent applications mentioned in this specification are incorporated herein by reference in their entireties.

SUMMARY OF THE DISCLOSURE

Provided herein is a gene editing multi-site (GEMS) construct for insertion into a genome at an insertion site, wherein said GEMS construct comprises: flanking insertion sequences, wherein each of said flanking insertion sequences is homologous to a genome sequence at said insertion site; and a GEMS sequence between said flanking insertion sequences, wherein said GEMS sequence comprises a plurality of nuclease recognition sequences, wherein each of said plurality of nuclease recognition sequences comprises a guide target sequence and a protospacer adjacent motif (PAM) sequence, wherein said guide target sequence binds a guide polynucleotide following insertion of said GEMS construct at said insertion site.

In some embodiments, said GEMS construct is at least 95% identical to a sequence as shown in SEQ ID NOs: 2 or 84. In some embodiments, a sequence identity of said GEMS construct to said SEQ ID NOs: 2 or 84 is calculated by BLASTN. In some embodiments, said guide polynucleotide comprises a guide RNA. In some embodiments, said plurality of nuclease recognition sequences comprises at least three nuclease recognition sequences. In some embodiments, said plurality of nuclease recognition sequences comprises at least five nuclease recognition sequences. In some embodiments, said plurality of nuclease recognition sequences comprises at least seven nuclease recognition sequences. In some embodiments, said plurality of nuclease recognition sequences comprises at least ten nuclease recognition sequences. In some embodiments, said plurality of nuclease recognition sequences comprises greater than ten nuclease recognition sequences.

In some embodiments, said GEMS construct comprises sequences, wherein a sequence of a first nuclease recognition sequence guide target sequence differs between said first nuclease recognition sequence and said second nuclease recognition sequence. In some embodiments, each of said plurality of nuclease recognition sequences comprises a different sequence than another of said plurality of nuclease recognition sequences. In some embodiments, each of said guide target sequence in said plurality of nuclease recognition sequences is different from another of said guide target sequence in said plurality of nuclease recognition sequences. In some embodiments, said guide target sequence is from about 17 to about 24 nucleotides in length. In some embodiments, said guide target sequence is 20 nucleotides in length. In some embodiments, said guide target sequence is GC-rich. In some embodiments, said guide target sequence has from about 40% to about 80% of G and C nucleotides. In some embodiments, said guide target sequence has less than 40% G and C nucleotides. In some embodiments, said guide target sequence has more than 80% G and C nucleotides. In some embodiments, at least one of said plurality of nuclease recognition sequences is a Cas9 nuclease recognition sequence. In some embodiments, multiple of said plurality of nuclease recognition sequences are Cas9 nuclease recognition sequences. In some embodiments, said guide target sequence is AT-rich. In some embodiments, said guide target sequence has from about 40% to about 80% of A and T nucleotides. In some embodiments, said guide target sequence has less than 40% A and T nucleotides. In some embodiments, said guide target sequence has more than 80% A and T nucleotides.

In some embodiments, at least one of said plurality of nuclease recognition sequences in said GEMS construct is a Cpf1 nuclease recognition sequence. In some embodiments, multiple of said plurality of nuclease recognition sequences are Cpf1 nuclease recognition sequence. In some embodiments, each of said PAM sequence in said plurality of nuclease recognition sequences is different from another of said PAM sequence in said plurality of nuclease recognition sequences. In some embodiments, said PAM sequence is independently selected from the group consisting of: CC, NG, YG, NGG, NAA, NAT, NAG, NAC, NTA, NTT, NTG, NTC, NGA, NGT, NGC, NCA, NCT, NCG, NCC, NRG, TGG, TGA, TCG, TCC, TCT, GGG, GAA, GAC, GTG, GAG, CAG, CAA, CAT, CCA, CCN, CTN, CGT, CGC, TAA, TAC, TAG, TGG, TTG, TCN, CTA, CTG, CTC, TTC, AAA, AAG, AGA, AGC, AAC, AAT, ATA, ATC, ATG, ATT, AWG, AGG, GTG, TTN, YTN, TTTV, TYCV, TATV, NGAN, NGNG, NGAG, NGCG, NGGNG, NGRRT, NGRRN, NNGRRT, NNAAAAN, NNNNGATT, NAAAAC, NNAAAAAW, NNAGAA, NNNNACA, GNNNCNNA, NNNNGATT, NNAGAAW, NNGRR, NNNNNNN, TGGAGAAT, AAAAW, GCAAA, and TGAAA.

In some embodiments, said GEMS sequence further comprises a polynucleotide spacer, wherein said polynucleotide spacer separates at least one of said plurality of nuclease recognition sequences from an adjacent nuclease recognition sequence of said plurality of nuclease recognition sequences. In some embodiments, said polynucleotide spacer is from about 2 to about 10,000 nucleotides in length. In some embodiments, said polynucleotide spacer is from about 25 to about 50 nucleotides in length. In some embodiments, said polynucleotide spacer is a plurality of polynucleotide spacers. In some embodiments, at least one of said polynucleotide spacers in said plurality of polynucleotide spacers is the same as another polynucleotide spacer in said plurality of polynucleotide spacers. In some embodiments, each of said polynucleotide spacers is different than another of said plurality of polynucleotide spacers. In some embodiments, at least one of said flanking insertion sequences has a length of at least 12 nucleotides. In some embodiments, at least one of said flanking insertion sequences has a length of at least 18 nucleotides. In some embodiments, at least one of said flanking insertion sequences has a length of at least 50 nucleotides. In some embodiments, at least one of said flanking insertion sequences has a length of at least 100 nucleotides. In some embodiments, at least one of said flanking insertion sequences has a length of at least 500 nucleotides. In some embodiments, said flanking insertion sequences comprise a pair of flanking insertion sequences, and said pair of flanking insertion sequences flank said GEMS sequence.

In some embodiments, at least one flanking insertion sequence of said pair of flanking insertion sequences of said GEMS construct comprises an insertion sequence that is homologous to a sequence of a safe harbor site of said genome. In some embodiments, said safe harbor site is an adeno-associated virus site 1 (AAVs1) site. In some embodiments, said safe harbor site comprises a Rosa26 site. In some embodiments, said safe harbor site comprises a C—C motif receptor 5 (CCR5) site. In some embodiments, a sequence of a first insertion sequence differs from a sequence of a second insertion sequence of said pair of insertion sequences. In some embodiments, said insertion into said genome is by homologous recombination. In some embodiments, at least one insertion sequence of said pair of insertion sequences comprises a meganuclease recognition sequence. In some embodiments, said meganuclease recognition sequence comprises an I-SceI meganuclease recognition sequence.

In some embodiments, said GEMS construct further comprises a reporter gene. In some embodiments, said reporter gene encodes a fluorescent protein. In some embodiments, said fluorescent protein is green fluorescent protein (GFP). In some embodiments, said reporter gene is regulated by an inducible promoter. In some embodiments, said inducible promoter is induced by an inducer. In some embodiments, said inducer is doxycycline, isopropyl-β-thiogalactopyranoside (IPTG), galactose, a divalent cation, lactose, arabinose, xylose, N-acyl homoserine lactone, tetracycline, a steroid, a metal, or an alcohol. In some embodiments, said inducer is heat or light.

Provided herein is a host cell comprising the GEMS construct as provided herein. In some embodiments, said host cell is a eukaryotic cell. In some embodiments, said host cell is a mammalian cell. In some embodiments, said mammalian cell is a human cell. In some embodiments, said host cell is a stem cell. In some embodiments, said stem cell is independently selected from the group consisting of an adult stem cell, a somatic stem cell, a non-embryonic stem cell, an embryonic stem cell, a hematopoietic stem cell, a pluripotent stem cell, and a trophoblast stem cell. In some embodiments, said trophoblast stem cell is a mammalian trophoblast stem cell. In some embodiments, said mammalian trophoblast stem cell is a human trophoblast stem cell. In some embodiments, said host cell is a non-stem cell. In some embodiments, said host cell is a T-cell. In some embodiments, said T-cell is independently selected from the group consisting of an αβ T-cell, an NK T-cell, a γδ T-cell, a regulatory T-cell, a T helper cell and a cytotoxic T-cell.

Provided herein is a method of manufacturing a host cell as provided herein, wherein the method comprises introducing into a cell said GEMS construct as provided herein.

Provided herein is a method of manufacturing a host cell comprising: introducing into a cell a gene editing multi-site (GEMS) construct for insertion into a genome at an insertion site, wherein said GEMS construct comprises (i) flanking insertion sequences, wherein each of said flanking insertion sequences is homologous to a genome sequence at said insertion site; and (ii) a GEMS sequence between said flanking insertion sequences, wherein said GEMS sequence comprises a plurality of nuclease recognition sequences, wherein each of said plurality of nuclease recognition sequences comprises a guide target sequence and a protospacer adjacent motif (PAM) sequence, wherein said guide target sequence binds a guide polynucleotide following insertion of said GEMS construct at said insertion site.

In some embodiments, the method of manufacturing the host cell further comprises introducing into said cell a nuclease for mediating integration of said GEMS construct into said genome. In some embodiments, said nuclease when bound to said guide polynucleotide recognizes said nuclease recognition sequence of said plurality of nuclease recognition sequences. In some embodiments, said nuclease is an endonuclease. In some embodiments, said endonuclease comprises a meganuclease, wherein at least one of said flanking insertion sequences comprises a consensus sequence of said meganuclease. In some embodiments, said meganuclease is I-SceI. In some embodiments, said nuclease comprises a CRISPR-associated nuclease.

In some embodiments, the method of manufacturing the host cell further comprises introducing into said cell a guide polynucleotide for mediating integration of said GEMS construct into said genome. In some embodiments, said guide polynucleotide is a guide RNA. In some embodiments, said guide RNA recognizes a sequence of said genome at said insertion site. In some embodiments, said insertion site is at a safe harbor site of the genome. In some embodiments, said safe harbor site comprises an AAVs1 site. In some embodiments, said safe harbor site is a Rosa26 site. In some embodiments, said safe harbor site is a C—C motif receptor 5 (CCR5) site. In some embodiments, said GEMS construct is integrated at said insertion site.

In some embodiments, the method of manufacturing the host cell further comprises introducing a donor nucleic acid sequence into said host cell for insertion into said GEMS construct at said nuclease recognition sequence. In some embodiments, said donor nucleic acid sequence is integrated at said nuclease recognition sequence. In some embodiments, said donor nucleic acid sequence encodes a therapeutic protein. In some embodiments, said therapeutic protein comprises a chimeric antigen receptor (CAR). In some embodiments, said CAR is a CD19 CAR or a portion thereof. In some embodiments, said therapeutic protein comprises dopamine or a portion thereof. In some embodiments, said therapeutic protein comprises insulin, proinsulin, or a portion thereof.

In some embodiments, the method of manufacturing the host cell further comprises introducing into said host cell (i) a second guide polynucleotide, wherein said guide polynucleotide recognizes a second nuclease recognition sequence of said plurality of nuclease recognition sequences; (ii) a second nuclease, wherein said second nuclease recognizes said second nuclease recognition sequence when bound to said second guide polynucleotide; and (iii) a second donor nucleic acid sequence for integration at said second nuclease recognition sequence. In some embodiments, the method further comprising propagating said host cell.

Provided herein is a method of engineering a genome for receiving a donor nucleic acid sequence: introducing into the host cell as described herein: (i) a guide polynucleotide that recognizes said guide target sequence; (ii) a nuclease that when bound to said guide polynucleotide recognizes a nuclease recognition sequence of said plurality of nuclease recognition sequences; and (iii) a donor nucleic acid sequence for integration into said GEMS construct at said nuclease recognition sequence. In some embodiments, said nuclease cleaves said GEMS sequence when bound to said guide polynucleotide to form a double-stranded break in said GEMS sequence. In some embodiments, said donor nucleic acid sequence is integrated into said GEMS sequence at said double-stranded break. In some embodiments, said donor nucleic acid sequence encodes a therapeutic protein. In some embodiments, said therapeutic protein comprises a chimeric antigen receptor (CAR), a T-cell receptor (TCR), a B-cell receptor (BCR), an αβ receptor, or a γδ T-receptor. In some embodiments, said CAR is a CD19 CAR or a portion thereof. In some embodiments, said therapeutic protein comprises dopamine or a portion thereof. In some embodiments, said therapeutic protein comprises insulin, proinsulin, or a portion thereof.

In some embodiments, the method of engineering a genome further comprises introducing into the host cell as described herein (i) a second guide polynucleotide, wherein said second guide polynucleotide recognizes a second nuclease recognition sequence of said plurality of nuclease recognition sequences; (ii) a second nuclease, wherein said second nuclease recognizes said second nuclease recognition sequence when bound to said second guide polynucleotide; and (iii) a second donor nucleic acid sequence for integration within said second nuclease recognition sequence. In some embodiments, said host cell is a eukaryotic cell. In some embodiments, said host cell is a stem cell.

In some embodiments, the method of engineering a genome further comprises differentiating said stem cell into a T-cell. In some embodiments, said T-cell is independently selected from the group consisting of an αβ T-cell, an NK T-cell, a γδ T-cell, a regulatory T-cell, a T helper cell and a cytotoxic T-cell. In some embodiments, said differentiating occurs prior to said introducing said guide polynucleotide and said nuclease into said host cell. In some embodiments, said differentiating occurs after said introducing said guide polynucleotide and said nuclease into said host cell. In some embodiments, said insertion site is within a safe harbor site of said genome. In some embodiments, said safe harbor site comprises an AAVs1 site. In some embodiments, said safe harbor site is a Rosa26 site. In some embodiments, said safe harbor site is a C—C motif receptor 5 (CCR5) site.

In some embodiments, the method of engineering a genome comprises the PAM sequence independently selected from the group consisting of: CC, NG, YG, NGG, NAA, NAT, NAG, NAC, NTA, NTT, NTG, NTC, NGA, NGT, NGC, NCA, NCT, NCG, NCC, NRG, TGG, TGA, TCG, TCC, TCT, GGG, GAA, GAC, GTG, GAG, CAG, CAA, CAT, CCA, CCN, CTN, CGT, CGC, TAA, TAC, TAG, TGG, TTG, TCN, CTA, CTG, CTC, TTC, AAA, AAG, AGA, AGC, AAC, AAT, ATA, ATC, ATG, ATT, AWG, AGG, GTG, TTN, YTN, TTTV, TYCV, TATV, NGAN, NGNG, NGAG, NGCG, NGGNG, NGRRT, NGRRN, NNGRRT, NNAAAAN, NNNNGATT, NAAAAC, NNAAAAAW, NNAGAA, NNNNACA, GNNNCNNA, NNNNGATT, NNAGAAW, NNGRR, NNNNNNN, TGGAGAAT AAAAW, GCAAA, and TGAAA.

In some embodiments, the method of engineering a genome comprises a nuclease. In some embodiments, said nuclease is a CRISPR-associated nuclease. In some embodiments, said CRISPR-associated nuclease is a Cas9 enzyme. In some embodiments, said nuclease is a Cpf1 enzyme. In some embodiments, said PAM sequence is not required for said integration. In some embodiments, said nuclease is an Argonaute enzyme. In some embodiments, the method is for treating a disease. For example, the disease can be an autoimmune disease, cancer, diabetes, or Parkinson's disease. In some embodiments, disclosed herein is a host cell produced by any of methods described herein.

BRIEF DESCRIPTION OF THE DRAWINGS

The features of the present disclosure are set forth with particularity in the appended claims. A better understanding of the features and advantages of the present will be obtained by reference to the following detailed description that sets forth illustrative embodiments, in which the principles of the disclosure are utilized, and the accompanying drawings of which:

FIG. 18B discloses SEQ ID NOS 85, 85, 85, 85-86 and 86, respectively, in order of appearance. FIG. 18D discloses SEQ ID NOS 87, 87, 87, 87-89, 89, 89 and 89-91, respectively, in order of appearance.

FIG. 19D discloses SEQ ID NOS 92, 92, 92 and 92-94, respectively, in order of appearance. FIG. 19E discloses SEQ ID NOS 95, 95, 95, 95-96, 95, 97-102, 101, 101 and 103-104, respectively, in order of appearance.

FIG. 19F discloses SEQ ID NOS 105-106, 105, 105, 107-111 and 111-113, respectively, in order of appearance.

FIG. 24B discloses SEQ ID NOS 114-115, 115, 115, 115 and 115-117, respectively, in order of appearance. FIG. 24D discloses SEQ ID NOS 118-124, 124, 124-126 and 126, respectively, in order of appearance.

FIG. 25 shows an exemplary GEMS sequence with multiple gene editing sites (SEQ ID NO: 2).

DETAILED DESCRIPTION OF THE DISCLOSURE

Figure 1:
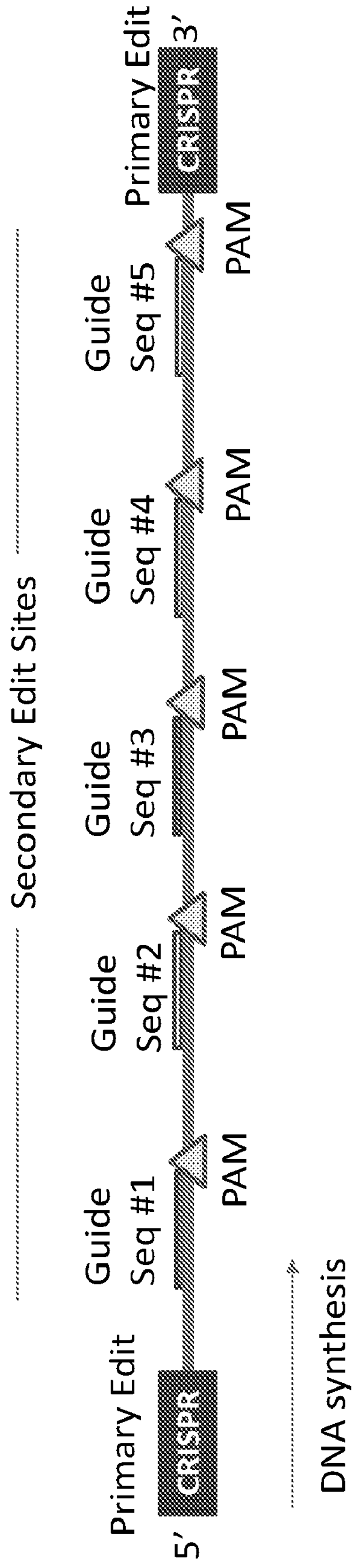
FIG. 1 shows a representation of a gene editing multi-site (GEMS), flanked by CRISPR sites that are 5' and 3' to the GEMS. The GEMS as shown include protospacer adjacent motif (PAM) compatible with different crRNA as a part of the guide RNA.

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms “a,” “an” and “the” include plural referents unless the context clearly dictates otherwise.

In this application, the use of “or” means “and/or” unless stated otherwise. The terms “and/or” and “any combination thereof” and their grammatical equivalents as used herein, can be used interchangeably. These terms can convey that any combination is specifically contemplated. Solely for illustrative purposes, the following phrases “A, B, and/or C” or “A, B, C, or any combination thereof” can mean “A individually; B individually; C individually; A and B; B and C; A and C; and A, B, and C.” The term “or” can be used conjunctively or disjunctively, unless the context specifically refers to a disjunctive use.

Furthermore, use of the term “including” as well as other forms, such as “include”, “includes,” and “included,” is not limiting.

Reference in the specification to “some embodiments,” “an embodiment,” “one embodiment” or “other embodiments” means that a particular feature, structure, or characteristic described in connection with the embodiments is included in at least some embodiments, but not necessarily all embodiments, of the present disclosures.

As used in this specification and claim(s), the words “comprising” (and any form of comprising, such as “comprise” and “comprises”), “having” (and any form of having, such as “have” and “has”), “including” (and any form of including, such as “includes” and “include”) or “containing” (and any form of containing, such as “contains” and “contain”) are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term “about” in relation to a reference numerical value and its grammatical equivalents as used herein can include the numerical value itself and a range of values plus or minus 10% from that numerical value.

The term “about” or “approximately” means within an acceptable error range for the particular value as determined by one of ordinary skill in the art, which will depend in part on how the value is measured or determined, i.e., the limitations of the measurement system. For example, “about” can mean within 1 or more than 1 standard deviation, per the practice in the art. Alternatively, “about” can mean a range of up to 20%, up to 10%, up to 5%, or up to 1% of a given value. In another example, the amount “about 10” includes 10 and any amounts from 9 to 11. In yet another example, the term “about” in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term “about” can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "multiple gene editing site(s)" and "gene editing multi-site(s) (GEMS)" are used interchangeably herein. A GEMS construct can comprises primary endonuclease recognition sites and a multiple gene editing site or a gene editing multi-site. In some embodiments, one or more of the primary endonuclease recognition sites are positioned upstream of the multiple gene editing site, and one or more of the primary endonuclease recognition sites are positioned downstream of the multiple gene editing site (FIGS. 1, 2A-2B, and 3). A GEMS construct can comprise flanking insertion sequences, wherein each of said flanking insertion sequences are homologous to a genome sequence at said insertion site; and a GEMS sequence adjacent to said flanking insertion sequences, wherein said GEMS sequence comprises a plurality of nuclease recognition sequences, wherein each of said plurality of nuclease recognition sequences comprises a guide target sequence and a protospacer adjacent motif (PAM) sequence, wherein said guide target sequence binds a guide polynucleotide following insertion of said GEMS construct at said insertion site. In an embodiment, the GEMS construct can further comprise a polynucleotide spacer which separates at least one nuclease recognition sequence from an adjacent nuclease recognition sequence. In some embodiment, the GEMS construct comprises a pair of homology arms which flank the GEMS sequence. In some embodiments, at least one homology arm of the pair of homology arms comprises a homology arm sequence that is homologous to a sequence of a safe harbor site of a host cell genome. In an embodiment, the plurality of nuclease recognition sequences is a plurality of editing sites (e.g., a plurality of PAMs), which each comprise a secondary endonuclease recognition site. The primary endonuclease recognition sites (e.g., insertion site) upstream and downstream of the multiple gene editing site facilitate insertion of the GEMS into the genome of a host cell. Thus, the GEMS constructs can be used, for example, to transfect a host cell and, once in the host cell, the upstream and downstream primary endonuclease recognition sites facilitate insertion of the multiple gene editing site into a chromosome. Once the multiple gene editing site is inserted into a chromosome, the host cell can be further modified with donor nucleic acid sequences or donor genes or portions thereof that are inserted into one or more of the editing sites of the multiple gene editing site. In some embodiments, insertion of the multiple gene editing site into a chromosome is stable integration into the chromosome.

The term "flanking insertion sequence" refers to a nucleotide sequences homologous to a genome sequence at the insertion site; wherein the GEMS sequence adjacent to the flanking insertion sequences is inserted at the insertion site. The flanking insertion sequences can comprise a pair of flanking insertion sequences, and said pair of flanking insertion sequences flank said GEMS sequence. In some cases, at least one flanking insertion sequence of said pair of flanking insertion sequences can comprise an insertion sequence that is homologous to a sequence of a safe harbor site (e.g., AAVs1, Rosa26, CCR5) of said genome. In some cases, the flanking insertion sequence is recognized by meganuclease, zinc finger nuclease, TALEN, CRISPR/Cas9, CRISPR/Cpf1, and/or Argonaut.

The term "host cell" refers to a cell comprising and capable of integrating one or more GEMS construct into its genome. The GEMS construct provided herein can be inserted into any suitable host cell. In some cases, the GEMS construct is integrated into a safe harbor site (e.g., Rosa26, AAVS1, CCR5). In some cases, the host cell is a stem cell. The host cell can be a prokaryotic or eukaryotic cell. Insertion of the construct can proceed according to any technique suitable in the art. For example, transfection, lipofection, or temporary membrane disruption such as electroporation or deformation can be used to insert the construct into the host cell. Viral vectors or non-viral vectors can be used to deliver the construct in some aspects. In an embodiment, the host cell can be competent for any endonuclease described herein. Competency for the endonuclease permits integration of the multiple gene editing site into the host cell genome. The host cell can be a primary isolate, obtained from a subject and optionally modified as necessary to make the cell competent for any required endonuclease. In some aspects, the host cell is a cell line. In some aspects, the host cell is a primary isolate or progeny thereof. In some aspects, the host cell is a stem cell. The stem cell can be an embryonic stem cell, a non-embryonic stem cell or an adult stem cell. The stem cell is preferably pluripotent, and not yet differentiated or begun a differentiation process. In some aspects, the host cell is a fully differentiated cell. When the host cell, transfected with the GEMS construct, divides, the multiple gene editing site of the construct can be integrated with the host cell genome such that progeny of the host cell can carry the multiple gene editing site. A host cell comprising an integrated multiple gene editing site can be cultured and expanded in order to increase the number of cells available for receiving donor gene sequences. Stable integration ensures subsequent generations of cells can have the multiple gene editing sites.

Figure 7:
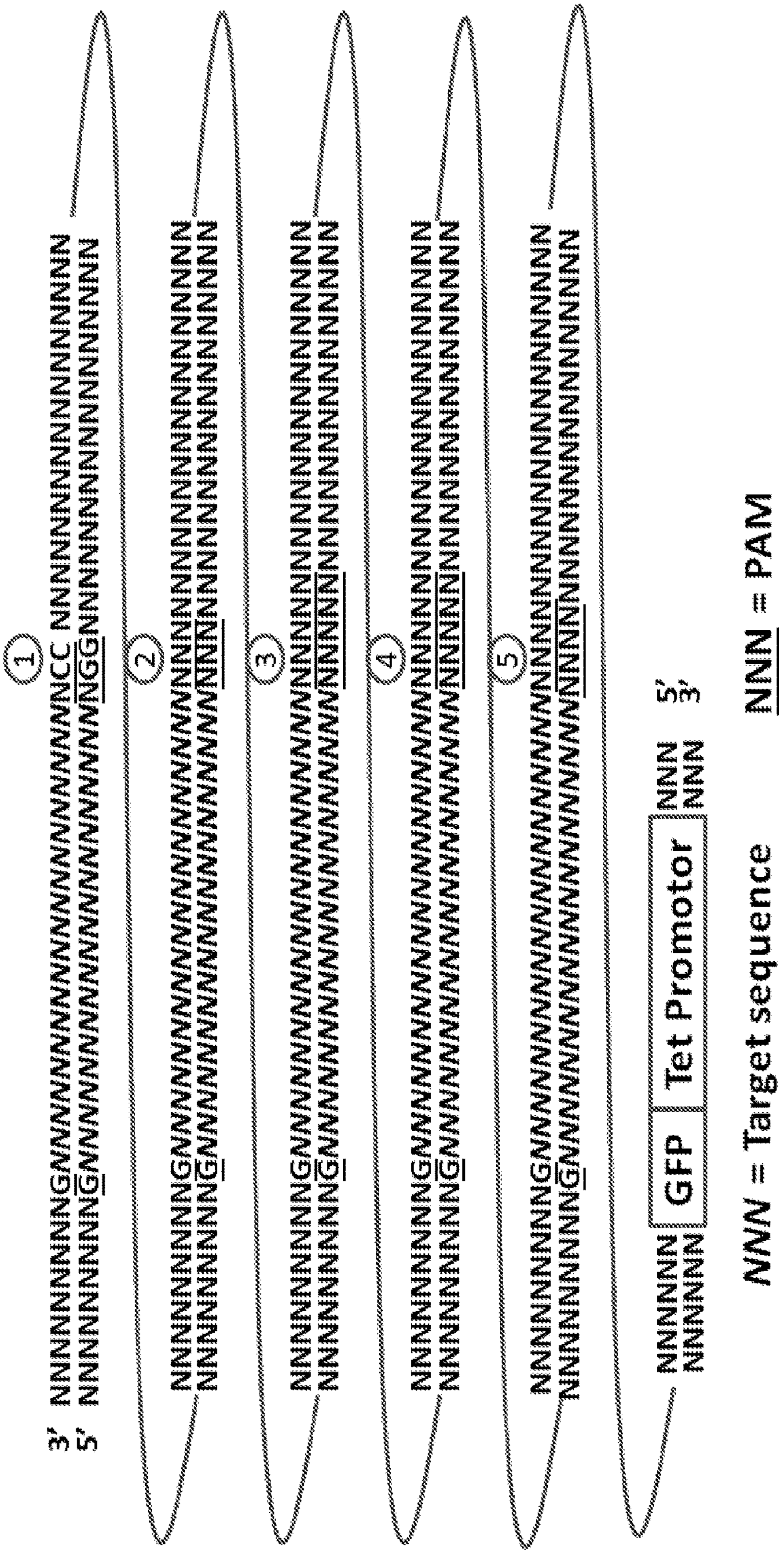
FIG. 7 shows a representation of an exemplary GEMS construct having a Tet-inducible green fluorescent protein (GFP) tag to confirm insertion of the GEMS into the chromosome of a cell.
Figure 8:
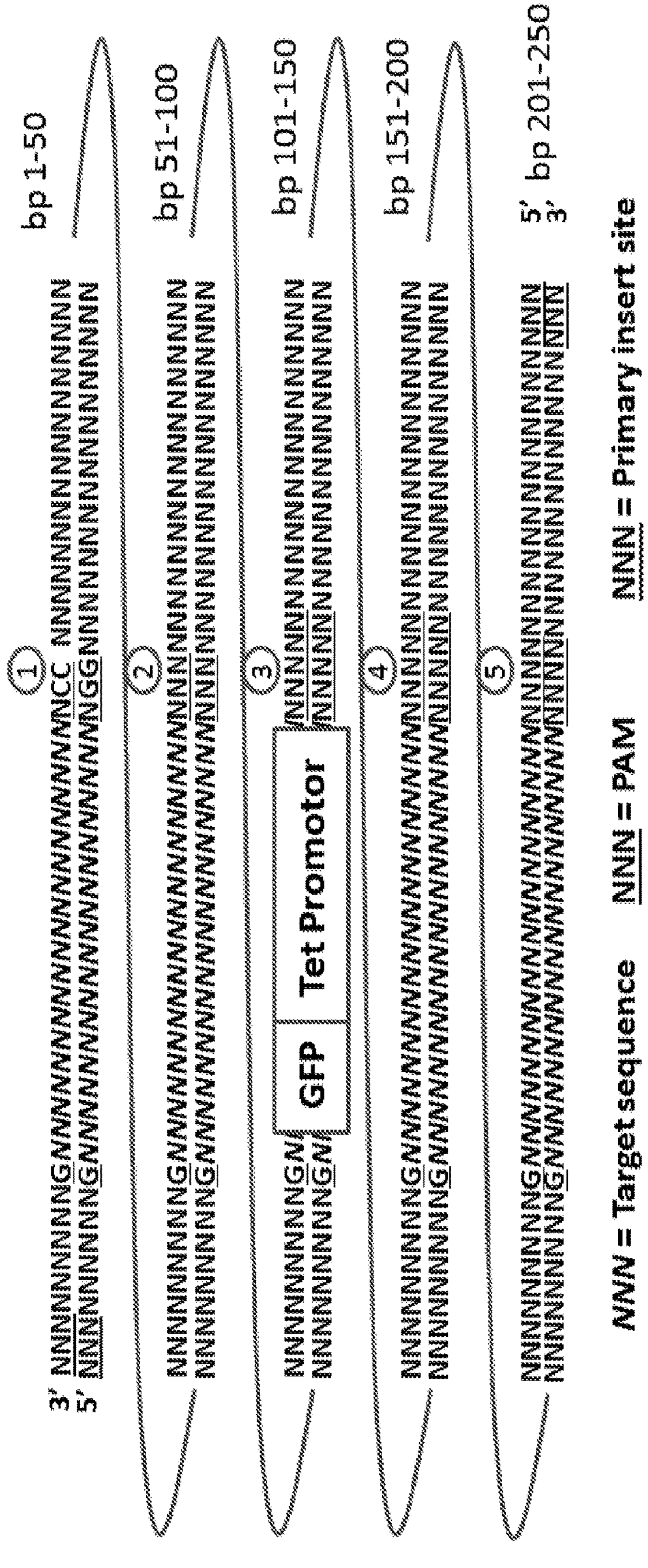
FIG. 8 shows a representation of an exemplary GEMS construct having a Tet-inducible green fluorescent protein (GFP) tag inserted into one of the target sequences.

The term "donor nucleic acid sequence(s)", "donor gene (s)" or "donor gene(s) of interest" refers to the nucleic acid sequence(s) or gene(s) inserted into the host cell genome at the multiple gene editing site. Donor nucleic acid sequences can be DNA. Donor nucleic acid sequences can be provided on an additional plasmid or other suitable vector that is inserted into the host cell. Transfection, lipofection, or temporary membrane disruption such as electroporation or deformation can be used to insert the vector comprising the donor nucleic acid sequence into the host cell. The donor nucleic acid sequences can be exogenous genes, or portions thereof, including engineered genes. The donor nucleic acid sequences can encode any protein or portion thereof that the user desires that the host cell express. The donor nucleic acid sequences (including genes) can further comprise a reporter gene, which can be used to confirm expression. The expression product of the reporter gene can be substantially inert such that its expression along with the donor gene of interest does not interfere with the intended activity of the donor gene expression product, or otherwise interfere with other natural processes in the cell, or otherwise cause deleterious effects in the cell. The donor nucleic acid sequence can also comprise regulatory elements that permit controlled expression of the donor gene. For example, the donor nucleic acid sequence can comprise a repressor operon or inducible operon. The expression of the donor nucleic acid sequence can thus be under regulatory control such that the gene is only expressed under controlled conditions. In some aspects, the donor nucleic acid sequence includes no regulatory elements, such that the donor gene is effectively constitutively expressed. In some embodiments, the donor nucleic acid sequence encoding is the green fluorescent protein (GFP) (SEQ ID NO: 12) under a tetracycline (Tet)-inducible promoter (FIGS. 7-8).

In some embodiments, the donor nucleic acid encodes a CAR construct (e.g., CD19 CAR). In some embodiments, the donor nucleic acid sequences comprise a nucleotide sequence of SEQ ID NO: 20. In some embodiments, the donor nucleic acid sequences comprise a nucleotide sequence of SEQ ID NO: 21. In some embodiments, the donor nucleic acid sequences comprise a nucleotide sequence of SEQ ID NO: 22. In some embodiments, the donor nucleic acid sequences comprise a nucleotide sequence of SEQ ID NO: 23. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 20. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 21. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 22. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 23.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"Polynucleotide(s)", "oligonucleotide(s)", "nucleic acid (s)", "nucleotide(s)", "polynucleic acid(s)", or any grammatical equivalent as used herein refers to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs. The nucleic acid sequences and vectors disclosed or contemplated herein can be introduced into a cell by, for example, transfection, transformation, or transduction.

"Transfection," "transformation," or "transduction" as used herein refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346:776-777 (1990)); and strontium phosphate DNA co-precipitation (Brash et al., Mol. Cell Biol., 7:2031-2034 (1987)). Phage, viral, or non-viral vectors can be introduced into host cells, after growth of infectious particles in suitable packaging cells, many of which are commercially available. In some embodiments, lipofection, nucleofection, or temporary membrane disruption (e.g., electroporation or deformation) can be used to introduce one or more exogenous polynucleotides into the host cell.

A "safe harbor" region or "safe harbor" site is a portion of the chromosome where one or more donor genes, including transgenes, can integrate, with substantially predictable expression and function, but without inducing adverse effects on the host cell or organism, including but not limited to, without perturbing endogenous gene activity or promoting cancer or other deleterious condition. See, Sadelain M et al. (2012) Nat. Rev. Cancer 12:51-58. In an embodiment, the safe harbor site is the adeno-associated virus site 1 (AAVS1), a naturally occurring site of integration of AAV virus on chromosome 19. In an embodiment, the safe harbor site is the chemokine (C—C motif) receptor 5 (CCR5) gene, a chemokine receptor gene known as an HIV-1 coreceptor. In an embodiment, the safe harbor site is the human ortholog of the mouse Rosa26 locus, a locus extensively validated in the murine setting for the insertion of ubiquitously expressed transgenes. By way of example, in humans, there is a safe harbor locus on chromosome 19 (PPP1R12C) that is known as AAVS1. In mice, the Rosa26 locus is known as a safe harbor locus. The human AAVS1 site is particularly useful for receiving transgenes in embryonic stem cells and for pluripotent stem cells.

"Polypeptide", "peptide" and their grammatical equivalents as used herein refer to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The terms "identical" and its grammatical equivalents as used herein or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.,* 2:482 (1981); by the alignment algorithm of Needleman and Wunsch, *J. Mol. Biol.,* 48:443 (1970); by the search for similarity method of Pearson and Lipman, *Proc. Nat. Acad. Sci U.S.A.,* 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene,* 73:237-244 (1988) and Higgins and Sharp, CABIOS, 5:151-153 (1989); Corpet et al., Nucleic Acids Res., 16:10881-10890 (1988); Huang et al., *Computer Applications in the Biosciences,* 8:155-165 (1992); and Pearson et al., *Methods in Molecular Biology,* 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

"CD19", cluster of differentiation 19 or B-lymphocyte antigen CD19, is a protein that in human is encoded by the CD19 gene. The CD19 gene encodes a cell surface molecule that assembles with the antigen receptor of B lymphocytes in order to decrease the threshold for antigen receptor-dependent stimulation. CD19 is expressed on follicular dendritic cells and B cells. In fact, it is present on B cells from earliest recognizable B-lineage cells during development to B-cell blasts but is lost on maturation to plasma cells. It primarily acts as a B cell co-receptor in conjunction with CD21 and CD81. Upon activation, the cytoplasmic tail of CD19 becomes phosphorylated, which leads to binding by Src-family kinases and recruitment of PI-3 kinase. As on T cells, several surface molecules form the antigen receptor and form a complex on B lymphocytes. The (almost) B cell-specific CD19 phosphoglycoprotein is one of these molecules. The others are CD21 and CD81. These surface immunoglobulin (sIg)-associated molecules facilitate signal transduction. On B cells, anti-immunoglobulin antibody mimicking exogenous antigen causes CD19 to bind to sIg and internalize with it. The reverse process has not been demonstrated, suggesting that formation of this receptor complex is antigen-induced. This molecular association has been confirmed by chemical studies.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. Vector also can comprise a selectable marker gene.

The term "selectable marker gene" as used herein refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77:3567 (1980); O'Hare et al., Proc. Natl. Acad. Sci. USA, 78:1527 (1981); Mulligan & Berg, Proc. Natl. Acad. Sci. USA, 78:2072 (1981); Colberre-Garapin et al., J. Mol. Biol., 150:1 (1981); Santerre et al., Gene, 30:147 (1984); Kent et al., Science, 237:901-903 (1987); Wigler et al., Cell, 11:223 (1977); Szybalska & Szybalski, Proc. Natl. Acad. Sci. USA, 48:2026 (1962); Lowy et al., Cell, 22:817 (1980); and U.S. Pat. Nos. 5,122,464 and 5,770,359.

The term "coding sequence" as used herein refers to a segment of a polynucleotide that codes for protein. The region or sequence is bounded nearer the 5' end by a start codon and nearer the 3' end with a stop codon. Coding sequences can also be referred to as open reading frames.

The term "operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "induce", "induction" and its grammatical equivalents as used herein refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off with an inducer at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters, isopropyl-B-thiogalactopyranoside (IPTG) inducible promoter.

As used herein, the term "guide RNA" and its grammatical equivalents can refer to an RNA which can be specific for a target DNA and can form a complex with Cas protein. An RNA/Cas complex can assist in "guiding" Cas protein to a target DNA.

The term "protospacer adjacent motif (PAM)" or PAM-like motif refers to a 2-6 base pair DNA sequence immediately following the DNA sequence targeted by the Cas9 nuclease in the CRISPR bacterial adaptive immune system. In some embodiments, the PAM can be a 5' PAM (i.e., located upstream of the 5' end of the protospacer). In other embodiments, the PAM can be a 3' PAM (i.e., located downstream of the 5' end of the protospacer).

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

"T helper cells" (TH cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H9$, $T_H17$, $T_H22$ or $T_{FH}$ (T follicular helper cells), which secrete different cytokines to facilitate different types of immune responses. Signaling from the APCs directs T cells into particular subtypes.

"Cytotoxic T cells" (TC cells, or CTLs) or "cytotoxic T lymphocytes" destroy virus-infected cells and tumor cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

"Memory T cells" are a subset of antigen-specific T cells that persist long-term after an infection has resolved. They quickly expand to large numbers of effector T cells upon re-exposure to their cognate antigen, thus providing the immune system with memory against past infections. Memory T cells comprise three subtypes: central memory T cells ($T_{CM}$ cells) and two types of effector memory T cells ($T_{EM}$ cells and $T_{EMRA}$ cells). Memory cells can be either CD4+ or CD8+. Memory T cells typically express the cell surface proteins CD45RO, CD45RA and/or CCR7.

"Regulatory T cells" (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

"Natural killer cells" or "NK cells" are a type of cytotoxic lymphocyte critical to the innate immune system. The role NK cells play is analogous to that of cytotoxic T cells in the vertebrate adaptive immune response. NK cells provide rapid responses to viral-infected cells, acting at around 3 days after infection, and respond to tumor formation. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction. They were named "natural killers" because of the initial notion that they do not require activation to kill cells that are missing "self" markers of MHC class 1. This role is especially important because harmful cells that are missing MHC I markers cannot be detected and destroyed by other immune cells, such as T lymphocyte cells. NK cells (belonging to the group of innate lymphoid cells) are defined as large granular lymphocytes (LGL) and constitute the third kind of cells differentiated from the common lymphoid progenitor-generating B and T lymphocytes. NK cells are known to differentiate and mature in the bone marrow, lymph nodes, spleen, tonsils, and thymus, where they then enter into the circulation. NK cells differ from natural killer T cells (NKTs) phenotypically, by origin and by respective effector functions; often, NKT cell activity promotes NK cell activity by secreting interferon gamma. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice.

"Natural killer T cells" (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both T helper ($T_H$) and cytotoxic T (TC) cells (i.e., cytokine production and release of cytolytic/cell killing molecules). They are also able to recognize and eliminate some tumor cells and cells infected with herpes viruses.

"Adoptive T cell transfer" refers to the isolation and ex vivo expansion of tumor specific T cells to achieve greater number of T cells than what can be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

The term "antibody" as used herein includes IgG (including IgG1, IgG2, IgG3, and IgG4), IgA (including IgA1 and IgA2), IgD, IgE, or IgM, and IgY, and is meant to include whole antibodies, including single-chain whole antibodies, and antigen-binding (Fab) fragments thereof. Antigen-binding antibody fragments include, but are not limited to, Fab, Fab' and $F(ab')_2$, Fd (consisting of VH and CH1), single-chain variable fragment (scFv), single-chain antibodies, disulfide-linked variable fragment (dsFv) and fragments comprising either a VL or VH domain. The antibodies can be from any animal origin. Antigen-binding antibody fragments, including single-chain antibodies, can comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies can be monoclonal, polyclonal, chimeric, humanized, and human monoclonal and polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antibody like molecules" can be for example proteins that are members of the Ig-superfamily which are able to selectively bind a partner. MHC molecules and T cell receptors are such molecules. In one embodiment, the antibody-like molecule is an TCR. In one embodiment, the TCR has been modified to increase its MHC binding affinity.

The terms "fragment of an antibody," "antibody fragment," "functional fragment of an antibody," "antigen-binding portion" or its grammatical equivalents are used interchangeably herein to mean one or more fragments or portions of an antibody that retain the ability to specifically bind to an antigen (see, generally, Holliger et al., Nat. Biotech., 23 (9): 1126-1129 (2005)). The antibody fragment desirably comprises, for example, one or more CDRs, the variable region (or portions thereof), the constant region (or portions thereof), or combinations thereof. Non-limiting examples of antibody fragments include (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242:423-426 (1988); Huston et al., Proc. Natl. Acad. Sci. USA, 85:5879-5883 (1988); and Osbourn et al., Nat. Biotechnol., 16:778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites.

"Tumor antigen" as used herein refers to any antigenic substance produced or overexpressed in tumor cells. It can, for example, trigger an immune response in the host. Alternatively, for purposes of this disclosure, tumor antigens can be proteins that are expressed by both healthy and tumor cells, but because they identify a certain tumor type, they can be a suitable therapeutic target. In some embodiments, the tumor antigen is CD19, CD20, CD30, CD33, CD38, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, or any combination thereof. In some embodiments, the tumor antigen is 1p19q, ABL1, AKTI, ALK, APC, AR, ATM, BRAF, BRCA1, BRCA2, cKIT, cMET, CSFIR, CTNNB1, EGFR, EGFRVIII, ER, ERBB2 (HER2), FGFR1, FGFR2, FLT3, GNA11, GNAQ, GNAS, HER2, HRAS, IDH1, IDH2, JAK2, KDR (VEGFR2), KRAS, MGMT, MGMT-Me, MLH1, MPL, NOTCH1, NRAS, PDGFRA, Pgp, PIK3CA, PR, PTEN, RET, RRMI, SMO, SPARC, TLE3, TOP2A, TOPO1, TP53, TS, TUBB3, VHL, CDH1, ERBB4, FBXW7, HNFIA, JAK3, NPM1, PTPN11, RB1, SMAD4, SMARCB1, STK1, MLH1, MSH2, MSH6, PMS2, microsatellite instability (MSI), ROS1, ERCC1, or any combination thereof.

The term "chimeric Antigen Receptor" (CAR), "artificial T cell receptor", "chimeric T cell receptor", or "chimeric immunoreceptor" as used herein refers to an engineered receptor, which grafts an arbitrary specificity onto an immune effector cell. CARs typically have an extracellular domain (ectodomain), which comprises an antigen-binding domain, a transmembrane domain, and an intracellular (endodomain) domain. In some embodiments, CAR does not actually recognize the entire antigen; instead it binds to only a portion of the antigen's surface, an area called the antigenic determinant or epitope.

"Epitope", "antigenic determinant", "antigen recognition moiety", "antigen recognition domain", and their grammatical equivalents refer to a molecule or portion of an antigen to which specifically e.g., an antibody or a receptor binds. In one embodiment, the antigen recognition moiety is in an antibody, antibody like molecule or fragment thereof and the antigen is a tumor antigen.

A "functional variant" of a protein used herein refers to a polypeptide, or a protein having substantial or significant sequence identity or similarity to the reference polypeptide, and retains the biological activity of the reference polypeptide of which it is a variant. In some embodiments, a functional variant, for example, comprises the amino acid sequence of the reference protein with at least or about 1, 2, 3, 4, 5, 6, 7, 8, 9, 10, 11, 12, 13, 14, 15, 16, 17, 18, 19, or 20 conservative amino acid substitutions. Functional variants encompass, for example, those variants of the CAR described herein (the parent CAR) that retain the ability to recognize target cells to a similar extent, the same extent, or to a higher extent, as the parent CAR. In reference to a nucleic acid sequence encoding the parent CAR, a nucleic acid sequence encoding a functional variant of the CAR can be for example, about 10% identical, about 25% identical, about 30% identical, about 50% identical, about 65% identical, about 70% identical, about 75% identical, about 80% identical, about 85% identical, about 90% identical, about 95% identical, or about 99% identical to the nucleic acid sequence encoding the parent CAR.

The term "functional portion," when used in reference to a CAR, refers to any part or fragment of a CAR described herein, which part or fragment retains the biological activity of the CAR of which it is a part (the parent CAR). In reference to a nucleic acid sequence encoding the parent CAR, a nucleic acid sequence encoding a functional portion of the CAR can encode a protein comprising, for example, about 10%, 25%, 30%, 50%, 68%, 80%, 90%, 95%, or more, of the parent CAR.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —$NH_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the parent CAR.

"Proliferative disease" as referred to herein means a unifying concept that excessive proliferation of cells and turnover of cellular matrix contribute significantly to the pathogenesis of several diseases, including cancer is presented.

"Patient" or "subject" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, non-human primates, cats, dogs, pigs, cattle, cats, horses, goats, sheep, rodents (e.g., mice, rabbits, rats, or guinea pigs) and other mammalians that can benefit from the therapies disclosed herein. Exemplary human patients can be male and/or female.

"Patient in need thereof" or "subject in need thereof" is referred to herein as a patient diagnosed with or suspected of having a disease or disorder, for instance, but not restricted to a proliferative disorder such as cancer. In some cases, a cancer is a solid tumor or a hematologic malignancy. In some instances, the cancer is a solid tumor. In other instances, the cancer is a hematologic malignancy. In some cases, the cancer is a metastatic cancer. In some cases, the cancer is a relapsed or refractory cancer. In some instances, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments leukemia can be, for instance, acute lymphoblastic leukemia (ALL), acute myeloid leukemia (AML), chronic lymphocytic leukemia (CLL) and chronic myeloid leukemia (CML).

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treatment", "treating", or its grammatical equivalents refers to obtaining a desired pharmacologic and/or physiologic effect. In embodiments, the effect is therapeutic, i.e., the effect partially or completely cures a disease and/or adverse symptom attributable to the disease. To this end, the inventive method comprises administering a therapeutically effective amount of the composition comprising the host cells expressing the inventive nucleic acid sequence, or a vector comprising the inventive nucleic acid sequences.

The term "therapeutically effective amount", therapeutic amount", "immunologically effective amount", "anti-tumor effective amount", "tumor-inhibiting effective amount" or its grammatical equivalents refers to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

Some numerical values disclosed throughout are referred to as, for example, "X is at least or at least about 100; or 200 [or any numerical number]." This numerical value includes the number itself and all of the following:

i) X is at least 100;
ii) X is at least 200;
iii) X is at least about 100; and
iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:

i) X being administered on between day 1 and day 2;
ii) X being administered on between day 2 and day 3;
iii) X being administered on between about day 1 and day 2;
iv) X being administered on between about day 2 and day 3;
v) X being administered on between day 1 and about day 2;
vi) X being administered on between day 2 and about day 3;
vii) X being administered on between about day 1 and about day 2; and
viii) X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

Gene Editing Multi-Sites (GEMS)

Gene modified cell therapies are rapidly moving through clinical development and are the new drug frontier. However, these therapies are individualized solutions and therefore lack economy of scale and have limited patient access. These challenges offer the opportunity to create solutions that can support the economy of scale and make the therapy available to all patients in need. One solution can be to create "off the shelf" products. These products are derived from a donor and then expanded to be used in many recipients. Off the shelf products need to overcome some challenge to become of therapeutic and commercial value. Such challenge include overcoming rejection and sensitization; improve reliability of the gene modifications to reduce safety risks and cost; expanding therapeutic cell to high numbers (~109 cells, or more, per treatment); increasing dose to donor ratios (doses generated per donor) which will decrease development and manufacturing cost.

Provided herein is a nucleic acid construct comprising a multiple gene editing site or a gene editing multi-sites (GEMS) for facilitating gene editing and genetic engineering. The construct comprises DNA, and can be in the form of a plasmid. The term "multiple gene editing sites" and "gene editing multi-sites" are used interchangeably herein. The GEMS system can offer significant benefits, such as plug and play system to reduce development cost; exact known location of gene insert which enhances safety; standard tools to insert any gene construct allowing customization; and a possibility to be introduced in any source cell type preferably a self-renewing source. In some embodiments, the GEMS construct comprises eukaryotic nucleotides. In an embodiment, an exemplary GEMS sequence with multiple gene editing sites is as shown in FIG. 25. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

In some cases, the GEMS construct comprises at least one homology arm of at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 30 nucleotides, at least 40 nucleotides, at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, or at least 1,000 nucleotides. In some embodiments, at least one homology arm of the pair of homology arms comprises a homology arm sequence that is homologous to a sequence of a safe harbor site of a host cell genome. In some embodiments, the AAVs1 5' homology arm sequence comprises a nucleotide sequence of SEQ ID NO: 7. In some embodiments, the AAVs1 3' homology arm sequence comprises a nucleotide sequence of SEQ ID NO: 8.

The GEMS construct comprises primary endonuclease recognition sites and a multiple gene editing site. In some embodiments, one or more of the primary endonuclease recognition sites are positioned upstream of the multiple gene editing site, and one or more of the primary endonuclease recognition sites are positioned downstream of the multiple gene editing site (FIGS. 1, 2A-2B, and 3). The multiple gene editing site, in turn, comprises a plurality of editing sites, which each comprise a secondary endonuclease recognition site.

The primary endonuclease recognition sites upstream and downstream of the multiple gene editing site facilitate insertion of the multiple gene editing site into the genome of a host cell. Thus, the constructs can be used, for example, to transfect a recipient cell and, once in the recipient cell, the upstream and downstream primary endonuclease recognition sites facilitate insertion of the multiple gene editing site into a chromosome. Once the multiple gene editing site is inserted into a chromosome, the cell can be further modified with donor genes or portions thereof that are inserted into one or more of the editing sites of the multiple gene editing site. In some embodiments, insertion of the multiple gene editing site into a chromosome is stable integration into the chromosome.

Figure 4:
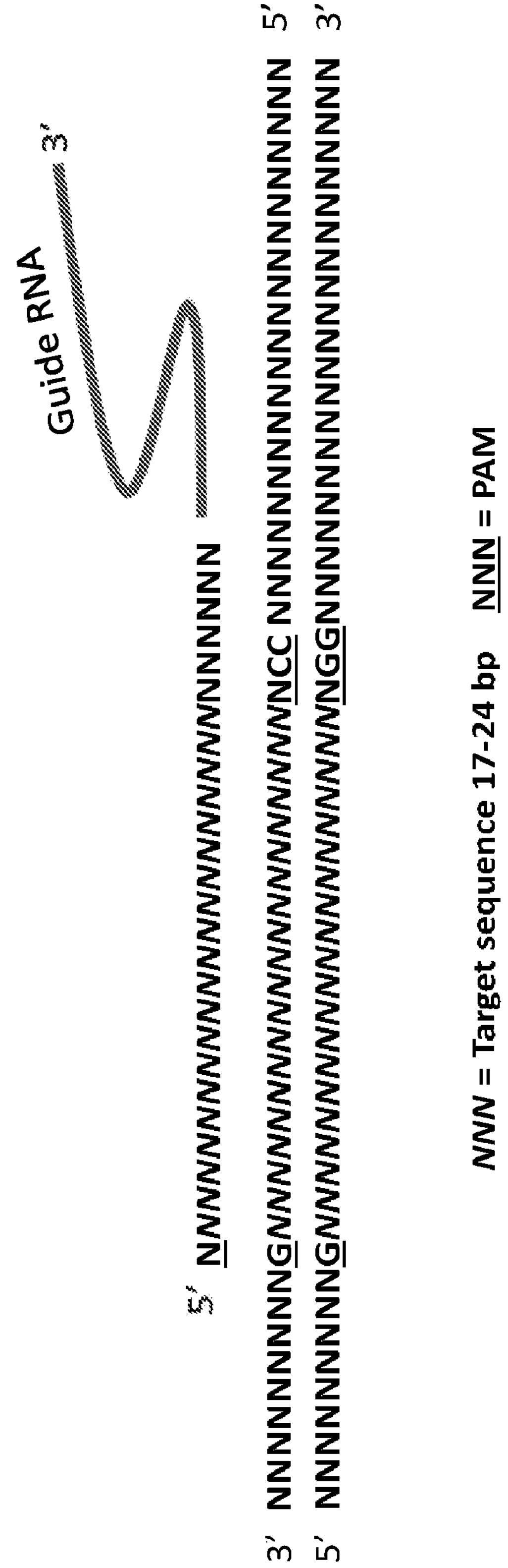
FIG. 4 shows a representation of a single editing site from a GEMS construct. The target locus in a chromosome includes a target sequence of about 17-24 bases, which is flanked by the PAM sequence. A guide RNA (gRNA) with a PAM recognition site complementary to the PAM sequence can align with the target and PAM sequence, and thereafter recruit the Cas9 enzyme.
Figure 5:
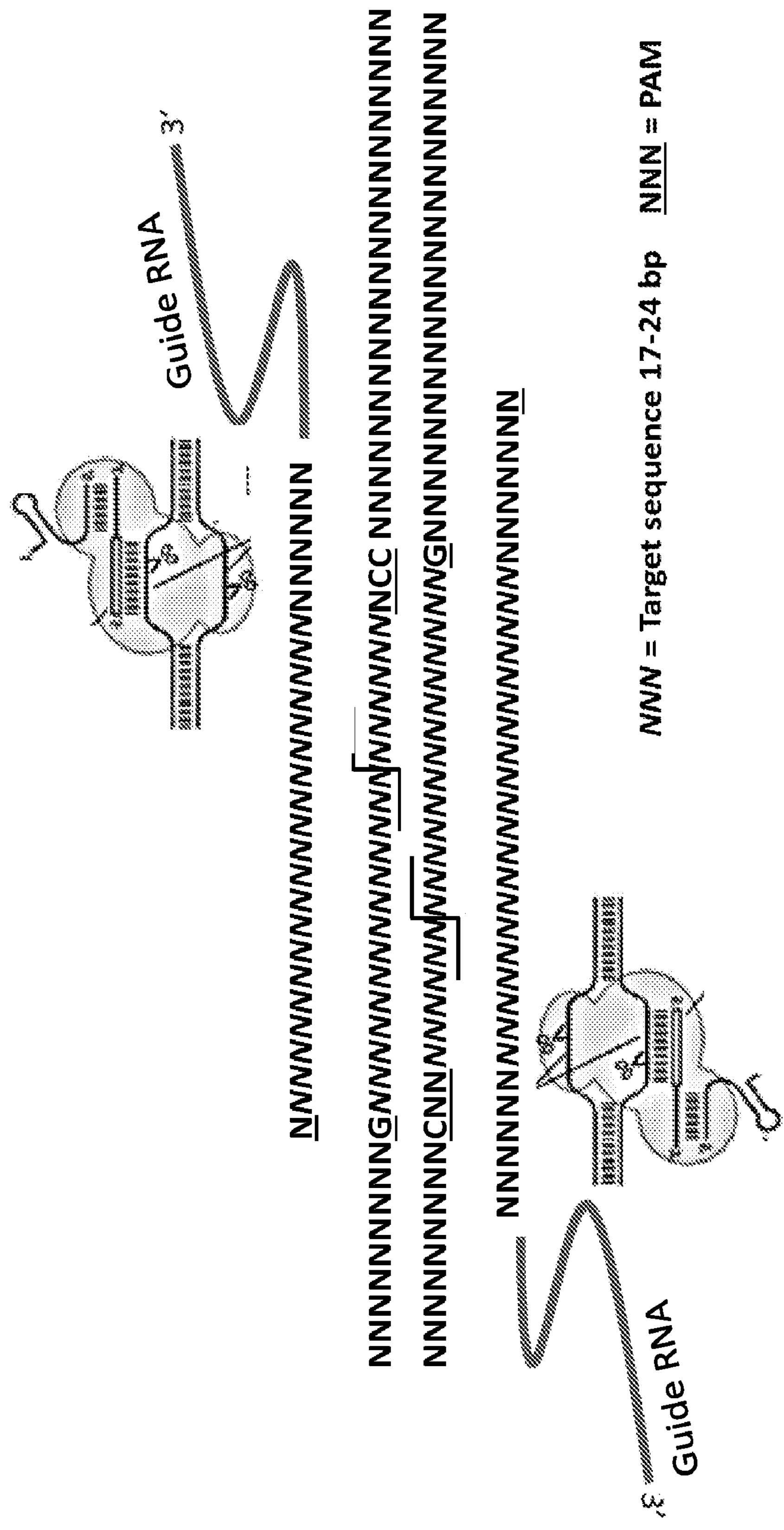
FIG. 5 shows a representation of double editing sites from a GEMS construct. The target locus in the chromosome includes two target sequences of about 17-24 bases, which are flanked by a PAM sequence on the chromosomal sense strand and anti-sense strand respectively. A guide RNA (gRNA) with a PAM recognition site complementary to the PAM sequence can align with the target and PAM sequence, and thereafter recruit the Cas9 enzyme.
Figure 6:
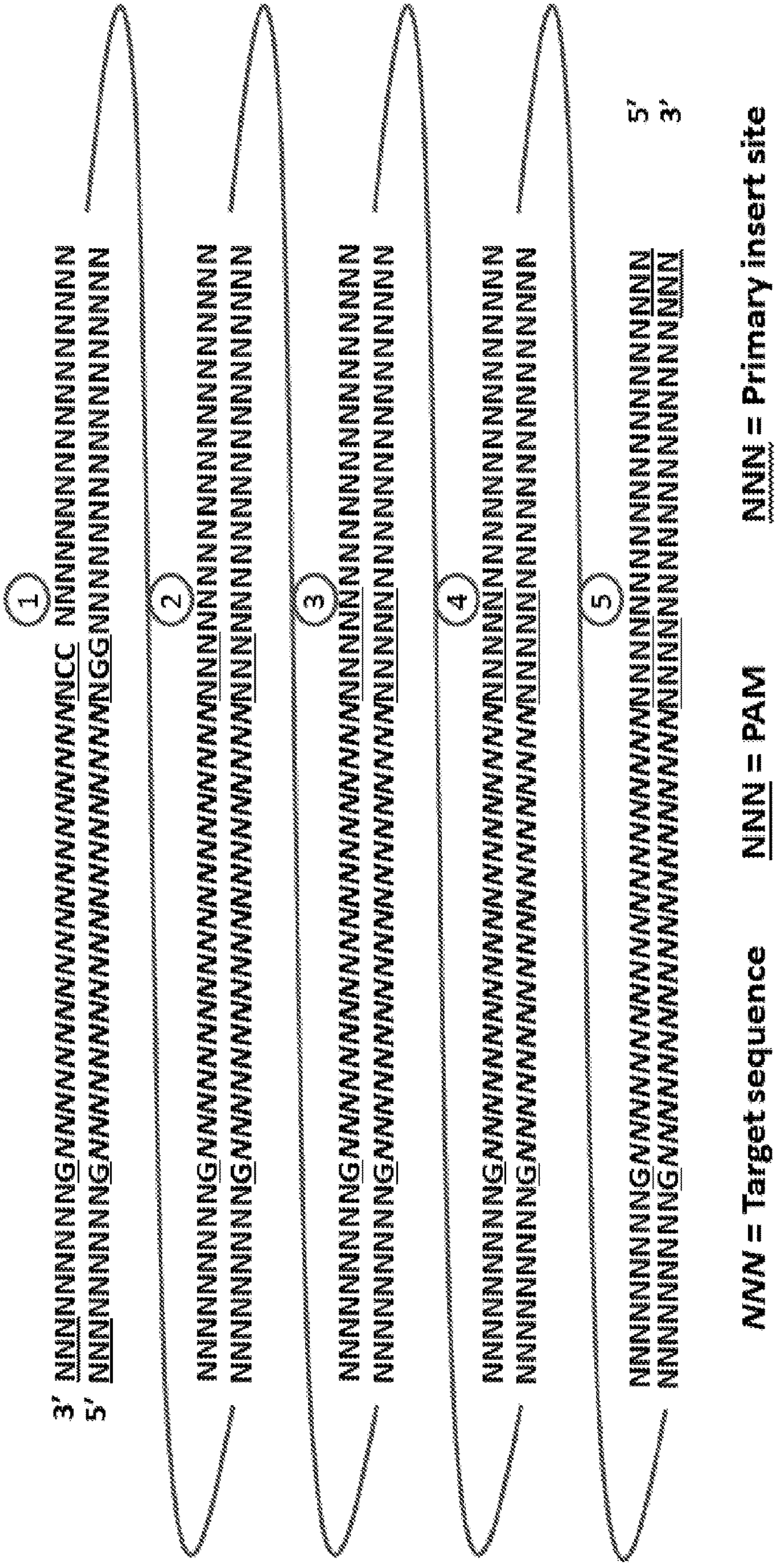
FIG. 6 shows a representation of an exemplary GEMS construct. The GEMS is flanked upstream and downstream by the insertion site, where the construct is to be inserted into the chromosome of a cell.

In some embodiments, within the multiple gene editing site, each of the plurality of secondary endonuclease recognition sites (e.g., PAM) can be contiguous with other secondary endonuclease recognition sites (e.g., PAM), but each secondary endonuclease recognition site can be separated from an adjacent recognition site by a polynucleotide spacer (FIGS. 4-6). The polynucleotide spacer can comprise any suitable number of nucleotides. The spacer length can be from about 2 nucleotides (base pairs in a double stranded construct) to about 10,000 or more nucleotides. In some embodiments, the space length is about 2 to about 5 nucleotides, from about 5 to about 10 nucleotides, from about 10 to about 20 nucleotides, from about 20 to about 30 nucleotides, from about 30 to about 40 nucleotides, from about 40 to about 50 nucleotides, from about 50 to about 100 nucleotides, from about 100 to about 200 nucleotides, from about 200 to about 300 nucleotides, from about 300 to about 400 nucleotides, from about 400 to about 500 nucleotides, from about 500 to about 1,000 nucleotides, from about 1,000 to about 2,000 nucleotides, from about 2,000 to about 5,000 nucleotides, or from about 5,000 to about 10,000 nucleotides. In some aspects, the spacer length is from about 5 to about 1000 nucleotides, from about 10 to about 100 nucleotides, or from about 25 to about 50 nucleotides.

In an embodiment, the GEMS construct is targeted to and stably integrates into a safe harbor region (e.g., Rosa26, AAVS1, CCR5) of a chromosome. A "safe harbor" region is a portion of the chromosome where one or more donor genes, including transgenes, can integrate, with substantially predictable expression and function, but without inducing adverse effects on the host cell or organism, including but not limited to, without perturbing endogenous gene activity or promoting cancer or other deleterious condition. See, Sadelain M et al. (2012) Nat. Rev. Cancer 12:51-58. By way of example, in humans, there is a safe harbor locus on chromosome 19 (PPP1R12C) that is known as AAVS1. In mice, the Rosa26 locus is known as a safe harbor locus. The human AAVS1 site is particularly useful for receiving transgenes in embryonic stem cells and for pluripotent stem cells. The human AAVS1 site is preferred for use in accordance with some aspects of the construct. In some embodiments, AAVs1 5' homology arm sequence comprises a nucleotide sequence of SEQ ID NO: 7. In some embodiments, AAVs1 3' homology arm sequence comprises a nucleotide sequence of SEQ ID NO: 8. In some embodiments, AAVs1 CRISPR targeting sequence comprises a nucleotide sequence of SEQ ID NO: 10. In some embodiments, AAVs1 CRISPR gRNA sequence comprises a nucleotide sequence of SEQ ID NO: 10.

To insert the multiple gene editing site of the construct into the safe harbor locus (e.g., Rosa26, AAVS1, CCR5), endonuclease activity in the cell is used. In some embodiments, the construct comprises one or more primary endonuclease recognition sequences that allow the construct to be cleaved by an endonuclease in the cell in order to generate a donor sequence comprising the multiple gene editing site. This donor sequence comprising the multiple gene editing site can then be inserted into a safe harbor locus. A compatible endonuclease recognizes the recognition sequence, and cleaves the construct accordingly. In some embodiments, the primary endonuclease recognition sequences are in common with endonuclease recognition sequences present at the safe harbor locus. In this way, the endonuclease can cleave the safe harbor locus, allowing insertion of the free (cleaved from the construct) multiple gene editing site donor sequence into the cleaved safe harbor locus. This insertion can proceed via homologous or non-homologous end joining (NHEJ) in the cell. Thus, the primary endonuclease recognition sequences can be tailored to nucleases that produce compatible ends at the site of the double stranded breaks in the construct DNA and in the safe harbor locus.

The methods described herein allows a DNA construct (e.g., GEMS construct, a gene of interest) entry into a host cell by e.g., calcium phosphate/DNA co-precipitation, microinjection of DNA into a nucleus, electroporation, bacterial protoplast fusion with intact cells, transfection, lipofection, infection, particle bombardment, sperm mediated gene transfer, or any other technique known by one skilled in the art.

Methods described herein can take advantage of a CRISPR/Cas system. For example, double-strand breaks (DSBs) can be generated using a CRISPR/Cas system, e.g., a type II CRISPR/Cas system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of a target sequence. In some embodiments, the target sequence of each secondary endonuclease recognition site in the multiple gene editing site can be the same, although in some aspects, the target sequence of each secondary endonuclease recognition site can be different from other target sequences in the multiple gene editing site. The target sequence can be from about 10 to about 30 nucleotides in length, from about 15 to about 25 nucleotides in length, and from about 17 to about 24 nucleotides in length (FIGS. 4-6). In some aspects, the target sequence is about 20 nucleotides in length.

In some embodiments, the target sequence can be GC-rich, such that at least about 40% of the target sequence is made up of G or C nucleotides. The GC content of the target sequence can from about 40% to about 80%, though GC content of less than about 40% or greater than about 80% can be used. In some embodiments, the target sequence can be AT-rich, such that at least about 40% of the target sequence is made up of A or T nucleotides. The AT content of the target sequence can from about 40% to about 80%, though AT content of less than about 40% or greater than about 80% can be used.

Site Specific Modification

Inserting one or more GEMS constructs disclosed herein can be site-specific. For example, one or more transgenes can be inserted adjacent to Rosa26, AAVS1, or CCR5. In some embodiments, the GEMS sequence adjacent to the flanking insertion sequences is inserted at the insertion site. The flanking insertion sequences can comprise a pair of flanking insertion sequences, and said pair of flanking insertion sequences flank said GEMS sequence. In some cases, at least one flanking insertion sequence of said pair of flanking insertion sequences can comprise an insertion sequence that is homologous to a sequence of a safe harbor site (e.g., AAVs1, Rosa26, CCR5) of said genome. In some cases, the flanking insertion sequence is recognized by meganuclease, zinc finger nuclease, TALEN, CRISPR/Cas9, CRISPR/Cpf1, and/or Argonaut. In some cases, the flanking sequence has a length of about 14 to 40 nucleotides. In some cases, the flanking sequence has a length of about 18 to 36 nucleotides. In some cases, the flanking sequence has a length of about 28 to 40 nucleotides. In some cases, the flanking sequence has a length of about 19 to 22 nucleotides. In some cases, the flanking sequence has a length of at least 18 nucleotides. In some cases, the flanking sequence has a length of at least 50 nucleotides. In some cases, the flanking sequence has a length of at least 100 nucleotides. In some cases, the flanking sequence has a length of at least 500 nucleotides.

Modification of a targeted locus of a cell can be produced by introducing DNA into cells, where the DNA has homology to the target locus. DNA can include a marker gene, allowing for selection of cells comprising the integrated construct. Homologous DNA in a target vector can recombine with a chromosomal DNA at a target locus. The DNA construct to be inserted can be flanked on both sides by homologous DNA sequences, a 3' recombination arm, and a 5' recombination arm. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17. In some embodiments, AAVs1 3' homology arm sequence comprises a nucleotide sequence of SEQ ID NO: 8. In some embodiments, AAVs1 CRISPR targeting sequence comprises a nucleotide sequence of SEQ ID NO: 10. In some embodiments, AAVs1 CRISPR gRNA sequence comprises a nucleotide sequence of SEQ ID NO: 10.

A variety of enzymes can catalyze insertion of foreign DNA into a host genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, fC31 integrase (a serine recombinase derived from *Streptomyces* phage fC31), or bacteriophage derived site-specific recombinases (including Flp, lambda integrase, bacteriophage HK022 recombinase, bacteriophage R4 integrase and phage TP901-1 integrase).

Cre/lox recombination is a tyrosine family site-specific recombinase technology, used to carry out deletions, insertions, translocations and inversions at specific sites in the DNA of cells. It allows the DNA modification to be targeted to a specific cell type or be triggered by a specific external stimulus. It can be implemented both in eukaryotic and prokaryotic systems. The Cre/lox system consists of a single enzyme, Cre recombinase, that recombines a pair of short target sequences called the Lox sequences. This system can be implemented without inserting any extra supporting proteins or sequences. The Cre enzyme and the original Lox site called the LoxP sequence are derived from bacteriophage P1. Placing Lox sequences appropriately allows genes to be activated, repressed, or exchanged for other genes. At a DNA level many types of manipulations can be carried out. The activity of the Cre enzyme can be controlled so that it is expressed in a particular cell type or triggered by an external stimulus like a chemical signal or a heat shock.

Flp/FRT recombination is a site-directed recombination technology used to manipulate an organism's DNA under controlled conditions in vivo. It is analogous to Cre/lox recombination but involves the recombination of sequences between short flippase recognition target (FRT) sites by the recombinase flippase (Flp) derived from the 2 μm plasmid of baker's yeast *Saccharomyces cerevisiae*. The Flp protein is a tyrosine family site-specific recombinase. This family of recombinases performs its function via a type IB topoisomerase mechanism causing the recombination of two separate strands of DNA. Recombination is carried out by a repeated two-step process. The initial step causes the creation of a Holliday junction intermediate. The second step promotes the resulting recombination of the two complementary strands.

The CRISPR/Cas system can be used to perform site specific insertion. For example, a nick on an insertion site in the genome can be made by CRISPR/Cas to facilitate the insertion of a transgene at the insertion site.

Certain aspects disclosed herein can utilize vectors. Any plasmids and vectors can be used as long as they are replicable and viable in a selected host. Vectors known in the art and those commercially available (and variants or derivatives thereof) can be engineered to include one or more recombination sites for use in the methods. Vectors that can be used include, but not limited to, bacterial expression vectors (such as pBs, pQE-9 (Qiagen), phagescript, PsiX174, pBluescript SK, pB5KS, pNH8a, pNH16a, pNH18a, pNH46a (Stratagene), pTrc99A, pKK223-3, pKK233-3, pDR540, pRIT5 (Pharmacia), and variants or derivatives thereof), eukaryotic expression vectors (such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, pYACneo (Clontech), pSVK3, pSVL, pMSG, pCH110, pKK232-8 (Pharmacia, Inc.), p3'SS, pXT1, pSG5, pPbac, pMbac, pMClneo, pOG44 (Stratagene, Inc.), pYES2, pAC360, pBlueBa-cHis A, B, and C, pVL1392, pBlueBac111, pCDM8, pcDNA1, pZeoSV, pcDNA3, pREP4, pCEP4, pEBVHis (Invitrogen, Corp.), pWLneo, pSv2cat, pOG44, pXT1, pSG (Stratagene) pSVK3, pBPv, pMSG, pSVL (Pharmiacia), and variants or derivatives thereof), and any other plasmids and vectors replicable and viable in the host cell.

Vectors known in the art and those commercially available (and variants or derivatives thereof) can in accordance with the present disclosure be engineered to include one or more recombination sites for use in the methods of the present disclosure. These vectors can be used to express a gene, e.g., a transgene, or portion of a gene of interest. A gene of portion or a gene can be inserted by using known methods, such as restriction enzyme-based techniques.

One or more recombinases can be introduced into a host cell before, concurrently with, or after the introduction of a target vector (e.g., a GEMS vector). The recombinase can be directly introduced into a cell as a protein, for example, using liposomes, coated particles, or microinjection. Alternately, a polynucleotide, either DNA or messenger RNA, encoding the recombinase can be introduced into the cell using a suitable expression vector. The targeting vector components can be useful in the construction of expression cassettes containing sequences encoding a recombinase of interest. However, expression of the recombinase can be regulated in other ways, for example, by placing the expression of the recombinase under the control of a regulatable promoter (i.e., a promoter whose expression can be selectively induced or repressed).

Recombinases for use in the practice of the present disclosure can be produced recombinantly or purified as previously described. Polypeptides having the desired recombinase activity can be purified to a desired degree of purity by methods known in the art of protein ammonium sulfate precipitation, purification, including, but not limited to, size fractionation, affinity chromatography, HPLC, ion exchange chromatography, heparin agarose affinity chromatography (e.g., Thorpe & Smith, Proc. Nat. Acad. Sci. 95:5505-5510, 1998.).

In one embodiment, the recombinases can be introduced into the eukaryotic cells that contain the recombination attachment sites at which recombination is desired by any suitable method. Methods of introducing functional proteins, e.g., by microinjection or other methods, into cells are well known in the art. Introduction of purified recombinase protein ensures a transient presence of the protein and its function, which is often a preferred embodiment. Alternatively, a gene encoding the recombinase can be included in an expression vector used to transform the cell, in which the recombinase-encoding polynucleotide is operably linked to a promoter which mediates expression of the polynucleotide in the eukaryotic cell. The recombinase polypeptide can also be introduced into the eukaryotic cell by messenger RNA that encodes the recombinase polypeptide. It is generally preferred that the recombinase be present for only such time as is necessary for insertion of the nucleic acid fragments into the genome being modified. Thus, the lack of permanence associated with most expression vectors is not expected to be detrimental. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide. In other embodiments, the recombinase gene is introduced into a transgenic eukaryotic organism. Transgenic cells or animals can be made that express a recombinase constitutively or under cell-specific, tissue-specific, developmental-specific, organelle-specific, or small molecule-inducible or repressible promoters. The recombinases can be also expressed as a fusion protein with other peptides, proteins, nuclear localizing signal peptides, signal peptides, or organelle-specific signal peptides (e.g., mitochondrial or chloroplast transit peptides to facilitate recombination in mitochondria or chloroplast).

For example, a recombinase can be from the Integrase or Resolvase families. The Integrase family of recombinases has over one hundred members and includes, for example, FLP, Cre, and lambda integrase. The Integrase family, also referred to as the tyrosine family or the lambda integrase family, uses the catalytic tyrosine's hydroxyl group for a nucleophilic attack on the phosphodiester bond of the DNA. Typically, members of the tyrosine family initially nick the DNA, which later forms a double strand break. Examples of tyrosine family integrases include Cre, FLP, SSV1, and lambda (2) integrase. In the resolvase family, also known as the serine recombinase family, a conserved serine residue forms a covalent link to the DNA target site (Grindley, et al., (2006) Ann Rev Biochem 16:16).

In one embodiment, the recombinase is an isolated polynucleotide sequence comprising a nucleic acid sequence that encodes a recombinase selecting from the group consisting of a SPBc2 recombinase, a SF370.1 recombinase, a Bxb1 recombinase, an A118 recombinase and a QRv1 recombinase. Examples of serine recombinases are described in detail in U.S. Pat. No. 9,034,652, hereby incorporated by reference in its entirety.

In one embodiment, a method for site-specific recombination comprises providing a first recombination site and a second recombination site; contacting the first and second recombination sites with a prokaryotic recombinase polypeptide, resulting in recombination between the recombination sites, wherein the recombinase polypeptide can mediate recombination between the first and second recombination sites, the first recombination site is attP or attB, the second recombination site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB.

Further embodiments provide for the introduction of a site-specific recombinase into a cell whose genome is to be modified. One embodiment relates to a method for obtaining site-specific recombination in an eukaryotic cell comprises providing a eukaryotic cell that comprises a first recombination attachment site and a second recombination attachment site; contacting the first and second recombination attachment sites with a prokaryotic recombinase polypeptide, resulting in recombination between the recombination attachment sites, wherein the recombinase polypeptide can mediate recombination between the first and second recombination attachment sites, the first recombination attachment site is a phage genomic recombination attachment site (attP)

or a bacterial genomic recombination attachment site (attB), the second recombination attachment site is attB or attP, and the recombinase is selected from the group consisting of a *Listeria monocytogenes* phage recombinase, a *Streptococcus pyogenes* phage recombinase, a *Bacillus subtilis* phage recombinase, a *Mycobacterium tuberculosis* phage recombinase and a *Mycobacterium smegmatis* phage recombinase, provided that when the first recombination attachment site is attB, the second recombination attachment site is attP, and when the first recombination attachment site is attP, the second recombination attachment site is attB. In an embodiment the recombinase is selected from the group consisting of an A118 recombinase, a SF370.1 recombinase, a SPBc2 recombinase, a QRv1 recombinase, and a Bxb1 recombinase. In one embodiment the recombination results in integration.

Nuclease Recognition Sites

In an embodiment, the GEMS construct comprises a plurality of nuclease recognition sequences, wherein each of the plurality of nuclease recognition sequences comprises a guide target sequence linked to a PAM sequence, wherein the guide target sequence binds to a guide polynucleotide (e.g., gRNA) following insertion of the GEMS construct at the insertion site. In an embodiment, the nuclease is an endonuclease. The term "nuclease recognition site(s) and "nuclease recognition sequence(s)" are used interchangeably herein. In an embodiment, the GEMS construct can further comprise a polynucleotide spacer or a plurality of polynucleotide spacers which separates at least one nuclease recognition sequence from an adjacent nuclease recognition sequence. The polynucleotide space can be about 2 to about 10,000 nucleotides in length. The polynucleotide space can be about 25 to about 50 nucleotides in length. The polynucleotide space can be about 2 nucleotides, about 5 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, about 60 nucleotides, about 70 nucleotides, about 80 nucleotides, about 90 nucleotides, about 100 nucleotides, about 1,000 nucleotides, about 2,000 nucleotides, about 3,000 nucleotides, about 4,000 nucleotides, about 5,000 nucleotides, about 6,000 nucleotides, about 7,000 nucleotides, about 8,000 nucleotides, about 9,000 nucleotides, and about 10,000 nucleotides in length. In some cases, a first polynucleotide spacer separating a nuclease recognition sequence from an adjacent nuclease recognition sequence is the same sequence as a second polynucleotide spacer separating the nuclease recognition sequence from another adjacent nuclease recognition sequence. In some cases, a first polynucleotide spacer separating a nuclease recognition sequence from an adjacent nuclease recognition sequence has a different sequence than a second polynucleotide spacer separating the nuclease recognition sequence from another adjacent nuclease recognition sequence.

In an embodiment, the GEMS construct comprises one or more primary nuclease recognition sequences for insertion into a chromosome of a host cell at e.g., a safe harbor region (e.g., Rosa26, AAVS1, CCR5). In an embodiment, the construct comprises a multiple gene editing site, which comprises a plurality of secondary nuclease recognition sequences that allow for insertion of one or more donor nucleic acid sequences into the chromosome at e.g., the safe harbor region via the multiple gene editing site. In some embodiments, the one or more donor nucleic acid sequences can comprise a gene, or a portion thereof, encoding any polypeptide of interest or portion thereof. The gene can encode, for example, a therapeutic protein, or an immune protein, or a signal protein, or any other protein that the practitioner intends to be expressed in the host cell. In some embodiments, the therapeutic protein is a CD19 CAR. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17. In some embodiments, AAVs1 3' homology arm sequence comprises a nucleotide sequence of SEQ ID NO: 8. In some embodiments, AAVs1 CRISPR targeting sequence comprises a nucleotide sequence of SEQ ID NO: 10. In some embodiments, AAVs1 CRISPR gRNA sequence comprises a nucleotide sequence of SEQ ID NO: 10.

The plurality of secondary nuclease recognition sites can comprise a plurality of recognition sequences for a zinc finger nuclease (ZFN), a transcription activator-like effector nuclease (TALEN), a clustered regularly interspaced short palindromic repeats (CRISPR) associated nuclease (Cas), an Argonaute protein taken from *Pyrococcus furiosus* (PfAgo), or a combination thereof. For example, a multiple gene editing site can comprise a plurality of different secondary nuclease recognition sites, which can differ in the type of nuclease that recognizes the site (e.g., ZFN, TALEN, or Cas), and which can differ among the recognition site sequences themselves. There are numerous recognition sequences for each type of nuclease, such that the multiple gene editing site can comprise different recognition sequences for the same type of endonuclease.

In some embodiments, one or more primary nuclease recognition sequences in GEMS construct can comprise a zinc finger nuclease (ZFN) recognition sequence, a transcription activator-like effector nuclease (TALEN) recognition sequence, a clustered regularly interspaced short palindromic repeats (CRISPR) associated nuclease, or a meganuclease recognition sequence. ZFNs and TALENs can be fused to the FokI endonuclease. FIGS. 1, 2A-2B, and 3 show a non-limiting example of a portion of the construct comprising a multiple gene editing site, flanked on its 5' and 3' ends by CRISPR recognition sequences (the primary endonuclease recognition sequences).

A ZFN generally comprises a zinc finger DNA binding protein and a DNA-cleavage domain. As used herein, a "zinc finger DNA binding protein" or "zinc finger DNA binding domain" is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein (ZFP). Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data.

As used herein, the term "transcription activator-like effector nuclease" or "TAL effector nuclease" or "TALEN" refers to a class of artificial restriction endonucleases that are generated by fusing a TAL effector DNA binding domain to a DNA cleavage domain. In some embodiments, the TALEN is a monomeric TALEN that can cleave double stranded DNA without assistance from another TALEN. The term "TALEN" is also used to refer to one or both members of a pair of TALENs that are engineered to work together to cleave DNA at the same site. TALENs that work together can be referred to as a left-TALEN and a right-TALEN, which references the handedness of DNA.

Meganuclease refers to a double-stranded endonuclease having a large oligonucleotide recognition site, e.g., DNA sequences of at least 12 base pairs (bp) or from 12 bp to 40 bp. The meganuclease can also be referred to as rare-cutting or very rare-cutting endonuclease. The meganuclease of the present disclosure can be monomeric or dimeric. The meganuclease can include any natural meganuclease such as a homing endonuclease, but can also include any artificial or man-made meganuclease endowed with high specificity, either derived from homing endonucleases of group I introns and inteins, or other proteins such as zinc finger proteins or group II intron proteins, or compounds such as nucleic acid fused with chemical compounds.

In some embodiments, the meganuclease can be one of four separated families on the basis of well conserved amino acids motifs, namely the LAGLIDADG family, the GIY-YIG family, the His-Cys box family, and the HNH family (Chevalier et al., 2001, N.A.R, 29, 3757-3774). According to one embodiment, the meganuclease is a I-Dmo I, PI-Sce I, I-SceI, PI-Pfu I, I-Cre I, I-Ppo I, or a hybrid homing endonuclease I-Dmo I/I-Cre I called E-Dre I (Chevalier et al., 2001, Nat Struct Biol, 8, 312-316). In some cases, the meganuclease is the I-SceI meganuclease, which recognizes the nucleic acid sequence TAGGGATAACAGGGTAAT (SEQ ID NO: 1). In some cases, the GEMS construct comprises the I-SceI meganuclease recognition sequence (primary endonuclease recognition sequence) upstream, downstream, or both upstream and downstream of the multiple gene editing site.

In some embodiments, a host cell to which the GEMS construct is transfected is preferably competent for the endonuclease (expresses the endonuclease) that recognizes the primary endonuclease recognition sequence. For competency, the cell can be a cell that naturally expresses the particular endonuclease that recognizes the primary recognition sequences of the construct, or the cell can be separately transfected with a gene encoding the endonuclease such that the cell expresses an exogenous endonuclease. For example, where the GEMS construct includes a ZFN recognition sequence as the primary endonuclease recognition sequence, the cell can be competent for a zinc finger nuclease, which serves as the primary endonuclease to cleave the construct for insertion of the multiple gene editing site into the chromosome. For example, where the GEMS construct includes a TALEN recognition sequence as the primary endonuclease recognition sequence, the cell can be competent for a transcription activator-like effector nuclease, which serves as the primary endonuclease to cleave the construct for insertion of the multiple gene editing site into the chromosome. For example, where the GEMS construct includes a meganuclease recognition sequence as the primary endonuclease recognition sequence, the cell can be competent for a meganuclease which serves as the primary endonuclease to cleave the construct for insertion of the multiple gene editing site into the chromosome. For example, where the GEMS construct comprises the I-SceI meganuclease recognition sequence as the primary endonuclease recognition sequence, the cell to which the construct is transfected can be a I-SceI meganuclease-competent cell, and the I-SceI meganuclease serves as the primary endonuclease, which serves as the primary endonuclease to cleave the construct for insertion of the multiple gene editing site into the chromosome.

The number of nuclease recognition sequences in the GEMS construct can vary. In an embodiment, the multiple gene editing site comprises a plurality of nuclease recognition sites. In an embodiment, the plurality of nuclease recognition sites is a plurality of Cas nuclease recognition sequences. The GEMS construct can comprise at least two nuclease recognition sites. The GEMS construct can comprise at least three nuclease recognition sequences. The GEMS construct can comprise at least four nuclease recognition sequences. The GEMS construct can comprise at least five nuclease recognition sequences. The GEMS construct can comprise at least six nuclease recognition sequences. The GEMS construct can comprise at least seven nuclease recognition sequences. The GEMS construct can comprise at least eight nuclease recognition sequences. The GEMS construct can comprise at least nine nuclease recognition sequences. The GEMS construct can comprise at least ten nuclease recognition sequences. The GEMS construct can comprise more than ten nuclease recognition sequences. The GEMS construct can comprise more than fifteen nuclease recognition sequences. The GEMS construct can comprise more than twenty nuclease recognition sequences. The GEMS construct can comprise a first nuclease recognition sequence that is different from a sequence of a second nuclease recognition sequence. The GEMS construct can comprises a plurality of nuclease recognition sequences, wherein each of nuclease recognition sequences are different from each other. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

CRISPR/Cas9 System

Clustered Regularly Interspaced Short Palindromic Repeats (CRISPR) is a family of DNA sequences in bacteria. The sequences contain snippets of DNA from viruses that have attacked the bacterium. These snippets are used by the bacterium to detect and destroy DNA from similar viruses during subsequent attacks. These sequences play a key role in a bacterial defense system, and form the basis of a technology known as CRISPR/Cas9 that effectively and specifically changes genes within organisms.

Methods described herein can take advantage of a CRISPR/Cas system. For example, double-strand breaks (DSBs) can be generated using a CRISPR/Cas system, e.g., a type II CRISPR/Cas system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of a target sequence.

In some embodiments, the target sequence of each secondary endonuclease recognition site in the multiple gene editing site can be the same, although in some aspects, the target sequence of each secondary endonuclease recognition site can be different from other target sequences in the multiple gene editing site. The target sequence can be from about 10 to about 30 nucleotides in length, from about 15 to about 25 nucleotides in length, and from about 17 to about 24 nucleotides in length (FIGS. 4-6). In some aspects, the target sequence is about 20 nucleotides in length.

In some embodiments, the target sequence can be GC-rich, such that at least about 40% of the target sequence is made up of G or C nucleotides. The GC content of the target sequence can from about 40% to about 80%, though GC content of less than about 40% or greater than about 80% can be used. In some embodiments, the target sequence can be AT-rich, such that at least about 40% of the target sequence is made up of A or T nucleotides. The AT content of the target sequence can from about 40% to about 80%, though AT content of less than about 40% or greater than about 80% can be used.

Cas proteins that can be used herein include class 1 and class 2. Non-limiting examples of Cas proteins include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csml, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csfl, Csf2, CsO, Csf4, Csdl, Csd2, Cstl, Cst2, Csh1, Csh2, Csal, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within about 1, 2, 3, 4, 5, 6, 7, 8, 9, 10, 15, 20, 25, 50, 100, 200, 500, or more base pairs from the first or last nucleotide of a target sequence.

A vector that encodes a CRISPR enzyme that is mutated to with respect, to a corresponding wild-type enzyme such that the mutated CRISPR enzyme lacks the ability to cleave one or both strands of a target polynucleotide containing a target sequence can be used. Cas9 can refer to a polypeptide with at least or at least about 50%, 60%, 70%, 80%, 90%, 91%, 92%, 93%, 94%, 95%, 96%, 97%, 98%, 99%, or 100% sequence identity and/or sequence homology to a wild type exemplary Cas9 polypeptide (e.g., Cas9 from *S. pyogenes*). Cas9 can refer to a polypeptide with at most or at most about 50%, 60%, 70%, 80%, 90%, 91%, 92%, 93%, 94%, 95%, 96%, 97%, 98%, 99%, or 100% sequence identity and/or sequence homology to a wild type exemplary Cas9 polypeptide (e.g., from *S. pyogenes*). Cas9 can refer to the wild type or a modified form of the Cas9 protein that can comprise an amino acid change such as a deletion, insertion, substitution, variant, mutation, fusion, chimera, or any combination thereof.

In some embodiments, the methods described herein can utilize an engineered CRISPR system. The Engineered CRISPR system contains two components: a guide RNA (gRNA or sgRNA) or a guide polynucleotide; and a CRISPR-associated endonuclease (Cas protein). The gRNA is a short synthetic RNA composed of a scaffold sequence necessary for Cas-binding and a user-defined ~20 nucleotide spacer that defines the genomic target to be modified. Thus, a skilled artisan can change the genomic target of the CRISPR specificity is partially determined by how specific the gRNA targeting sequence is for the genomic target compared to the rest of the genome. In some embodiments, the sgRNA is any one of sequences in SEQ ID NOs: 24-32 (Table 6). In some embodiments, AAVs1 CRISPR targeting sequence comprises a nucleotide sequence of SEQ ID NO: 9. In some embodiments, AAVs1 CRISPR gRNA sequence comprises a nucleotide sequence of SEQ ID NO: 10. In some embodiments, GEMS sequence targeting sequence comprises a nucleotide sequence of SEQ ID NO: 14. In some embodiments, GEMS sequence guide RNA sequence comprises a nucleotide sequence of SEQ ID NO: 15.

The Cas9 nuclease has two functional endonuclease domains: RuvC and HNH. Cas9 undergoes a second conformational change upon target binding that positions the nuclease domains to cleave opposite strands of the target DNA. The end result of Cas9-mediated DNA cleavage is a double-strand break (DSB) within the target DNA (~3-4 nucleotides upstream of the PAM sequence). The resulting DSB is then repaired by one of two general repair pathways: (1) the efficient but error-prone non-homologous end joining (NHEJ) pathway; or (2) the less efficient but high-fidelity homology directed repair (HDR) pathway.

The "efficiency" of non-homologous end joining (NHEJ) and/or homology directed repair (HDR) can be calculated by any convenient method. For example, in some cases, efficiency can be expressed in terms of percentage of successful HDR. For example, a surveyor nuclease assay can be used can be used to generate cleavage products and the ratio of products to substrate can be used to calculate the percentage. For example, a surveyor nuclease enzyme can be used that directly cleaves DNA containing a newly integrated restriction sequence as the result of successful HDR. More cleaved substrate indicates a greater percent HDR (a greater efficiency of HDR). As an illustrative example, a fraction (percentage) of HDR can be calculated using the following equation [(cleavage products)/(substrate plus cleavage products)] (e.g., b+c/a+b+c), where “a” is the band intensity of DNA substrate and “b” and “c” are the cleavage products.

In some cases, efficiency can be expressed in terms of percentage of successful NHEJ. For example, a T7 endonuclease I assay can be used to generate cleavage products and the ratio of products to substrate can be used to calculate the percentage NHEJ. T7 endonuclease I cleaves mismatched heteroduplex DNA which arises from hybridization of wild-type and mutant DNA strands (NHEJ generates small random insertions or deletions (indels) at the site of the original break). More cleavage indicates a greater percent NHEJ (a greater efficiency of NHEJ). As an illustrative example, a fraction (percentage) of NHEJ can be calculated using the following equation: (1-(1-(b+c/a+b+c)).sup. 1/2). times. 100, where “a” is the band intensity of DNA substrate and “b” and “c” are the cleavage products (Ran et. al., Cell. 2013 Sep. 12; 154 (6): 1380-9).

The NHEJ repair pathway is the most active repair mechanism, and it frequently causes small nucleotide insertions or deletions (indels) at the DSB site. The randomness of NHEJ-mediated DSB repair has important practical implications, because a population of cells expressing Cas9 and a gRNA or a guide polynucleotide can result in a diverse array of mutations. In most cases, NHEJ gives rise to small indels in the target DNA that result in amino acid deletions, insertions, or frameshift mutations leading to premature stop codons within the open reading frame (ORF) of the targeted gene. The ideal end result is a loss-of-function mutation within the targeted gene.

While NHEJ-mediated DSB repair often disrupts the open reading frame of the gene, homology directed repair (HDR) can be used to generate specific nucleotide changes ranging from a single nucleotide change to large insertions like the addition of a fluorophore or tag.

In order to utilize HDR for gene editing, a DNA repair template containing the desired sequence can be delivered into the cell type of interest with the gRNA(s) and Cas9 or Cas9 nickase. The repair template can contain the desired edit as well as additional homologous sequence immediately upstream and downstream of the target (termed left & right homology arms). The length of each homology arm can be dependent on the size of the change being introduced, with larger insertions requiring longer homology arms. The repair template can be a single-stranded oligonucleotide, double-stranded oligonucleotide, or a double-stranded DNA plasmid. The efficiency of HDR is generally low (<10% of modified alleles) even in cells that express Cas9, gRNA and an exogenous repair template. The efficiency of HDR can be enhanced by synchronizing the cells, since HDR takes place during the S and G2 phases of the cell cycle. Chemically or genetically inhibiting genes involved in NHEJ can also increase HDR frequency.

In some embodiments, Cas9 is a modified Cas9. A given gRNA targeting sequence can have additional sites throughout the genome where partial homology exists. These sites are called off-targets and need to be considered when designing a gRNA. In some embodiments, AAVs1 CRISPR targeting sequence comprises a nucleotide sequence of SEQ ID NO: 9. In some embodiments, GEMS sequence targeting sequence comprises a nucleotide sequence of SEQ ID NO: 14. In some embodiments, GEMS site guide RNA sequence comprises a nucleotide sequence of SEQ ID NO: 15. In addition to optimizing gRNA design, CRISPR specificity can also be increased through modifications to Cas9. Cas9 generates double-strand breaks (DSBs) through the combined activity of two nuclease domains, RuvC and HNH. Cas9 nickase, a D10A mutant of SpCas9, retains one nuclease domain and generates a DNA nick rather than a DSB. Thus, two nickases targeting opposite DNA strands are required to generate a DSB within the target DNA (often referred to as a double nick or dual nickase CRISPR system). This requirement dramatically increases target specificity, since it is unlikely that two off-target nicks can be generated within close enough proximity to cause a DSB. The nickase system can also be combined with HDR-mediated gene editing for specific gene edits.

In some embodiments, the modified Cas9 is a high fidelity Cas9 enzyme. In some embodiments, the high fidelity Cas9 enzyme is SpCas9 (K855A), eSpCas9 (1.1), SpCas9-HF1, or hyper accurate Cas9 variant (HypaCas9). The modified Cas9 eSpCas9 (1.1) contains alanine substitutions that weaken the interactions between the HNH/RuvC groove and the non-target DNA strand, preventing strand separation and cutting at off-target sites. Similarly, SpCas9-HF1 lowers off-target editing through alanine substitutions that disrupt Cas9’s interactions with the DNA phosphate backbone. HypaCas9 contains mutations (SpCas9 N692A/M694A/Q695A/H698A) in the REC3 domain that increase Cas9 proofreading and target discrimination. All three high fidelity enzymes generate less off-target editing than wildtype Cas9.

In some cases, Cas9 is a variant Cas9 protein. A variant Cas9 polypeptide has an amino acid sequence that is different by one amino acid (e.g., has a deletion, insertion, substitution, fusion) when compared to the amino acid sequence of a wild type Cas9 protein. In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 protein. In some cases, the variant Cas9 protein has no substantial nuclease activity. When a subject Cas9 protein is a variant Cas9 protein that has no substantial nuclease activity, it can be referred to as “dCas9.”

In some cases, a variant Cas9 protein has reduced nuclease activity. For example, a variant Cas9 protein exhibits less than about 20%, less than about 15%, less than about 10%, less than about 5%, less than about 1%, or less than about 0.1%, of the endonuclease activity of a wild-type Cas9 protein, e.g., a wild-type Cas9 protein.

In some cases, a variant Cas9 protein can cleave the complementary strand of a guide target sequence but has reduced ability to cleave the non-complementary strand of a double stranded guide target sequence. For example, the variant Cas9 protein can have a mutation (amino acid substitution) that reduces the function of the RuvC domain. As a non-limiting example, in some embodiments, a variant Cas9 protein has a D10A (aspartate to alanine at amino acid position 10) and can therefore cleave the complementary strand of a double stranded guide target sequence but has reduced ability to cleave the non-complementary strand of a double stranded guide target sequence (thus resulting in a single strand break (SSB) instead of a double strand break (DSB) when the variant Cas9 protein cleaves a double stranded target nucleic acid) (see, for example, Jinek et al., Science. 2012 Aug. 17; 337 (6096): 816-21).

In some cases, a variant Cas9 protein can cleave the non-complementary strand of a double stranded guide target sequence but has reduced ability to cleave the complementary strand of the guide target sequence. For example, the variant Cas9 protein can have a mutation (amino acid substitution) that reduces the function of the HNH domain (RuvC/HNH/RuvC domain motifs). As a non-limiting example, in some embodiments, the variant Cas9 protein has an H840A (histidine to alanine at amino acid position 840) mutation and can therefore cleave the non-complementary strand of the guide target sequence but has reduced ability to cleave the complementary strand of the guide target sequence (thus resulting in a SSB instead of a DSB when the variant Cas9 protein cleaves a double stranded guide target sequence). Such a Cas9 protein has a reduced ability to cleave a guide target sequence (e.g., a single stranded guide target sequence) but retains the ability to bind a guide target sequence (e.g., a single stranded guide target sequence).

In some cases, a variant Cas9 protein has a reduced ability to cleave both the complementary and the non-complementary strands of a double stranded target DNA. As a non-limiting example, in some cases, the variant Cas9 protein harbors both the D10A and the H840A mutations such that the polypeptide has a reduced ability to cleave both the complementary and the non-complementary strands of a double stranded target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors W476A and W1126A mutations such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors P475A, W476A, N477A, D1125A, W1126A, and D1127A mutations such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors H840A, W476A, and W1126A, mutations such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors H840A, D10A, W476A, and W1126A, mutations such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors, H840A, P475A, W476A, N477A, D1125A, W1126A, and D1127A mutations such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

As another non-limiting example, in some cases, the variant Cas9 protein harbors D10A, H840A, P475A, W476A, N477A, D1125A, W1126A, and D1127A mutations such that the polypeptide has a reduced ability to cleave a target DNA. Such a Cas9 protein has a reduced ability to cleave a target DNA (e.g., a single stranded target DNA) but retains the ability to bind a target DNA (e.g., a single stranded target DNA).

In some cases, when a variant Cas9 protein harbors W476A and W1126A mutations or when the variant Cas9 protein harbors P475A, W476A, N477A, D1125A, W1126A, and D1127A mutations, the variant Cas9 protein does not bind efficiently to a PAM sequence. Thus, in some such cases, when such a variant Cas9 protein is used in a method of binding, the method need not include a PAM-mer. In other words, in some cases, when such a variant Cas9 protein is used in a method of binding, the method can include a guide RNA, but the method can be performed in the absence of a PAM-mer (and the specificity of binding is therefore provided by the targeting segment of the guide RNA).

Other residues can be mutated to achieve the above effects (i.e. inactivate one or the other nuclease portions). As non-limiting examples, residues D10, G12, G17, E762, H840, N854, N863, H982, H983, A984, D986, and/or A987 can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the variant Cas9 protein can still bind to target DNA in a site-specific manner (because it is still guided to a target DNA sequence by a guide RNA) as long as it retains the ability to interact with the guide RNA.

Alternatives to *S. pyogenes* Cas9 can include RNA-guided endonucleases from the Cpf1 family that display cleavage activity in mammalian cells. CRISPR from *Prevotella* and *Francisella* 1 (CRISPR/Cpf1) is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. Unlike Cas9 nucleases, the result of Cpf1-mediated DNA cleavage is a double-strand break with a short 3' overhang. Cpf1's staggered cleavage pattern can open up the possibility of directional gene transfer, analogous to traditional restriction enzyme cloning, which can increase the efficiency of gene editing. Like the Cas9 variants and orthologues described above, Cpf1 can also expand the number of sites that can be targeted by CRISPR to AT-rich regions or AT-rich genomes that lack the NGG PAM sites favored by SpCas9. The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alpha-helical recognition lobe of Cas9. Cpf1 CRISPR-Cas domain architecture shows that Cpf1 is functionally unique, being classified as Class 2, type V CRISPR system. The Cpf1 loci encode Cas1, Cas2 and Cas4 proteins more similar to types I and III than from type II systems. Functional Cpf1 doesn't need the trans-activating CRISPR RNA (tracrRNA), therefore, only CRISPR (crRNA) is required. This benefits genome editing because Cpf1 is not only smaller than Cas9, but also it has a smaller sgRNA molecule (proximately half as many nucleotides as Cas9). The Cpf1-crRNA complex cleaves target DNA or RNA by identification of a protospacer adjacent motif 5'-YTN-3' in contrast to the G-rich PAM targeted by Cas9. After identification of PAM, Cpf1 introduces a sticky-end-like DNA double-stranded break of 4 or 5 nucleotides overhang.

Protospacer Adjacent Motif

The protospacer adjacent motif (PAM) or PAM-like motif refers to a 2-6 base pair DNA sequence immediately following the DNA sequence targeted by the Cas9 nuclease in the CRISPR bacterial adaptive immune system. In some embodiments, the PAM can be a 5' PAM (i.e., located upstream of the 5' end of the protospacer). In other embodiments, the PAM can be a 3' PAM (i.e., located downstream of the 5' end of the protospacer). The PAM sequence is essential for target binding, but the exact sequence depends on a type of Cas protein. Non-limiting examples of Cas proteins include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof.

In an embodiment, the multiple gene editing site comprises a plurality of secondary endonuclease recognition sites for the CRISPR-associated endonuclease Cas9. In an embodiment, each secondary recognition site is specific to a Cas9 enzyme from a different species of bacteria. A Cas9 nuclease recognition site can comprises a targeting sequence coupled to a nucleotide protospacer adjacent motif (PAM) sequence. In some embodiments, AAVs1 CRISPR targeting sequence comprises a nucleotide sequence of SEQ ID NO: 9. In some embodiments, GEMS sequence targeting sequence comprises a nucleotide sequence of SEQ ID NO: 14. In some embodiments, GEMS sequence guide RNA sequence comprises a nucleotide sequence of SEQ ID NO: 15. Different bacteria species encode different Cas9 nuclease proteins, which recognize different PAM sequences. Thus, to facilitate Cas9-facilitated insertion of donor genes into the multiple gene editing site, the multiple gene editing site can comprise a plurality of secondary endonuclease recognition sites for Cas9 that each comprise a target sequence coupled to a PAM sequence (FIGS. 4-6).

Figure 2A:
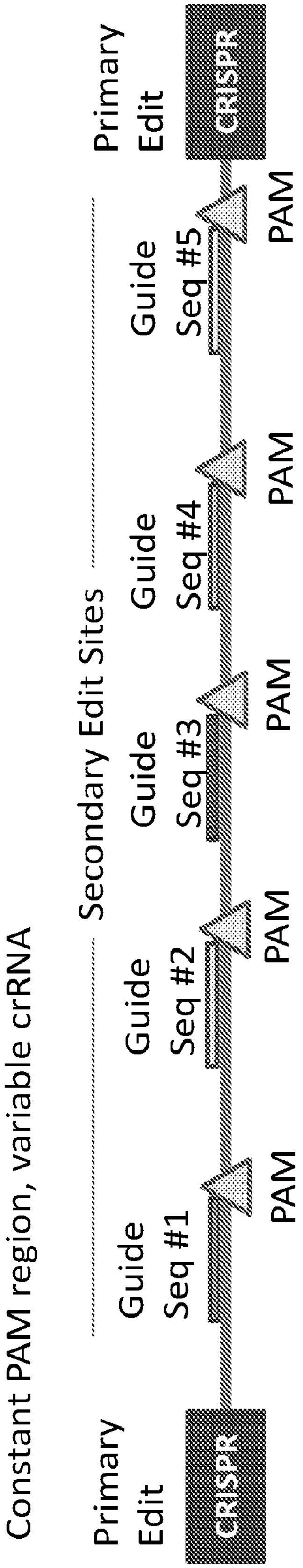
FIG. 2A shows a representation of different embodiments of GEMS construct. The GEMS has multiple different crRNA sequences in combination with a fixed Cas9 nuclease.
Figure 2B:
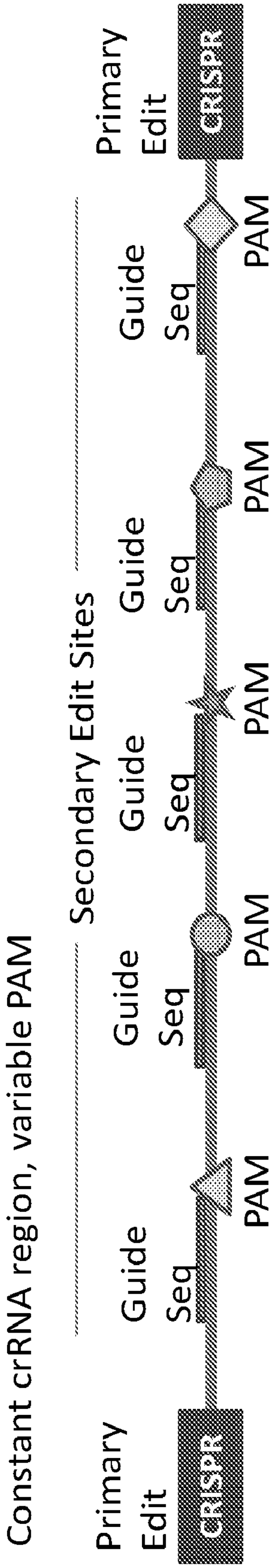
FIG. 2B shows a representation of different embodiments of GEMS construct. The GEMS has multiple different PAM sequences represented by the different shapes combined with fixed crRNA sequences.
Figure 3:
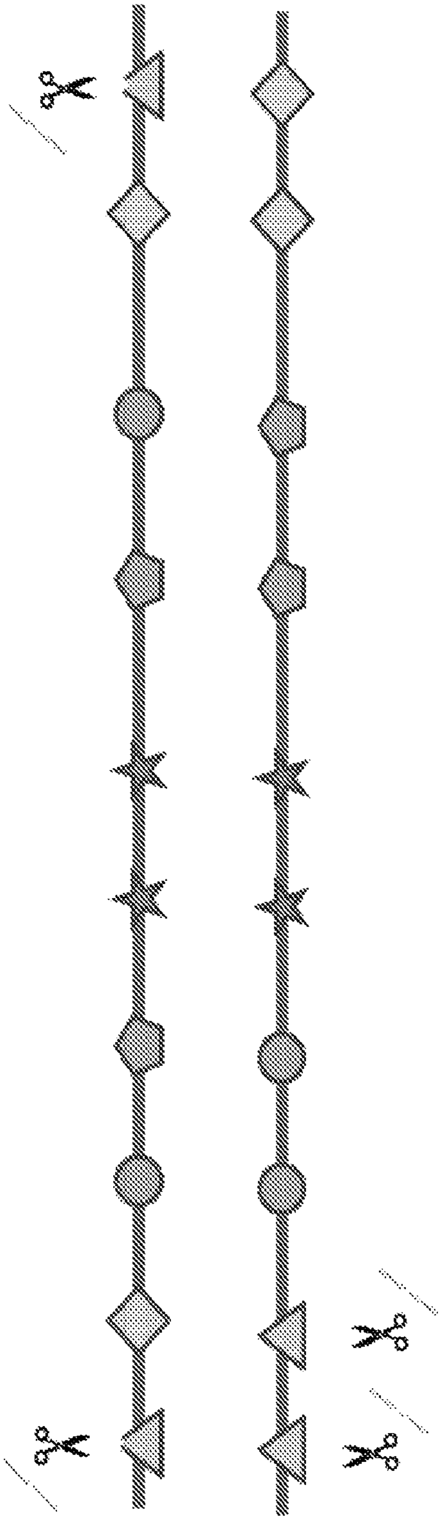
FIG. 3 shows a representation of different embodiments of GEMS construct. The GEMS has multiple different PAM sequences, but each PAM sequence is provided as a pair, with each oriented in a different direction. In an embodiment, the first PAM sequence in the pair is oriented in the 5' to 3' direction, and the second PAM sequence in the pair is oriented in the 3' to 5' direction.

Each Cas9 nuclease target sequence can be coupled to a PAM sequence. Among the Cas9 nuclease recognition sites in the multiple gene editing site, each PAM sequence can be different from the other PAM sequences (e.g., variable PAM region and constant crRNA region) (FIG. 2B), even if the target sequence is the same among the Cas9 nuclease recognition sites. In some cases, each PAM sequence can be the same as the other PAM sequences, though in such cases, the target sequence can be different among the Cas9 nuclease recognition sites (e.g., constant PAM region and variable crRNA region) (FIG. 2A).

The PAM sequence can be any PAM sequence known in the art. Suitable PAM sequences include, but are not limited to, CC, NG, YG, NGG, NAA, NAT, NAG, NAC, NTA, NTT, NTG, NTC, NGA, NGT, NGC, NCA, NCT, NCG, NCC, NRG, TGG, TGA, TCG, TCC, TCT, GGG, GAA, GAC, GTG, GAG, CAG, CAA, CAT, CCA, CCN, CTN, CGT, CGC, TAA, TAC, TAG, TGG, TTG, TCN, CTA, CTG, CTC, TTC, AAA, AAG, AGA, AGC, AAC, AAT, ATA, ATC, ATG, ATT, AWG, AGG, GTG, TTN, YTN, TTTV, TYCV, TATV, NGAN, NGNG, NGAG, NGCG, AAAAW, GCAAA, TGAAA, NGGNG, NGRRT, NGRRN, NNGRRT, NNAAAAN, NNNNGATT, NAAAAC, NNAAAAAW, NNAGAA, NNNNACA, GNNNCNNA, NNNNGATT, NNAGAAW, NNGRR, NNNNNNN and TGGAGAAT, and any variation thereof. Different PAM sequences recognized by different Cas9 enzyme species are listed in Tables 1-2.

TABLE 1

Cas Enzyme and PAM Sequences

| Cas9 Species | PAM Sequence |
|---|---|
| *Streptococcus pyogenes* (Sp); SpCas9 | 3'NGG |
| SpCas9 D1135E variant | 3'NGG (reduced NAG binding) |
| SpCas9 VRER variant (D1135V, G1218R, R1335E, T1337R) | 3'NGCG |
| SpCas9 EQR variant (D1135E, R1335Q, T1337R) | 3'NGAG |
| SpCas9 VQR variant (D1335V, R1335Q, T1337R) | 3'NGAN or NGNG |
| *Staphylococcus aures* (Sa); SaCas9 | 3'NNGRRT or NNGRR(N) |
| *Acidaminococcus* sp. (AsCpf1) and *Lachnospiraceae bacterium* (LbCpf1) | 5'TTTV |
| AsCpf1 RR variant | 5'TYCV |
| LbCpf1 RR variant | 5'TYCV |
| AsCpf1 RVR variant | 5'TATV |
| *Neisseria meningitides* (Nm) | 3'NNNNGATT |

TABLE 1-continued

| Cas Enzyme and PAM Sequences | |
|---|---|
| Cas9 Species | PAM Sequence |
| *Streptococcus thermophiles* (St) | 3'NNAGAAW |
| *Treponema denticola* (Td) | 3'NAAAAC |
| Additional Cas9 species | PAM sequence may not be characterized |

*Y is a pyrimidine; N is any nucleotide base; W is A or T.

TABLE 2

| Variable PAMs | | | |
|---|---|---|---|
| 5' to 3' Strand | | 3' to 5' Strand | |
| NGRRT (CgAAt) | *Staphylococcus aures* (Sa); *Neisseria meningitis* | NGAG (Tgag) | *Staphylococcus pyogenes* v1 EQR variant (Spv1) |
| NGGNG (CggAg) | *Streptococcus thermophiles* A (St-A) (CRISPR3) | NGCG (cgcg) | *Staphylococcus pyogenes* VRER variant (Svrer) |
| NAAAAC (Gaaaac) | *Treponema denticola* (Td) | NNNNGATT (CTAGgatt) | *Neiseria Meningitis* (Mn) |
| GCAAA | *Streptococcus thermophiles* B (St LMG18311) | NNAGAAW (GCagaaT) | *Staphylococcus Thermophiles* (St) |
| TGGAGAAT | | TAA | *Haloferax valcanii* |
| GNNNCNNA (gAGAcGAa) | *Pasteurella multocida* (Pm) | AAAAW (aaaaT) | *Staphylococcus thermophiles* B (StB) |
| TGAAA | *Lactobacillus casei* (Lc) | NNAAAAAW (CGaaaaaT) | |

In some embodiments, the PAM sequence can be on the sense strand or the antisense strand (FIGS. 2A, 2B, 3, 4, and Tables 3-5). The PAM sequence can be oriented in any direction. For example, the Cas9 nuclease recognition sites (the secondary endonuclease recognition sites) in the multiple gene editing site, which comprises a target sequence and a PAM sequence, can be on either or both of the sense strand or antisense strand of the construct, and can be oriented in any direction. In an embodiment, the gene editing site crRNA sequence can be 5'-NNNNNNNNNNNNNNNNNNNN-gRNA-3' (Table 3). In an embodiment, the gene editing site crRNA sequence can be 3'-gRNA-NNNNNNNNNNNNNNNNNNNN-5' (Table 4).

TABLE 3

| GEMS Editing Site crRNA Sequences (PAM on 5' to 3' strand; sense, non-template strand) | |
|---|---|
| SEQ ID NO | Sequences |
| 33 | UGAAUUAGAUUUGCGUUACU |
| 34 | UCACAAUCACUCAAGAAGCA |
| 35 | CUUUAGACACAGUAAGACAA |
| 36 | CCCGCAAUAGAGAGCUUUGA |
| 37 | GAACGUATCUGCAUGUCUAG |

TABLE 3-continued

| GEMS Editing Site crRNA Sequences (PAM on 5' to 3' strand; sense, non-template strand) | |
|---|---|
| SEQ ID NO | Sequences |
| 38 | CAUGCCUUUAGAAUUCAGUA |
| 39 | UGUGUUAGCGCGCUGAUCUG |
| 40 | UACGAAGUCGAGAUAAAAUG |
| 41 | GCAUAACCAGUACGCAAGAU |
| 42 | UUUUGCUACAUCUUGUAAUA |
| 43 | AUUAUAAUAUUCAGUAGAAA |
| 44 | CAGCTACGAGUCACGAUGUA |
| 45 | CAAUGACAAUAGCGAUAACG |

TABLE 3-continued

| GEMS Editing Site crRNA Sequences (PAM on 5' to 3' strand; sense, non-template strand) | |
|---|---|
| SEQ ID NO | Sequences |
| 46 | GUUACGUUCGCGAAGCGUUG |
| 47 | GCGUAACAACUUCUGAGUUG |

*5'-NNNNNNNNNNNNNNNNNNNN-gRNA-3'

TABLE 4

| GEMS Editing Site crRNA Sequences (PAM on 3' to 5' strand; anti-sense, template strand) | |
|---|---|
| SEQ ID NO | Sequences |
| 48 | AACAAUACAUACGUGUUCGU |
| 49 | UGCATCGCAAGCTCAUCGCG |
| 50 | AGCGUGUUCGUGUCAGAGCA |
| 51 | UCUACGAGACGCGCGACGUU |
| 52 | UACGAUAAAUAAUUGCGCAG |
| 53 | AAUUAAGAUUUCGUUAGCUU |
| 54 | AACAAUGUGCGCAUGACAUA |
| 55 | GACUGCGCAAUACGAUUUAG |
| 56 | GCAGUAACGUUCAUCUGCGC |
| 57 | AGCUAACGAAAGAGUAGCAU |
| 58 | UAGACGCUCGCUAAAUCUUU |
| 59 | UCGCACUGUCGAGCUAUCAC |
| 60 | GACUAGCGUCACGUAAGAGU |
| 61 | AGCUAGCAUGUAUCUAGGAC |
| 62 | UGCGCGUGCGUCGACAUAUU |

*3'-gRNA-NNNNNNNNNNNNNNNNNNNN-5'

TABLE 5

| GEMS 2.0 Editing Site crRNA Sequences | |
|---|---|
| SEQ ID NO | Sequences |
| 63 | AUCCGUAUUCCGACGUACGA |
| 64 | CGUACUGUGAUACACGCGAC |
| 65 | GGCGCUCCGAUAAAUCGCUA |
| 66 | AUUACCGAUACGAUACGAAC |
| 67 | ACGGACGCGCAACCGUCGUC |
| 68 | UAAUCGGUUGCGCCGCUCGG |
| 69 | UUAUUUACCCCGCGCGAGGU |
| 70 | GUUGUAUCGUACGUCGGUCU |
| 71 | AGUAUUCGAGUACGCGUCGA |

TABLE 5-continued

| GEMS 2.0 Editing Site crRNA Sequences | |
|---|---|
| SEQ ID NO | Sequences |
| 72 | GUAUUCGAGUACGCGUCGAU |
| 73 | GCGUGCGAUCGUACCGUGUA |
| 74 | CGCAUGGCAAUCUACGCGCG |
| 75 | GUGAACCGACCCGGUCGAUC |
| 76 | UUCUUCGAUACGGUACGAAU |
| 77 | UUUAUAUGGGACGCGUACGC |
| 78 | AGAGUGGCCGCGAUAAUCGA |
| 79 | UAAUCCUCGCGGUAACCGGU |
| 80 | AGAGUGGGCGCGAAUAUCGU |

In an embodiment, *S. pyogenes* Cas9 (SpCas9) can be used as a CRISPR endonuclease for genome engineering. However, others can be used. In some cases, a different endonuclease can be used to target certain genomic targets. In some cases, synthetic SpCas9-derived variants with non-NGG PAM sequences can be used. Additionally, other Cas9 orthologues from various species have been identified and these "non-SpCas9s" can bind a variety of PAM sequences that can also be useful for the present disclosure. For example, the relatively large size of SpCas9 (approximately 4 kb coding sequence) can lead to plasmids carrying the SpCas9 cDNA that cannot be efficiently expressed in a cell. Conversely, the coding sequence for *Staphylococcus aureus* Cas9 (SaCas9) is approximately 1 kilo base shorter than SpCas9, possibly allowing it to be efficiently expressed in a cell. Similar to SpCas9, the SaCas9 endonuclease is capable of modifying target genes in mammalian cells in vitro and in mice in vivo. In some cases, a Cas protein can target a different PAM sequence. In some cases, a target gene can be adjacent to a Cas9 PAM, 5'-NGG, for example. In other cases, other Cas9 orthologs can have different PAM requirements. For example, other PAMs such as those of *S. thermophilus* (5'-NNAGAA for CRISPR1 and 5'-NGGNG for CRISPR3) and *Neisseria* meningiditis (5'-NNNNGATT) can also be found adjacent to a target gene. A transgene of the present disclosure can be inserted adjacent to any PAM sequence from any Cas, or Cas derivative, protein. In some cases, a PAM can be found every, or about every, 8 to 12 base pairs in the GEMS construct. A PAM can be found every 1 to 15 base-pairs in in the GEMS construct. A PAM can also be found every 5 to 20 base-pairs in in the GEMS construct. In some cases, a PAM can be found every 5, 6, 7, 8, 9, 10, 11, 12, 13, 14, 15, 16, 17, 18, 19, 20, or more base-pairs in the GEMS construct. In an embodiment, a PAM can be found at or between every 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 base pairs in the GEMS construct. In an embodiment, a PAM can be found at or between more than 100 base pairs, more than 200 base pairs, more than 300 base pairs, more than 400 base pairs, or more than 500 base pairs in the GEMS construct. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

In some embodiments, for a *S. pyogenes* system, a target gene sequence can precede (i.e., be 5' to) a 5'-NGG PAM, and a 20-nt guide RNA sequence can base pair with an opposite strand to mediate a Cas9 cleavage adjacent to a PAM. In some cases, an adjacent cut can be or can be about 3 base pairs upstream of a PAM. In some cases, an adjacent cut can be or can be about 10 base pairs upstream of a PAM. In some cases, an adjacent cut can be or can be about 0-20 base pairs upstream of a PAM. For example, an adjacent cut can be next to, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 base pairs upstream of a PAM. An adjacent cut can also be downstream of a PAM by 1 to 30 base pairs.

In an embodiment, the GEMS construct comprises a plurality of the secondary endonuclease recognition site. In an embodiment, the plurality of the secondary endonuclease recognition site is a plurality of PAM. Each PAM in the plurality of PAM can be in any orientation (5' or 3'). The number of PAM sequences in the GEMS construct can vary. In an embodiment, the GEMS construct comprises a plurality of PAM. In an embodiment, the GEMS construct can comprise one or more PAM. In an embodiment, the GEMS construct can comprise two or more PAM. In an embodiment, the GEMS construct can comprise three or more PAM. In an embodiment, the GEMS construct can comprise four or more PAM. In an embodiment, the GEMS construct can comprise five or more PAM. In an embodiment, the GEMS construct can comprise six or more PAM. In an embodiment, the GEMS construct can comprise seven or more PAM. In an embodiment, the GEMS construct can comprise eight or more PAM. In an embodiment, the GEMS construct can comprise nine or more PAM. In an embodiment, the GEMS construct can comprise ten or more PAM. In an embodiment, the GEMS construct can comprise eleven or more PAM. In an embodiment, the GEMS construct can comprise twelve or more PAM. In an embodiment, the GEMS construct can comprise thirteen or more PAM. In an embodiment, the GEMS construct can comprise fourteen or more PAM. In an embodiment, the GEMS construct can comprise fifteen or more PAM. In an embodiment, the GEMS construct can comprise sixteen or more PAM. In an embodiment, the GEMS construct can comprise seventeen or more PAM. In an embodiment, the GEMS construct can comprise eighteen or more PAM. In an embodiment, the GEMS construct can comprise nineteen or more PAM. In an embodiment, the GEMS construct can comprise twenty or more PAM. In an embodiment, the GEMS construct can comprise thirty or more PAM. In an embodiment, the GEMS construct can comprise forty or more PAM.

A vector that encodes a CRISPR enzyme comprising one or more nuclear localization sequences (NLSs) can be used. For example, there can be or be about 1, 2, 3, 4, 5, 6, 7, 8, 9, 10 NLSs used. A CRISPR enzyme can comprise the NLSs at or near the ammo-terminus, about or more than about 1, 2, 3, 4, 5, 6, 7, 8, 9, 10 NLSs at or near the carboxy-terminus, or any combination of these (e.g., one or more NLS at the ammo-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise about 6 NLSs. An NLS is considered near the N- or C-terminus when the nearest amino acid to the NLS is within about 50 amino acids along a polypeptide chain from the N- or C-terminus, e.g., within 1, 2, 3, 4, 5, 10, 15, 20, 25, 30, 40, or 50 amino acids.

Guide Polynucleotides

As used herein, the term "guide polynucleotide(s)" refer to a polynucleotide which can be specific for a target sequence and can form a complex with Cas protein. In an embodiment, the guide polynucleotide is a guide RNA. As used herein, the term "guide RNA (gRNA)" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a host cell at least one guide RNA or guide polynucleotide, e.g., DNA encoding at least one guide RNA. A guide RNA or a guide polynucleotide can interact with a RNA-guided endonuclease to direct the endonuclease to a specific target site, at which site the 5' end of the guide RNA base pairs with a specific protospacer sequence in a chromosomal sequence.

A guide RNA or a guide polynucleotide can comprise two RNAs, e.g., CRISPR RNA (crRNA) and transactivating crRNA (tracrRNA). A guide RNA or a guide polynucleotide can sometimes comprise a single-chain RNA, or single guide RNA (sgRNA) formed by fusion of a portion (e.g., a functional portion) of crRNA and tracrRNA. A guide RNA or a guide polynucleotide can also be a dual RNA comprising a crRNA and a tracrRNA. Furthermore, a crRNA can hybridize with a target DNA. In some embodiments, the sgRNA is any one of sequences in SEQ ID NOs: 24-32. In an embodiment, a guide RNA can be a fixed guide RNA with PAM variants. For example, the GEMS construct can be designed to comprise a crRNA sequence of 5'-CUUACUACAUGUGCGUGUUC-(gRNA)-3' (SEQ ID NO: 85), wherein PAM can be on sense, non-template strand. For example, the GEMS construct can be designed to comprise a crRNA sequence of 3'-(gRNA) AAAUGAGCAGCAUACUAACA-5' (SEQ ID NO: 86), wherein PAM can be on anti-sense, template strand.

In some embodiments, the gRNA is any one of sequences in SEQ ID NOs: 24-32 (Table 6). In some embodiments, AAVs1 CRISPR targeting sequence comprises a nucleotide sequence of SEQ ID NO: 9. In some embodiments, AAVs1 CRISPR gRNA sequence comprises a nucleotide sequence of SEQ ID NO: 10. In some embodiments, GEMS sequence targeting sequence comprises a nucleotide sequence of SEQ ID NO: 14. In some embodiments, GEMS sequence guide RNA sequence comprises a nucleotide sequence of SEQ ID NO: 15.

As discussed above, a guide RNA or a guide polynucleotide can be an expression product. For example, a DNA that encodes a guide RNA can be a vector comprising a sequence coding for the guide RNA. A guide RNA or a guide polynucleotide can be transferred into a cell by transfecting the cell with an isolated guide RNA or plasmid DNA comprising a sequence coding for the guide RNA and a promoter. A guide RNA or a guide polynucleotide can also be transferred into a cell in other way, such as using virus-mediated gene delivery.

A guide RNA or a guide polynucleotide can be isolated. For example, a guide RNA can be transfected in the form of an isolated RNA into a cell or organism. A guide RNA can be prepared by in vitro transcription using any in vitro transcription system known in the art. A guide RNA can be transferred to a cell in the form of isolated RNA rather than in the form of plasmid comprising encoding sequence for a guide RNA.

A guide RNA or a guide polynucleotide can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA or a guide polynucleotide can be complementary to sequence at a target site in a chromosomal sequence such that the first region of the guide RNA can base pair with the target site. In some cases, a first region of a guide RNA can comprise from or from about 10 nucleotides to 25 nucleotides (i.e., from 10 nucleotides to nucleotides; or from about 10 nucleotides to about 25 nucleotides; or from 10 nucleotides to about 25 nucleotides; or from about 10 nucleotides to 25 nucleotides) or more. For example, a region of base pairing between a first region of a guide RNA and a target site in a chromosomal sequence can be or can be about 10, 11, 12, 13, 14, 15, 16, 17, 18, 19, 20, 22, 23, 24, 25, or more nucleotides in length. Sometimes, a first region of a guide RNA can be or can be about 19, 20, or 21 nucleotides in length.

A guide RNA or a guide polynucleotide can also comprises a second region that forms a secondary structure. For example, a secondary structure formed by a guide RNA can comprise a stem (or hairpin) and a loop. A length of a loop and a stem can vary. For example, a loop can range from or from about 3 to 10 nucleotides in length, and a stem can range from or from about 6 to 20 base pairs in length. A stem can comprise one or more bulges of 1 to 10 or about 10 nucleotides. The overall length of a second region can range from or from about 16 to 60 nucleotides in length. For example, a loop can be or can be about 4 nucleotides in length and a stem can be or can be about 12 base pairs.

A guide RNA or a guide polynucleotide can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than or more than about 4 nucleotides in length. For example, the length of a third region can range from or from about 5 to 60 nucleotides in length.

A guide RNA or a guide polynucleotide can target any exon or intron of a gene target. In some cases, a guide can target exon 1 or 2 of a gene, in other cases; a guide can target exon 3 or 4 of a gene. A composition can comprise multiple guide RNAs that all target the same exon or in some cases, multiple guide RNAs that can target different exons. An exon and an intron of a gene can be targeted.

A guide RNA or a guide polynucleotide can target a nucleic acid sequence of or of about 20 nucleotides. A target nucleic acid can be less than or less than about 20 nucleotides. A target nucleic acid can be at least or at least about 5, 10, 15, 16, 17, 18, 19, 20, 21, 22, 23, 24, 25, 30, or anywhere between 1-100 nucleotides in length. A target nucleic acid can be at most or at most about 5, 10, 15, 16, 17, 18, 19, 20, 21, 22, 23, 24, 25, 30, 40, 50, or anywhere between 1-100 nucleotides in length. A target nucleic acid sequence can be or can be about 20 bases immediately 5' of the first nucleotide of the PAM. A guide RNA can target a nucleic acid sequence. A target nucleic acid can be at least or at least about 1-10, 1-20, 1-30, 1-40, 1-50, 1-60, 1-70, 1-80, 1-90, or 1-100 nucleotides.

A guide polynucleotide, for example, a guide RNA, can refer to a nucleic acid that can hybridize to another nucleic acid, for example, the target nucleic acid or protospacer in a genome of a cell. A guide polynucleotide can be RNA. A guide polynucleotide can be DNA. The guide polynucleotide can be programmed or designed to bind to a sequence of nucleic acid site-specifically. A guide polynucleotide can comprise a polynucleotide chain and can be called a single guide polynucleotide. A guide polynucleotide can comprise two polynucleotide chains and can be called a double guide polynucleotide. A guide RNA can be introduced into a cell or embryo as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III). Plasmid vectors that can be used to express guide RNA include, but are not limited to, px330 vectors and px333 vectors. In some cases, a plasmid vector (e.g., px333 vector) can comprise at least two guide RNA-encoding DNA sequences.

A DNA sequence encoding a guide RNA or a guide polynucleotide can also be part of a vector. Further, a vector can comprise additional expression control sequences (e.g., enhancer sequences, Kozak sequences, polyadenylation sequences, transcriptional termination sequences, etc.), selectable marker sequences (e.g., GFP or antibiotic resistance genes such as puromycin), origins of replication, and the like. A DNA molecule encoding a guide RNA can also be linear. A DNA molecule encoding a guide RNA or a guide polynucleotide can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

A guide polynucleotide can comprise one or more modifications to provide a nucleic acid with a new or enhanced feature. A guide polynucleotide can comprise a nucleic acid affinity tag. A guide polynucleotide can comprise synthetic nucleotide, synthetic nucleotide analog, nucleotide derivatives, and/or modified nucleotides.

In some cases, a gRNA or a guide polynucleotide can comprise modifications. A modification can be made at any location of a gRNA or a guide polynucleotide. More than one modification can be made to a single gRNA or a guide polynucleotide. A gRNA or a guide polynucleotide can undergo quality control after a modification. In some cases, quality control can include PAGE, HPLC, MS, or any combination thereof.

A modification of a gRNA or a guide polynucleotide can be a substitution, insertion, deletion, chemical modification, physical modification, stabilization, purification, or any combination thereof.

A gRNA or a guide polynucleotide can also be modified by 5'adenylate, 5' guanosine-triphosphate cap, 5'N7-Methylguanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencer 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, or any combination thereof.

In some cases, a modification is permanent. In other cases, a modification is transient. In some cases, multiple modifications are made to a gRNA or a guide polynucleotide. A gRNA or a guide polynucleotide modification can alter physio-chemical properties of a nucleotide, such as their conformation, polarity, hydrophobicity, chemical reactivity, base-pairing interactions, or any combination thereof.

A modification can also be a phosphorothioate substitute. In some cases, a natural phosphodiester bond can be susceptible to rapid degradation by cellular nucleases and; a modification of internucleotide linkage using phosphorothioate (PS) bond substitutes can be more stable towards hydrolysis by cellular degradation. A modification can increase stability in a gRNA or a guide polynucleotide. A modification can also enhance biological activity. In some cases, a phosphorothioate enhanced RNA gRNA can inhibit RNase A, RNase T1, calf serum nucleases, or any combinations thereof. These properties can allow the use of PS-RNA gRNAs to be used in applications where exposure to nucleases is of high probability in vivo or in vitro. For example, phosphorothioate (PS) bonds can be introduced between the last 3-5 nucleotides at the 5'- or 3'-end of a gRNA which can inhibit exonuclease degradation. In some cases, phosphorothioate bonds can be added throughout an entire gRNA to reduce attack by endonucleases.

Promoter

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Non-limiting exemplary promoters include the simian virus 40 (SV40) early promoter, mouse mammary tumor virus long terminal repeat (LTR) promoter, human immunodeficiency virus (HIV) long terminal repeat (LTR) promoter, adenovirus major late promoter (Ad MLP), a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), mouse mammary tumor virus (MMTV), moloney murine leukemia virus (MoMuLV) promoter, an avian leukemia virus promoter, an Epstein-Barr virus immediate early promoter, an actin promoter, a myosin promoter, an elongation factor-1, promoter, an hemoglobin promoter, a creatine kinase promoter, and an Ovian leukemia virus promoter. U6 promoters are useful for expression non-coding RNAs (e.g., targeter-RNAs, activator-RNAs, single guide RNAs) in eukaryotic cells.

The present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. An inducible promoter allows control of the expression using one or more chemical, biological, and/or environmental inducers. Non-limiting exemplary inducers include doxycycline, isopropyl-β-thiogalactopyranoside (IPTG), galactose, a divalent cation, lactose, arabinose, xylose, N-acyl homoserine lactone, tetracycline, a steroid, a metal, an alcohol, heat, or light.

Examples of inducible promoters include, but are not limited to T7 RNA polymerase promoter, T3 RNA polymerase promoter, Isopropyl-beta-thiogalactopyranoside (IPTG)-regulated promoter, lactose induced promoter, heat shock promoter, tetracycline-regulated promoter, steroid-regulated promoter, metal-regulated promoter, estrogen receptor-regulated promoter, and the like. Inducible promoters can therefore be regulated by molecules including, but not limited to, doxycycline; RNA polymerase, e.g., T7 RNA polymerase; an estrogen receptor; an estrogen receptor fusion; and the like.

An inducible promoter utilizes a ligand for dose-regulated control of expression of said at least two genes. In some cases, a ligand can be selected from a group consisting of ecdysteroid, 9-cis-retinoic acid, synthetic analogs of retinoic acid, N,N'-diacylhydrazines, oxadiazolines, dibenzoylalkyl cyanohydrazines, N-alkyl-N,N'-diaroylhydrazines, N-acyl-N-alkylcarbonylhydrazines, N-aroyl-N-alkyl-N'-aroylhydrazines, arnidoketones, 3,5-di-tert-butyl-4-hydroxy-N-isobutyl-benzamide, 8-O-acetylharpagide, oxysterols, 22 (R) hydroxycholesterol, 24 (S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide), and any combination thereof.

Expression control sequences can also be used in constructs. For example, an expression control sequence can comprise a constitutive promoter, which is expressed in a wide variety of cell types. For example, among suitable strong constitutive promoters and/or enhancers are expression control sequences from DNA viruses (e.g., SV40, polyoma virus, adenoviruses, adeno-associated virus, pox viruses, CMV, HSV, etc.) or from retroviral LTRs. Tissue-specific promoters can also be used and can be used to direct expression to specific cell lineages.

In some embodiments, the promoter is an inducible promoter. In some embodiments, the promoter is a non-inducible promoter. In some cases, the promoter can be a tissue-specific promoter. Herein "tissue-specific" refers to regulated expression of a gene in a subset of tissues or cell types. In some cases, a tissue-specific promoter can be regulated spatially such that the promoter drives expression only in certain tissues or cell types of an organism. In other cases, a tissue-specific promoter can be regulated temporally such that the promoter drives expression in a cell type or tissue differently across time, including during development of an organism. In some cases, a tissue-specific promoter is regulated both spatially and temporally. In certain embodiments, a tissue-specific promoter is activated in certain cell types either constitutively or intermittently at particular times or stages of the cell type. For example, a tissue-specific promoter can be a promoter that is activated when a specific cell such as a T cell or a NK cell is activated. T cells can be activated in a variety of ways, for example, when presented with peptide antigens by MHC class II molecules or when an engineered T cells comprising an antigen binding polypeptide engages with an antigen. In one instance, such an engineered T cell or NK cell expresses a chimeric antigen receptor (CAR) or T-cell receptor (TCR).

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters can also be referred to as enhancers, transcriptional control elements, control sequences, etc. Any convenient spatially restricted promoter can be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) can depend on the organism. For example, various spatially restricted promoters are known for plants, flies, worms, mammals, mice, etc. Thus, a spatially restricted promoter can be used to regulate the expression of a nucleic acid encoding e.g., a reporter gene, a therapeutic protein, or a nuclease in a wide variety of different tissues and cell types, depending on the organism. Some spatially restricted promoters are also temporally restricted such that the promoter is in the "ON" state or "OFF" state during specific stages of embryonic development or during specific stages of a biological process.

For illustration purposes, non-limiting examples of spatially restricted promoters include neuron-specific promoters, adipocyte-specific promoters, cardiomyocyte-specific promoters, smooth muscle-specific promoters, or photoreceptor-specific promoters. Non-limiting examples of neuron-specific spatially restricted promoters include a neuron-specific enolase (NSE) promoter (e.g., EMBL HSENO2, X51956); an aromatic amino acid decarboxylase (AADC) promoter; a neurofilament promoter (e.g., GenBank HUMNFL, L04147); a synapsin promoter (e.g., GenBank HUMSYNIB, M55301); a thy-1 promoter (e.g., Chen et al. (1987) Cell 51:7-19; and Llewellyn, et al. (2010) Nat. Med. 16 (10): 1161-1166); a serotonin receptor promoter (e.g., GenBank S62283); a tyrosine hydroxylase promoter (TH) (e.g., Oh et al. (2009) Gene Ther 16:437; Sasaoka et al. (1992) Mol. Brain Res. 16:274; Boundy et al. (1998 J. Neurosci. 18:9989; and Kaneda et al. (1991) Neuron 6:583-594); a GnRH promoter (e.g., Radovick et al. (1991) Proc. Natl. Acad. Sci. USA 88:3402-3406); an L7 promoter (e.g., Oberdick et al. (1990) Science 248:223-226); a DNMT promoter (e.g., Bartge et al. (1988 Proc. Natl. Acad. Sci. USA 85:3648-3652); an enkephalin promoter (e.g., Comb et al. (1988 EMBO J. 17:3793-3805); a myelin basic protein (MBP) promoter; a Ca2+-calmodulin-dependent protein kinase II-alpha (CamKII.alpha.) promoter (e.g., Mayford et al. (1996) Proc. Natl. Acad. Sci. USA 93:13250; and Casanova et al. (2001) Genesis 31:37); and a CMV enhancer/platelet-derived growth factor-β promoter (e.g., Liu et al. (2004) Gene Therapy 11:52-60).

Non-limiting examples of adipocyte-specific spatially restricted promoters include aP2 gene promoter/enhancer, e.g., a region from −5.4 kb to +21 bp of a human aP2 gene (e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (e.g., Knight et al. (2003) Proc. Natl. Acad. Sci. USA 100:14725); a fatty acid translocase (FAT/CD36) promoter (e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (e.g., Mason et al. (1998 Endocrinol. 139:1013; and Chen et al. (1999) Biochem. Biophys. Res. Comm. 262:187); an adiponectin promoter (e.g., Kita et al. (2005) Biochem. Biophys. Res. Comm. 331:484; and Chakrabarti (2010) Endocrinol. 151:2408; an adipsin promoter (e.g., Platt et al. (1989) Proc. Natl. Acad. Sci. USA 86:7490); and a resistin promoter (e.g., Seo et al. (2003) Molec. Endocrinol. 17:1522).

Non-limiting examples of cardiomyocyte-specific spatially restricted promoters include control sequences derived from the following genes: myosin light chain-2, a-myosin heavy chain, AE3, cardiac troponin C, and cardiac actin (Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051).

One example of a suitable promoter is the immediate early cytomegalovirus (CMV) promoter sequence. This promoter sequence is a strong constitutive promoter sequence capable of driving high levels of expression of any polynucleotide sequence operatively linked thereto. In an embodiment, the CMV promoter sequence comprises a nucleotide sequence of SEQ ID NO: 11. In some embodiments, the CMV promoter comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 11.

Another example of a suitable promoter is human elongation growth factor 1 alpha 1 (hEF1a1). In embodiments, the vector construct comprising the CARs and/or TCRs of the present disclosure comprises hEF1a1 functional variants. In an embodiment, the EF-1 alpha promoter sequence comprises a nucleotide sequence of SEQ ID NO: 18. In some embodiments, the EF-1 alpha promoter comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 18.

Reporter System

In some aspects, the multiple gene editing site further comprises a reporter gene, which confirms that the multiple gene editing site has been successfully been inserted into the host cell genome. The reporter gene can encode a protein that does not does not interfere with insertion of donor genes, or interfere with other natural processes in the cell, or otherwise cause deleterious effects in the cell. The reporter gene can encode a detectable protein such as a fluorescent protein, including green fluorescent protein (GFP) (SEQ ID NO: 12) or related proteins such as yellow fluorescent protein, blue fluorescent protein, or red fluorescent protein. The reporter gene can be under control of an inducer (i.e., an inducible promoter). In an embodiment, the inducer is an alcohol, tetracycline, a steroid, a metal or isopropyl-β-thiogalactopyranoside (IPTG). In an embodiment, the inducer is heat or light. For example, as shown in FIGS. 7-8, the multiple gene editing site of the construct can comprise the gene encoding GFP as a reporter, with the GFP gene under a tetracycline (Tet) promoter, which inhibits the expression of the GFP protein until the cell is exposed to tetracycline. In an embodiment, the GFP sequence comprises a nucleotide sequence of SEQ ID NO: 12. In some embodiments, the GFP sequence comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 12.

In order to assess GEMS insertion and/or the expression of donor nucleotide sequences (e.g., CAR or portions thereof), the expression vector to be introduced into a cell can also contain either a selectable marker gene or a reporter gene or both to facilitate identification and selection of expressing cells from the population of cells sought to be transfected or infected through viral vectors. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

In other aspects, the selectable marker can be carried on a separate piece of DNA and used in a co-transfection procedure. Both selectable markers and reporter genes can be flanked with appropriate regulatory sequences to enable expression in the host cells. Useful selectable markers include, for example, antibiotic-resistance genes, such as puromycin resistance gene (puro), neomycin resistance gene (neo) (SEQ ID NO: 13), blasticidin resistance gene (bla) (SEQ ID NO: 19), and ampicillin resistance gene and the like. In an embodiment, the puromycin resistance gene sequence comprises a nucleotide sequence of SEQ ID NO: 13. In some embodiments, the puromycin resistance gene sequence comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 13. In an embodiment, the blasticidin resistance gene sequence comprises a nucleotide sequence of SEQ ID NO: 19. In some embodiments, the blasticidin resistance gene sequence comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 19.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes can include genes encoding luciferase, beta-galactosidase, chloramphenicol acetyl transferase, secreted alkaline phosphatase, or the green fluorescent protein gene (e.g., Ui-Tei et al., FEBS Letters 479:79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

Regardless of the method used to introduce exogenous nucleic acids into the host, in order to confirm the presence of the recombinant DNA sequence in the host cell, a variety of assays can be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

Host Cells

The GEMS construct provided herein can be inserted into any suitable cell. The term "host cell" as used herein refers to an in vivo or in vitro eukaryotic cell (a cell from a unicellular or multicellular organism, e.g., a cell line) which can be, or has been, used as a recipient for the GEMS construct, and further any of donor nucleic acid sequences (e.g., encoding a therapeutic protein) as described herein inserted into the GEMS sequence. The term "host cell" includes the progeny of the original cell which has been targeted (e.g., transfected with a GEMS construct, a construct encoding a nuclease and/or a guide polynucleotide). It is understood that the progeny of a single cell is not necessarily be completely identical in morphology or in genomic or total DNA complement as the original parent, due to natural, accidental, or deliberate mutation. A host cell can be any eukaryotic cell having DNA that can be targeted by a Cas9 targeting complex (e.g., a eukaryotic single-cell organism, a somatic cell, a germ cell, a stem cell, a plant cell, an algal cell, an animal cell, in invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell).

Insertion of the construct can proceed according to any technique suitable in the art. For example, transfection, lipofection, or temporary membrane disruption such as electroporation or deformation can be used to insert the construct into the host cell. Viral vectors or non-viral vectors can be used to deliver the construct in some aspects. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

In an embodiment, the host cell can be non-competent, and nucleases (e.g., endonucleases) can be transfected to the host cell. In an embodiment, the host cell can be competent for at least the primary endonuclease and, also for the secondary endonuclease. Competency for the primary endonuclease permits integration of the multiple gene editing site into the host cell genome. The host cell can be a primary isolate, obtained from a subject and optionally modified as necessary to make the cell competent for either or both of the primary endonuclease and the secondary endonuclease.

In some aspects, the host cell is a cell line. In some aspects, the host cell is a primary isolate or progeny thereof. In some aspects, the host cell is a stem cell. The stem cell can be an embryonic stem cell or an adult cell. The stem cell is preferably pluripotent, and not yet differentiated or begun a differentiation process. In some aspects, the host cell is a fully differentiated cell. When the host cell, transfected with the construct, divides, the multiple gene editing site of the construct can be integrated with the host cell genome such that progeny of the host cell can carry the multiple gene editing site. A host cell comprising an integrated multiple gene editing site can be cultured and expanded in order to increase the number of cells available for receiving donor gene sequences. Stable integration ensures subsequent generations of cells can have the multiple gene editing sites.

The host cell can be further manipulated at locations outside of the multiple gene editing site. For example, the host cell can have one or more genes knocked out, or can have one or more genes knocked down with siRNA, shRNA, or other suitable nucleic acid for gene knock down. The host cell can also or alternatively have other genes edited or revised via any suitable editing technique. Such manipulations outside of the multiple gene editing site can, for example, permit the assessment of the effects of the donor nucleic acid sequence, or the protein it encodes, on the cell when other genes are knocked out, knocked down, or otherwise altered.

In some embodiments, the host cell manipulations outside of the multiple gene editing site, as well as manipulations by way of the addition of donor nucleic acid sequences, can favorably enhance the immunogenicity profile of the donor cell. Thus, for example, via added donor nucleic acid sequences, the host cell can express one or more markers that impart compatibility with the immune system of the subject to which the host cell is administered in a therapeutic context. Alternatively, via knockout or knockdown manipulations, the host cell can lack expression of one or more markers that would cause the cell to be recognized and destroyed by the immune system of the subject to which the host cell is administered in a therapeutic context.

In some embodiments, the host cell can be one or more cells from tissues or organs, the tissues or organs including brain, lung, liver, heart, spleen, pancreas, small intestine, large intestine, skeletal muscle, smooth muscle, skin, bones, adipose tissues, hairs, thyroid, trachea, gall bladder, kidney, ureter, bladder, aorta, vein, esophagus, diaphragm, stomach, rectum, adrenal glands, bronchi, ears, eyes, retina, genitals, hypothalamus, larynx, nose, tongue, spinal cord, or ureters, uterus, ovary and testis. For example, the host cell can be from brain, heart, liver, skin, intestine, lung, kidney, eye, small bowel, pancreas, or spleen.

In some embodiments, the host cell can be one or more of trichocytes, keratinocytes, gonadotropes, corticotropes, thyrotropes, somatotropes, lactotrophs, chromaffin cells, parafollicular cells, *glomus* cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic a cells, pancreatic B cells, pancreatic 8 cells, pancreatic F cells (e.g., PP cells), pancreatic & cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula *densa* cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, splenocytes (e.g., T lymphocytes, B lymphocytes, dendritic cells, microphages, leukocytes), trophoblast stem cells, or any combination thereof.

In some cases, the host cell is a T cell. In some cases, the T cell is an αβ T-cell, an NK T-cell, a γδ T-cell, a regulatory T-cell, a T helper cell, or a cytotoxic T-cell.

Stem Cells

In some cases, the host cell is a stem cell. In some cases, the host cell is an adult stem cell. In some cases, the host cell is an embryonic stem cell. In some cases, the host cell is a non-embryonic stem cell. In some cases, the host ells are derived from non-stem cells. In some cases, the host cells are derived from stem cells (e.g., embryonic stem cells, non-embryonic stem cells, pluripotent stem cells, placental stem cells, induced pluripotent stem cells, trophoblast stem cells etc.).

The term "stem cell" is used herein to refer to a cell (e.g., plant stem cell, vertebrate stem cell) that has the ability both to self-renew and to generate a differentiated cell type (Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and can or cannot retain the capacity to proliferate further. Stem cells can be characterized by both the presence of specific markers (e.g., proteins, RNAs, etc.) and the absence of specific markers. Stem cells can also be identified by functional assays both in vitro and in vivo, particularly assays relating to the ability of stem cells to give rise to multiple differentiated progeny. In an embodiment, the host cell is an adult stem cell, a somatic stem cell, a non-embryonic stem cell, an embryonic stem cell, hematopoietic stem cell, an include pluripotent stem cells, and a trophoblast stem cell.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282 (5391): 1145-7) whereas induced pluripotent stem cells (iPSCs) are derived from somatic cells (Takahashi et. al, Cell. 2007 Nov. 30; 131 (5): 861-72; Takahashi et. al, Nat Protoc. 2007; 2 (12): 3081-9; Yu et. al, Science. 2007 Dec. 21; 318 (5858): 1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs can be in the form of an established cell line, they can be obtained directly from primary embryonic tissue, or they can be derived from a somatic cell.

By "embryonic stem cell" (ESC) is meant a PSC that is isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells can be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, each of which is incorporated herein by its entirety. Methods for proliferating hESCs in the undifferentiated form are described in WO 99/20741, WO 01/51616, and WO 03/020920, each of which is incorporated herein by its entirety.

By "embryonic germ stem cell" (EGSC) or "embryonic germ cell" or "EG cell", it is meant a PSC that is derived from germ cells and/or germ cell progenitors, e.g. primordial germ cells, i.e. those that can become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98:113; Shamblott, M., et al. (1998) Proc. Natl. Acad. Sci. USA, 95:13726; and Koshimizu, U., et al. (1996) Development, 122:1235, each of which are incorporated herein by its entirety.

By "induced pluripotent stem cell" or "iPSC", it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs can be found in, for example, U.S. Patent Publication Nos. US20090047263, US20090068742, US20090191159, US20090227032, US20090246875, and US20090304646, each of which are incorporated herein by its entirety. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell", it is meant any cell in an organism that, in the absence of experimental manipulation, does not ordinarily give rise to all types of cells in an organism. In other words, somatic cells are cells that have differentiated sufficiently that they do not naturally generate cells of all three germ layers of the body, i.e. ectoderm, mesoderm and endoderm. For example, somatic cells can include both neurons and neural progenitors, the latter of which is able to naturally give rise to all or some cell types of the central nervous system but cannot give rise to cells of the mesoderm or endoderm lineages.

Trophoblast Stem Cells

Trophoblast stem cells (TS cells) are precursors of differentiated placenta cells. In some instances, a TS cell is derived from a blastocyst polar trophectoderm (TE) or an extraembryonic ectoderm (ExE) cell. In some cases, TS is capable of indefinite proliferation in vitro in an undifferentiated state, and is capable of maintaining the potential multilineage differentiation capabilities in vitro. In some instances, a TS cell is a mammalian TS cell. Exemplary mammals include mouse, rat, rabbit, sheep, cow, cat, dog, monkey, ferret, bat, kangaroo, seals, dolphin, and human. In some embodiments, a TS cell is a human TS (hTS) cell.

In some instances, TS cells are obtained from fallopian tubes. Fallopian tubes are the site of fertilization and the common site of ectopic pregnancies, in which biological events such as the distinction between inner cell mass (ICM) and trophectoderm and the switch from totipotency to pluripotency with major epigenetic changes take place. In some instances, these observations provide support for fallopian tubes as a niche reservoir for harvesting blastocyst-associated stem cells at the preimplantation stage. Blastocyst is an early-stage preimplantation embryo, and comprises ICM which subsequently forms into the embryo, and an outer layer termed trophoblast which gives rise to the placenta.

In some embodiments, a TS cell is a stem cell used for generation of a progenitor cell such as for example a hepatocyte. In some embodiments, a TS cell is derived from ectopic pregnancy. In some embodiments, the TS cell is a human TS cell. In one embodiment, the human TS cell derived from ectopic pregnancies does not involve the destruction of a human embryo. In another embodiment, the human TS cell derived from ectopic pregnancies does not involve the destruction of a viable human embryo. In another embodiment, the human TS cell is derived from trophoblast tissue associated with non-viable ectopic pregnancies. In another embodiment, the ectopic pregnancy cannot be saved. In another embodiment, the ectopic pregnancy would not lead to a viable human embryo. In another embodiment, the ectopic pregnancy threatens the life of the mother. In another embodiment, the ectopic pregnancy is tubal, abdominal, ovarian or cervical.

During normal blastocyst development, ICM contact per se or its derived diffusible 'inducer' triggers a high rate of cell proliferation in the polar trophectoderm, leading to cell movement toward the mural region throughout the blastocyst stage and can continue even after the distinction of the trophectoderm from the ICM. The mural trophectoderm cells overlaying the ICM are able to retain a 'cell memory' of ICM. At the beginning of the implantation, the mural cells opposite the ICM cease division because of the mechanical constraints from the uterine endometrium. However, in an ectopic pregnancy in which the embryo is located within the fallopian tube, constraints do not exist in the fallopian tubes which result in continuing division of polar trophectoderm cells to form extraembryonic ectoderm (ExE) in the stagnated blastocyst. In some instances, the ExE-derived TS cells exist for up to 20 days in a proliferation state. As such, until clinical intervention occurs, the cellular processes can yield an indefinite number of hTS cells in the preimplantation embryos and such cells can retain cell memory from ICM.

In some instances, TS cells possess specific genes of ICM (e.g., OCT4, NANOG, SOX2, FGF4) and trophectoderm (e.g., CDX2, Fgfr-2, Eomes, BMP4), and express components of the three primary germ layers, mesoderm, ectoderm, and endoderm. In some instances, TS cells express embryonic stem (e.g., human embryonic stem) cell-related surface markers such as specific stage embryonic antigen (SSEA)-1, -3 and -4 and mesenchymal stem cell-related markers (e.g., CD 44, CD90, CK7 and Vimentin). In other instances, hematopoietic stem cell markers (e.g., CD34, CD45, α6-integrin, E-cadherin, and L-selectin) are not expressed.

Mammalian Trophoblast Stem Cells

In some embodiments, the host cell can be a mammalian trophoblast stem cell from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, a mammalian trophoblast stem cell herein is not from primates, e.g., monkeys, apes, humans. In another instance, a mammalian trophoblast stem cell herein is from primates, e.g., monkeys, apes, humans. In another instance, a mammalian trophoblast stem cell herein is human or humanized.

A mammalian trophoblast stem cell herein can be induced for differentiating into one or more kinds of differentiated cells prior to or after insertion of one or more GEMS constructs. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

In one instance, the differentiated cell is a progenitor cell, e.g., a pancreatic progenitor cell. In one instance, the differentiated cell is a pluripotent stem cell. In one instance, the differentiated cell is an endodermal, mesodermal, or ectodermal progenitor cell. In one instance, the differentiated cell is a definitive endoderm progenitor cell. In one instance, the differentiated cell is a pancreatic endoderm progenitor cell. In one instance, the differentiated cell is a multipotent progenitor cell. In one instance, the differentiated cell is an oligopotent progenitor cell. In one instance, the differentiated cell is a monopotent, bipotent, or tripotent progenitor cell. In one instance, the differentiated cell is an endocrine, exocrine, or duct progenitor cell, e.g., an endocrine progenitor cell. In one instance, the differentiated cell is a beta-cell. In one instance, the differentiated cell is an insulin-producing cell. One or more differentiated cells can be used in any method disclosed herein.

In one aspect, provided herein are one or more differentiated cells comprising one or more GEMS constructs. In one instance, the isolated differentiated cell is a human cell. In one instance, the isolated differentiated cell has a normal karyotype. In one instance, the isolated differentiated cell has one or more immune-privileged characteristics, e.g., low or absence of CD33 expression and/or CD133 expression. One or more isolated differentiated cells disclosed herein can be used in any method disclosed herein.

In another aspect, provided herein is an isolated progenitor cell that expresses one or more transcription factors comprising Foxa2, Pdx1, Ngn3, Ptfla, Nkx6.1, or any combination thereof. In one instance, the isolated progenitor cell expresses two, three, or four transcription factors of Foxa2, Pdx1, Ngn3, Ptfla, Nkx6.1. In one instance, the isolated progenitor cell expresses Foxa2, Pdx1, Ngn3, Ptfla, and Nkx6.1. In one instance, the isolated progenitor cell is an induced pluripotent stem cell. In one instance, the isolated progenitor cell is derived from a mammalian trophoblast stem cell, e.g., an hTS cell. In one instance, the isolated progenitor cell is a pancreatic progenitor cell. In one instance, the isolated progenitor cell is an endodermal, mesodermal, or ectodermal progenitor cell. In one instance, the isolated progenitor cell is a definitive endoderm progenitor cell. In one instance, the isolated progenitor cell is a pancreatic endoderm progenitor cell. In one instance, the isolated progenitor cell is a multipotent progenitor cell. In one instance, the isolated progenitor cell is an oligopotent progenitor cell. In one instance, the isolated progenitor cell is a monopotent, bipotent, or tripotent progenitor cell. In one instance, the isolated progenitor cell is an endocrine, exocrine, or duct progenitor cell, e.g., an endocrine progenitor cell. In one instance, the isolated progenitor cell is a beta-cell. In one instance, the isolated progenitor cell is an insulin-producing cell. In one instance, the isolated progenitor cell is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, the isolated progenitor cell is a human cell. In one instance, the isolated progenitor cell has a normal karyotype. In one instance, the isolated progenitor cell has one or more immune-privileged characteristics, e.g., low or absence of CD33 expression and/or CD133 expression. An isolated progenitor cell disclosed herein can be used in any method disclosed herein.

In another aspect, provided herein is an isolated progenitor cell that expresses betatrophin, betatrophin mRNA, C-peptide, and insulin, wherein the isolated progenitor cell is differentiated from a mammalian trophoblast stem cell. In one instance, the isolated progenitor cell is from rodents (e.g, mice, rats, guinea pigs, hamsters, squirrels), rabbits, cows, sheep, pigs, dogs, cats, monkeys, apes (e.g., chimpanzees, gorillas, orangutans), or humans. In one instance, the isolated progenitor cell is a pancreatic progenitor cell. In one instance, the isolated progenitor cell is a human cell. In one instance, the isolated progenitor cell has a normal karyotype. In one instance, the isolated progenitor cell has one or more immune-privileged characteristics, e.g., low or absence of CD33 expression and/or CD133 expression. One or more isolated progenitor cells disclosed herein can be used in any method disclosed herein. In one instance, an isolated progenitor cell herein is an insulin-producing cell. One or more isolated progenitor cells herein can be used in any method disclosed herein. In one instance, a differentiated cell herein is an insulin-producing cell. In one instance, a differentiated cell herein is a neurotransmitter producing cell.

Human Trophoblast Stem Cells

Human fallopian tubes are the site of fertilization and the common site of ectopic pregnancies in women, where several biological events take place such as the distinction between inner cell mass (ICM) and trophectoderm and the switch from totipotency to pluripotency with the major epigenetic changes. These observations provide support for fallopian tubes as a niche reservoir for harvesting blastocyst-associated stem cells at the preimplantation stage. Ectopic pregnancy accounts for 1 to 2% of all pregnancies in industrialized countries and are much higher in developing countries. Given the shortage in availability of human embryonic stem cells (hES cells) and fetal brain tissue, described herein is the use of human trophoblast stem cells (hTS cells) derived from ectopic pregnancy as a substitution for scarcely available hES cells for generation of progenitor cells.

In some embodiments, the hTS cells derived from ectopic pregnancies do not involve the destruction of a human embryo. In another instance, the hTS cells derived from ectopic pregnancies do not involve the destruction of a viable human embryo. In another instance, the hTS cells are derived from trophoblast tissue associated with non-viable ectopic pregnancies. In another instance, the ectopic pregnancy cannot be saved. In another instance, the ectopic pregnancy would not lead to a viable human embryo. In another instance, the ectopic pregnancy threatens the life of the mother. In another instance, the ectopic pregnancy is tubal, abdominal, ovarian or cervical.

In some embodiments, during blastocyst development, ICM contact per se or its derived diffusible 'inducer' triggers a high rate of cell proliferation in the polar trophectoderm, leading to cell movement toward the mural region throughout the blastocyst stage and can continue even after the distinction of the trophectoderm from the ICM. The mural trophectoderm cells overlaying the ICM are able to retain a 'cell memory' of ICM. Normally, at the beginning of implantation the mural cells opposite the ICM cease division because of the mechanical constraints from the uterine endometrium. However, no such constraints exist in the fallopian tubes, resulting in the continuing division of polar trophectoderm cells to form extraembryonic ectoderm (ExE) in the stagnated blastocyst of an ectopic pregnancy. In some embodiments, the ExE-derived TS cells exist for at least a 4-day window in a proliferation state, depending on the interplay of ICM-secreted fibroblast growth factor 4 (FGF4) and its receptor fibroblast growth factor receptor 2 (Fgfr2). In another instance, the ExE-derived TS cells exist for at least a 1-day, at least a 2-day, at least a 3-day, at least a 4-day, at least a 5-day, at least a 6-day, at least a 7-day, at least a 8-day, at least a 9-day, at least a 10-day, at least a 11-day, at least a 12-day, at least a 13-day, at least a 14-day, at least a 15-day, at least a 16-day, at least a 17-day, at least a 18-day, at least a 19-day, at least a 20-day window in a proliferation state. Until clinical intervention occurs, these cellular processes can yield an indefinite number of hTS cells in the preimplantation embryos; such cells retaining cell memory from ICM, reflected by the expression of ICM-related genes.

Method of Differentiating Host Stem Cells

In an embodiment, the host stem cell can be differentiated prior to or after insertion of one or more GEMS constructs. In some embodiments, the GEMS construct comprises a GEMS sequence of SEQ ID NO: 2. In some embodiments, the GEMS construct comprises a GEMS sequence of SEQ ID NO: 84. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 2. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 84. In some embodiments, the GEMS construct comprises a nucleotide sequence of SEQ ID NO: 81, SEQ ID NO: 82, and/or SEQ ID NO: 83. In some embodiments, the GEMS construct comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 81, SEQ ID NO: 82, and/or SEQ ID NO: 83. In some embodiments, the GEMS construct comprises GEMS site 16 5' homology arm sequence comprising a nucleotide sequence of SEQ ID NO: 16. In some embodiments, the GEMS construct comprises GEMS site 16 3' homology arm sequence comprising a nucleotide sequence of SEQ ID NO: 17.

In one of many aspects, provided herein is a method of differentiating the host stem cell. In an embodiment, the host stem cell is a mammalian trophoblast stem cell. In one instance, the mammalian trophoblast stem cell is a human trophoblast stem (hTS) cell. In one instance, the differentiated cell is a pluripotent stem cell. In one instance, the differentiated cell is a progenitor cell, e.g., a pancreatic progenitor cell. In one instance, the differentiated cell is an endodermal, mesodermal, or ectodermal progenitor cell, e.g., a definitive endoderm progenitor cell. In one instance, the differentiated cell is a pancreatic endoderm progenitor cell. In one instance, the differentiated cell is a multipotent progenitor cell. In one instance, the differentiated cell is an oligopotent progenitor cell. In one instance, the differentiated cell is a monopotent, bipotent, or tripotent progenitor cell. In one instance, the differentiated cell is an endocrine, exocrine, or duct progenitor cell, e.g., an endocrine progenitor cell. In one instance, the differentiated cell is a beta-cell. In one instance, the differentiated cell is an insulin-producing cell. One or more differentiated cells can be used in any method disclosed herein.

In some embodiments, the mammalian trophoblast stem cell herein is from rodents (e.g, mice, rats, guinea pigs, hamsters, squirrels), rabbits, cows, sheep, pigs, dogs, cats, monkeys, apes (e.g., chimpanzees, gorillas, orangutans), or humans.

In some embodiments, the method of differentiating the host stem cells activates miR-124. In one instance, the method of differentiating the host stem cells activates miR-124 spatiotemporarily, e.g., between about 1 hour to about 8 hours, at a definitive endoderm stage. In one instance, the method of differentiating the host stem cells elevates miR-124 expression. In one instance, the method of differentiating the host stem cells deactivates miR-124. In one instance, the method of differentiating the host stem cells decreases miR-124 expression. In one instance, the method of differentiating the host stem cells comprises contacting the mammalian trophoblast stem cell with one or more agents, e.g., proteins or steroid hormones. In one instance, the one or more agents comprise a growth factor, e.g., a fibroblast growth factor (FGF). In one instance, the FGF is one or more of FGF1, FGF2, FGF3, FGF4, FGF5, FGF6, FGF7, FGF8, FGF9, or FGF10. In one instance, the one or more agents comprise FGF2 (basic fibroblast growth factor, bFGF). In one instance, the method of differentiating the host stem cells comprises contacting the host stem cell with no more than about 200 ng/ml of FGF (e.g., bFGF), e.g., from 100 to 200 ng/mL. In one instance, the method of differentiating the host stem cells comprises contacting the host stem cell with no more than about 100 ng/mL of FGF (e.g., bFGF), e.g., from about 0.1 to 1 ng/ml; or from about 1 to about 100 ng/ml of FGF (e.g., bFGF). In one instance, the concentration of FGF (e.g., bFGF) used herein is from about: 0.1-1, 1-10, 10-20, 20-30, 30-40, 40-50, 50-60, 50-70, 80-90, or 90-100 ng/mL. In one instance, the concentration of FGF (e.g., bFGF) used herein is about: 0.1, 0.2, 0.4, 0.6, 0.8, 1, 2, 3, 4, 5, 6, 7, 8, 9, 10, 11, 12, 13, 14, 15, 16, 17, 18, 19, 20, 25, 30, 35, 40, 45, 50, 60, 70, 80, or 90 ng/mL. In one instance, the one or more agents further comprise an antioxidant or reducing agent (e.g., 2-mercaptoethanol). In one instance, the one or more agents further comprise a vitamin (e.g., nicotinamide). In one instance, the method of differentiating host stem cell comprises contacting the mammalian trophoblast stem cell with FGF (e.g., bFGF), 2-mercaptoethanol, and nicotinamide. In one instance, the concentration of antioxidant/reducing agent (e.g., 2-mercaptoethanol) is no more than about 10 mmol/L, e.g., from about 0.1 to about 10 mmol/L. In one instance, the concentration of antioxidant/reducing agent (e.g., 2-mercaptoethanol) is from about: 0.1-1, 1-2, 2-3, 3-4, 4-5, 5-6, 6-7, 7-8, 8-9, or 9-10 mmol/L. In one instance, the concentration of antioxidant/reducing agent (e.g., 2-mercaptoethanol) is about: 0.2, 0.5, 1, 1.5, 2, 3, 4, 5, 6, 7, 8, or 9 mmol/L. In one instance, the concentration of antioxidant/reducing agent (e.g., 2-mercaptoethanol) is about 1 mmol/L. In one instance, the concentration of vitamin (e.g., nicotinamide) is no more than about 100 mmol/L, e.g., from about 1 to about 100 mmol/L. In one instance, the concentration of vitamin (e.g., nicotinamide) is from about: 1-10, 10-20, 20-30, 30-40, 40-50, 50-60, 50-70, 80-90, or 90-100 mmol/L. In one instance, the concentration of vitamin (e.g., nicotinamide) is about: 2, 4, 6, 8, 10, 12, 14, 16, 18, 20, 30, 40, 50, 60, 70, 80, or 90 mmol/L. In one instance, the concentration of vitamin (e.g., nicotinamide) is about 10 mmol/L.

In one instance, the method of differentiating the host stem cells comprises contacting the host stem cell with one or more agents to regulate activity or expression level of cAMP Responsive Element Binding Protein 1 (CREB1). In one instance, the one or more agents regulate CREB1 phosphorylation. In one instance, the one or more agents comprise a vitamin metabolite, e.g., retinoic acid. In one instance, the one or more agents comprise a CREB1-binding protein. In one instance, the one or more agents regulate one or more factors comprising mix11, Cdx2, Oct4, Sox17, Foxa2, or GSK3B.

In one instance, the one or more agents comprise an exogenous miR-124 precursor or an exogenous anti-miR-124. In one instance, the host stem cell is transfected with the exogenous miR-124 precursor or the exogenous anti-miR-124. In one instance, cis-regulatory element (CRE) of TGACGTCA of promoters of the miR-124 is modulated. In some embodiments, the miR-124 is miR-124a, miR-124b, miR-124c, miR-124d, or miR-124e. In one instance, the miR-124 is miR-124a, e.g., *Homo sapiens* miR-124a (hsa-miR-124a).

In one instance, the host stem cell differentiates into the differentiated cell within one day after the start of the differentiating. In some embodiments, induction of differentiation of the host stem cells comprises culturing an undifferentiated host stem cell in a medium comprising a growth factor (e.g., bFGF) under conditions (e.g., 12, 24, 48, 76, or 96 hours) sufficient to induce the differentiation. The medium can further comprise serum (e.g., FBS), carbohydrates (e.g., glucose), antioxidants/reducing agents (e.g., β-mercaptonethanol), and/or vitamins (e.g., nicotinamide). Yield of the differentiated cells is measured, e.g., insulin+/Ngn3+ cells or insulin+/glucagon+ cells as indicators for pancreatic progenitors. In one instance, FBS and insulin levels are positively correlated during FGF (e.g., bFGF) induction, e.g., as indicated by Western blot analysis.

In some embodiments, upon cell induction (e.g, by bFGF), a time-course analysis, e.g, for 4, 8, 16, 24, 32, 40, or 48 hours, can be conducted to monitor levels of transcription factors identifying the cascading stages of cell differentiation development. In some embodiments, declining Mix11 and high levels of T and Gsc can imply a transition from the host stem cells to mesendoderm. In some embodiments, dominant pluripotency transcription factors at each stage of differentiation include Cdx2 for mesendoderm, Oct4 or Nanog for DE, Cdx2 or Nanog for primitive gut endoderm, or Sox2 for pancreatic progenitors. In some embodiments, FGF (e.g., bFGF) induces multifaceted functions of miR-124a via upregulation of Oct4, Sox17, or Foxa2, but downregulation of Smad4 or Mix11 at the DE stage.

In some embodiments, during cell differentiation, levels of proteins or hormones characteristic to the target differentiated cells are also measured with a time-course analysis, e.g., for 4, 8, 16, 24, 32, 40, or 48 hours. For example, betatrophin, C-peptide, and insulin are measured, e.g., with qPCR analysis, for pancreatic progenitor production.

In some embodiments, a growth factor is used to induce differentiation of the host stem cell. In one instance, the growth factor is FGF (e.g., bFGF), bone morphogenetic protein (BMP), or vascular endothelial growth factor (VEGF). In some embodiments, an effective amount of a growth factor is no more than about 100 ng/ml, e.g., about: 1, 2, 5, 10, 15, 20, 25, 30, 35, 40, 45, 50, 60, 70, 80, 90, or 100 ng/mL. In one instance, the host stem cell is a mammalian trophoblast stem cell. In one instance, the mammalian trophoblast stem cell is an hTS cell.

In some embodiments, a culture medium used to differentiate the host stem cell can further comprise an effective amount of a second agent that works synergistically with a first agent to induce differentiation into a mesendoderm direction. In some embodiments, the first and second agents are different growth factors. In some embodiments, the first agent is added to the culture medium before the second agent. In some embodiments, the second agent is added to the culture medium before the first agent. In one instance, the first agent is FGF (e.g., bFGF). In some embodiments, the second agent is BMP, e.g., BMP2, BMP7, or BMP4, added before or after the first agent. In some embodiments, an effective amount of a BMP is no more than about 100 ng/ml, e.g., about: 1, 2, 5, 10, 15, 20, 25, 30, 35, 40, 45, 50, 60, 70, 80, 90, or 100 ng/mL. In one instance, the host stem cell is a mammalian trophoblast stem cell. In one instance, the mammalian trophoblast stem cell is an hTS cell.

In some embodiments, a culture medium used to differentiate the host stem cell (e.g., a mammalian trophoblast stem cell) can comprise feeder cells. Feeder cells are cells of one type that are co-cultured with cells of another type, to provide an environment in which the cells of the second type can grow. In some embodiments, a culture medium used is free or essentially free of feeder cells. In some embodiments, a GSK-3 inhibitor is used to induce differentiation of the host stem cell.

Method of Manufacturing Host Cells

Provided herein is a method of manufacturing a host cell comprising: introducing into said host cell a gene editing multi-site (GEMS) construct element for insertion into a genome at an insertion site, wherein said GEMS construct element comprises a (i) homology arm, wherein said homology arm comprises a homology sequence that is homologous to a genome sequence at said insertion site; and (ii) a GEMS sequence adjacent to said homology arm, wherein said GEMS sequence comprises a plurality of nuclease recognition sequences, wherein each of said plurality of nuclease recognition sequences comprises a guide target sequence linked to a protospacer adjacent motif (PAM) sequence, wherein said guide target sequence binds a guide polynucleotide following insertion of said GEMS construct element at said insertion site.

In some embodiments, the method further comprises introducing into said host cell an endonuclease for mediating integration of said GEMS construct element into said genome. In some embodiments, said nuclease is an endonuclease. In some embodiments, said endonuclease comprises a meganuclease, wherein said homology sequence of said homology arm comprises a consensus sequence of said meganuclease. In some embodiments,, said meganuclease is I-Scel. In some embodiments, said endonuclease comprises a CRISPR-associated nuclease.

In some embodiments, the method further comprises introducing into said host cell a guide RNA for mediating integration of said GEMS construct element into said genome. In some embodiments, said guide RNA recognizes a sequence of said genome at said insertion site. In some embodiments, said insertion site is at a safe harbor site of the genome. In some embodiments, said safe harbor site comprises an AAVs1 site, a Rosa26 site, or a C—C motif receptor 5 (CCR5) site. In some embodiments, said GEMS construct element is integrated at said insertion site. In some embodiments, the method further comprises introducing said guide polynucleotide into said host cell. In some embodiments, said guide polynucleotide is a guide RNA. In some embodiments, the method further comprises introducing a nuclease into said host cell, wherein said nuclease when bound to said guide polynucleotide recognizes said nuclease recognition sequence of said plurality of nuclease recognition sequences. In some embodiments, said nuclease is a CRISPR-associated nuclease. In some embodiments, the method further comprises introducing a donor nucleic acid sequence into said host cell for insertion into said GEMS construct element within said nuclease recognition sequence. In some embodiments, said donor nucleic acid sequence is integrated within said nuclease recognition sequence. In some embodiments, said donor nucleic acid sequence polynucleotide encodes a therapeutic protein. In some embodiments, said therapeutic protein comprises a chimeric antigen receptor (CAR). In some embodiments, said CAR is a CD19 CAR or a portion thereof. In some embodiments, said therapeutic protein comprises dopamine or a portion thereof. In some embodiments, said therapeutic protein comprises insulin, proinsulin, or a portion thereof.

In some embodiments, the donor nucleic acid sequences comprise a nucleotide sequence of SEQ ID NO: 20. In some embodiments, the donor nucleic acid sequences comprise a nucleotide sequence of SEQ ID NO: 21. In some embodiments, the donor nucleic acid sequences comprise a nucleotide sequence of SEQ ID NO: 22. In some embodiments, the donor nucleic acid sequences comprise a nucleotide sequence of SEQ ID NO: 23. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 20. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 21. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 22. In some embodiments, the donor nucleic acid sequences comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 23.

In some embodiments, the method further comprises introducing into said host cell (i) a second guide polynucleotide, wherein said guide polynucleotide recognizes a second nuclease recognition sequence of said plurality of nuclease recognition sequences; (ii) a second nuclease, wherein said second nuclease recognizes said second nuclease recognition sequence when bound to said second guide polynucleotide; and (iii) a second donor nucleic acid sequence for integration within said second nuclease recognition sequence. In some embodiments, the method further comprises propagating said host cell.

Provided herein is a method of editing a genome comprising: obtaining a host cell that comprises a gene editing multi-site (GEMS) construct element inserted into a genome of said host cell at an insertion site, wherein said GEMS construct element comprises a GEMS sequence, wherein said GEMS sequence comprises a plurality of nuclease recognition sequences, wherein each of said plurality of nuclease recognition sequences comprises a guide target sequence linked to a protospacer adjacent motif (PAM) sequence; and introducing into said host cell: (i) a guide polynucleotide that recognizes said guide target sequence; and (ii) a nuclease that when bound to said guide polynucleotide recognizes a nuclease recognition sequence of said plurality of nuclease recognition sequences.

In some embodiments, said nuclease cleaves said GEMS sequence when bound to said guide polynucleotide to form a double-stranded break in said GEMS sequence. In some embodiments, the method further comprises introducing into said host cell a donor nucleic acid sequence, wherein said donor nucleic acid sequence is integrated into said GEMS sequence at said double-stranded break. In some embodiments, said donor nucleic acid sequence encodes a therapeutic protein. In some embodiments, said therapeutic protein comprises a chimeric antigen receptor (CAR). In some embodiments, said CAR is a CD19 CAR or a portion thereof. In some embodiments, said therapeutic protein comprises dopamine or a portion thereof. In some embodiments, said therapeutic protein comprises insulin, proinsulin, or a portion thereof.

In some embodiments, the method of editing a genome further comprises introducing into said host cell (i) a second guide polynucleotide, wherein said guide polynucleotide recognizes a second nuclease recognition sequence of said plurality of nuclease recognition sequences; (ii) a second nuclease, wherein said second nuclease recognizes said second nuclease recognition sequence when bound to said second guide polynucleotide; and (iii) a second donor nucleic acid sequence for integration within said second nuclease recognition sequence. In some embodiments, said host cell is a stem cell. In some embodiments, the method further comprises differentiating said stem cell into a T-cell. In some embodiments, said T-cell is selected from the group consisting of an αβ T-cell, an NK T-cell, a γδ T-cell, a regulatory T-cell, a T helper cell and a cytotoxic T-cell. In some embodiments, said differentiating occurs prior to said introducing said guide polynucleotide and said nuclease into said host cell. In some embodiments, said differentiating occurs after said introducing said guide polynucleotide and said nuclease into said host cell. In some embodiments, said insertion site is within a safe harbor site of said genome. In some embodiments, said safe harbor site comprises an AAVs1 site, a Rosa26 site, or a C—C motif receptor 5 (CCR5) site.

In some embodiments, said PAM sequence is selected from the group consisting of: CC, NG, YG, NGG, NAA, NAT, NAG, NAC, NTA, NTT, NTG, NTC, NGA, NGT, NGC, NCA, NCT, NCG, NCC, NRG, TGG, TGA, TCG, TCC, TCT, GGG, GAA, GAC, GTG, GAG, CAG, CAA, CAT, CCA, CCN, CTN, CGT, CGC, TAA, TAC, TAG, TGG, TTG, TCN, CTA, CTG, CTC, TTC, AAA, AAG, AGA, AGC, AAC, AAT, ATA, ATC, ATG, ATT, AWG, AGG, GTG, TTN, YTN, TTTV, TYCV, TATV, NGAN, NGNG, NGAG, NGCG, AAAAW, GCAAA, TGAAA, NGGNG, NGRRT, NGRRN, NNGRRT, NNAAAAN, NNNNGATT, NNAGAAW, NAAAAC, NNAAAAAW, NNAGAA, NAAAAC, NNNNACA, GNNNCNNA, NNNNGATT, NNAGAAW, NNGRR, NNNNNNN and TGGAGAAT. In some embodiments, said nuclease is a CRISPR-associated nuclease. In some embodiments, said CRISPR-associated nuclease is a Cas9 enzyme.

Enriching

In some embodiments, subject methods include (i) a step of enriching the host cell population for the cells that are in a desired phase(s) of the cell cycle, and/or (ii) a step of blocking the host cell at a desired phase in the cell cycle. The cell cycle is the series of events that take place in a cell leading to its division and duplication (replication) that produces two daughter cells. Two major phases of the cell cycle are the S phase (DNA synthesis phase), in which DNA duplication occurs, and the M phase (mitosis), in which the chromosomes segregation and cell division occurs. The eukaryotic cell cycle is traditionally divided into four sequential phases: G1, S, G2, and M. G1, S, and G2 together can collectively be referred to as “interphase”. Under certain conditions, cells can delay progress through G1 and can enter a specialized resting state known as GO (G zero), in which they can remain for days, weeks, or even years before resuming proliferation. The period of transition from one state to another can be referred to using a hyphen, for example, G1/S, G2/M, etc. As is known in the art, various checkpoints exist throughout the cell cycle at which a cell can monitor conditions to determine whether cell cycle progression should occur. For example, the G2/M DNA damage checkpoint serves to prevent cells from entering mitosis (M-phase) with genomic DNA damage.

A step of enriching a population of eukaryotic cells for cells in a desired phase of the cell cycle (e.g., Gl, S, G2, M, Gl/S, G2/M, G0, etc., or any combination thereof), and can be performed using any convenient method (e.g., a cell separation method and/or a cell synchronization method).

In some cases, the method includes a step of enriching a population of the host cells for cells in the GO phase of the cell cycle. For example, in some cases, a subject method includes: (a) enriching a population of eukaryotic cells for cells in the GO phase of the cell cycle; and (b) contacting the GEMS construct and/or the donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide polynucleotide.

In some cases, the method includes a step of enriching a population of host cells for cells in the Gl phase of the cell cycle. For example, in some cases, the method includes: (a) enriching a population of the host cells for cells in the Gl phase of the cell cycle; and (b) contacting the GEMS construct and/or the donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide RNA comprising.

In some cases, the method includes a step of enriching a population of the host cells for cells in the G2 phase of the cell cycle. For example, in some cases, the method includes: (a) enriching a population of the host cells for cells in the G2 phase of the cell cycle; and (b) contacting the GEMS construct and/or donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide RNA.

In some cases, the method includes a step of enriching a population of the host cells for cells in the S phase of the cell cycle. For example, in some cases, the method includes: (a) enriching a population of the host cells for cells in the S phase of the cell cycle; and (b) contacting the GEMS construct and/or donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide RNA.

In some cases, the method includes a step of enriching a population of the host cells for cells in the M phase of the cell cycle. For example, in some cases, the method includes: (a) enriching a population of the host cells for cells in the M phase of the cell cycle; and (b) contacting the GEMS construct and/or donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide RNA.

In some cases, the method includes a step of enriching a population of the host cells for cells in the Gl/S transition of the cell cycle. For example, in some cases, the method includes: (a) enriching a population of the host cells for cells in the Gl/S transition of the cell cycle; and (b) contacting the GEMS construct and/or donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide RNA.

In some cases, the method includes a step of enriching a population of the host cells for cells in the G2/M transition of the cell cycle. For example, in some cases, the method includes: (a) enriching a population of the host cells for cells in the G2/M transition of the cell cycle; and (b) contacting the GEMS construct and/or donor nucleic acid sequences with a Cas9 targeting complex (e.g., via introducing into the host cell(s) at least one component of a Cas9 targeting complex) (e.g., contacting the GEMS construct and/or donor nucleic acid sequences with (i) a Cas9 protein; and (ii) a guide RNA.

By “enrich” is meant increasing the fraction of desired cells in the resulting cell population. For example, in some cases, enriching includes selecting desirable cells (e.g., cells that are in the desired phase of the cell cycle) away from undesirable cells (e.g., cells that are not in the desired phase of the cell cycle), which can result in a smaller population of cells, but a greater fraction (i.e., higher percentage) of the cells of the resulting cell population will be desirable cells (e.g., cells that are in the desired phase of the cell cycle). Cell separation methods can be an example of this type of enrichment. In other cases, enriching includes converting undesirable cells (e.g., cells that are not in the desired phase of the cell cycle) into desirable cells (e.g., cells that are in the desired phase of the cell cycle), which can result in a similar size population of cells as the starting population, but a greater fraction of those cells can be desirable cells (e.g., cells that are in the desired phase of the cell cycle). Cell synchronization methods can be an example of this type of enrichment. In some cases, enrichment can both change the overall size of the resulting cell population (compared to the size of the starting population) and increase the fraction of desirable cells. For example, multiple methods/techniques can be combined (e.g., to improve enrichment, to enrich for cells a more than one desired phase of the cell cycle, etc.).

In some cases, enriching includes a cell separation method. Any convenient cell separation method can be used to enrich for cells that are at various phases of the cell cycle. Suitable cell separation techniques for enrichment of cells at particular phases of the cell cycle include, but are not limited to: (i) mitotic shake-off (M-phase; mechanical separation on the basis of cell adhesion properties, e.g., adherent cells in the mitotic phase detach from the surface upon gentle shaking, tapping, or rinsing); (ii) countercurrent centrifugal elutriation (CCE) (G1, S, G2/M, and intermediate states; physical separation on the basis of cell size and density); and (iii) flow cytometry and cell sorting (e.g., GO, G1, S, G2/M; physical separation based on specific intracellular, e.g., DNA, content) and cell surface and/or size properties).

Mitotic shake-off generally includes dislodgment of low adhesive, mitotic cells by agitation (see for example, Beyrouthy et. al., PLOS ONE 3, e3943 (2008); Schorl, C. & Sedivy, Methods 41, 143-150 (2007)). Countercurrent centrifugal elutriation (CCE) generally includes the separation of cells according to their sedimentation velocity in a gravitational field where the liquid containing the cells is made to flow against the centrifugal force with the sedimentation rate of cells being proportional to their size (see for example, Grosse et. al., Prep Biochem Biotechnol. 2012; 42 (3): 217-33; Banfalvi et. al., Nat. Protoc. 3, 663-673 (2008)). Flow cytometry methods generally include the characterization of cells according to antibody and/or ligand and/or dye-mediated fluorescence and scattered light in a hydrodynamically focused stream of liquid with subsequent electrostatic, mechanical or fluidic switching sorting (see for example, Coquelle et. al., Biochem. Pharmacol. 72, 1396-1404 (2006); Juan et. al., Cytometry 49, 170-175 (2002)). For more information related to cell separation techniques, refer to, for example, Rosner et al., Nat Protoc. 2013 March; 8 (3): 602-26.

In some cases, enriching includes a cell synchronization method (i.e., synchronizing the cells of a cell population). Cell synchronization is a process by which cells at different stages of the cell cycle within a cell population (i.e., a population of cells in which various individual cells are in different phases of the cycle) are brought into the same phase. Any convenient cell synchronization method can be used in the subject methods to enrich for cells that are at a desired phase(s) of the cell cycle. For example, cell synchronization can be achieved by blocking cells at a desired phase in the cell cycle, which allows the other cells to cycle until they reach the blocked phase. For example, suitable methods of cell synchronization include, but are not limited to: (i) inhibition of DNA replication, DNA synthesis, and/or mitotic spindle formation (e.g., sometimes referred to herein as contacting a cell with a cell cycle blocking composition); (ii) mitogen or growth factor withdrawal (GO, G1, GO/G1; growth restriction-induced quiescence via, e.g., serum starvation and/or amino acid starvation); and (iii) density arrest (G1; cell-cell contact-induced activation of specific transcriptional programs) (see for example, Rosner et al., Nat Protoc. 2013 March; 8 (3): 602-26), which is hereby incorporated by reference in its entirety, and see references cited therein).

Various methods for cell synchronization is known to one of ordinary skill in the art and any convenient method can be used. For additional methods for cell synchronization (e.g., synchronization of plant cells), see, for example, Sharma, Methods in Cell Science, 1999, Volume 21, Issue 2-3, pp 73-78 ("Synchronization in plant cells—an introduction"); Dolezel et al., Methods in Cell Science, 1999, Volume 21, Issue 2-3, pp 95-107 ("Cell cycle synchronization in plant root meristems"); Kumagai-Sano et al., Nat Protoc. 2006; 1 (6): 2621-7; and Cools et al., The Plant Journal (2010) 64, 705-714; and Rosner et al., Nat Protoc. 2013 March; 8 (3): 602-26; all of which are hereby incorporated by reference in their entirety.

Checkpoint Inhibitors

In some embodiments, a cell (or cells of a cell population), is blocked at a desired phase of the cell cycle (e.g., by contacting the cell with a cycle blocking composition such as a checkpoint inhibitor). In some embodiments, cells of a cell population are synchronized (e.g., by contacting the cells with a cell cycle blocking composition). A cell cycle blocking composition (e.g., checkpoint inhibitors) can include one or more cell cycle blocking agents. The terms "cell cycle blocking agent" and "checkpoint inhibitor" refer to an agent that blocks (e.g., reversibly blocks (pauses), irreversibly blocks) a cell at a particular point in the cell cycle such that the cell cannot proceed further. Suitable cell cycle blocking agents include reversible cell cycle blocking agents. Reversible cell cycle blocking agents do not render the cell permanently blocked. In other words, when reversible cell cycle blocking agent is removed from the cell medium, the cell is free to proceed through the cell cycle. Cell cycle blocking agents are sometimes referred to in the art as cell synchronization agents because when such agents contact a cell population (e.g., a population having cells that are at different stages of the cell cycle), the cells of the population become blocked at the same phase of the cell cycle, thus synchronizing the population of cells relative to that particular phase of the cell cycle. When the cell cycle blocking agent used is reversible, the cells can then be "released" from cell cycle block.

Suitable cell cycle blocking agents include, but are not limited to: nocodazole (G2, M, G2/M; inhibition of microtubule polymerization), colchicine (G2, M, G2/M; inhibition of microtubule polymerization); demecolcine (colcemid) (G2, M, G2/M; inhibition of microtubule polymerization); hydroxyurea (G1, S, G1/S; inhibition of ribonucleotide reductase); aphidicolin (G1, S, G1/S; inhibition of DNA polymerase-alpha and DNA polymerase-delta); lovastatin (G1; inhibition of HMG-COA reductase/cholesterol synthesis and the proteasome); mimosine (G1, S, G1/S; inhibition of thymidine, nucleotide biosynthesis, inhibition of Ctf4/chromatin binding); thymidine (G1, S, Gl/S; excess thymidine-induced feedback inhibition of DNA replication); latrunculin A (M; delays anaphase onset, actin polymerization inhibitor, disrupts interpolar microtubule stability); and latrunculin B (M; actin polymerization inhibitor).

Suitable cell cycle blocking agents can include any agent that has the same or similar function as the agents above (e.g., an agent that inhibits microtubule polymerization, an agent that inhibits ribonucleotide reductase, an agent that inhibits DNA polymerase-alpha and/or DNA polymerase-delta, an agent that inhibits HMG-COA reductase and/or cholesterol synthesis, an agent that inhibits nucleotide biosynthesis, an agent that inhibits DNA replication, i.e., inhibit DNA synthesis, an agent that inhibits initiation of DNA replication, an agent that inhibits deoxycytosine synthesis, an agent that induces excess thymidine-induced feedback inhibition of DNA replication, and agent that disrupts interpolar microtubule stability, an agent that inhibits actin polymerization, and the like). Suitable agents that block G1 can include: staurosporine, dimethyl sulfoxide (DMSO), glycocorticosteroids, and/or mevalonate synthesis inhibitors. Suitable agents that block G2 phase can include CDK1 inhibitors e.g., RO-3306. Suitable agents that block M can include cytochalasin D.

Non-limiting examples of suitable cell cycle blocking agents include cobtorin; dinitroaniline; benefin (benluralin); butralin; dinitramine; ethalfluralin; oryzalin; pendimethalin; trifluralin; amiprophos-methyl; butamiphos dithiopyr; thiazopyr propyzamider-pronamide-tebutam DCPA (chlorthal-dimethyl); anisomycin; alpha amanitin; jasmonic acid; abscisic acid; menadione; cryptogeine; hydrogen peroxide; sodium permanganate; indomethacin; epoxomycin; lactacystein; icrf 193; olomoucine; roscovitine; bohemine; K252a; okadaic acid; endothal; caffeine; MG132; and cycline dependent kinase inhibitors. For more information regarding cell cycle blocking agents, see Merrill G F, Methods Cell Biol. 1998; 57:229-49, which is hereby incorporated by reference in its entirety.

Donor Nucleic Acid Sequences

The term "donor nucleic acid sequence(s)", "donor gene (s)" or "donor gene(s) of interest" refers to the nucleic acid sequence(s) or gene(s) inserted into the host cell genome at the multiple gene editing site. In an embodiment, the donor nucleic acid sequences encode a chimeric gene of interest (e.g., CAR). In an embodiment, the donor nucleic acid sequences encode a reporter gene. In an embodiment, the donor nucleic acid sequences encode a transgene. In an embodiment, the donor nucleic acid sequences encode dopamine or other neurotransmitter. In an embodiment, the donor nucleic acid sequences encode insulin or a pro-form of insulin, or other hormones.

In some embodiments, once the host cell has the multiple gene editing site integrated, the host cell can be competent to receive donor nucleic acid sequences to be further inserted into the genome at the multiple gene editing site. Donor nucleic acid sequences can be in DNA or RNA form, with DNA being preferred. Donor nucleic acid sequences can be provided on an additional plasmid or other suitable vector that is inserted into the host cell. Transfection, lipofection, or temporary membrane disruption such as electroporation or deformation can be used to insert the vector comprising the donor nucleic acid sequence into the host cell. Viral or non-viral vectors can be used to deliver the donor nucleic acid sequence in some aspects. The vector or plasmid comprising a donor nucleic acid sequence can comprises endonuclease recognition sequences upstream and downstream of the donor nucleic acid sequence, such that the vector can be cleaved by the same endonuclease that cleaves the multiple gene editing site.

The donor nucleic acid sequences can be exogenous genes, or portions thereof, including engineered genes. The donor nucleic acid sequences can encode any protein or portion thereof that the user desires that the host cell express. The donor nucleic acid sequences (including genes) can further comprise a reporter gene, which can be used to confirm expression. The expression product of the reporter gene can be substantially inert such that its expression along with the donor gene of interest does not interfere with the intended activity of the donor gene expression product, or otherwise interfere with other natural processes in the cell, or otherwise cause deleterious effects in the cell.

The donor nucleic acid sequence can also comprise regulatory elements that permit controlled expression of the donor gene. For example, the donor nucleic acid sequence can comprise a repressor operon or inducible operon. The expression of the donor nucleic acid sequence can thus be under regulatory control such that the gene is only expressed under controlled conditions. In some aspects, the donor nucleic acid sequence includes no regulatory elements, such that the donor gene is effectively constitutively expressed.

In some embodiments, the donor nucleic acid sequence encoding is the green fluorescent protein (GFP) (SEQ ID NO: 12) under a tetracycline (Tet)-inducible promoter (FIGS. 7-8). In an embodiment, a reporter gene (e.g., GFP) and a regulatory element inserted into the multiple gene editing site. Upon integration of e.g., the GFP and Tet-regulatory elements into the multiple gene editing site in the cell, exposure of the cell to e.g., tetracycline can induce the expression of e.g., GFP such that the expression can be confirmed and measured (FIGS. 7-8).

The number of donor nucleic acid sequences that can be inserted into the multiple gene editing site can vary. The number of potential donor nucleic acid sequences can be limited, for example, by the number of secondary endonuclease recognition sites in the multiple gene editing site and/or the number of donor nucleic acid sequences whose expression the cell is capable of tolerating.

The size of any given donor nucleic acid sequences that can be inserted into the multiple gene editing site can vary. The size can be limited by the number of donor nucleic acid sequences being inserted into the multiple gene editing site and/or the number or size of the donor nucleic acid sequences the cell is capable of tolerating.

Figure 9:
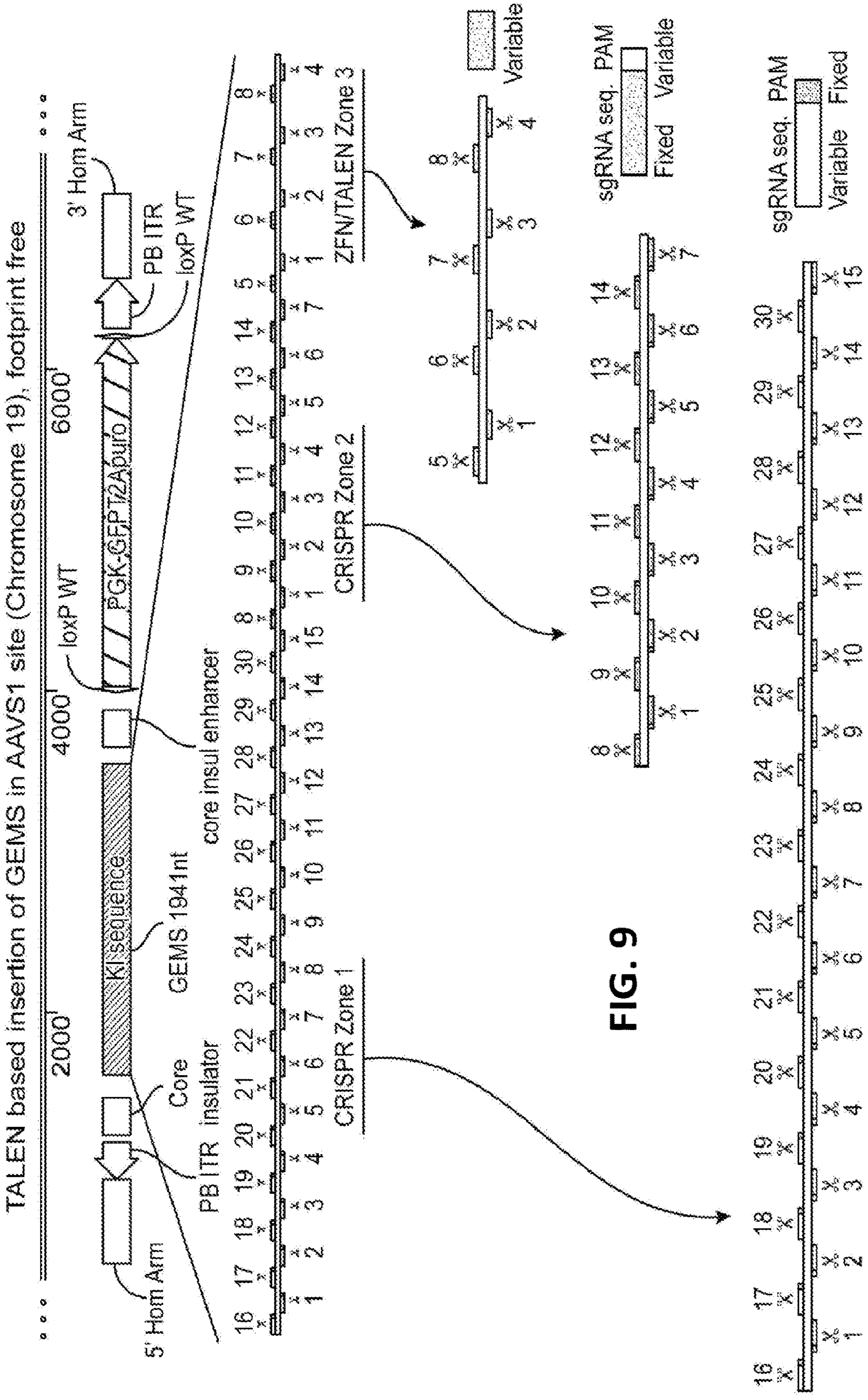
FIG. 9 shows an example of a GEMS design in this embodiment the GEMS contains 3 zones each allowing for gene editing using different methods. Zone 1, CRISPR edits using variable crRNA sequences in combination with a fixed PAM. Zone 2, CRISPR edits using variable PAMs combined with fixed crRNA sequences. Zone 3, ZNF/TALEN editing zone.

In some embodiments, the donor nucleic acid sequence can be inserted into any one of the secondary endonuclease recognition sites in the multiple gene editing site. Insertion can be facilitated by the particular secondary endonuclease, which cleaves the secondary endonuclease recognition site in the multiple gene editing site and also cleaves the secondary endonuclease recognition site in the vector. The latter cleavage frees the donor nucleic acid sequence for insertion into the cleaved multiple gene editing site. Insertion of the donor nucleic acid sequence can proceed via homologous or NHEJ in the cell. Thus, the secondary endonuclease recognition sequences can be tailored to nucleases that produce compatible ends at the site of the double stranded breaks in the vector DNA and in the multiple gene editing site. Multiple donor nucleic acid sequences can be sequentially inserted into the multiple gene editing site (FIG. 9).

The secondary endonuclease can be a ZFN, TALEN, or CRISPR associated nuclease such as Cas9 nuclease. In some aspects, the secondary endonuclease can be a CRISPR associated nuclease such that a CRISPR associated nuclease is used to insert each donor nucleic acid into the multiple gene editing sites. Cleavage of the multiple gene editing site via a CRISPR associated nuclease such as Cas9 nuclease occurs by way of a guide RNA (gRNA) or a guide polynucleotide that is specific to the target sequence and PAM sequence combination of a given secondary endonuclease recognition site in the multiple gene editing site. The gRNA or the guide polynucleotide comprises a protospacer element that is complementary to the target sequence, and a CRISPR RNA (crRNA) and a transactivation crRNA (tracrRNA) chimera. The gRNA or the guide polynucleotide recruits the Cas9 nuclease to form a complex, which complex recognizes the target sequence and PAM sequence at the multiple gene editing site, and thereafter, the nuclease cleaves the multiple gene editing site.

Figure 10A:
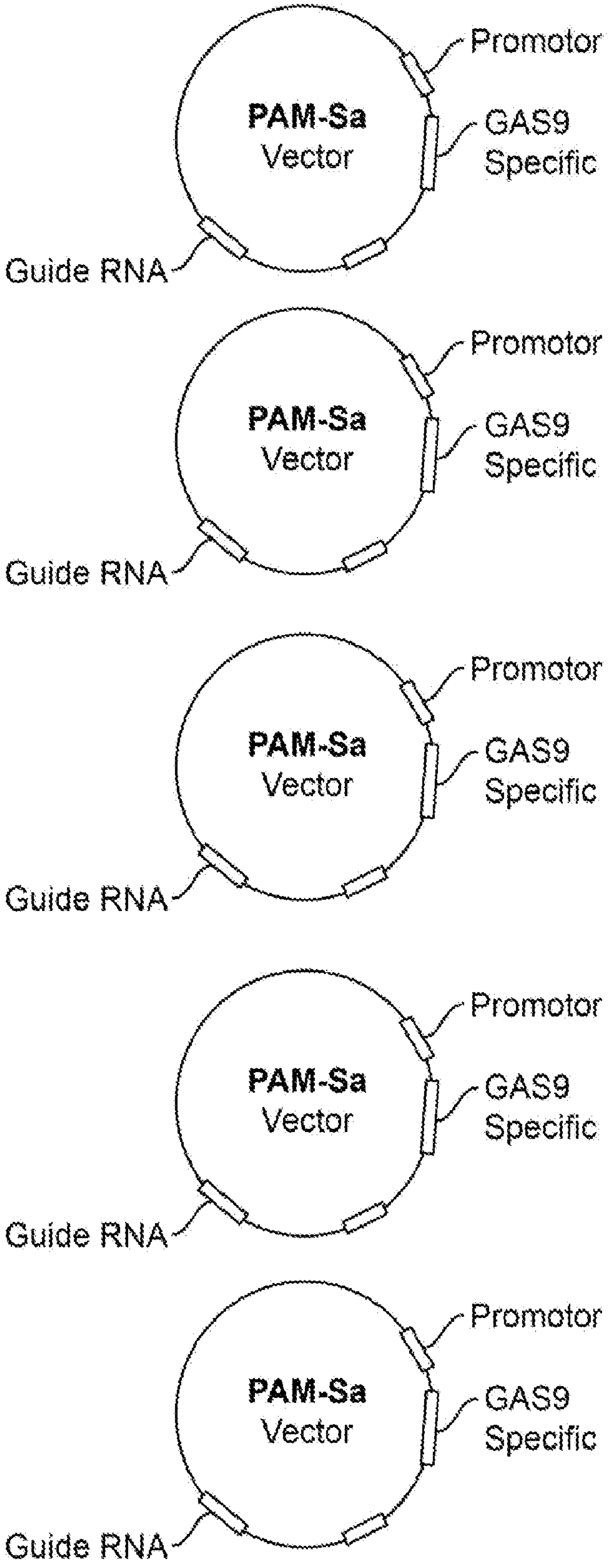
FIG. 10A shows five exemplary editing vectors, each allowing to edit a specific site on the GEMS.
Figure 10B:
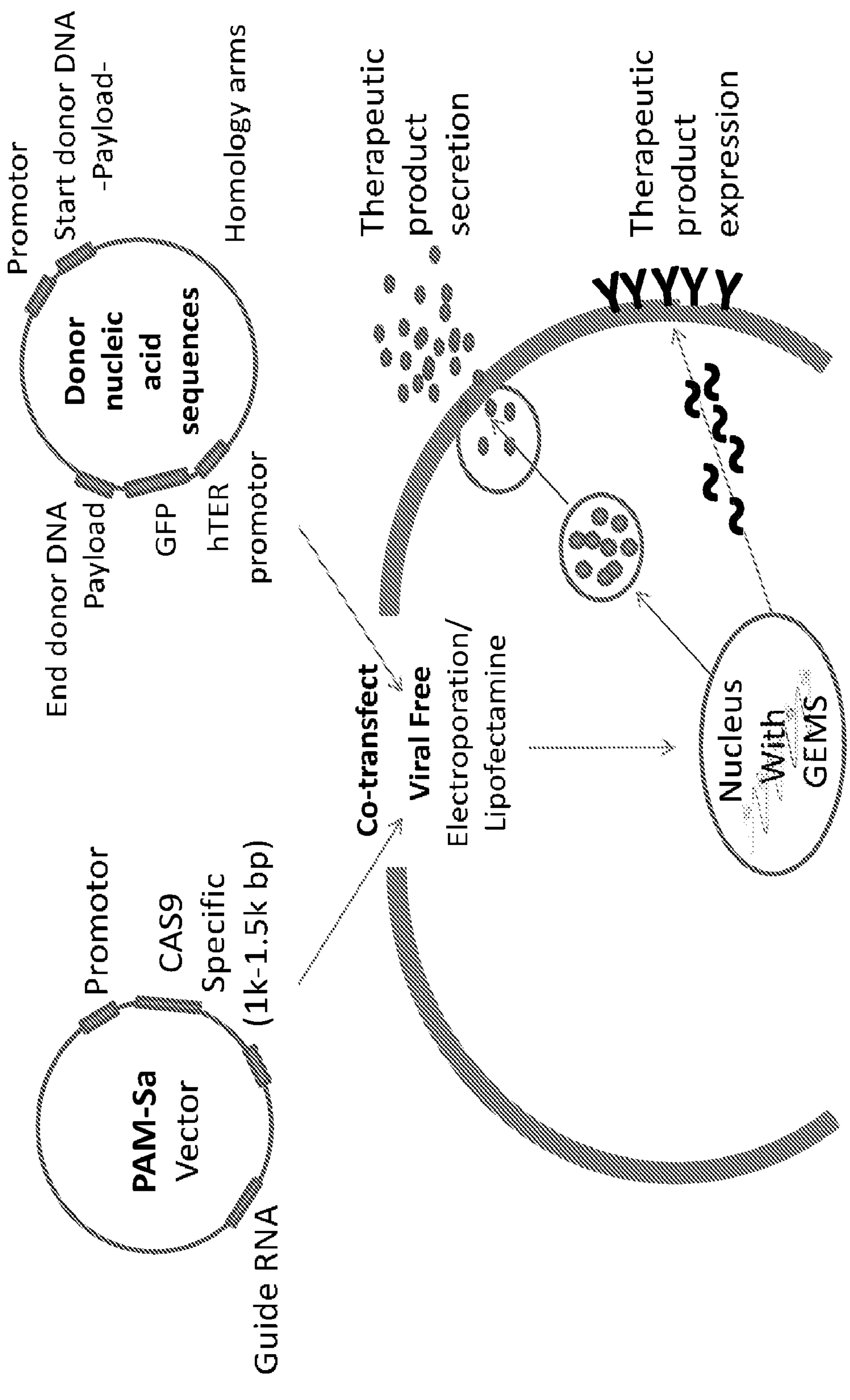
FIG. 10B is a schematic illustration of how the GEMS can be edited to express or secrete a therapeutic protein. In this embodiment, the guide RNA and Cas9 are delivered in a separate vector from the donor nucleic acid sequences.
Figure 11:
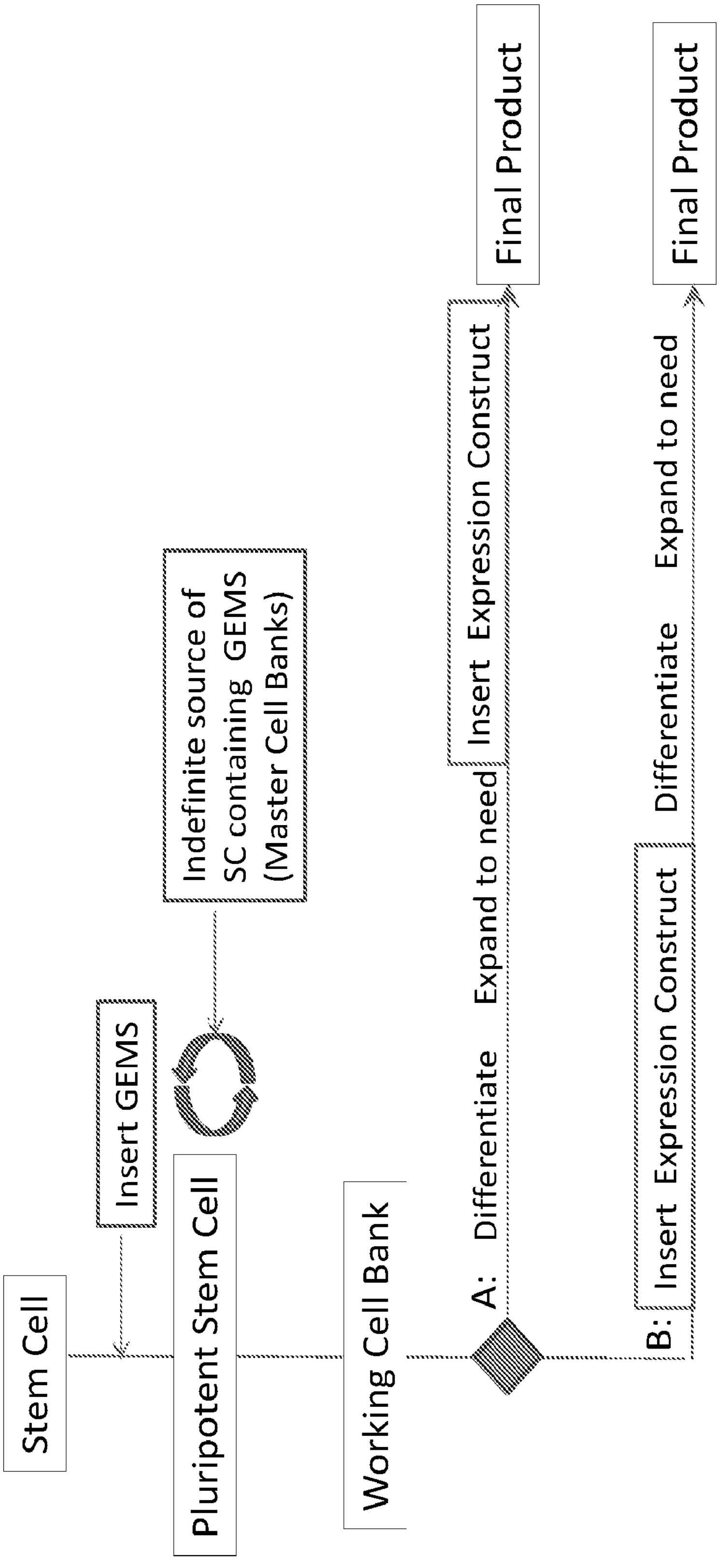
FIG. 11 shows potential uses of the construct in stem cells, in which the GEMS construct can be introduced into the stem cell before or after differentiation.

Following insertion of the donor nucleic acid sequence, the host cell can be further manipulated in order to express the protein encoded by the donor nucleic acid sequence, for example, cultured in the presence of inducers or repressors (FIGS. 10A and 10B). The host cell can also be cultured and propagated. In aspects where the host cell is a stem cell, the cell can be differentiated following insertion of the donor nucleic acid sequences (FIG. 11). The differentiated stem cell can be cultured and propagated.

Chimeric Antigen Receptor (CAR)

In an embodiment, the donor nucleic acid sequence is a chimeric antigen receptor (CAR). A CAR is an engineered receptor or an engineered receptor construct which grafts an exogenous specificity onto an immune effector cell. In some instances, a CAR comprises an extracellular domain (ectodomain) that comprises a target-specific binding element otherwise referred to as an antigen binding moiety or an antigen binding domain, a stalk region, a transmembrane domain and an intracellular (endodomain) domain. In some embodiments, CAR does not actually recognize the entire antigen; instead it binds to only a portion of the antigen's surface, an area called the antigenic determinant or epitope. In some instances, the intracellular domain further comprises one or more intracellular signaling domains or cytoplasmic signaling domains. In some instances, the intracellular domain further comprises a zeta chain portion. In some instances, a CAR as described herein further comprises one or more costimulatory domains and a signaling domain for T-cell activation.

In some embodiments, a CAR described herein comprises a target-specific binding element otherwise referred to as an antigen-binding moiety, an antigen binding domain or a predetermined cell surface protein. In embodiments, a CAR described herein engineered to target a tumor antigen of interest by way of engineering a desired antigen-binding moiety that specifically binds to an antigen on a tumor cell. In the context of the present disclosure, "tumor antigen" or "hyperproliferative disorder antigen" or "antigen associated with a hyperproliferative disorder," refers to antigens that are common to specific hyperproliferative disorders such as cancer.

In some embodiments, the antigen binding moiety of a CAR described herein is specific to or binds CD19. In embodiments, the antigen binding domain comprises a single chain antibody fragment (scFv) comprising a variable domain light chain (VL) and variable domain heavy chain (VH) of a target antigen specific monoclonal antibody. In embodiments, the scFv is humanized. In some embodiments, the antigen binding moiety can comprise VH and VL that are directionally linked, for example, from N to C terminus, VH-linker-VL or VL-linker-VH. In some instances, the antigen binding domain recognizes an epitope of the target. In some embodiments, described herein include a CAR or a CAR-T cell, in which the antigen binding domain comprises a F(ab')2, Fab', Fab, Fv, or scFv.

In some embodiments, CD19 scFv is encoded by a nucleotide sequence comprising SEQ ID NO: 20. In some embodiments, CD19 scFv is encoded by a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 20. In some embodiments, the CD19 CAR comprise a nucleotide sequence of SEQ ID NO: 20. In some embodiments, the CD19 CAR comprise a nucleotide sequence of SEQ ID NO: 21. In some embodiments, the CD19 CAR comprise a nucleotide sequence of SEQ ID NO: 22. In some embodiments, the CD19 CAR comprise a nucleotide sequence of SEQ ID NO: 23. In some embodiments, the CD19 CAR comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 20. In some embodiments, the CD19 CAR comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 21. In some embodiments, the CD19 CAR comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 22. In some embodiments, the CD19 CAR comprises a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 23.

In embodiments described herein, a CAR can comprise an extracellular antibody-derived single-chain variable domain (scFv) for target recognition, wherein the scFv can be connected by a flexible linker to a transmembrane domain and/or an intracellular signaling domain(s) that includes, for instance, CD3-ζ for T-cell activation. Normally when T cells are activated in vivo, they receive a primary antigen induced TCR signal with secondary costimulatory signaling from CD28 that induces the production of cytokines (e.g., IL-2 and IL-21), which then feed back into the signaling loop in an autocrine/paracrine fashion. With this in mind, a CAR can include a signaling domain, for instance, a CD28 cytoplasmic signaling domain or other costimulatory molecule signaling domains such as 4-1BB signaling domain. Chimeric CD28 co-stimulation improves T-cell persistence by up-regulation of anti-apoptotic molecules and production of IL-2, as well as expanding T cells derived from peripheral blood mononuclear cells (PBMC). In one embodiment, CARs are fusions of single-chain variable fragments (scFv) derived from monoclonal antibodies specific for hepatitis B virus antigen. In another embodiment, CARs are fused to transmembrane domain and CD3-ζ endodomain. Such molecules result in the transmission of a zeta signal in response to recognition by the scFv of its target.

In one embodiment of the CAR ectodomain, a signal peptide directs the nascent protein into the endoplasmic reticulum, for instance, if the receptor is to be glycosylated and anchored in the cell membrane. Any eukaryotic signal peptide sequence is envisaged to be functional. Generally, the signal peptide natively attached to the amino-terminal most component is used (e.g., in a scFv with orientation light chain-linker-heavy chain, the native signal of the light-chain is used). In embodiments, the signal peptide is GM-CSFRa or IgK. Other signal peptides that can be used include signal peptides from CD8a and CD28.

The antigen recognition domain can be a scFv. There can however be alternatives. An antigen recognition domain from native T-cell receptor (TCR) alpha and beta single chains are envisaged, as they have simple ectodomains (e.g., CD4 ectodomain to recognize HIV infected cells) and as well as other recognition components such as a linked e.g., cytokine (which leads to recognition of cells bearing the cytokine receptor). Almost anything that binds a given target, such as e.g., tumor associated antigen, with high affinity can be used as an antigen recognition region.

The transmembrane domain can be derived from either a natural or a synthetic source. Where the source is natural, the domain can be derived from any membrane-bound or transmembrane protein. Suitable transmembrane domains can include, but not limited to, the transmembrane region(s) of alpha, beta or zeta chain of the T-cell receptor; or a transmembrane region from CD28, CD3 epsilon, CD3-3, CD45, CD4, CD5, CD8alpha, CD9, CD16, CD22, CD33, CD37, CD64, CD80, CD86, CD134, CD137 or CD154. Alternatively the transmembrane domain can be synthetic and can comprise hydrophobic residues such as leucine and valine. In some embodiments, a triplet of phenylalanine, tryptophan and valine is found at one or both termini of a synthetic transmembrane domain. In some embodiments, the transmembrane domain comprises a CD8a transmembrane domain or a CD3-(transmembrane domain. In some embodiments, the transmembrane domain comprises a CD8a transmembrane domain. In other embodiments, the transmembrane domain comprises a CD3-ζ transmembrane domain. In some embodiments, CD8 hinge and transmembrane domain is encoded by a nucleotide sequence comprising SEQ ID NO: 21. In some embodiments, CD8 hinge and transmembrane domain is encoded by a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 21.

The intracellular signaling domain, also known as cytoplasmic domain, of the CAR of the present disclosure, is responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal. In some embodiments, the intracellular domain further comprises a signaling domain for T-cell activation. In some instances, the signaling domain for T-cell activation comprises a domain derived from TCRζ, FcRγ, FcRβ, CD3γ, CD3δ, CD3ε, CD5, CD22, CD79α, CD79β or CD66δ. In some cases, the signaling domain for T-cell activation comprises a domain derived from CD3-ζ. In some cases, the intracellular domain can comprise one or more costimulatory domains.

The cytoplasmic domain, also known as the intracellular signaling domain of a CAR described herein, is responsible for activation of at least one of the normal effector functions of the immune cell in which the CAR has been placed. The term "effector function" refers to a specialized function of a cell. Effector function of a T cell, for example, can be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in a CAR described herein can include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Signals generated through the TCR alone are generally insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner can contain signaling motifs which are known as immunoreceptor tyrosine-based activation motifs or ITAMs. Examples of ITAM-containing primary cytoplasmic signaling sequences that are of particular use in the present disclosure include, but not limited to, those derived from TCR zeta, FcR gamma, FcR beta, CD3 gamma, CD3 delta, CD3 epsilon, CD5, CD22, CD79a, CD79b, and CD66d. In embodiments, the cytoplasmic signaling molecule in a CAR described herein comprises a cytoplasmic signaling sequence derived from CD3 zeta.

In embodiments, the cytoplasmic domain of the CAR can be designed to comprise the CD3-¿ signaling domain by itself or combined with any other desired cytoplasmic domain(s) useful in the context of a CAR described herein. For example, the cytoplasmic domain of the CAR can comprise a CD3 chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. In embodiments, costimulatory molecules can be used together, e.g., CD28 and 4-1BB or CD28 and OX40. Thus, while the present disclosure in exemplified primarily with 4-1BBζ and CD8α as the co-stimulatory signaling element, other costimulatory elements are within the scope of the present disclosure. In some embodiments, 4-1BB endodomain is encoded by a nucleotide sequence comprising SEQ ID NO: 22. In some embodiments, 4-1BB endodomain is encoded by a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 22.

The cytoplasmic signaling sequences within the cytoplasmic signaling portion of a CAR described herein can be linked to each other in a random or specified order. In one embodiment, the cytoplasmic domain comprises the signaling domain of CD3-zeta and the signaling domain of CD28. In another embodiment, the cytoplasmic domain comprises the signaling domain of CD3-zeta and the signaling domain of 4-1BB. In yet another embodiment, the cytoplasmic domain is comprises the signaling domain of CD3-zeta and the signaling domains of CD28 and 4-1BB. In some embodiments, CD3 zeta domain is encoded by a nucleotide sequence comprising SEQ ID NO: 23. In some embodiments, 4CD3 zeta domain is encoded by a nucleotide sequence having at least 50%, 55%, 60%, 65%, 70%, 75%, 80%, 85%, 90%, 91%, 92%, 93%, 94%, 95%, 96%, 97%, 98%, 99%, 99.5% or 100% identity with the nucleotide sequence of SEQ ID NO: 23.

The costimulatory signaling region refers to a portion of the CAR comprising the intracellular signaling domain of a costimulatory molecule. Costimulatory molecules are cell surface molecules other than antigens receptors or their ligands that are required for an efficient response of lymphocytes to antigen. Exemplary costimulatory domains include, but are not limited to, CD8, CD27, CD28, 4-1BB (CD137), ICOS, DAP10, DAP12, OX40 (CD134), CD3-zeta or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), DAP10, DAP12 or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof. In some instances, a CAR described herein comprises at least one costimulatory domain DAP10 or a fragment thereof. In some instances, a CAR described herein comprises at least one costimulatory domain DAP12 or a fragment thereof.

In general, CARs exist in a dimerized form and are expressed as a fusion protein that links the extracellular scFv (VH linked to VL) region, a transmembrane domain, and intracellular signaling motifs. The endodomain of the first generation CAR induces T cell activation solely through CD3-ζ signaling. The second generation CAR provides activation signaling through CD3-ζ and CD28, or other endodomains such as 4-1BB or OX40. The 3rd generation CAR activates T cells via a CD3-ζ-containing combination of three signaling motifs such as CD28, 4-1BB, or OX40.

In embodiments, provided herein is an isolated nucleic acid encoding a chimeric antigen receptor (CAR), wherein the CAR comprises (a) a CD binding domain; (b) a transmembrane domain; (c) a costimulatory signaling domain comprising 4-1BB ζ or CD28, or both; and (d) a CD3 zeta signaling domain.

In embodiments, the CAR comprises a transmembrane domain that is fused to the extracellular domain of the CAR. In one embodiment, the transmembrane domain that naturally is associated with one of the domains in the CAR is used. In embodiments, the transmembrane domain is a hydrophobic alpha helix that spans the membrane.

The transmembrane domain can be derived from either a natural or a synthetic source. Where the source is natural, the domain can be derived from any membrane-bound or transmembrane protein. In some instances, a CAR comprises a transmembrane domain selected from a CD8a transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ. Transmembrane regions of particular use in this disclosure can be derived from (e.g., comprise at least the transmembrane region(s) of) the alpha, beta or zeta chain of the T-cell receptor, CD28, CD3 epsilon, CD45, CD4, CD5, CD8alpha, CD9, CD16, CD22, CD33, CD37, CD64, CD80, CD86, CD134, CD137 or CD154. Alternatively the transmembrane domain can be synthetic, in which case it will comprise predominantly hydrophobic residues such as leucine and valine. In embodiments, a triplet of phenylalanine, tryptophan and valine will be found at each end of a synthetic transmembrane domain.

Included in the scope of the present disclosure are nucleic acid sequences that encode functional portions of the CAR described herein. Functional portions encompass, for example, those parts of a CAR that retain the ability to recognize target cells, or detect, treat, or prevent a disease, to a similar extent, the same extent, or to a higher extent, as the parent CAR.

In embodiments, the CAR described herein contains additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity of the CAR, as compared to the biological activity of the parent CAR.

In some embodiments, a CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized, or conjugated.

Delivery System

The present disclosure also provides delivery systems, such as viral-based systems, in which a nucleic acid described herein is inserted. Representative viral expression vectors include, but are not limited to, adeno-associated viral vectors, adenovirus-based vectors (e.g., the adenovirus-based Per.C6 system available from Crucell, Inc. (Leiden, The Netherlands)), lentivirus-based vectors (e.g., the lentiviral-based pLPI from Life Technologies (Carlsbad, Calif.)), retroviral vectors (e.g., the pFB-ERV plus pCFB-EGSH), and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers.

Certain aspects disclosed herein can utilize vectors. Any plasmids and vectors can be used as long as they are replicable and viable in a selected host. Vectors known in the art and those commercially available (and variants or derivatives thereof) can be engineered to include one or more recombination sites for use in the methods. Vectors that can be used include, but not limited to, bacterial expression vectors (such as pBs, pQE-9 (Qiagen), phagescript, PsiX174, pBluescript SK, pB5KS, pNH8a, pNH16a, pNH18a, pNH46a (Stratagene), pTrc99A, pKK223-3, pKK233-3, pDR540, pRIT5 (Pharmacia), and variants or derivatives thereof), eukaryotic expression vectors (such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, pYACneo (Clontech), pSVK3, pSVL, pMSG, pCH110, pKK232-8 (Pharmacia, Inc.), p3'SS, pXT1, pSG5, pPbac, pMbac, pMClneo, pOG44 (Stratagene, Inc.), pYES2, pAC360, pBlueBa-cHis A, B, and C, pVL1392, pBlueBac111, pCDM8, pcDNA1, pZeoSV, pcDNA3, pREP4, pCEP4, pEBVHis (Invitrogen, Corp.), pWLneo, pSv2cat, pOG44, pXT1, pSG (Stratagene) pSVK3, pBPv, pMSG, pSVL (Pharmiacia), and variants or derivatives thereof), and any other plasmids and vectors replicable and viable in the host cell.

Vectors known in the art and those commercially available (and variants or derivatives thereof) can in accordance with the present disclosure be engineered to include one or more recombination sites for use in the methods of the present disclosure. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, Research Genetics, and Transposagen Pharmaceutical. Other vectors include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET9, pKK223-3, pKK233-3, pDR540, pRIT5 (Pharmacia), pSPORT1, pSPORT2, pCMVSPORT2.0 and pSY-SPORT1 (Invitrogen) and variants or derivatives thereof. Viral vectors can also be used, such as lentiviral vectors (see, for example, WO 03/059923; Tiscornia et al. PNAS 100:1844-1848 (2003)).

Additional vectors of interest include pTrxFus, pThioHis, pLEX, pTrcHis, pTrcHis2, pRSET, pBlueBacHis2, pcDNA3. 1/His, pcDNA3.1 (−)/Myc-His, pSecTag, pEBVHi5, pPIC9K, pPIC3.5K, pAO81S, pPICZ, pPICZA, pPICZB, pPICZC, pGAPZA, pGAPZB, pGAPZC, pBlueBac4.5, pBlueBacHis2, pMelBac, pSinReps, pSinHis, pllD, pND (SP 1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA 1.1/Amp, pcDNA3. 1, pcDNA3. 1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen;. lamda., ExCell,.lamda., gt11, pTrc99A, pKK223-3, pGEX-1 λ T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET32LIC, pET-30LIC, pBAC-2cp LIC, pBACgus-2cp LIC, pT7Blue-2 LIC, pT7Blue-2, lamda SCREEN-1, lamda BlueSTAR, pET-3abcd, pET-7abc, pET9abcd, pET1 labcd, pET12abc, pET-14b, pET-15b, pET-16b, pET-17b-pET-17xb, pET-19b, pET-20b(+), pET-21abcd(+), pET-22b (+), pET-23abcd(+), pET-24abcd(+), pET-25b(+), pET26b (+), pET-27b(+), pET-28abc(+), pET-29abc(+), pET-30abc (+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta VectaHyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2Basic, pSEAP2-Contral, pSEAP2-Promoter, pSEAP2-Enhancer, pßgal-Basic, pß-gal-Control, pBgal-Promoter, pßgal-Enhancer, pCMV, pTet-Off, pTet-On, pTK-Hyg, pRetro-Off, pRetro-On, pIRESIneo, pIRESihyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW3 1, BacPAK6, pTriplEx, λgt10, λgt11, pWE15, and λTriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/1-, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMClneo, pMClneo Poly A, pOG44, pOG45, pFRTBGAL, pNEOBGAL, pRS403, pRS404, pRS405, pRS406, pRS413, pRS414, pRS415, and pRS416 from Stratagene. Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

These vectors can be used to express a gene, e.g., a transgene, or portion of a gene of interest. A gene of portion or a gene can be inserted by using known methods, such as restriction enzyme-based techniques.

Additional suitable vectors include integrating expression vectors, which can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNATM5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

In some embodiments, the vectors comprise a hEF1al promoter to drive expression of transgenes, a bovine growth hormone poly A sequence to enhance transcription, a woodchuck hepatitis virus posttranscriptional regulatory element (WPRE), as well as LTR sequences derived from the pFUGW plasmid.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about-20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., Glycobiology 5:505-10 (1991)). However, compositions that have different structures in solution than the normal vesicular structure are also encompassed. For example, the lipids can assume a micellar structure or merely exist as non-uniform aggregates of lipid molecules. Also contemplated are lipofectamine-nucleic acid complexes.

Therapeutic Compositions

Figure 12:
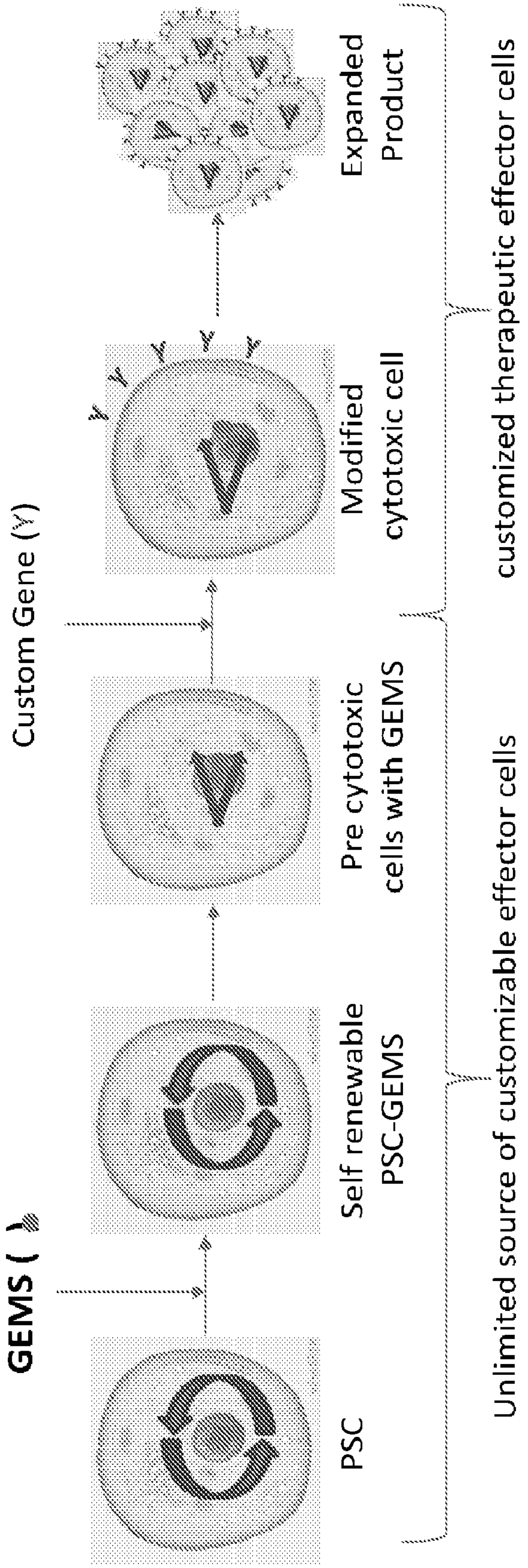
FIG. 12 shows a representation of the use of the GEMS construct to alter a cell phenotype in a desired manner. As shown, a gene “Y” is inserted into a cell being differentiated into a cytotoxic lineage, with the differentiated cell expressing the encoded protein and being clonally expanded.
Figure 13:
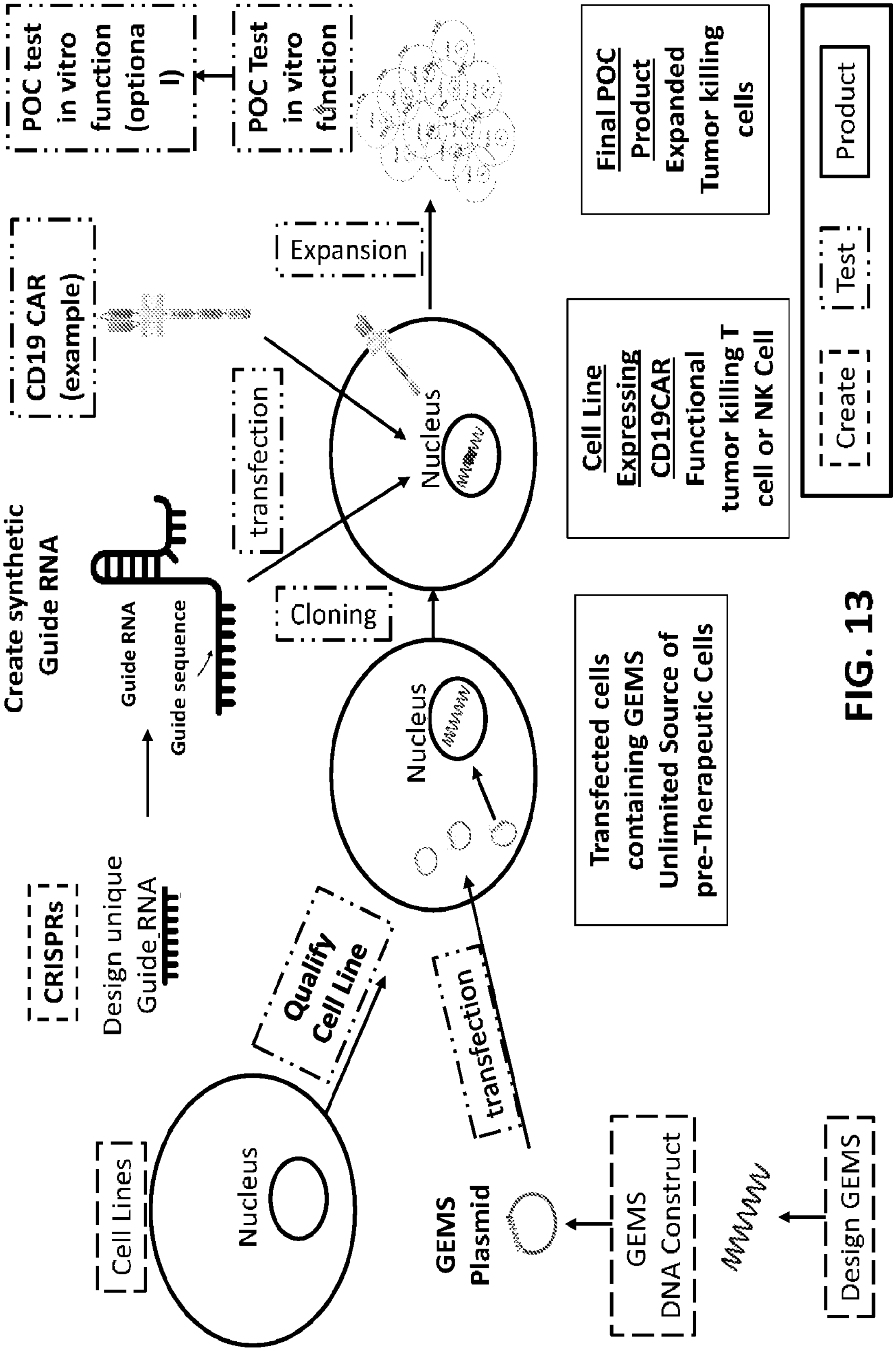
FIG. 13 is a schematic illustration of an exemplary process of developing gene edited cells expressing the donor DNA using GEMS modified cells.

In some aspects, the donor nucleic acid sequence encodes a therapeutic protein such as an antibody, a cytokine, a neurotransmitter, or a hormone. Thus, for example, when the host cell expresses the therapeutic protein, the host cell can serve as a therapeutic effector cell, or can have enhanced immunotherapeutic potential (FIGS. 10B and 11-13). In an embodiment, a pluripotent stem cell comprising the construct receives a donor nucleic acid sequence encoding a cytotoxic protein (Y), and is differentiated to a cytotoxic cell lineage and expanded, then expresses the cytotoxic protein (FIG. 12). In an embodiment, the host cells comprising the construct can be used in therapeutic modalities, and can be engineered according to donor nucleic acid sequences inserted into the multiple gene editing site of the construct.

In some aspects, the cell can secrete the protein encoded by the donor nucleic acid. Thus, the cell can have further use as an expression host cell, whereby the protein is secreted in the cell culture medium, and later harvested and purified.

The cells comprising a multiple gene editing site can be used to study the effects of the protein encoded by the donor gene on the cell, including the effects on signal pathway, or the capacity to differentiate and still express the donor gene protein. Clinically, the cells can be used to express therapeutic proteins or provide therapeutic support to immune cells.

In some aspects, one or more donor sequences can be removed from the multiple gene editing site. For example, where a donor sequence is positioned between secondary endonuclease recognition sites, such sites can be utilized to cleave the multiple gene editing site.

In some aspects, the multiple gene editing site itself can be removed. Removal of the multiple gene editing site can also remove any donor nucleic acid sequences inserted therein. A primary endonuclease recognition site can utilized to cleave the outer regions of the multiple gene editing site to facilitate its removal from the genome, including removal from the safe harbor site (e.g., Rosa26, AAVS1, CCR5). In some embodiments, AAVs1 3' homology arm sequence comprises a nucleotide sequence of SEQ ID NO: 8. In some embodiments, AAVs1 CRISPR targeting sequence comprises a nucleotide sequence of SEQ ID NO: 10. In some embodiments, AAVs1 CRISPR gRNA sequence comprises a nucleotide sequence of SEQ ID NO: 10.

In some embodiments, following insertion of the multiple gene editing site into a host cell, the host cell can be differentiated into neural lineage. The host cell can be a primary isolate stem cell, or stem cell line. The differentiation can occur prior to or following insertion of donor nucleic acid sequences into the multiple gene editing site in the stem cell host.

In some embodiments, the donor nucleic acid sequence can encode a chimeric antigen receptor. Following insertion of the multiple gene editing site into a host cell, the host cell can be differentiated into a cytotoxic T cell lineage or natural killer (NK) cell lineage. The host cell can be a primary isolate stem cell, or stem cell line. The differentiation can occur prior to or following insertion of donor nucleic acid sequences into the multiple gene editing site in the stem cell host. The donor nucleic acid sequences can encode one or more tumor targeting chimeric antigen receptors (CARs). The differentiated cells expressing the CARs can then be administered to cancer patients whose tumor cells express the CAR target. Without intending to be limited to any particular theory or mechanism of action, it is believed that the interaction of the CARs-expressing cytotoxic cells with tumor cells expressing CAR targets can facilitate killing of the tumor cells. The stem cells can be first isolated from the cancer patient, then returned to the patient following modification, differentiation, and expansion. The stem cells can be first isolated from a healthy donor, then administered to a cancer patient following modification, differentiation, and expansion. The cells can be directed to any tumor based on the CAR target, with the donor sequence tailored to the particular CARs expressed by the tumor.

In some embodiments, the donor nucleic acid sequence can encode dopamine or other neurotransmitter. The donor nucleic acid sequence encoding dopamine or other neurotransmitter can be under a regulatory control element, that modulates the level of dopamine or neurotransmitter expression according to the intake of a small molecule that affects the regulatory control element, for example, tetracycline to the tetracycline operon. The differentiated cells expressing dopamine can then be administered to a patient having a condition mediated by a dysregulation of dopamine expression, such as Parkinson's disease. Without intending to be limited to any particular theory or mechanism of action, it is believed that the expression of dopamine can mitigate the dysregulation of dopamine expression or other deficiency of dopamine, thereby treating the condition. The stem cells can be first isolated from the patient (e.g., Parkinson's Disease patient), then returned to the patient following modification, differentiation, and expansion. The stem cells can be first isolated from a healthy donor, then administered to the patient (e.g., Parkinson's Disease patient) following modification, differentiation, and expansion.

In some embodiments, the donor nucleic acid sequence can encode insulin or a pro-form of insulin, or other hormones. The differentiated cells expressing insulin or the pro-form thereof can then be administered to a patient having diabetes (Type 1 or Type 2), or other condition mediated by insulin dysregulation. Without intending to be limited to any particular theory or mechanism of action, it is believed that the expression of insulin can treat diabetes or other deficiency of insulin, thereby treating the condition. The stem cells can be first isolated from the patient (e.g., diabetes patient), then returned to the patient following modification, differentiation, and expansion. The stem cells can be first isolated from a healthy donor, then administered to the patient (e.g., diabetes patient) following modification, differentiation, and expansion.

The disclosure is not limited to the embodiments described and exemplified above, but is capable of variation and modification within the scope of the appended claims.

EXAMPLES

These examples are provided for illustrative purposes only and not to limit the scope of the claims provided herein.

Example 1. Engineering GEMS Sequence into the AAVs1 Site of HEK293T Cells

The GEMS donor plasmid (aavs1_cmvGFPpuro) was constructed in which the GEMS sequence (SEQ ID NO: 2) and a selection cassette are flanked by ~500 bp AAVS1 sequences surrounding the cutting site as the 5' and 3' homology arms to facilitate homology recombination. The selection cassette was composed of puromycin selection marker and GFP coding sequence, driven by CMV promoter. The selection cassette was flanked by loxP site sequences to facilitate the excision of the cassette by cre-loxP system if needed.

Two different transfection conditions were attempted to transfect the GEMS donor plasmid aavs1_cmvGFPpuro, a AAVS1 CRISPR/Cas9 single shot plasmid expressing Cas9 and AAVS1 targeting site sgRNA, and Cas9 mRNA into HEK293T cells by electroporation using the 4D-Nucleofector™ System from Lonza, and two control transfections were performed.

Figure 15:
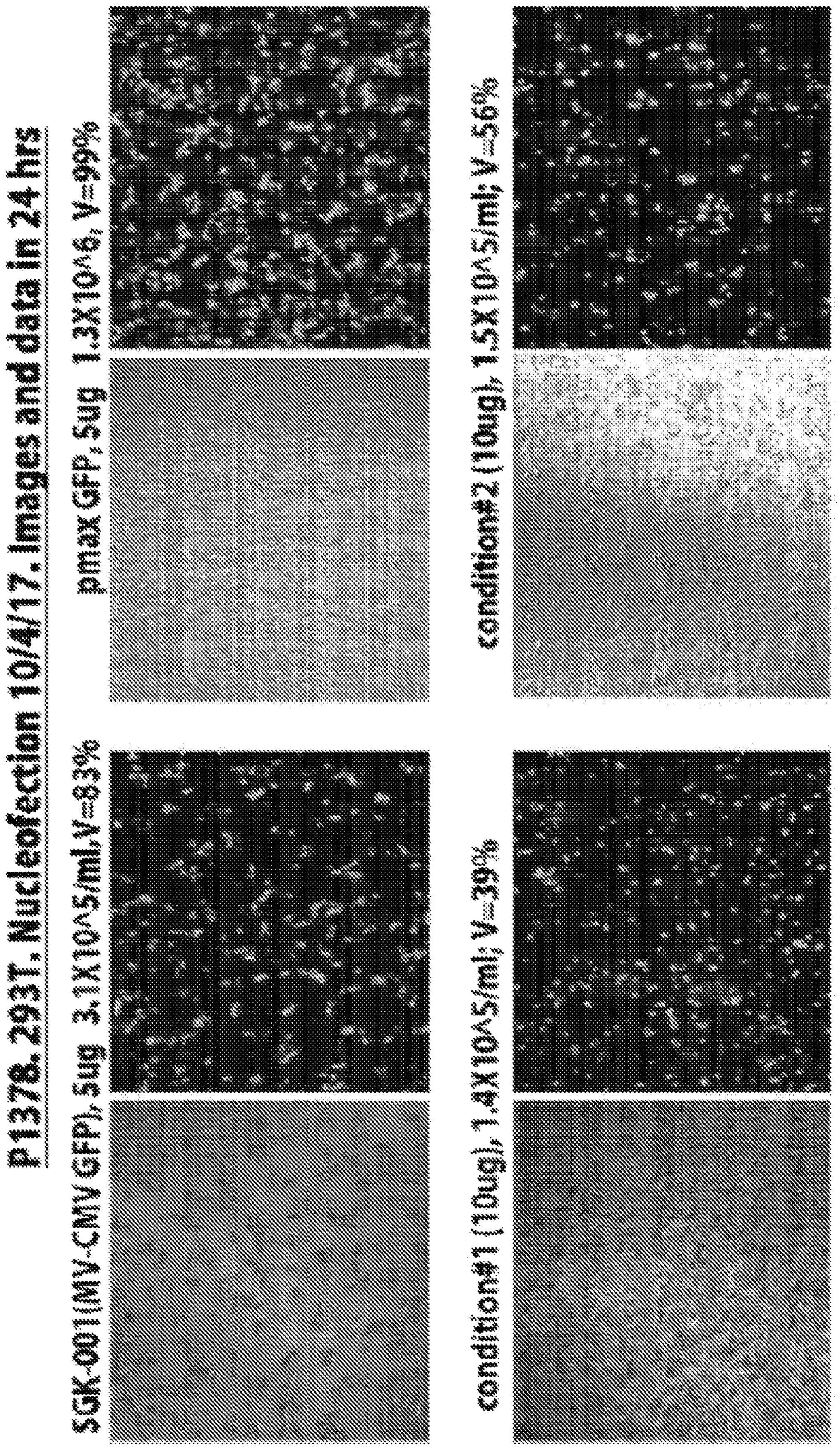
FIG. 15 is transfection efficiency of GEMS construct into AAVs1 site in HEK293T cells. HEK203 cells were transfected with GFP plasmid (green fluorescence) to assess transfection efficiency and viability of the cells post transfection. Combinations of two different amounts of GEMS donor plasmid, plasmid expressing gRNA and Cas9 mRNA, along with two different controls were transfected into HEK293T cells. The expression of GFP in the transfected cells were visualized by fluorescent microscope 24 hours post-transfection and cell viability were counted. High percentage of GFP positive cells with 39%-56% cell viability were produced by both conditions, indicating successful transfection.

Condition 1: 2 μg aavsl_cmvGFPpuro+4 μg AAVs1 CRISPR/Cas9 single shot plasmid+4 μg Cas9 mRNA Condition 2: 4 μg aavsl_cmvGFPpuro+4 μg AAVs1 CRISPR/Cas9 single shot plasmid+4 μg Cas9 mRNA Control 1: pMax GFP as positive control for Nucleofection efficiency Control 2: SGK-001 positive control for cmvGFP expression $1\times10^6$ HEK293T cells were used in each nucleofection. The expression of GFP in the nucleofected cells were visualized by fluorescent microscope 24 hours after nucleofection and cell viability was counted. High percentage of GFP positive cells with 39%-56% cell viability were produced by both conditions, indicating successful transfection (FIG. 15).

Figure 14:
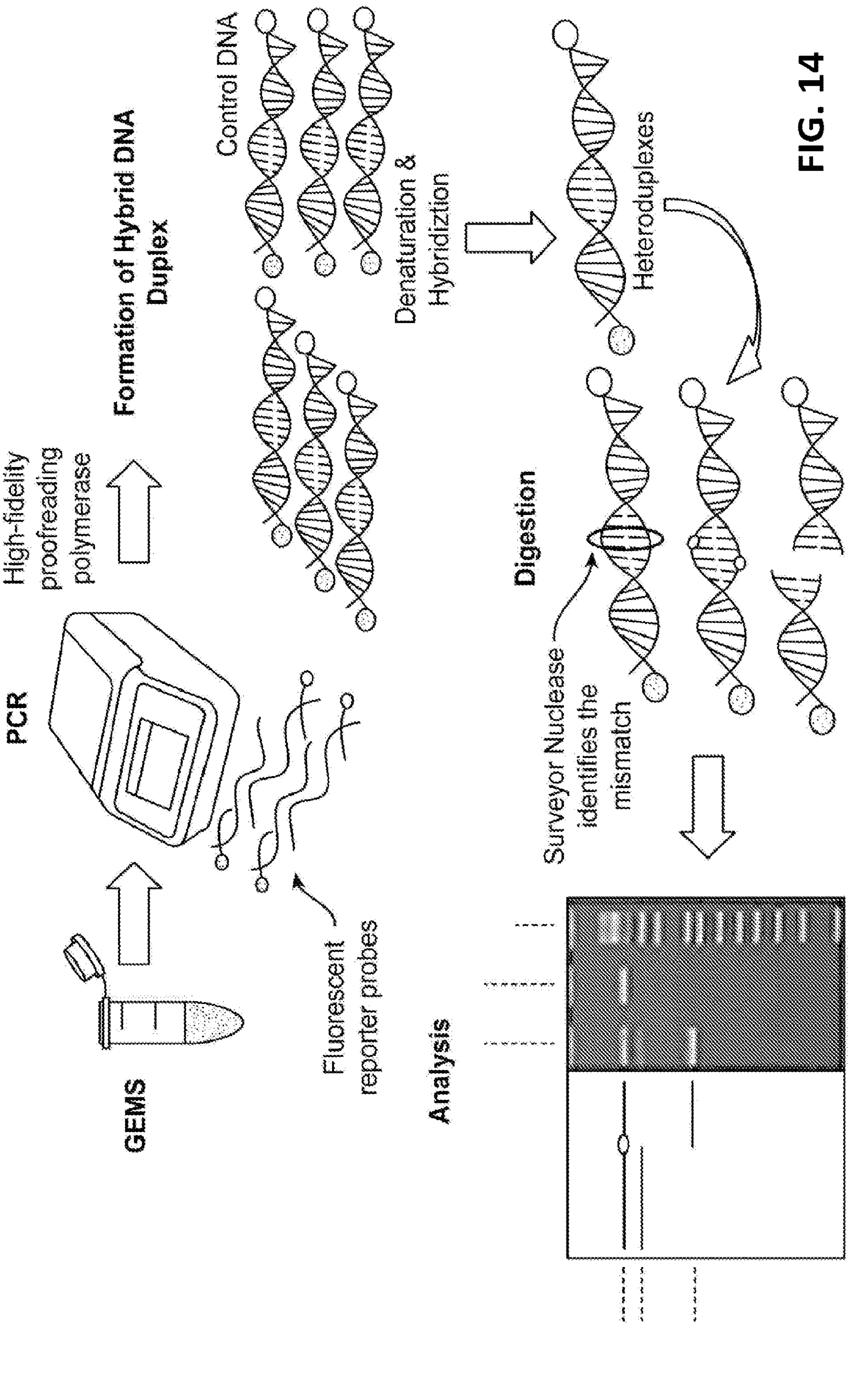
FIG. 14 is a schematic illustration of surveyor nuclease assay, an enzyme mismatch cleavage assay used to detect single base mismatches or small insertions or deletions (indels). The surveyor nuclease enzyme recognizes all base substitutions and insertions/deletions, and cleaves mismatched sites in both DNA strands with high specificity
Figure 16A:
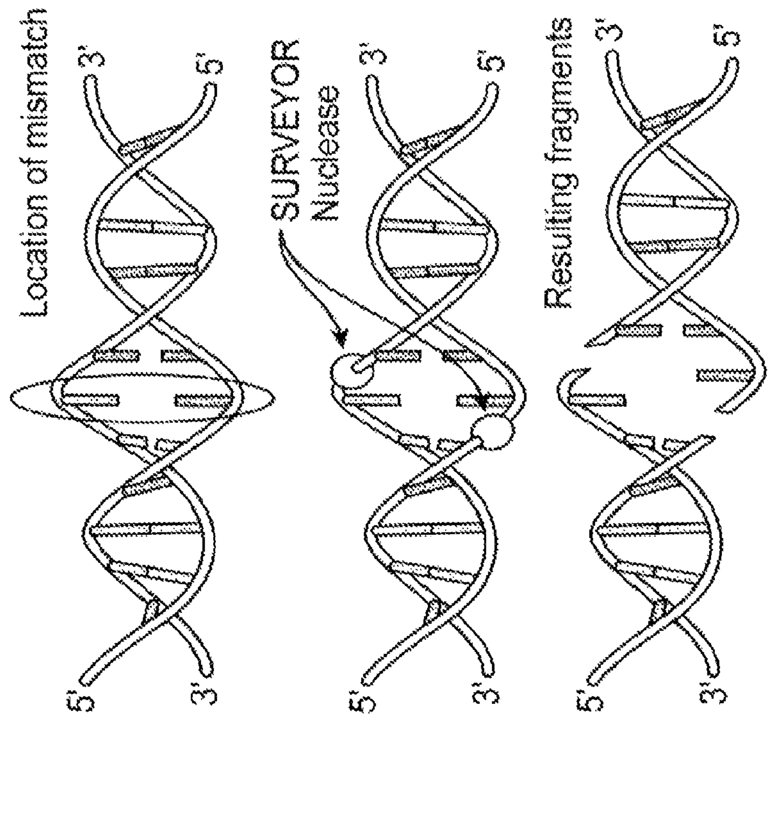
FIG. 16A is a schematic illustration of surveyor nuclease assay, an enzyme mismatch cleavage assay used to detect single base mismatches or small insertions or deletions (indels). The surveyor nuclease recognizes all base substitutions and insertions/deletions, and cleaves mismatched sites in both DNA strands with high specificity.
Figure 16B:
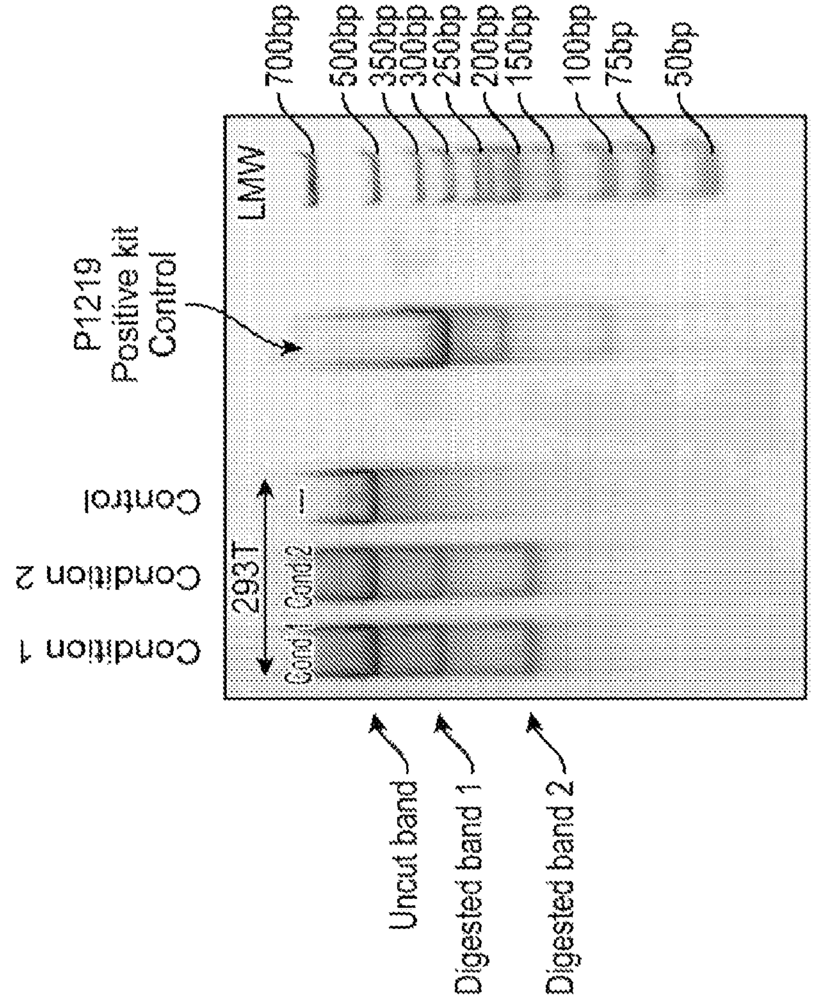
FIG. 16B shows cutting efficiency by CRISPR/Cas9 at AAVs1 site in transfected HEK293T cells. Quantitation of the intensity of DNA bands revealed a cutting efficiency of 24% and 15% for condition 1 and 2 respectively, which were typically expected for CRISPR/Cas9 activity.

Surveyor nuclease assays were performed to estimate the efficiency of CRISPR/Cas9 activity in transfected cells (FIGS. 14 and 16A). Briefly, five days after nucleofection, transfected cells were collected to prepare genomic DNA. The sequences of AAVs1 sites from transfected cells and reference untransfected cells were amplified by PCR. The PCR products were mixed together and hybridized to create heteroduplex between modified DNA and reference wild-type DNA. Surveyor nuclease was added to recognize and cleave mismatches in heteroduplexed DNA. The digested DNA fragments were analyzed by agarose gel electrophoresis. For both transfection conditions, two digested DNA fragments, resulted from the double-stranded cutting of AAVS1 site by CRISPR activity, were observed in addition to intact DNA fragment amplified by PCR (FIG. 16B). Quantitation of the intensity of DNA bands revealed a cutting efficiency of 24% and 15% for condition 1 and 2 respectively, which were typically expected for CRISPR/Cas9 activity.

Figure 17:
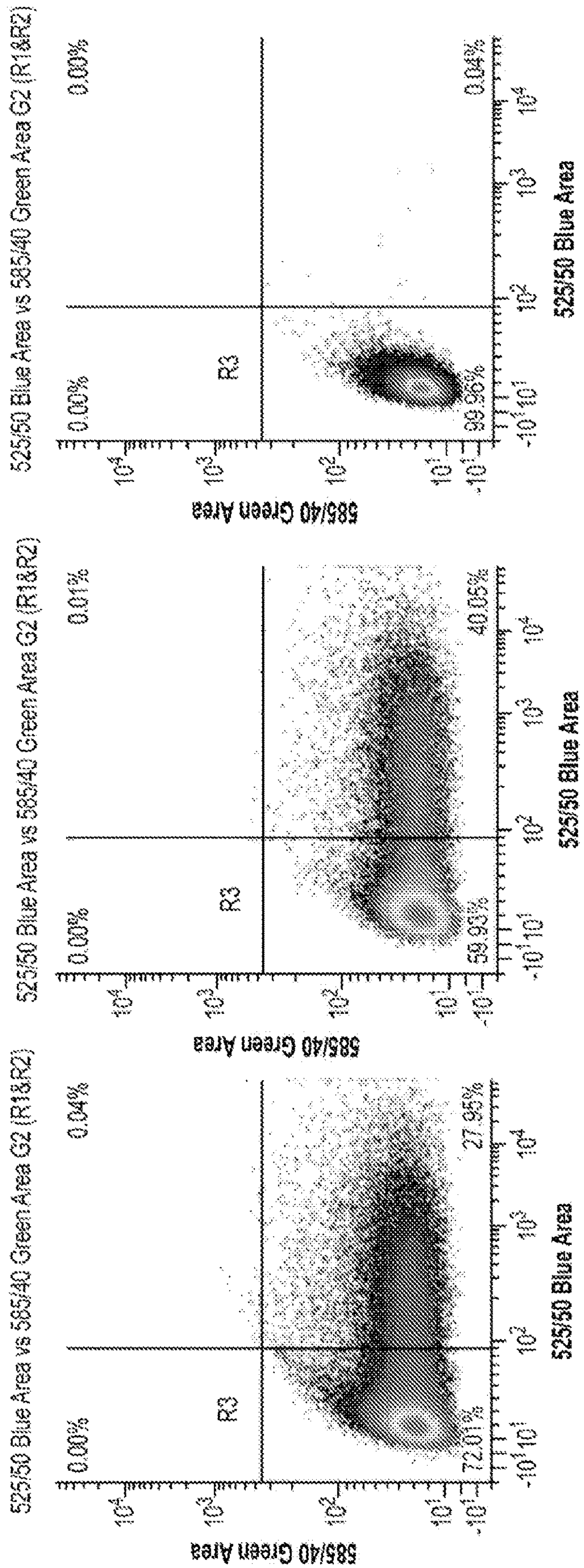
FIG. 17 shows flow cytometry analyses of GFP positive HEK293T cells enriched after puromycin selection. The cells were sorted by flow cytometry for GFP positive cells 16 days after transfection. In both condition 1 and 2, about 30-40% of the cell populations were GFP positive.

The transfected cells were cultured in media with puromycin to select puromycin resistant cells and GFP positive cells were enriched. 16 days after transfection, the cells were sorted by flow cytometry for GFP positive cells. In both condition 1 and 2, about 30-40% of the cell populations were GFP positive, although a wide range of GFP signal intensity was observed (FIG. 17).

Figure 18A:
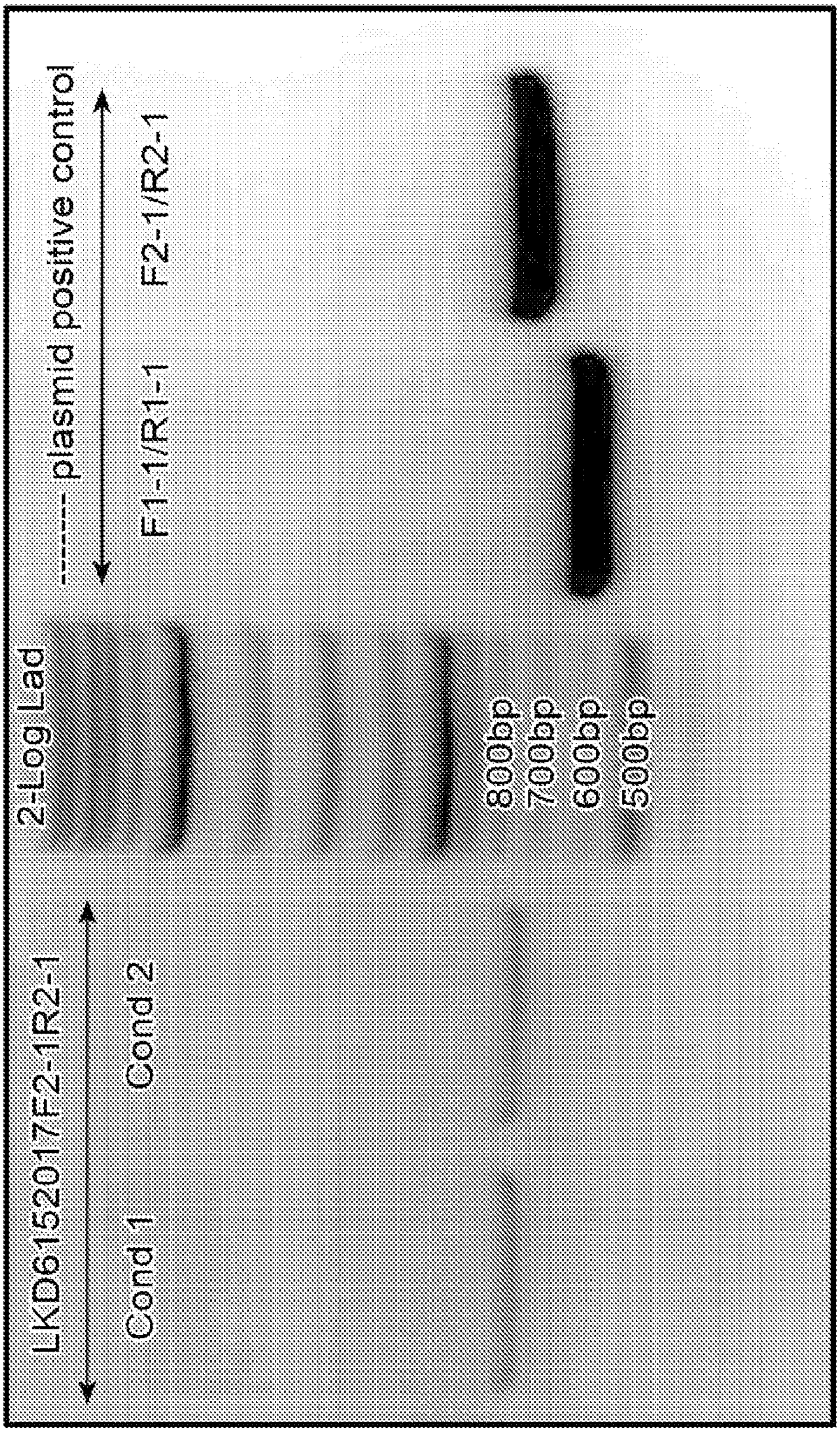
FIG. 18A is a gel electrophoresis of PCR products showing GEMS sequence inserted into HEK293T cell genome.
Figure 18B:
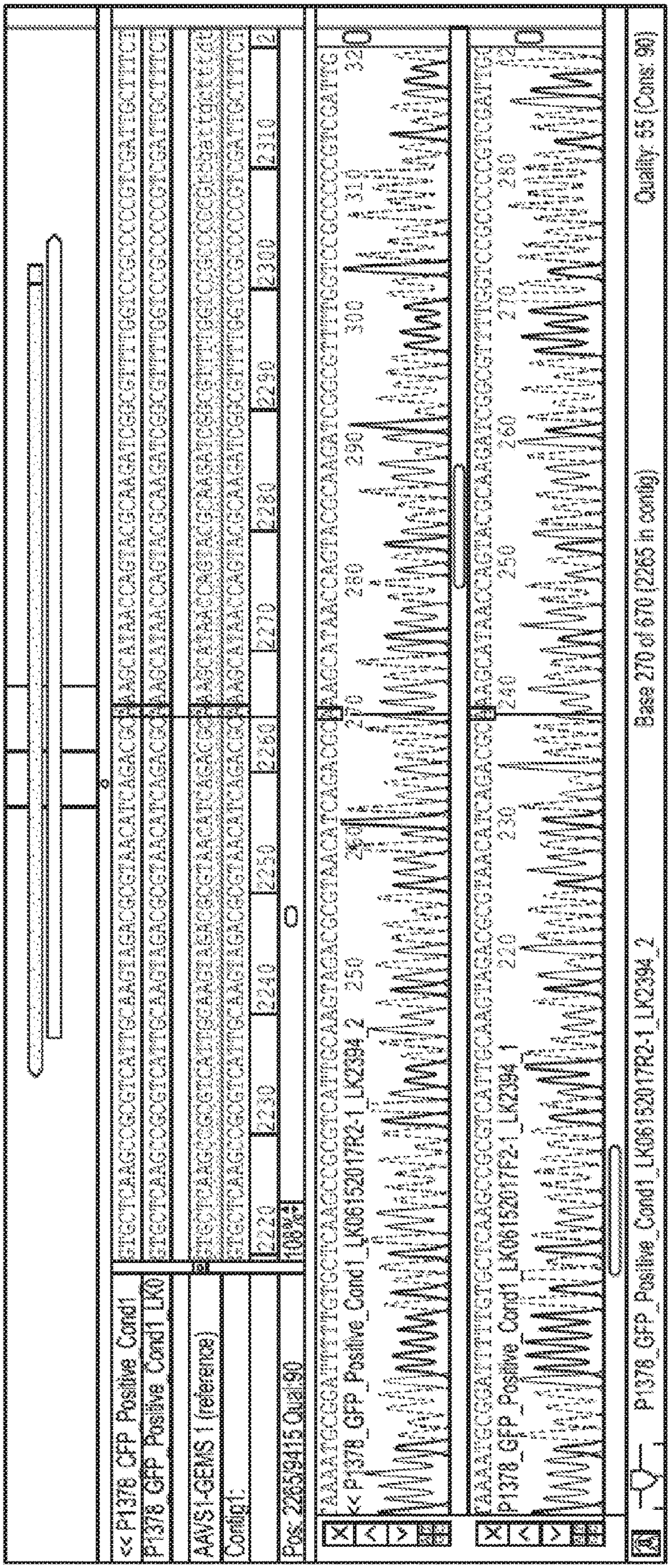
FIG. 18B shows sequencing of the PCR products of the inserted GEMs sequence.

The genomic DNA from puromycin resistant, GFP positive HEK293T cells were prepared. The GEMS sequence integrated into the cell genome was evaluated by PCR using primers specific to GEMS sequence followed by Sanger sequencing of the PCR product. For both condition 1 and 2, PCR products (728 bp) were amplified from the cell genomic DNA using primers (F2-1/R2-1) (SEQ ID NOs: 3-6) corresponding to GEMS sequence, indicating the successful integration of GEMS sequence in cell genome (FIG. 18A). The PCR products were further sequenced to confirm the identity of GEMS sequence (FIG. 18B). FIG. 18B shows sequencing of the PCR products of the inserted GEMs sequence.

Figure 18C:
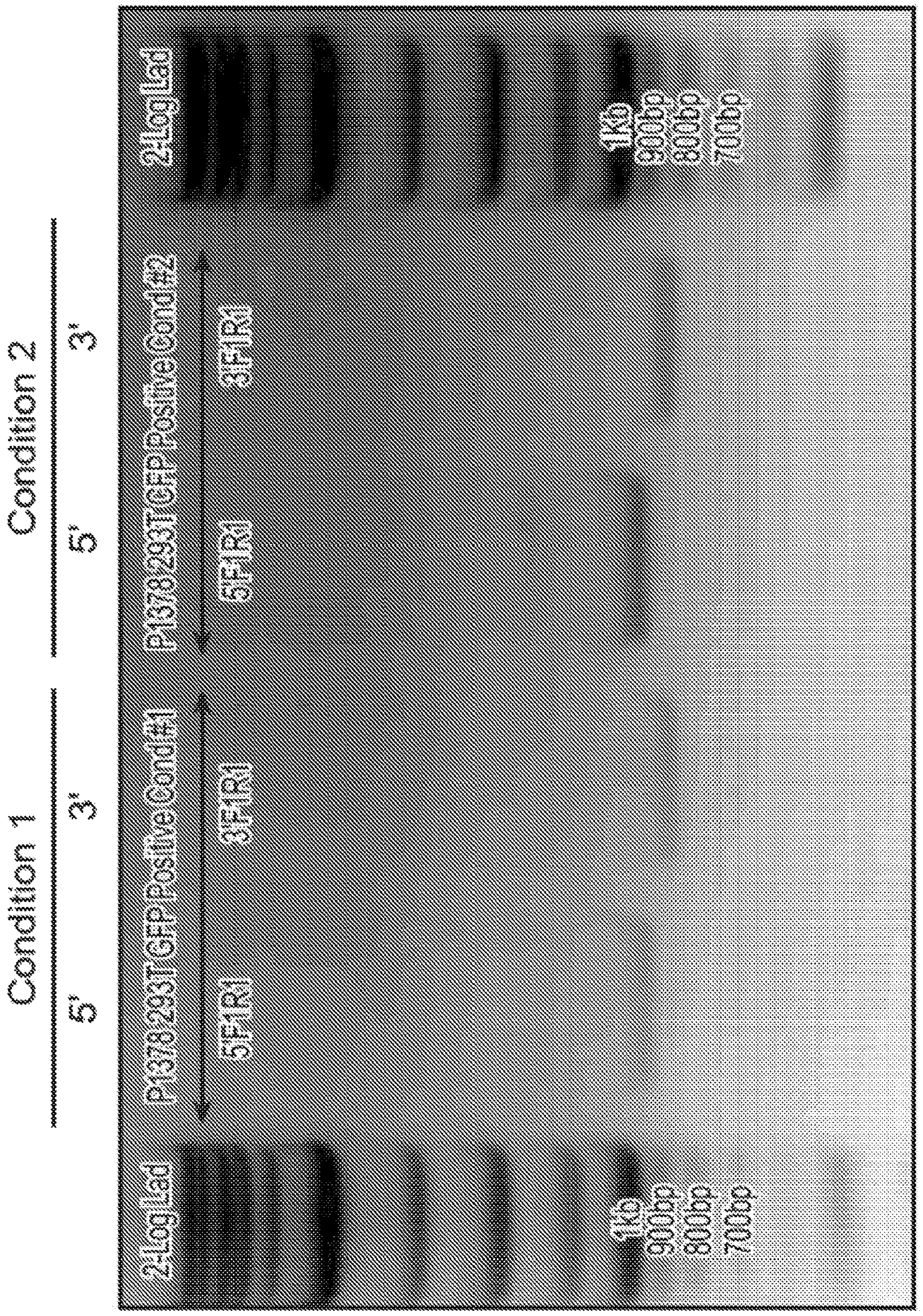
FIG. 18C shows a gel electrophoresis of PCR products of 5' and 3' junction sites of inserted GEMS cassette and AAVs1 site.
Figure 18D:
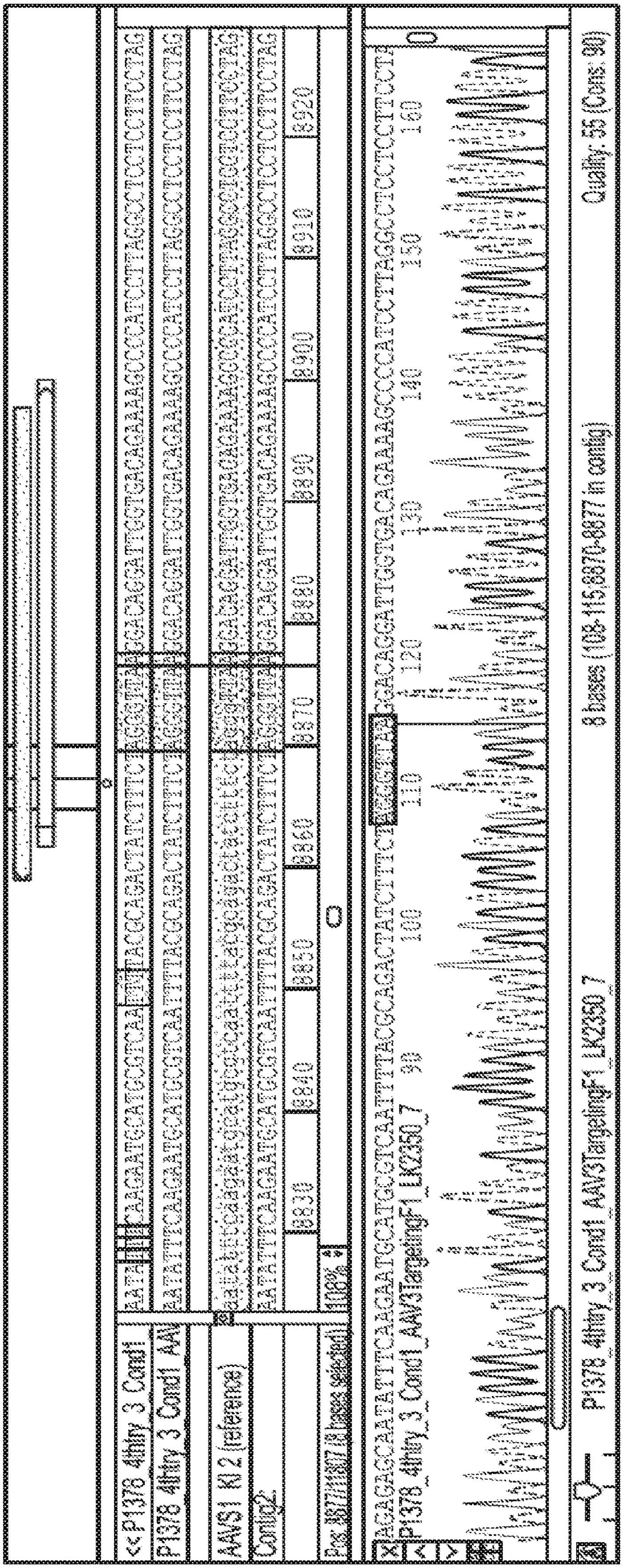
FIG. 18D shows sequencing of the PCR product of 3' junction sites. Correct junctions between AAVs1 site and 5' homology arm (upper panel) and between 5' homology arm and GEMS targeting cassette (lower panel) are shown.
Figure 18D:
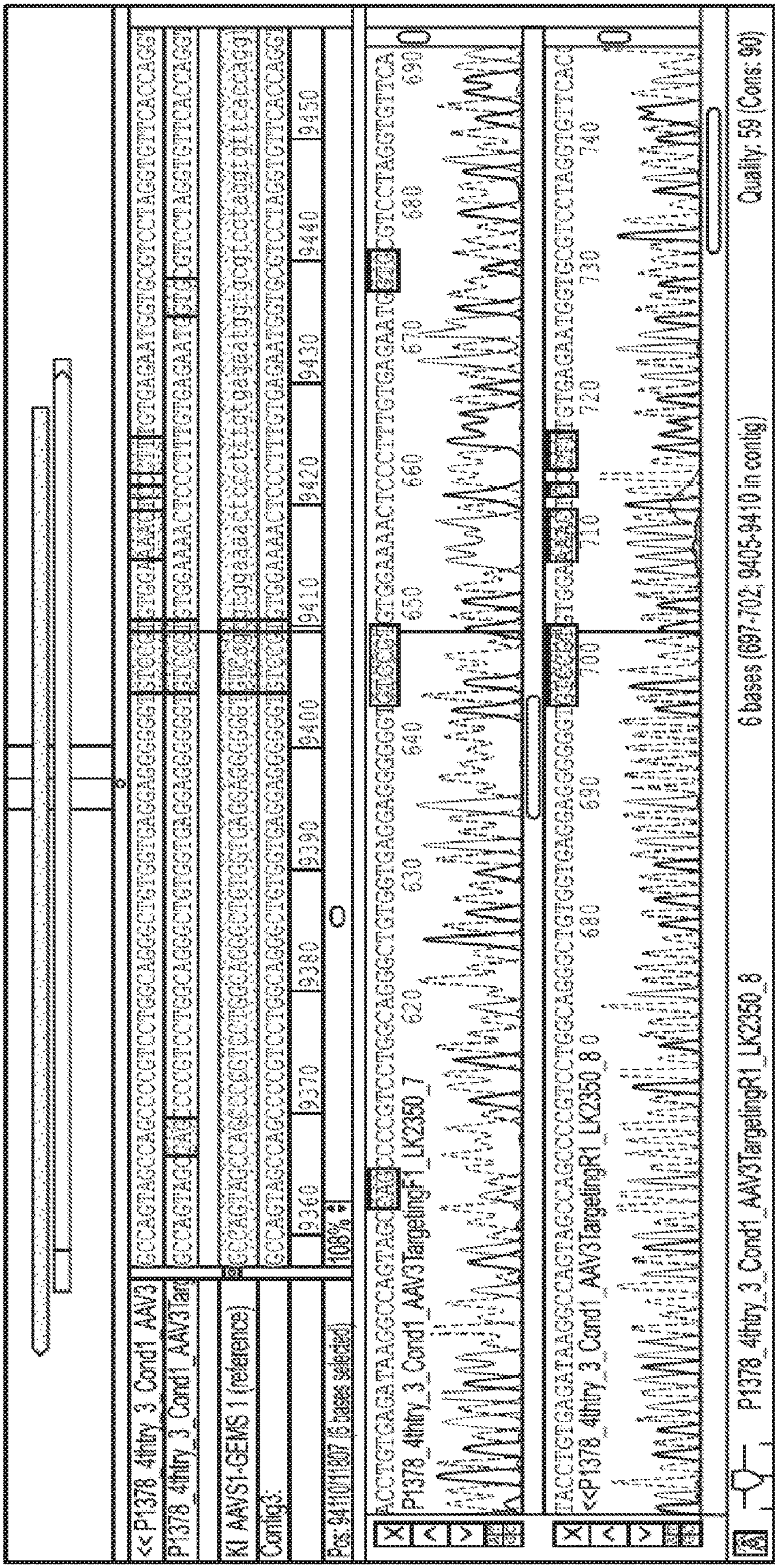

The proper insertion of GEMS into the AAVs1 site was evaluated by analyzing the 5' and 3' junction sites between the AAVs1 site and the inserted cassette by PCR using one primer specific to AAVs1 sequence and another primer specific to the inserted cassette sequence, followed by Sanger sequencing of the PCR product (SEQ ID NOs: 3-6). The appropriate 3' junction were confirmed by PCR with a correct 836 bp band (FIG. 18C) followed by Sanger sequencing (FIG. 18D), indicating successful targeted integration of GEMS sequence in the AAVs1 site. FIG. 18D shows sequencing of the PCR product of 3' junction sites. Correct junctions between AAVs1 site and 5' homology arm (upper panel) and between 5' homology arm and GEMS targeting cassette (lower panel) are shown. However, an incorrect 1 kb band was amplified by PCR for 5' junction site (FIG. 18C), which was proved to be an irrevant sequence.

Figure 19C:
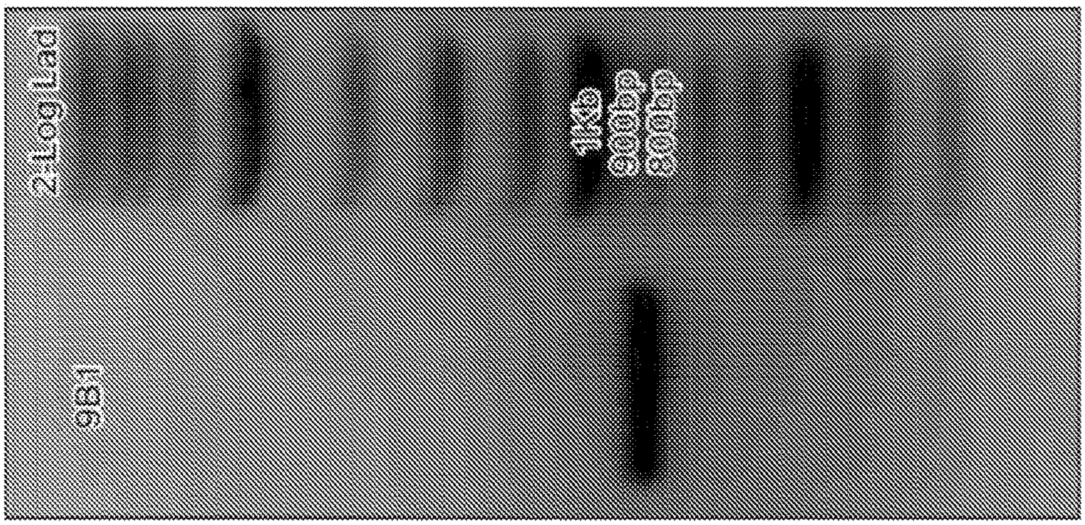
FIG. 19C is a gel electrophoresis showing PCR products of 3' junction sites of inserted GEMS cassette and AAVs1 site in the monoclonal GEMS modified HEK293T cell line (9B1).
Figure 19B:
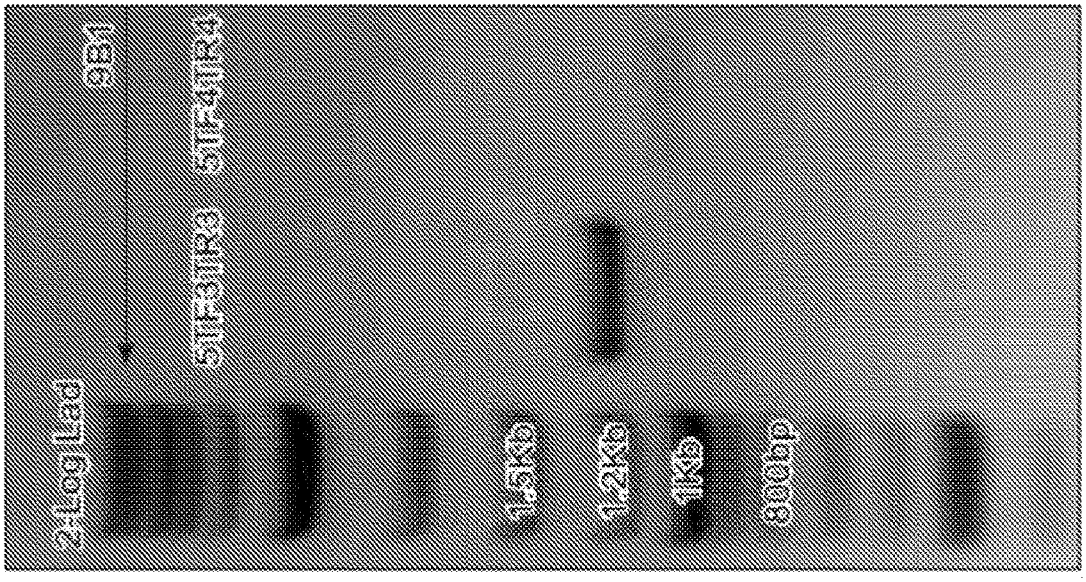
FIG. 19B is a gel electrophoresis showing PCR products of 5' junction sites of inserted GEMS cassette and AAVs1 site in the monoclonal GEMS modified HEK293T cell line (9B1).
Figure 19A:
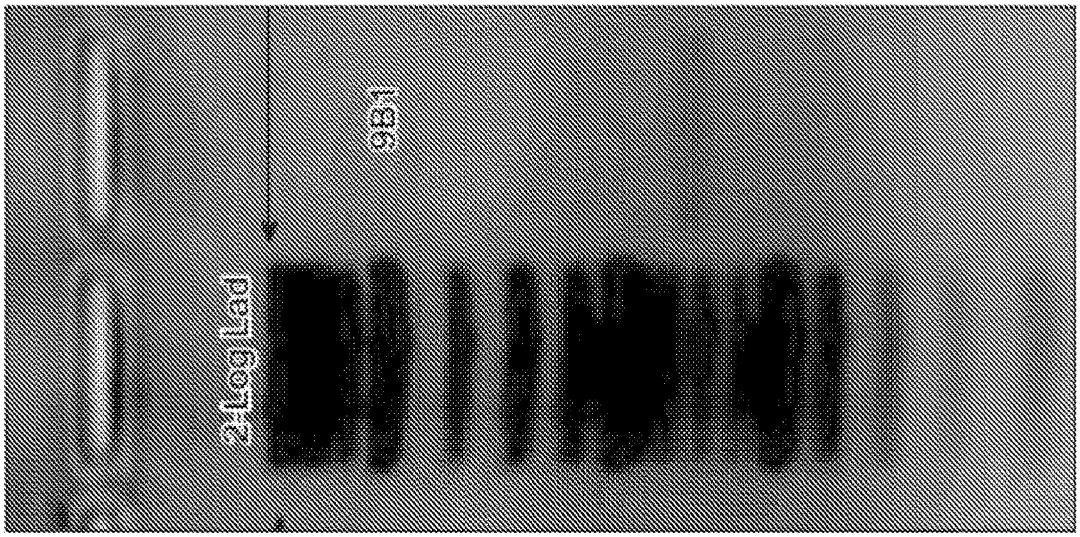
FIG. 19A is a gel electrophoresis of PCR products showing presence of GEMS sequence inserted into the genome of the monoclonal GEMS modified HEK293T cell line (9B1).
Figure 19D:
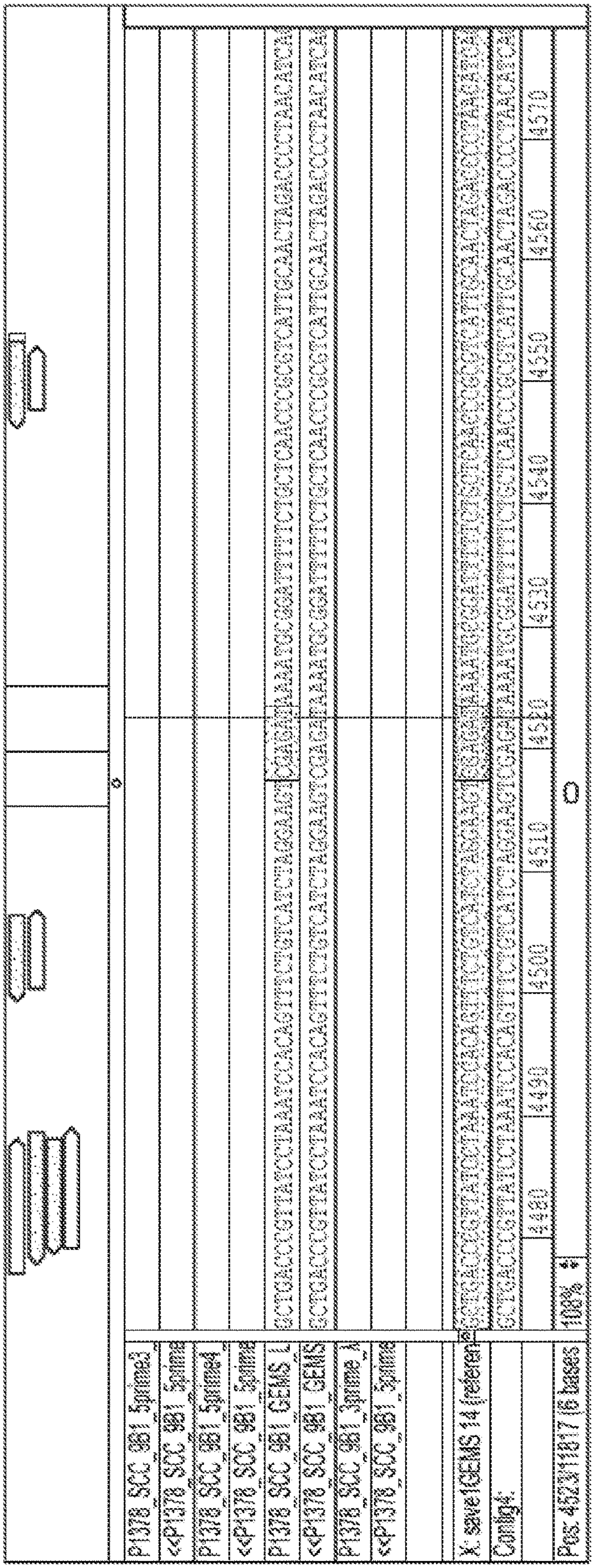
FIG. 19D shows sequencing of the PCR products of the inserted GEMs sequence from the monoclonal GEMS modified HEK293T cell line (9B1).
Figure 19D:
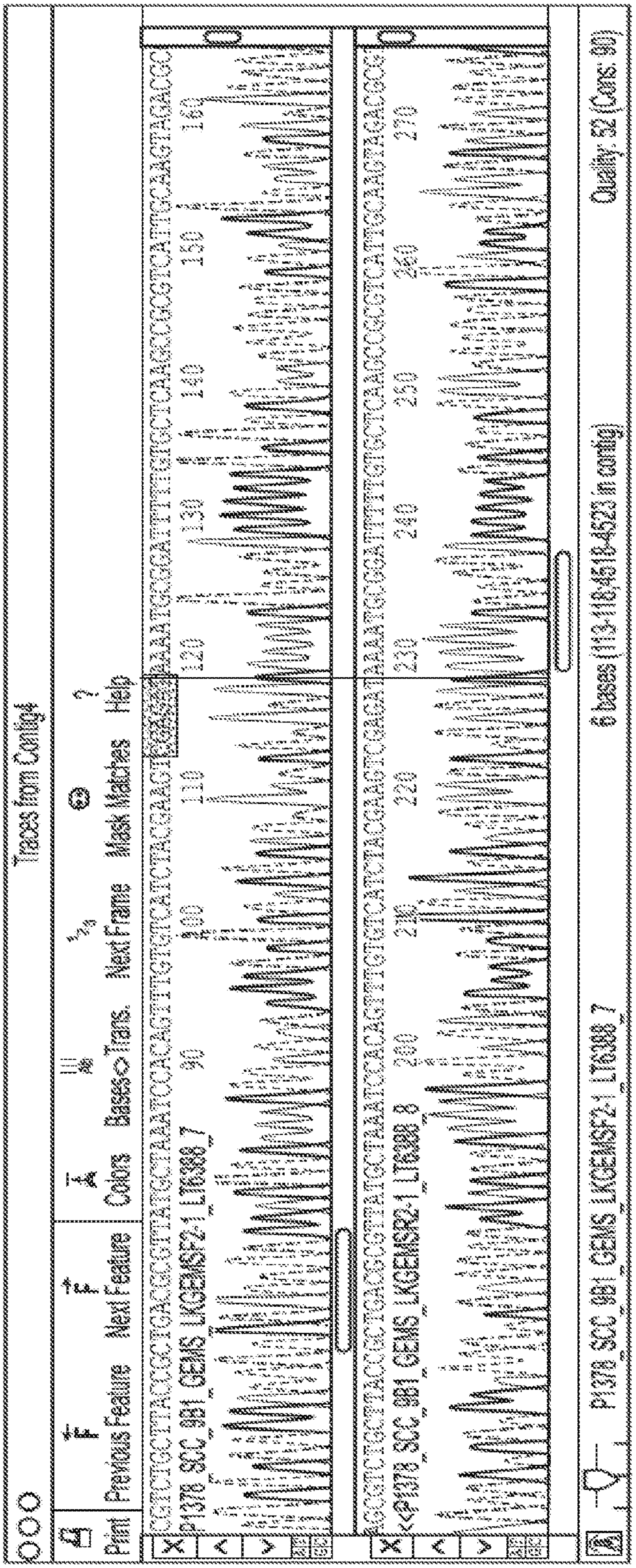
Figure 19E:
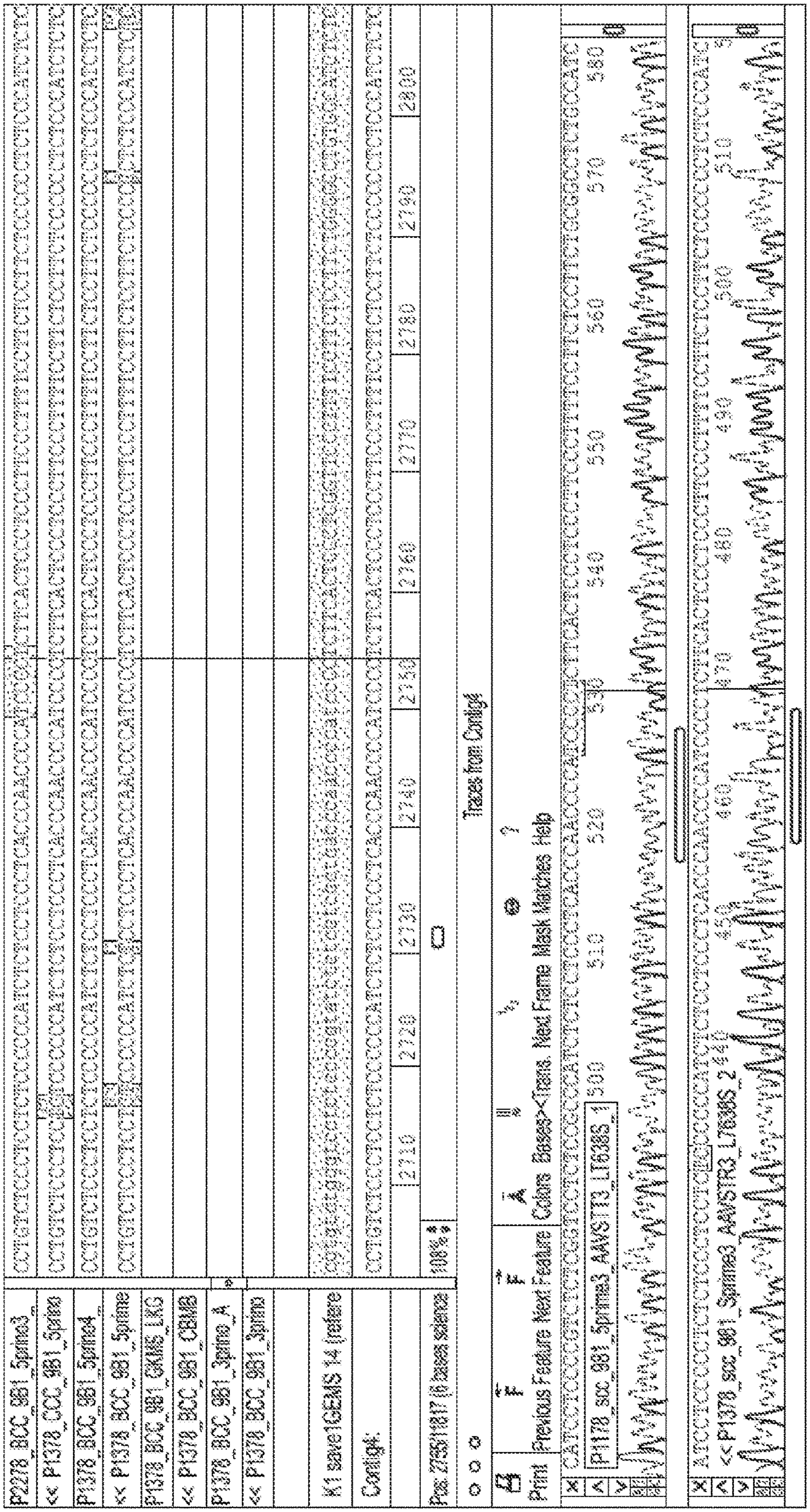
FIG. 19E shows sequencing of the 5' junction sites of inserted GEMS cassette and AAVs1 site from the monoclonal GEMS modified HEK293T cell line (9B1). Correct junctions between AAVs1 site and 5' homology arm (upper panel) and between 5' homology arm and GEMS targeting cassette (lower panel) are shown.
Figure 19E:
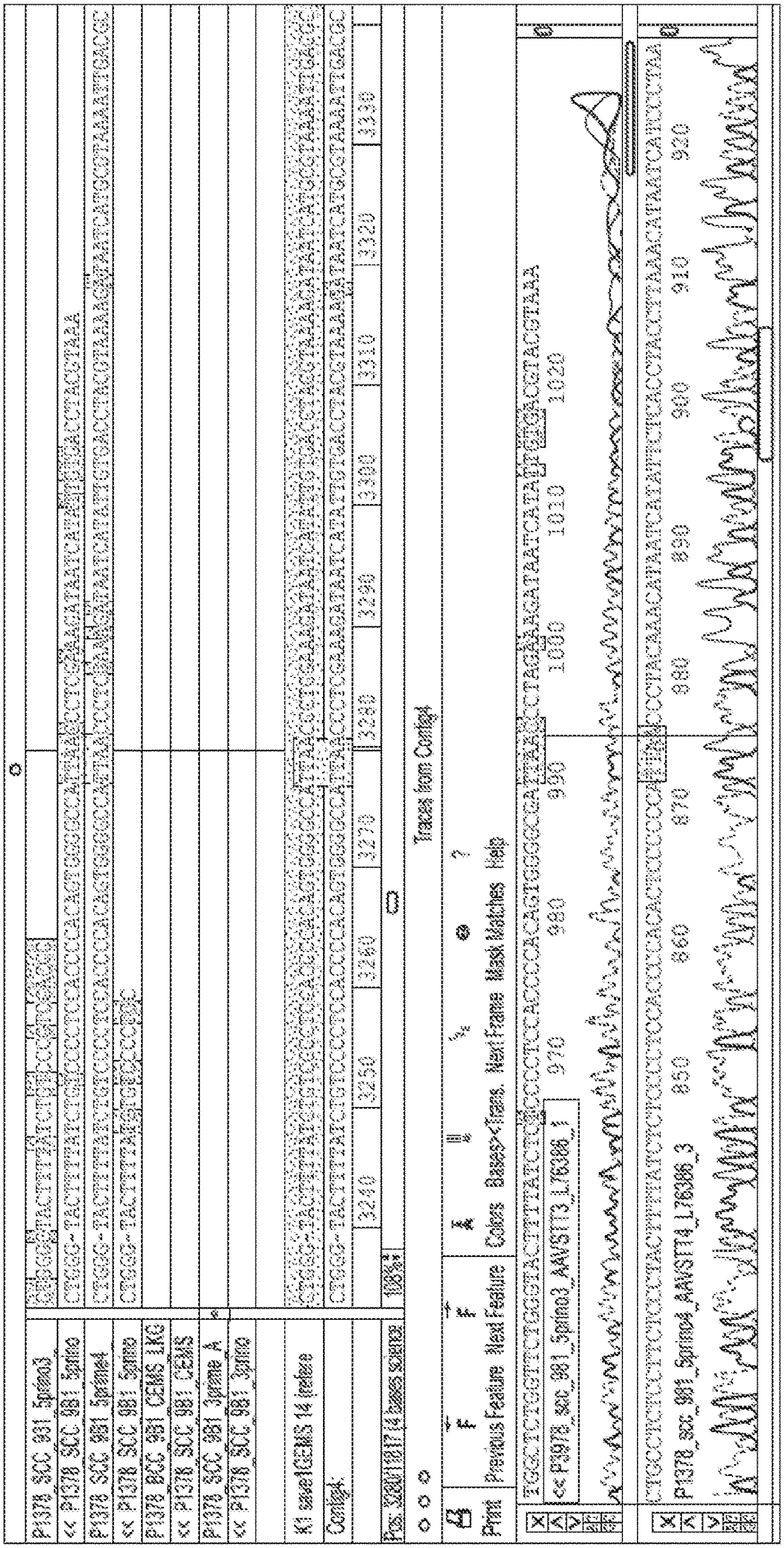
Figure 19F:
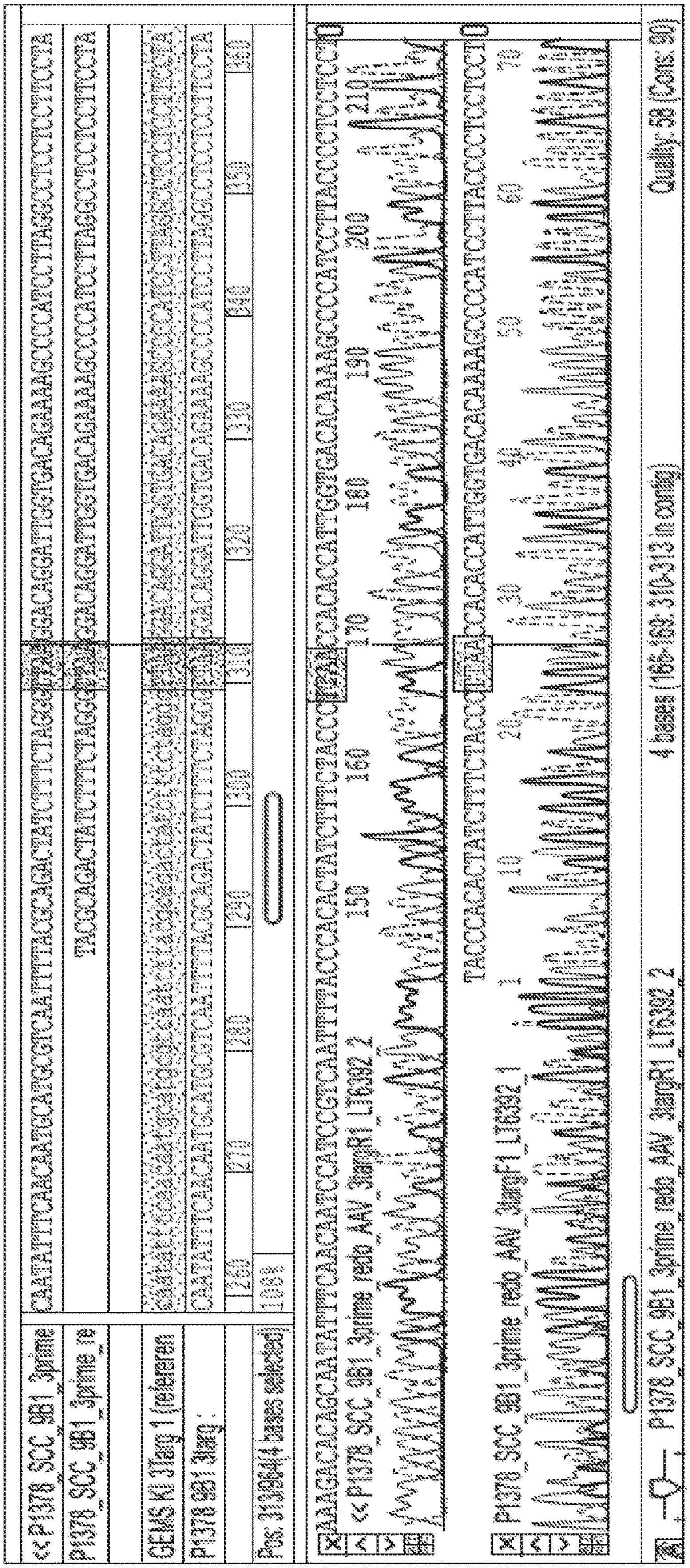
FIG. 19F shows sequencing of the 3' junction sites of inserted GEMS cassette and AAVs1 site from the monoclonal GEMS modified HEK293T cell line (9B1). Correct junctions between GEMS targeting cassette and 3' homology arm (upper panel) and between 3' homology arm and AAVs1 site (lower panel) are shown.
Figure 19F:
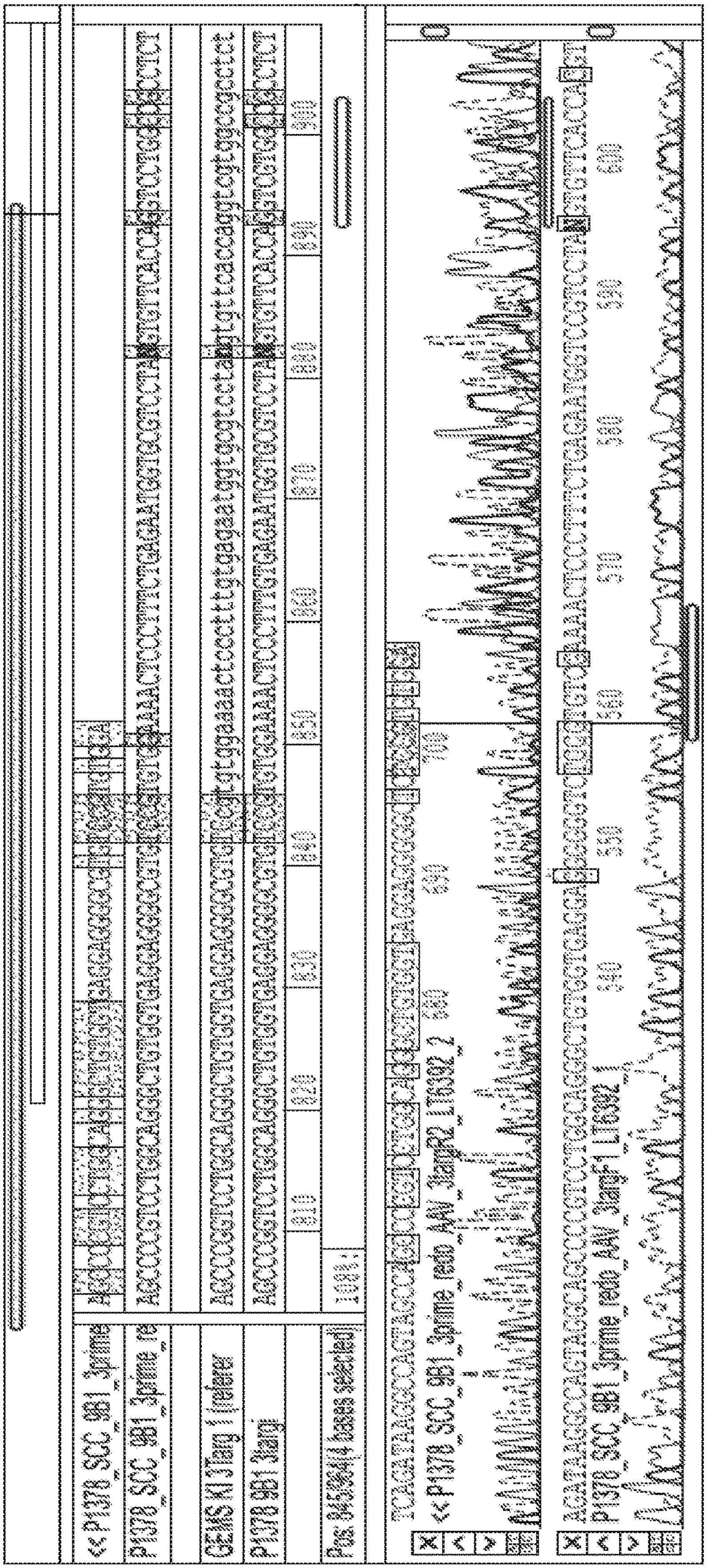

The pooled puromycin resistant, GFP positive cells were subjected to limited dilution into 96 well plate for single cell cloning. A monoclonal GEMS modified HEK293T cells line (9B1) was successfully established. The presence of the GEMS sequence inserted into cell genome of the monoclonal cell line was confirmed by PCR followed by Sanger sequencing (FIGS. 19A and 19D). The appropriate 5' junction and 3' junction were confirmed by PCR with a correct DNA bands followed by Sanger sequencing (FIGS. 19B, 19C, 19E, and 19F). FIG. 19D shows sequencing of the PCR products of the inserted GEMs sequence from the monoclonal GEMS modified HEK293T cell line (9B1). FIG. 19E shows sequencing of the 5' junction sites of inserted GEMS cassette and AAVs1 site from the monoclonal GEMS modified HEK293T cell line (9B1). Correct junctions between AAVs1 site and 5' homology arm (upper panel) and between 5' homology arm and GEMS targeting cassette (lower panel) are shown. FIG. 19F shows sequencing of the 3' junction sites of inserted GEMS cassette and AAVs1 site from the monoclonal GEMS modified HEK293T cell line (9B1). Correct junctions between GEMS targeting cassette and 3' homology arm (upper panel) and between 3' homology arm and AAVs1 site (lower panel) are shown.

GEMS sequence was successfully engineered into the AAVs1 site of HEK293T cells by CRISPR. This proof-of-concept study helped to establish standard protocols for cell transfection, assessment of CRISPR activity, stable cell line generation and validation of site-specific gene targeting, which can be referenced to engineer other cell types. The resulting GEMS modified HEK293T cell lines can be employed for further engineering CD19 CAR into the GEMS sequence.

Example 2. Engineering CD19 CAR into GEMS-Modified HEK293T cell

Figure 20:
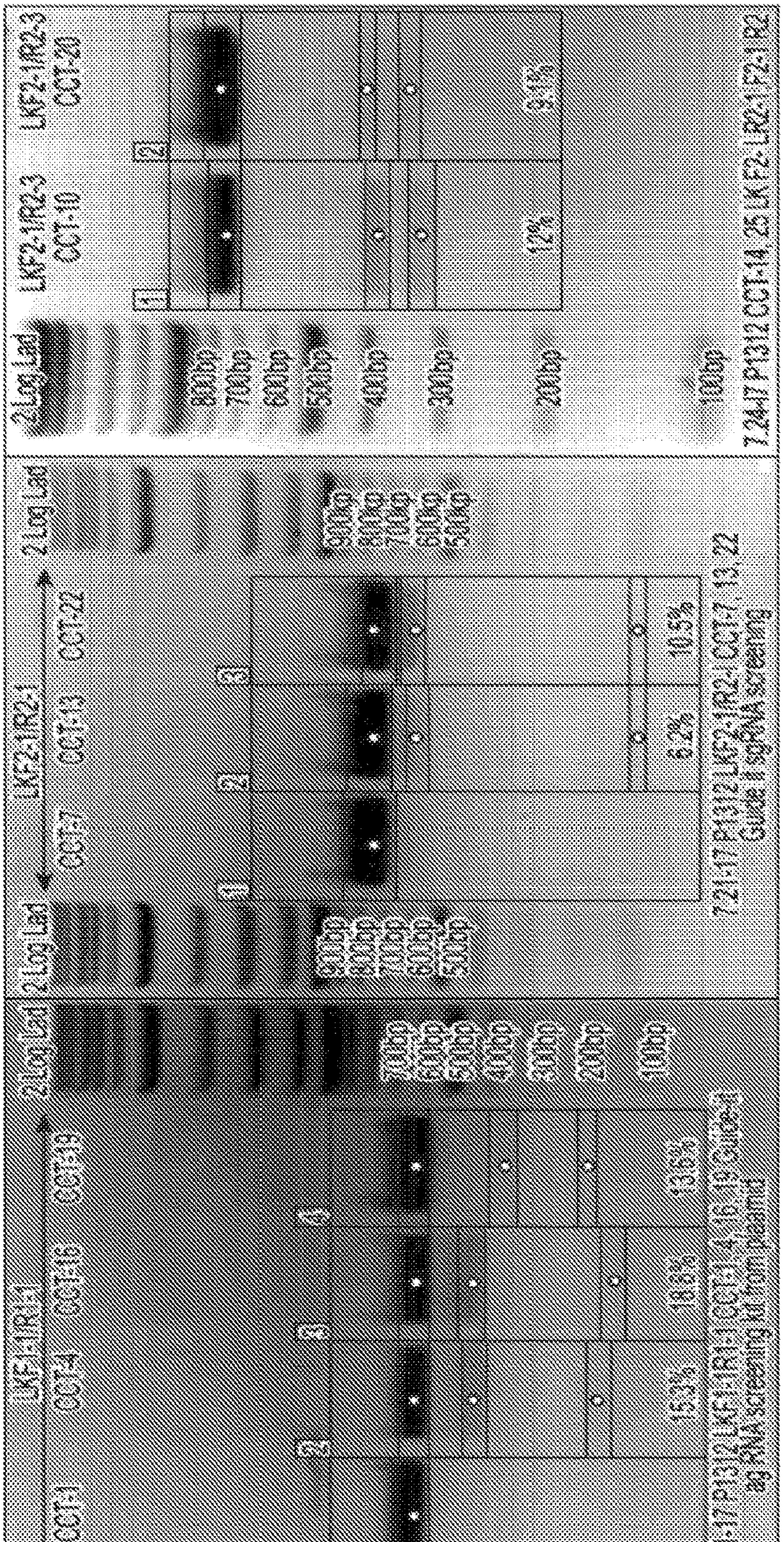
FIG. 20 shows cutting efficiency the designed sgRNAs in the in vitro nuclease assay. Nine designed sgRNA were tested in the in vitro assay for their ability to cut the GEMS sequence. Seven out of the nine sgRNAs cut the GEMS construct. Five out of the seven had cutting efficiencies between 10% and 25%, preferred range. Two out of seven showed efficiency below 10% and two did not cut.

To check whether Cas9-mediated CRISPR can cut the designed GEMS sequences (SEQ ID NO: 2) and to evaluate the cutting efficiencies, an in vitro nuclease assay was performed. Briefly, the GEMS DNA was PCR amplified, purified and resuspended in RNAase free water at about 100 ng/μl. 500 ng of Cas9 nuclease was pre-complexed with 1500 ng of each guide RNA corresponding to selective GEMS targeted sequences. This pre-complexed RNP was then added to 600 ng of the template DNA, in a total reaction volume of 10 μl, and incubated at 37° C. for 1 hour followed by inactivation at 70° C. for 10 min. The entire 10 μl reaction volume is then analyzed on TAE agarose gel. Nine designed sgRNA (Table 6; SEQ ID NOs 24-32) were tested in the Cell surveyor nuclease assay for their ability to cut the GEMS. Seven out of the nine sgRNAs cut the GEMS DNA. Five out of the seven had cutting efficiencies between 10% and 25% (preferred range). Two out of seven showed efficiency below 10% and two did not cut (FIG. 20; Table 6). The in vitro nuclease assay showed practical evidence that the designed sgRNAs can cut the designed GEMS DNA.

TABLE 6

Cutting Efficiencies of Tested sgRNAs

| SEQ ID NO | sgRNA | Sequence | % Cutting |
|---|---|---|---|
| 24 | CCT-16 | TGCTTGTGCATACATAACAA | 18.8 |
| 25 | CCT-04 | CCCGCAATAGAGAGCTTTGA | 15.3 |
| 26 | CCT-19 | TTGCAGCGCGCAGAGCATCT | 13.6 |
| 27 | CCT-10 | TTTTGCTACATCTTGTAATA | 12.0 |
| 28 | CCT-22 | ATACAGTACGCGTGTAACAA | 10.5 |
| 29 | CCT-25 | TACGATGAGAAAGCAATCGA | 9.1 |
| 30 | CCT-13 | CAATGACAATAGCGATAACG | 6.2 |
| 31 | CCT-01 | TGAATTAGATTTGCGTTACT | 0 |
| 32 | CCT-07 | TGTGTTAGCGCGCTGATCTG | 0 |

Based on the cutting efficiencies, site 16 of the GEMS sequences (CCT-16; SEQ ID NO: 24), which showed the highest cutting efficiency, was chosen as the site to engineer CD19 CAR into the GEMS-modified HEK293T cells as a proof-of-concept study. The CD19 CAR donor plasmid was constructed to express CD19 CAR composed of single chain Fv (scFv) (SEQ ID NO: 20) against CD19, a hinge and transmembrane domain followed by 4-1BB costimulatory endodomain (SEQ ID NO: 22) and the CD3-zeta intracellular signaling domain (SEQ ID NO: 23), under the control of e.g., EF-1α promoter (SEQ ID NO: 18). The CD19-CAR expression sequence, along with a blasticidin selection marker under e.g., CMV promoter (SEQ ID NO: 11), is flanked by GEMS sequence surrounding the cutting site (site 16) as the 5' and 3' homology arms (SEQ ID NOs: 16-17) to facilitate homology recombination.

Figure 21B:
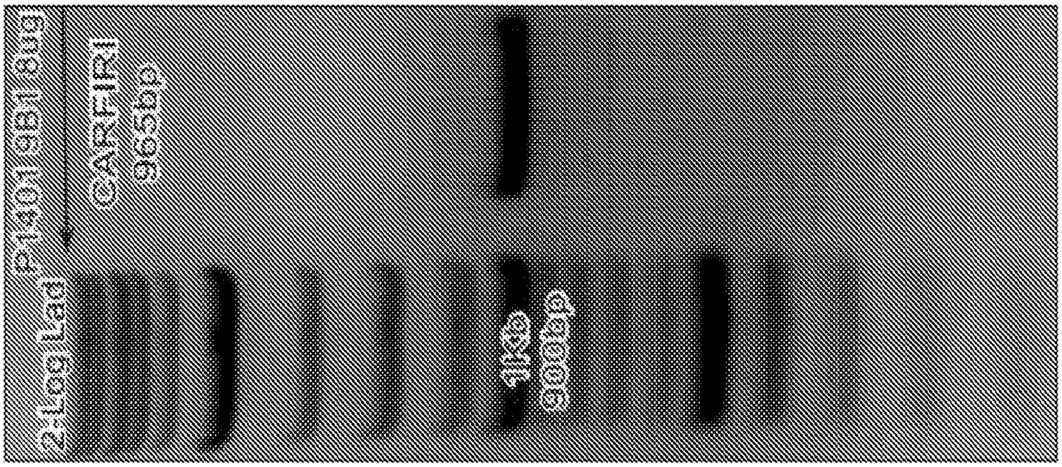
FIG. 21B is a gel electrophoresis of PCR products showing CD19 CAR sequence inserted into the cell genome of puromycin resistant GEMS modified HEK293T cells.
Figure 21A:
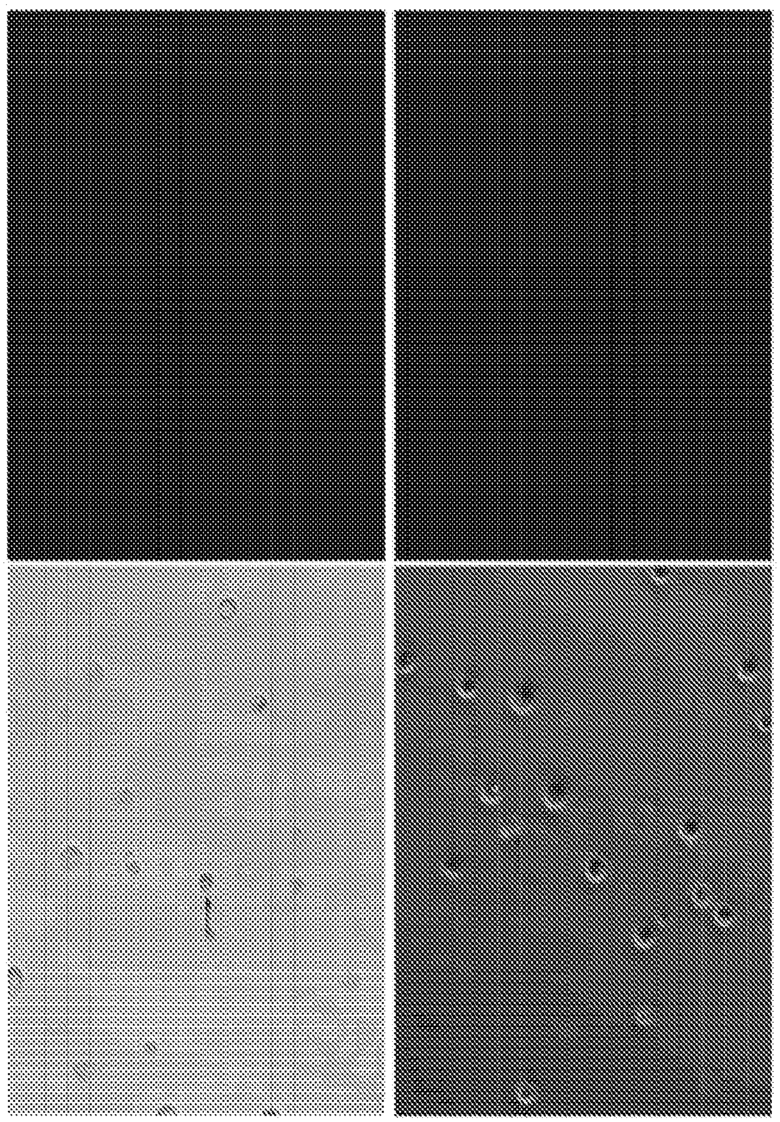
FIG. 21A shows the positive staining of CD19 CAR expression cells by immunostaining of pooled blasticidin resistant cells with Alexa Fluor 594 conjugated Goat anti-Human IgG F(ab')2 fragment antibody to detect the anti- CD19 scFv portion of CD19 CAR molecule.

Combinations of CD19 CAR donor plasmid, Cas9 expressing plasmid, and GEMS site 16 gRNA were transfected into the monoclonal GEMS modified HEK293T cell line (9B1) by nucleofection. The nucleofected cells were cultured in media with blasticidin to select blasticidin resistant cells. Sixteen days after nucleofection, the resistant cells were pooled together and they were able to survive with 40 μg/mL of blasticidin in the culture media while the parental native 9B1 cells could not survive (Table 7). The pooled cells were immunostained with Alexa Fluor 594 conjugated Goat anti-Human IgG F(ab')2 fragment antibody to detect the anti-CD19 scFv portion of CD19 CAR molecule. Positively stained cells were detected, indicating the expression of CD19 CAR in some of the pooled blasticidin resistant cells (FIG. 21A). Furthermore, the presence of CD19 CAR sequence in the pools of blasticidin resistant cells was confirmed by PCR (FIG. 21B).

TABLE 7

Percent Cell Viability of the GEMS-modified HEK293T (9B1) cells with CD19 CAR

| | % cell viability under 40 μg/ml blasticidin |
|---|---|
| Native 9B1 cells | 0% |
| 9B1 cells transfected with CD19 CAR donor plasmids | 100% |

The pooled cells can be further sorted by flow cytometry for CD19 CAR positive cells. Subsequently, the CD19 CAR positive cells can be subjected to single cell cloning. The insertion of CD19 CAR sequence into the site 16 of GEMS sequence can be verified by PCR followed by sanger sequencing of 5' and 3' junction sites between inserted cassette and site 16 targeting site.

Example 3. Engineering GEMS Sequence into the AAVs1 Site of NK92 Cells

Figure 22:
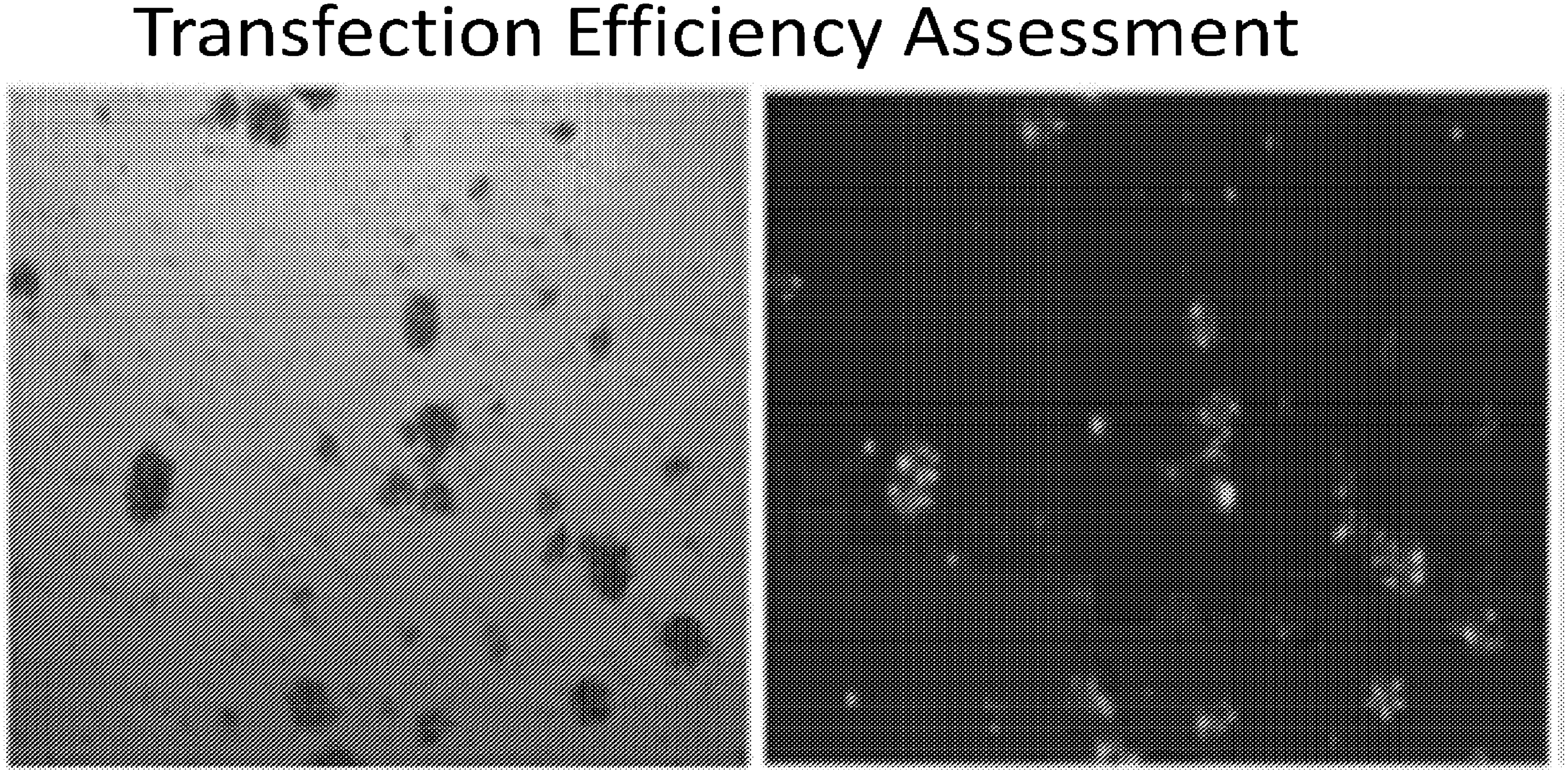
FIG. 22 shows transfection efficiency of GEMS construct into NK92 cells. NK92 cells were transfected with GFP plasmid (green fluorescence) to assess transfection efficiency and viability of the cells post transfection. Optimum conditions were established and yielded 60-70% transfection efficiency and retained 65% viability.
Figure 23:
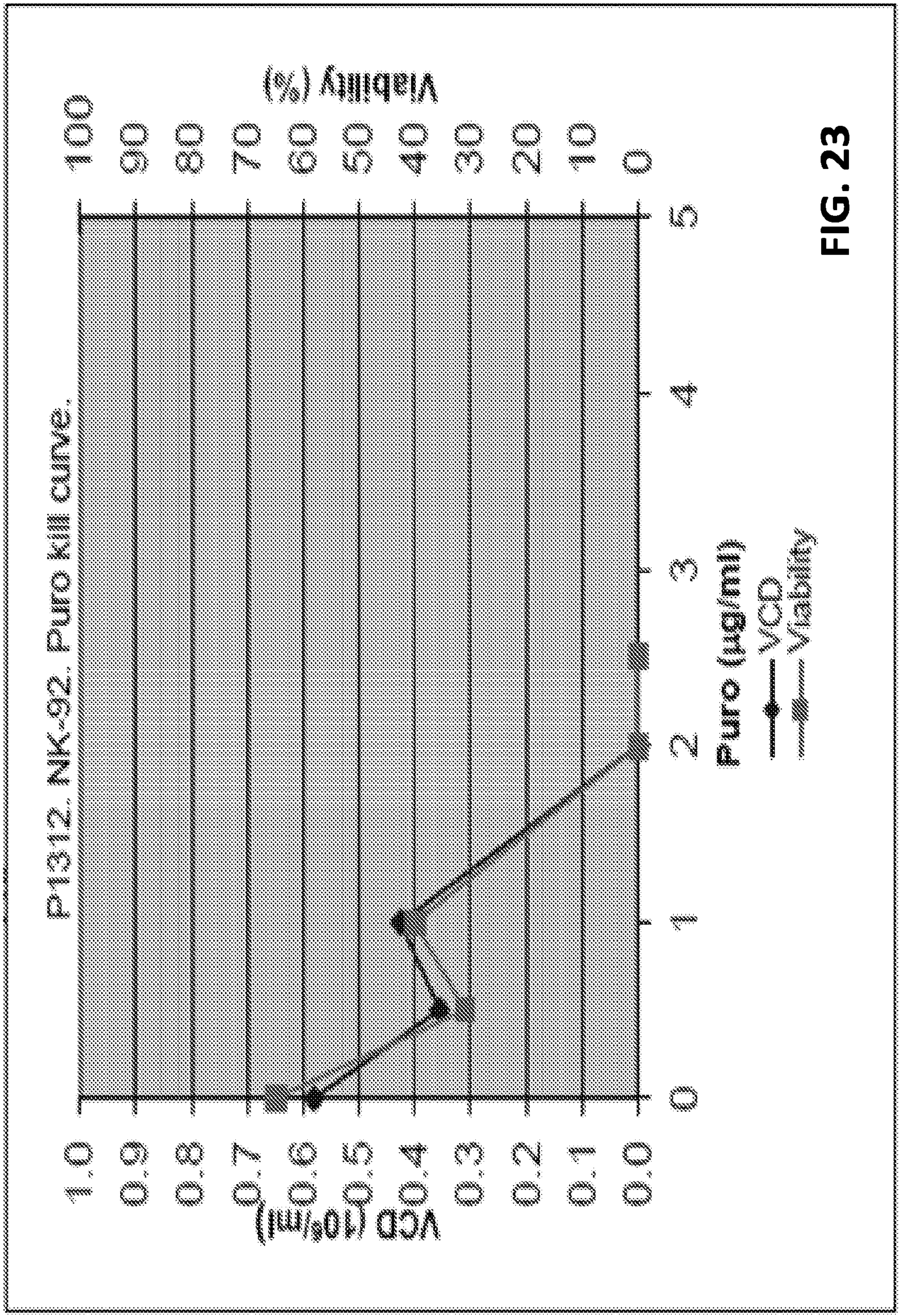
FIG. 23 shows puromycin sensitivity of NK92 cells transfected with GEMS-puromycin construct. NK92 cells were transfected with the GEMS-puromycin construct comprising the GEMS and a puromycin resistance gene. NK92 cells were culture in puromycin containing culture medium (0; 0.5; 1.0; 2.0; 2.5; 5; and 10 ug/ml). The NK92 showed no viability of cells present in cultures containing 2.0 ug/ml, or more, puromycin. VCD: viable cell density.

NK92 cells were transfected with GFP plasmid (green fluorescence) by electroporation using the 4D-Nucleofector™ System (Lonza). The viability pre, and post, nucleofection was assessed as well as the percentage of cells that became fluorescent by successful transfection of the GFP plasmid. Optimum conditions were established and yielded 60-70% transfection efficiency and retained 65% viability (FIG. 22). In addition, the puromycin sensitivity of the NK92 cells was tested. The NK92 cells were cultured in puromycin containing culture medium (0; 0.5; 1.0; 2.0; 2.5; 5.0; and 10 μg/ml). Viability as well as cell number was measured. The NK92 showed no viability of cells present in cultures containing more than 2.0 μg/ml puromycin (FIG. 23).

Several different transfection conditions were attempted to transfect the GEMS donor plasmid aavs1_cmvGFPpuro, a AAVS1 CRISPR/Cas9 single shot plasmid expressing Cas9 and AAVS1 targeting site sgRNA, and Cas9 mRNA into NK92 cells by electroporation using the 4D-Nucleofector™ System from Lonza. 1× 106 HEK293T cells were used in each nucleofection. The transfected cells were cultured in media with puromycin to select puromycin resistant cells and GFP positive cells were enriched. 20 days after transfection, the cells were sorted by flow cytometry for GFP positive cells.

Figure 24A:
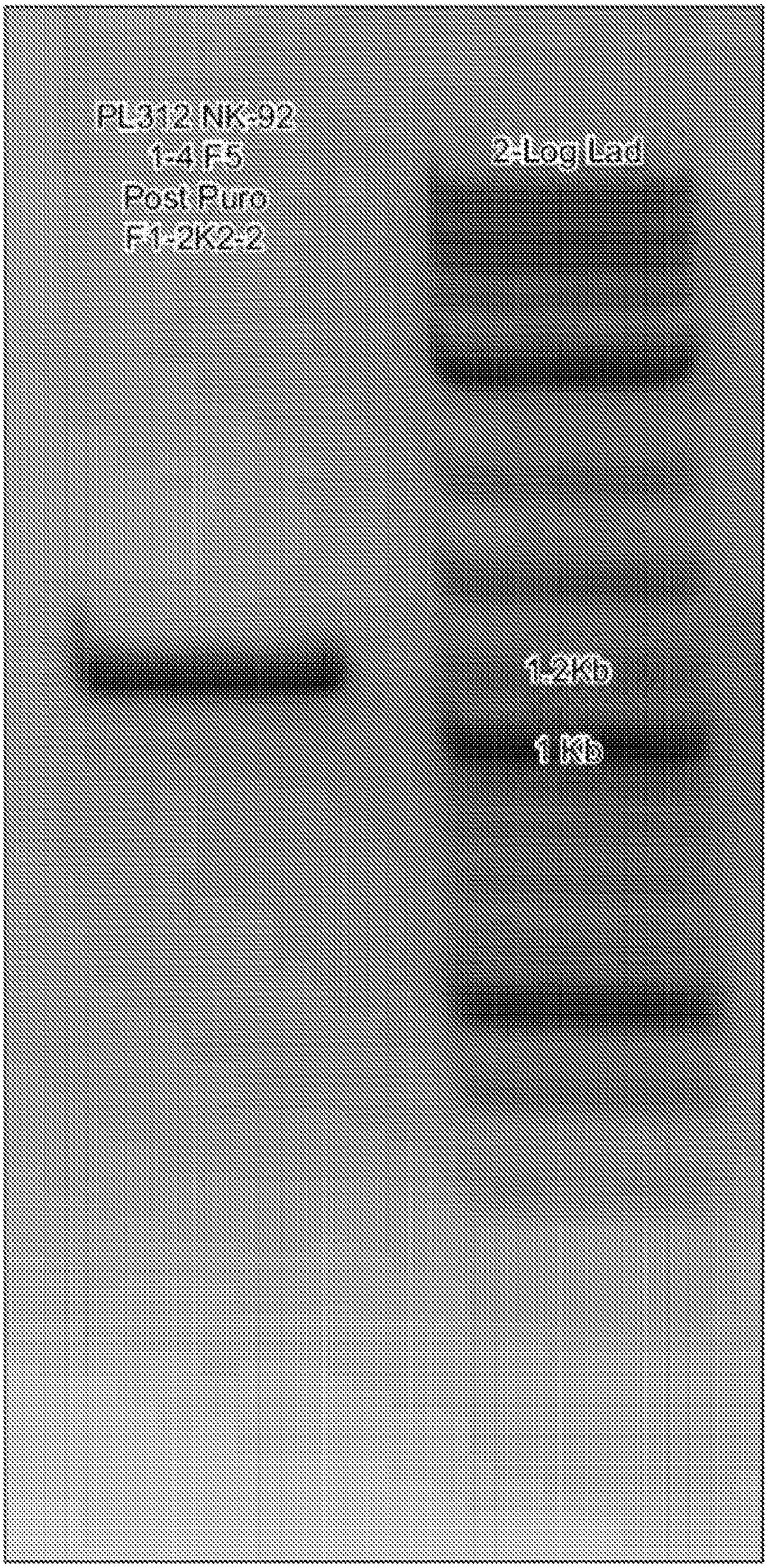
FIG. 24A is a gel electrophoresis of PCR products showing presence of GEMS sequence inserted into the genome of the pooled GFP positive NK92 cells.
Figure 24B:
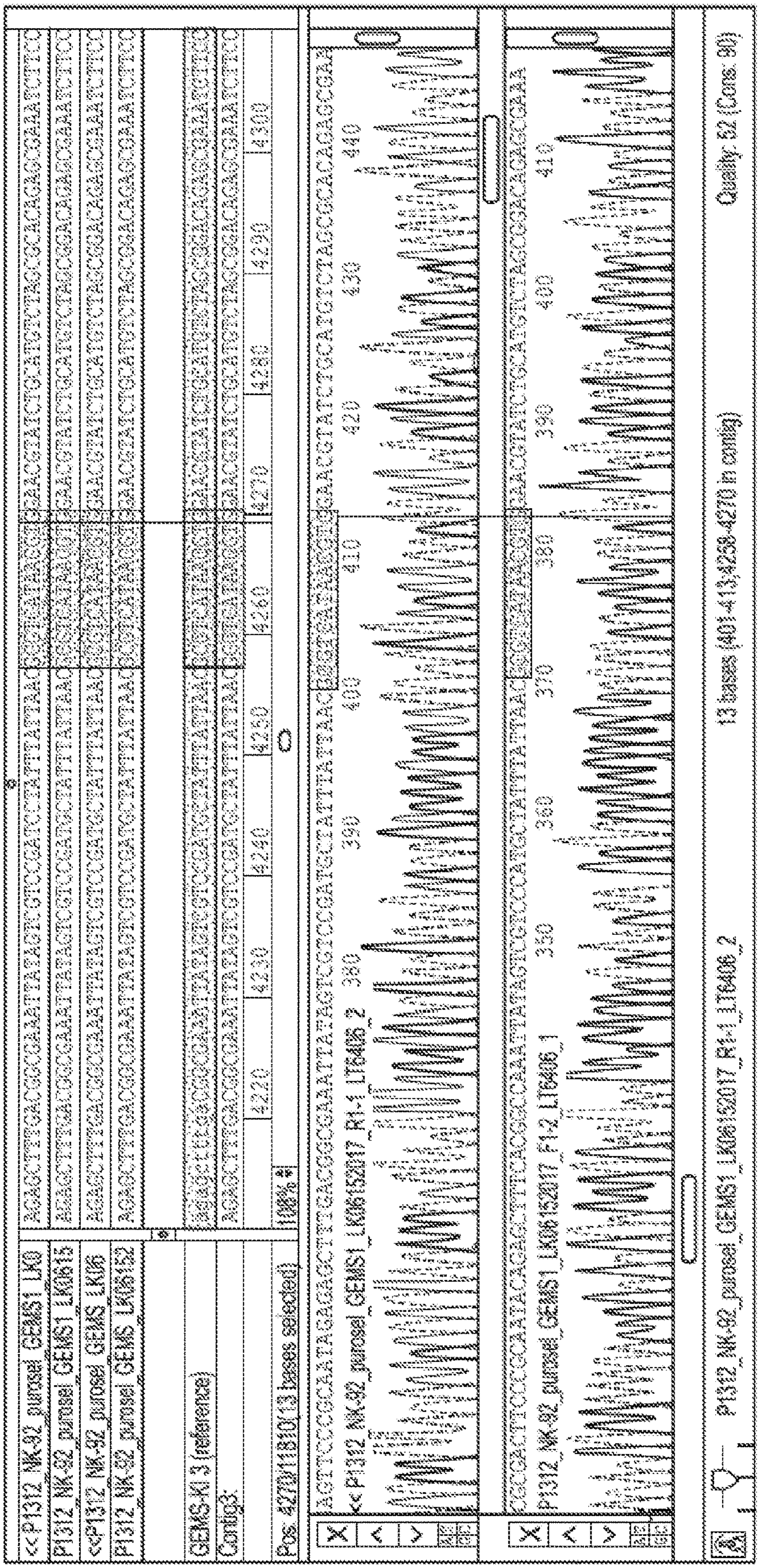
FIG. 24B shows sequencing of the PCR products of the inserted GEMs sequence from the pooled GFP positive NK92 cells.

The genomic DNA from puromycin resistant, GFP positive NK92 cells were prepared. The GEMS sequence (SEQ ID NO: 2) integrated into the cell genome was evaluated by PCR using primers specific to GEMS sequence followed by Sanger sequencing of the PCR product. PCR product (1147 bp) were amplified from the cell genomic DNA using primers (F1-2/R2-2) corresponding to GEMS sequence, indicating the successful integration of GEMS sequence in cell genome (FIG. 24A). The PCR products were further sequenced to confirm the identity of GEMS sequence (FIG. 24B). FIG. 24B shows sequencing of the PCR products of the inserted GEMs sequence.

Figure 24C:
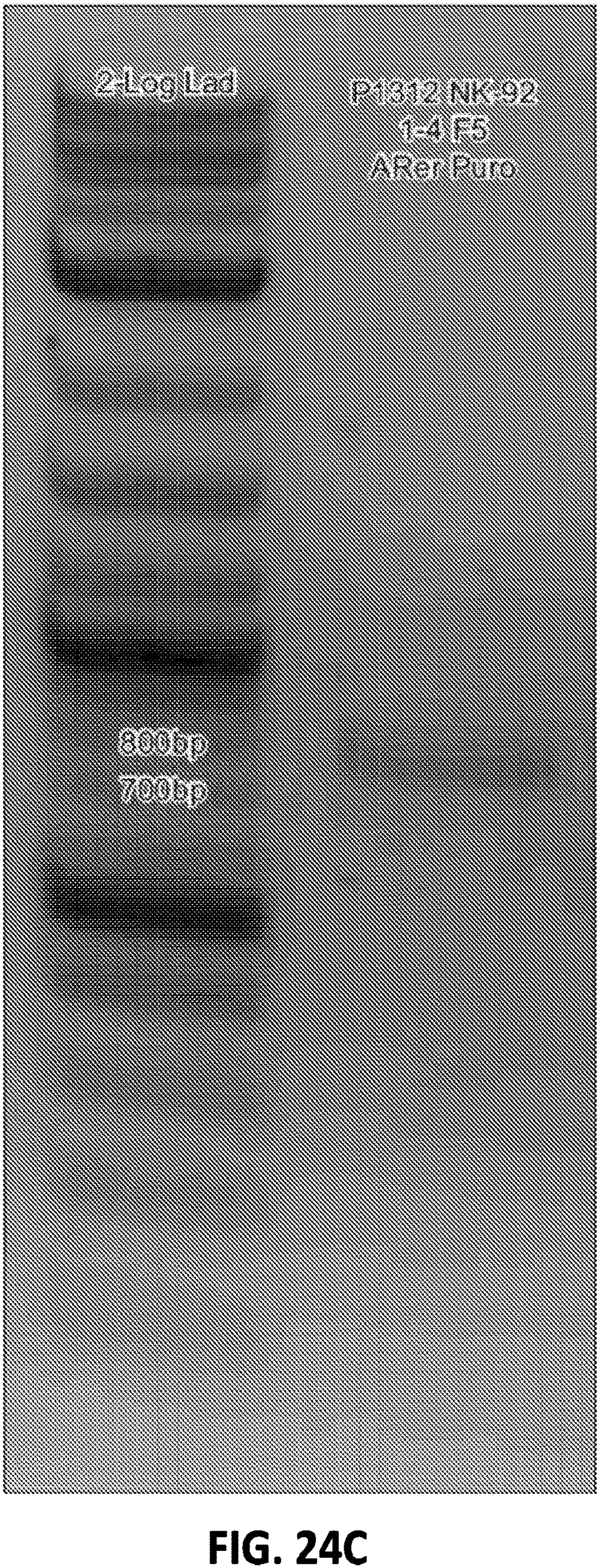
FIG. 24C is a gel electrophoresis showing PCR products of 5' junction sites of inserted GEMS cassette and AAVs1 site in the pooled GFP positive NK92 cells.
Figure 24D:
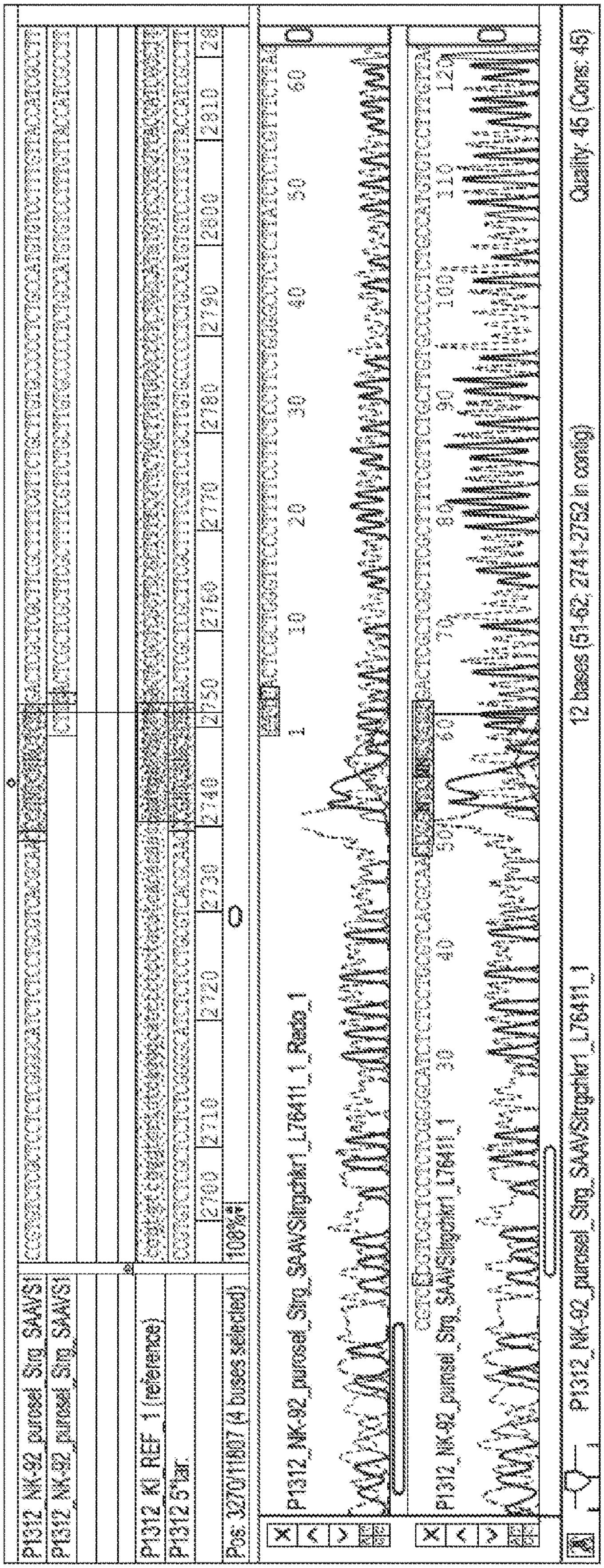
FIG. 24D shows sequencing of the 5' junction sites of inserted GEMS cassette and AAVs1 site from the pooled GFP positive NK92 cells. Correct junctions between AAVs1 site and 5' homology arm (upper panel) and between 5' homology arm and GEMS targeting cassette (lower panel) are shown.
Figure 24D:
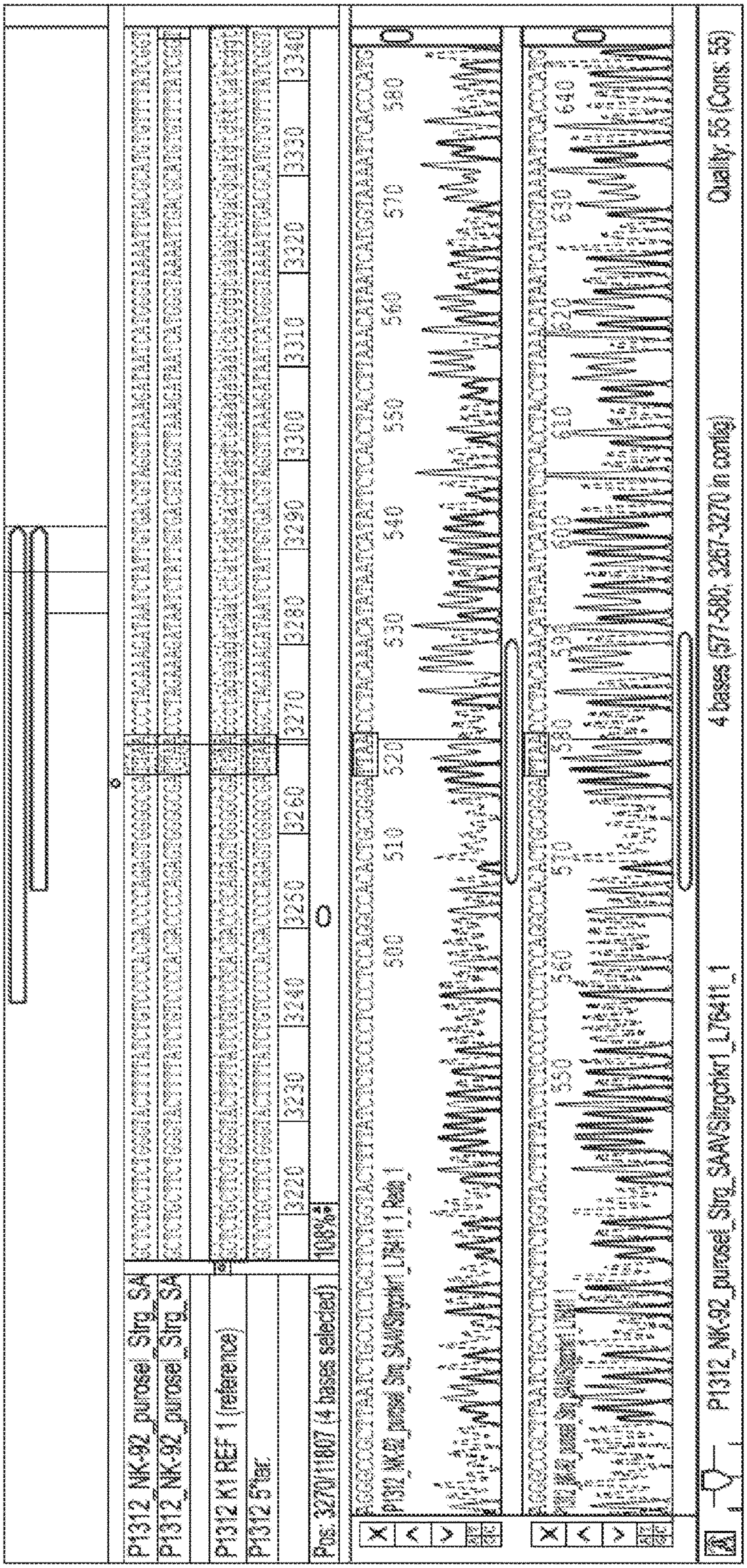

The proper insertion of GEMS into the AAVs1 site was evaluated by analyzing the 5' and 3' junction sites between the AAVs1 site and the inserted cassette by PCR using one primer specific to AAVs1 sequence and another primer specific to the inserted cassette sequence (SEQ ID NOs: 3-6), followed by Sanger sequencing of the PCR product. The appropriate 5' junction were confirmed by PCR with a correct 776 bp band (FIG. 24C) followed by Sanger sequencing (FIG. 24D), indicating successful targeted integration of GEMS sequence in the AAVs1 site. FIG. 24D shows sequencing of the 5' junction sites of inserted GEMS cassette and AAVs1 site from the pooled GFP positive NK92 cells. Correct junctions between AAVs1 site and 5' homology arm (upper panel) and between 5' homology arm and GEMS targeting cassette (lower panel) are shown.

Example 4. Engineering GEMS Sequence into the AAVs1 Site of Human Trophoblast Stem Cell (hTSC) Line

Establishment of Human Trophoblast Stem Cell (hTSC) Line

Human trophoblastic stem cells are prepared from tissues of healthy donors. The cells are maintained in culture media with proprietary growth factors. The expression of hTSC-specific markers and the pluripotency of the hTSC are evaluated.

Construction of Donor Plasmids for CRISPR-Mediated Genome Modification

To insert the GEMS sequence into the AAVS1 site of hTSC cell genome, a donor plasmid is constructed in which the GEMS sequence and a selection cassette are flanked by ~500 bp AAVS1 sequences surrounding the cutting site as the 5' and 3' homology arms to facilitate homology recombination. The selection cassette is composed of puromycin selection marker and GFP coding sequence, whose expressions are driven by e.g., CMV promoter. The selection cassette is flanked by loxP site sequences to facilitate the excision of the cassette by cre-loxP system if needed.

To insert a tumor targeting chimeric antigen receptor (CAR) into the GEMS sequence, a donor plasmid is constructed to express CD19 CAR composed of single chain Fv (scFv) against CD19, a hinge and transmembrane domain followed by 4-1BB costimulatory endodomain and the CD3-zeta intracellular signaling domain, under the control of e.g., EF-1α promoter. The CD19-CAR expression sequence, along with a blasticidin selection marker under e.g., CMV promoter, is flanked by GEMS sequence surrounding the cutting site as the 5' and 3' homology arms to facilitate homology recombination.

Establishment of GEMS-hTSC Cell Line

GEMS donor plasmid and AAVS1 CRISPR/Cas9 single shot plasmid are transfected into hTSC cells by electroporation using the 4D-Nucleofector™ System from Lonza. The viability pre, and post, nucleofection as well as the percentage of cells that become GFP signal positive are assessed 24 hours after transfection. The transfected cells are cultured in media with puromycin to select cells resistant to the killing by puromycin. Five days after transfection, transfected cells are collected to prepare genomic DNA. Surveyor nuclease assays are performed to estimate the efficiency of CRISPR/Cas9 activity in transfected cells.

Approximately two weeks after transfection, the puromycin resistant cells are sorted by flow cytometry to enrich GFP positive cells. Subsequently, the cells are plated into 96-well plate and single cell cloning is performed to generate monoclonal GEMS-modified hTSC cells. The GEMS sequence integrated into the cell genome is evaluated by PCR using primers specific to GEMS sequence followed by Sanger sequencing of the PCR product. The proper insertion of GEMS into the AAVS1 site is evaluated by analyzing the 5' and 3' junction sites between the AAVS1 site and the inserted cassette by PCR using one primer specific to AAVS1 sequence and another primer specific to the inserted cassette sequence, followed by Sanger sequencing of the PCR product. The puromycin-GFP selection cassette is excised from the genome of the established GEMS-hTSC cell lines by cre-loxP system. Whole genome sequencing is performed on established cell lines to assess on- and off-target insertion.

Example 5. Engineering CD19 CAR into the GEMS Sequence of GEMS Modified hTSC Cells Establishment of CD19 CAR-hTSC Cell Line CD19 CAR donor plasmid, Cas9 plasmid, and GEMS site-specific sgRNA expression plasmid are transfected into GEMS-hTSC cells by electroporation using the 4D-Nucleofector™ System. The transfected cells are cultured in media with blasticidin to select cells resistant to the killing by the antibiotics. Five days after transfection, transfected cells are collected to prepare genomic DNA. Surveyor nuclease assays are performed to estimate the efficiency of CRISPR/Cas9 activity in transfected cells.

Approximately two weeks after transfection, the blasticidin resistant cells are stained with fluorescence-labeled anti-hIgG Fab and sorted by flow cytometry to enrich CD19-scFv positive cells. Subsequently, the cells are plated into 96-well plate, and single cell cloning is performed to generate monoclonal CD19 CAR-modified hTSC cells. The CD19 CAR sequence integrated into the cell genome is evaluated by PCR using primers specific to CD19 CAR sequence followed by Sanger sequencing of the PCR product. The proper insertion of CD19 CAR into the specific GEMS site is evaluated by analyzing the 5' and 3' junction sites between the GEMS site and the inserted cassette by PCR using one primer specific to GEMS sequence and another primer specific to the inserted cassette sequence, followed by Sanger sequencing of the PCR product. Whole genome sequencing is performed on established CAR-hTSC cell lines to assess on- and off-target insertion.

The expression of CD19 CAR on the established CAR-hTSC cell lines are evaluated by Western blot analysis and immunostaining using anti-hIgG Fab recognizing CD19-scFv and antibodies recognizing 4-1BB costimulatory endodomain and the CD3-zeta intracellular signaling domain. The expression of hTSC-specific markers and the pluripotency of the CAR-hTSC cells are evaluated.

Induction of CD19 CAR-hTSC cell differentiation into CD19 CAR-NKT cells

The CD19 CAR-hTSC cells are induced to differentiate into CD19 CAR-NKT cells in culture media with proprietary differentiation factors. The differentiated CD19 CAR-NKT cells are enriched by flow sorting and the expression of NKT cell-specific markers are verified by immunostaining and RT-PCR.

To evaluate the functional activity of the NKT cells, the differentiated cells are co-cultured with K562 target cells in various effector: target cell ratio. The cytokines (e.g., TNFα, IFNγ) produced and CD107a degranulation from the differentiated NKT cells in response to stimulation with K562 target cells are evaluated. To evaluate the tumor cell killing activity of the differentiated NKT cells, the K562 cells are labeled by fluorescence and co-cultured with CAR-NKT cells in a cytotoxic assay. The killing of labeled K562 cells by the differentiated NKT cells is evaluated by flow cytometry.

Alternatively, the CD19 CAR can be introduced after GEMS-hTSC cells are differentiated into NKT cells.

Induction of CD19 CAR-hTSC Cell Differentiation into CD19 CAR-NK Cells

The CD19 CAR-hTSC cells can also be induced to differentiate into CD19 CAR-NK cells in culture media with proprietary differentiation factors. The differentiated CD19 CAR-NK cells are enriched by flow sorting and the expression of NK cell-specific markers are verified by immunostaining and RT-PCR.

Alternatively, the CD19 CAR can be introduced after GEMS-hTSC cells are differentiated into NK cells.

In Vitro Functional Evaluation of CD19-CAR Activity in CD19 CAR-NKT Cells or CD19 CAR-NK Cells To evaluate the CD19-CAR mediated tumor cell killing activity of differentiated CAR-NKT cells or CAR-NK cells in vitro, Raji cells expressing CD19 are labeled by fluorescence and co-cultured with CAR-NKT cells or CAR-NK cells in a cytotoxic assay in different effector: target cell ratio. The killing of labeled Raji cells by the differentiated NKT cells or CAR-NK cells is evaluated by flow cytometry. In addition to Raji cells, cytotoxic assays can also be set up with labeled CD19 positive primary leukemia cells isolated from patients as the target cells.

The evaluation of tumor cell killing activity, the cytokines (e.g., TNFα, IFNγ) produced and CD107a degranulation from the activated CAR-NKT cells or CAR-NK cells in response to stimulation with Raji and primary leukemia target cells are evaluated. Immunologic synapse formation between CAR-NKT cells and Raji/leukemia cells are evaluated by confocal microscope for CD19-CAR accumulation, cytotoxic granules accumulation, and polarization of microtubule-organizing center at the synapse.

In Vivo Functional Evaluation of CD19-CAR Activity in CAR-NKT Cells or CAR-NK Cells The in vivo anti-tumor activity of CAR-NKT cells or CAR-NK cells is evaluated in a xenogeneic lymphoma model. To establish the disease model, Raji cells are labeled by transduction with lentiviral vector encoding firefly luciferase. The labeled Raji cells are xenografted into NOD-SCID mice. The disease progression is monitored to evaluate the establishment of the mouse-human tumor model.

To evaluate the anti-tumor effects of CAR-NKT or CAR-NK cells, the cells are dosed intravenously into the mice xenografted with labeled Raji cells. The growth of firefly luciferase -labeled Raji tumor cells in mice is monitored by bioluminescence imaging. Blood and major disease-related organs (bone marrow, liver, spleen) from mice treated with CAR-NKT cells or CAR-NK cells are collected. The amplification of CAR-NKT cells or CAR-NK cells and the killing of Raji cells in these tissues are quantitated by flow cytometry.

The established CAR-NKT cells or CAR-NK cells can be further evaluated in clinical trials to treat CD19 positive B-cell lymphomas.

SEQUENCES

Provided herein is a representative list of certain sequences included in embodiments provided herein.

TABLE 8

| SEQ ID NO | Description | Sequence (5' to 3') |
|---|---|---|
| 1 | I-SceI meganuclease recognition site | TAGGGATAACAGGGTAAT |
| 2 | Second generation GEMS 2.0 | CCATCGTACGTCGGAATACGGATCTAATCAACTTTCTGCC GTACTGTGATACACGCGACAGGAACTGTGCGAAATCGCCA TAGCGATTTATCGGAGCGCCATTACGTACTCAGCTTATTAC CGATACGATACGAACAGGTCTAGCAAACTGCTGCCTGACG ACGGTTGCGCGTCCGTTAATACAGCACAAAAGTAATCGGT TGCGCCGCTCGGGGGATCGAGTTTAACTCACCTACGCTAC GCTAACGGGCGATCGTTCGTACGCGAGTTTTATTTACCCCG CGCGAGGTGGGCGAAATTATAGTCGTCCAAGACCGACGTA CGATACAACTCTAAATTTGCAGAATAGTATTCGAGTACGC GTCGATGGAAGTCATATCACGCGCCCATCGACGCGTACTC GAATACTGAACTCGCGTTCGACGCGTGCGATCGTACCGTG TACGGACTAGCGTCTGCTTACCTACGCTACGCTAACGGGC GATCACAGTTTGTGTCATCCGCATGGCAATCTACGCGCGA GGATTTTTGTGCTCAAGCCGGATCGACCGGGTCGGTTCAC TAACATCAGACGCAAATTCTTCGATACGGTACGAATAGGC GTTTTGGTCCGCCCCCGGCGTACGCGTCCCATATAAACTGT TGTCTAATTCAAAGAGTGGCCGCGATAATCGAAGGACATT TGTTACAAGACCTACCGGTTACCGCGAGGATTAATGTATC TTACACGTAAGAGTGGGCGCGAATATCGTAGG |
| 3 | 5' junction site forward primer (5'AAVS1 targCheckF1) | TTCCGGAGCACTTCCTTCT |
| 4 | 5' junction site reverse primer (5'AAVS1 targCheckR1) | CCGATAAAACACATGCGTCA |
| 5 | 3' junction site forward primer (3'AAVS1 targCheckF1) | CACGCGGTCGTTATAGTTCA |
| 6 | 3' junction site reverse primer (3'AAVS1 targCheckR1) | CGGAGGAATATGTCCCAGAT |
| 7 | AAVs1 5' homology arm | CGTCTTCACTCGCTGGGTTCCCTTTTCCTTCTCCTTCTGGGG CCTGTGCCATCTCTCGTTTCTTAGGATGGCCTTCTCCGACG GATGTCTCCCTTGCGTCCCGCCTCCCCTTCTTGTAGGCCTG CATCATCACCGTTTTTCTGGACAACCCCAAAGTACCCCGTC TCCCTGGCTTTAGCCACCTCTCCATCCTCTTGCTTTCTTTGC CTGGACACCCCGTTCTCCTGTGGATTCGGGTCACCTCTCAC TCCTTTCATTTGGGCAGCTCCCCTACCCCCCTTACCTCTCT AGTCTGTGCTAGCTCTTCCAGCCCCCTGTCATGGCATCTTC CAGGGGTCCGAGAGCTCAGCTAGTCTTCTTCCTCCAACCC GGGCCCCTATGTCCACTTCAGGACAGCATGTTTGCTGCCTC CAGGGATCCTGTGTCCCCGAGCTGGGACCACCTTATATTC CCAGGGCCGGTTAATGTGGCTCTGGTTCTGGGTACTTTTAT CTGTCCCCTCCACCCCACAGTGGGGC |
| 8 | AAVs1 3' homology arm | GGACAGGATTGGTGACAGAAAAGCCCCATCCTTAGGCCTC CTCCTTCCTAGTCTCCTGATATTGGGTCTAACCCCCACCTC CTGTTAGGCAGATTCCTTATCTGGTGACACACCCCCATTTC CTGGAGCCATCTCTCTCCTTGCCAGAACCTCTAAGGTTTGC TTACGATGGAGCCAGAGAGGATCCTGGGAGGGAGAGCTT GGCAGGGGGTGGGAGGGAAGGGGGGGATGCGTGACCTGC CCGGTTCTCAGTGGCCACCCTGCGCTACCCTCTCCCAGAAC CTGAGCTGCTCTGACGCGGCCGTCTGGTGCGTTTCACTGAT CCTGGTGCTGCAGCTTCCTTACACTTCCCAAGAGGAGAAG CAGTTTGGAAAAACAAAATCAGAATAAGTTGGTCCTGAGT TCTAACTTTGGCTCTTCACCTTTCTAGTCCCCAATTTATATT GTTCCTCCGTGCGTCAGTTTTACCTGTGAGATAAGGCCAGT AGCCAGCCCCGTCCTGGCAGGGCTGTGGTGAGGAGGGGG GTGTC |
| 9 | AAVs1 CRISPR targeting sequence | GGGGCCACTAGGGACAGGATTGG |

TABLE 8-continued

| Sequences | | |
|---|---|---|
| SEQ ID NO | Description | Sequence (5' to 3') |
| 10 | AAVs1 CRISPR guide RNA | GGGGCCACTAGGGACAGGATGTTTTAGAGCTAGAAATAGC AAGTTAAAATAAGGCTAGTCCGTTATCAACTTGAAAAAGT GGCACCGAGTCGGTGCTTTTTT |
| 11 | CMV promoter | ACATTGATTATTGACTAGTTATTAATAGTAATCAATTACGG GGTCATTAGTTCATAGCCCATATATGGAGTTCCGCGTTACA TAACTTACGGTAAATGGCCCGCCTGGCTGACCGCCCAACG ACCCCCGCCCATTGACGTCAATAATGACGTATGTTCCCAT AGTAACGCCAATAGGGACTTTCCATTGACGTCAATGGGTG GACTATTTACGGTAAACTGCCCACTTGGCAGTACATCAAG TGTATCATATGCCAAGTACGCCCCCTATTGACGTCAATGA CGGTAAATGGCCCGCCTGGCATTATGCCCAGTACATGACC TTATGGGACTTTCCTACTTGGCAGTACATCTACGTATTAGT CATCGCTATTACCATGGTGATGCGGTTTTGGCAGTACATCA ATGGGCGTGGATAGCGGTTTGACTCACGGGGATTTCCAAG TCTCCACCCCATTGACGTCAATGGGAGTTTGTTTTGGCACC AAAATCAACGGGACTTTCCAAAATGTCGTAACAACTCCGC CCCATTGACGCAAATGGGCGGTAGGCGTGTACGGTGGGAG GTCTATATAAGCAGAGCTCTCTGGCTAACTAGAGAACCCA CTGCTTACTGG |
| 12 | GFP | ATGGAGAGCGACGAGAGCGGCCTGCCCGCCATGGAGATC GAGTGCCGCATCACCGGCACCCTGAACGGCGTGGAGTTCG AGCTGGTGGGCGGCGGAGAGGGCACCCCCAAGCAGGGCC GCATGACCAACAAGATGAAGAGCACCAAAGGCGCCCTGA CCTTCAGCCCCTACCTGCTGAGCCACGTGATGGGCTACGG CTTCTACCACTTCGGCACCTACCCCAGCGGCTACGAGAAC CCCTTCCTGCACGCCATCAACAACGGCGGCTACACCAACA CCCGCATCGAGAAGTACGAGGACGGCGGCGTGCTGCACGT GAGCTTCAGCTACCGCTACGAGGCCGGCCGCGTGATCGGC GACTTCAAGGTGGTGGGCACCGGCTTCCCCGAGGACAGCG TGATCTTCACCGACAAGATCATCCGCAGCAACGCCACCGT GGAGCACCTGCACCCCATGGGCGATAACGTGCTGGTGGGC AGCTTCGCCCGCACCTTCAGCCTGCGCGACGGCGGCTACT ACAGCTTCGTGGTGGACAGCCACATGCACTTCAAGAGCGC CATCCACCCCAGCATCCTGCAGAACGGGGGCCCCATGTTC GCCTTCCGCCGCGTGGAGGAGCTGCACAGCAACACCGAGC TGGGCATCGTGGAGTACCAGCACGCCTTCAAGACCCCCAT CGCCTTCGCCAGATCCCGCGCTCAGTCGTCCAATTCTGCCG TGGACGGCACCGCCGGACCCGGCTCCACCGGATCTCGC ATGACCGAGTACAAGCCCACGGTGCGCCTCGCCACCCGCG ACGACGTCCCCAGGGCCGTCCGCACCCTCGCCGCCGCGTT CGCCGACTACCCCGCCACGCGCCACACCGTCGATCCGGAC CGCCACATCGAGCGGGTCACCGAGCTGCAAGAACTCTTCC TCACGCGCGTCGGGCTCGACATCGGCAAGGTGTGGGTCGC GGACGACGGCGCCGCGGTGGCGGTCTGGACCACGCCGGA GAGCGTCGAAGCGGGGGCGGTGTTCGCCGAGATCGGCCC |
| 13 | puromycin | GCGCATGGCCGAGTTGAGCGGTTCCCGGCTGGCCGCGCAG CAACAGATGGAAGGCCTCCTGGCGCCGCACCGGCCCAAG GAGCCCGCGTGGTTCCTGGCCACCGTCGGCGTCTCGCCCG ACCACCAGGGCAAGGGTCTGGGCAGCGCCGTCGTGCTCCC CGGAGTGGAGGCGGCCGAGCGCGCCGGGGTGCCCGCCTTC CTGGAGACCTCCGCGCCCCGCAACCTCCCCTTCTACGAGC GGCTCGGCTTCACCGTCACCGCCGACGTCGAGGTGCCCGA AGGACCGCGCACCTGGTGCATGACCCGCAAGCCCGGTGCC |
| 14 | GEMS site 16 targeting sequence | TGCTTGTGCATACATAACAACGG |
| 15 | GEMS site 16 guide RNA | TGCTTGTGCATACATAACAAGTTTTAGAGCTAGAAATAGC AAGTTAAAATAAGGCTAGTCCGTTATCAACTTGAAAAAGT GGCACCGAGTCGGTGC |

TABLE 8-continued

| Sequences | | |
|---|---|---|
| SEQ ID NO | Description | Sequence (5' to 3') |
| 16 | GEMS site 16 5' homology arm | GGGACAGCCCCCCCCCAAAGCCCCCAGGGATGTAATTACG TCCCTCCCCCGCTAGGGGGCAGCAGCGAGCCGCCCGGGGC TCCGCTCCGGTCCGGCGCTCCCCCCGCATCCCCGAGCCGG CAGCGTGCGGGGACAGCCCGGGCACGGGGAAGGTGGCAC GGGATCGCTTTCCTCTGAACGCTTCTCGCTGCTCTTTGAGC CTGCAGACACCTGGGGGGATACGGGGAAAAGGCCTCCAA GGCCAGCTTCCCACAATAAGTTGGGTGAATTTTGGCTCATT CCTCCTTTCTATAGGATTGAGGTCAGAGCTTTGTGATGGGA ATTCTGTGGAATGTGTGTCAGTTAGGGTGTGGAAAGTCCC GCGATCGCTCACGAGCAAGCGA |
| 17 | GEMS site 16 3' homology arm | GATATGTTAACGATGCTGAATTAGATTTGCGTTACTCGGA ACTGTGCGAAATCGCCGACGTAGCGTTCGAGTAGCGCATT ACGTACTCAGCTTTCACAATCACTCAAGAAGCACGGTCTA GCAAACTGCTGCCGTCGCACAAGCACAGTCTCGTTAATAC AGCACAAAAGCTTTAGACACAGTAAGACAACGGATCGAG TTTAACTCACCGAGATGCTCTGCGCGCTGCAACGTTCGTAC GCGAGTTCCCGCAATAGAGAGCTTTGACGGCGAAATTATA GTCGTCCGATGCTATTTATTAACGCGTCATAACGTGGAAC GTATCTGCATGTCTAGCGGACAGAGCGAAATCTTCCGTTA ATTCTAAAGCAATCGAATCTAAATTTGCAGAATCATGCCT TTAGAATTCAGTACGGAAGTCATATCACGCGCCGTTGTTA CACGCGTACTGTATTGAACTCGCGTTCGACTGTGTTAGCGC GCTGATCTGCGGACTAGCGTCTGCTTACCGCTGACGCGTT ATGCTAAATCCACAGTTTGTGTCATCTACGAAGTCGAGAT AAAATGCGGATTTTTGTGCTCAAGCCGCGTCATTGCAAG CGTGAGGCTCCGGTGCCCGTCAGTGGGCAGAGCGCACATC GCCCACAGTCCCCGAGAAGTTGGGGGGAGGGGTCGGCAA TTGAACCGGTGCCTAGAGAAGGTGGCGCGGGGTAAACTG GGAAAGTGATGTCGTGTACTGGCTCCGCCTTTTTCCCGAG GGTGGGGGAGAACCGTATATAAGTGCAGTAGTCGCCGTGA ACGTTCTTTTTCGCAACGGGTTTGCCGCCAGAACACAGGT AAGTGCCGTGTGTGGTTCCCGCGGGCCTGGCCTCTTTACG GGTTATGGCCCTTGCGTGCCTTGAATTACTTCCACCTGGCT GCAGTACGTGATTCTTGATCCCGAGCTTCGGGTTGGAAGT GGGTGGGAGAGTTCGAGGCCTTGCGCTTAAGGAGCCCCTT CGCCTCGTGCTTGAGTTGAGGCCTGGCCTGGGCGCTGGGG CCGCCGCGTGCGAATCTGGTGGCACCTTCGCGCCTGTCTC GCTGCTTTCGATAAGTCTCTAGCCATTTAAAATTTTTGATG ACCTGCTGCGACGCTTTTTTTCTGGCAAGATAGTCTTGTAA ATGCGGGCCAAGATCTGCACACTGGTATTTCGGTTTTTGG |
| 18 | EF-1alpha promoter | GGCCGCGGGCGGCGACGGGGCCCGTGCGTCCCAGCGCAC ATGTTCGGCGAGGCGGGGCCTGCGAGCGCGGCCACCGAG AATCGGACGGGGGTAGTCTCAAGCTGGCCGGCCTGCTCTG GTGCCTGGCCTCGCGCCGCCGTGTATCGCCCCGCCCTGGG CGGCAAGGCTGGCCCGGTCGGCACCAGTTGCGTGAGCGGA AAGATGGCCGCTTCCCGGCCCTGCTGCAGGGAGCTCAAAA TGGAGGACGCGGCGCTCGGGAGAGCGGGCGGGTGAGTCA CCCACACAAAGGAAAAGGGCCTTTCCGTCCTCAGCCGTCG CTTCATGTGACTCCACGGAGTACCGGGCGCCGTCCAGGCA CCTCGATTAGTTCTCGAGCTTTTGGAGTACGTCGTCTTTAG GTTGGGGGGAGGGGTTTTATGCGATGGAGTTTCCCCACAC TGAGTGGGTGGAGACTGAAGTTAGGCCAGCTTGGCACTTG ATGTAATTCTCCTTGGAATTTGCCCTTTTTGAGTTTGGATC TTGGTTCATTCTCAAGCCTCAGACAGTGGTTCAAAGTTTTT TTCTTCCATTTCAGGTGTCGTGA |
| 19 | blasticidin | ATGGCCAAGCCTTTGTCTCAAGAAGAATCCACCCTCATTG AAAGAGCAACGGCTACAATCAACAGCATCCCCATCTCTGA AGACTACAGCGTCGCCAGCGCAGCTCTCTCTAGCGACGGC CGCATCTTCACTGGTGTCAATGTATATCATTTTACTGGGGG ACCTTGTGCAGAACTCGTGGTGCTGGGCACTGCTGCTGCT GCGGCAGCTGGCAACCTGACTTGTATCGTCGCGATCGGAA ATGAGAACAGGGGCATCTTGAGCCCCTGCGGACGGTGCCG ACAGGTGCTTCTCGATCTGCATCCTGGGATCAAAGCCATA GTGAAGGACAGTGATGGACAGCCGACGGCAGTTGGGATT CGTGAATTGCTGCCCTCTGGTTATGTGTGGGAGGGC |
| 20 | CD19 scFv | GAAATTGTGATGACCCAGTCACCCGCCACTCTTAGCCTTTC ACCCGGTGAGCGCGCAACCCTGTCTTGCAGAGCCTCCCAA GACATCTCAAAATACCTTAATTGGTATCAACAGAAGCCCG GACAGGCTCCTCGCCTTCTGATCTACCACACCAGCCGGCT CCATTCTGGAATCCCTGCCAGGTTCAGCGGTAGCGGATCT |

TABLE 8-continued

| Sequences | | |
|---|---|---|
| SEQ ID NO | Description | Sequence (5' to 3') |
| | | GGGACCGACTACACCCTCACTATCAGCTCACTGCAGCCAG AGGACTTCGCTGTCTATTTCTGTCAGCAAGGGAACACCCT GCCCTACACCTTTGGACAGGGCACCAAGCTCGAGATTAAA GGTGGAGGTGGCAGCGGAGGAGGTGGGTCCGGCGGTGGA GGAAGCCAGGTCCAACTCCAAGAAAGCGGACCGGGTCTT GTGAAGCCATCAGAAACTCTTTCACTGACTTGTACTGTGA GCGGAGTGTCTCTCCCCGATTACGGGGTGTCTTGGATCAG ACAGCCACCGGGGAAGGGTCTGGAATGGATTGGAGTGATT TGGGGCTCTGAGACTACTTACTACAACTCATCCCTCAAGTC ACGCGTCACCATCTCAAAGGACAACTCTAAGAATCAGGTG TCACTGAAACTGTCATCTGTGACCGCAGCCGACACCGCCG TGTACTATTGCGCTAAGCATTACTATTATGGCGGGAGCTA CGCAATGGATTACTGGGGACAGGGTACTCTGGTCACCGTG TCCAGC |
| 21 | CD8 hinge and domain transmembrane | ACCACTACCCCAGCACCGAGGCCACCCACCCCGGCTCCTA CCATCGCCTCCCAGCCTCTGTCCCTGCGTCCGGAGGCATGT AGACCCGCAGCTGGTGGGGCCGTGCATACCCGGGGTCTTG ACTTCGCCTGCGATATCTACATTTGGGCCCCTCTGGCTGGT ACTTGCGGGGTCCTGCTGCTTTCACTCGTGATCACTCTTTA CTGT |
| 22 | 4-1BB endodomain | AAGCGCGGTCGGAAGAAGCTGCTGTACATCTTTAAGCAAC CCTTCATGAGGCCTGTGCAGACTACTCAAGAGGAGGACGG CTGTTCATGCCGGTTCCCAGAGGAGGAGGAAGGCGGCTGC GAACTG |
| 23 | CD3 zeta domain | CGCGTGAAATTCAGCCGCAGCGCAGATGCTCCAGCCTACA AGCAGGGGCAGAACCAGCTCTACAACGAACTCAATCTTGG TCGGAGAGAGGAGTACGACGTGCTGGACAAGCGGAGAGG ACGGGACCCAGAAATGGGCGGGAAGCCGCGCAGAAAGAA TCCCCAAGAGGGCCTGTACAACGAGCTCCAAAAGGATAA GATGGCAGAAGCCTATAGCGAGATTGGTATGAAAGGGGA ACGCAGAAGAGGCAAAGGCCACGACGGACTGTACCAGGG ACTCAGCACCGCCACCAAGGACACCTATGACGCTCTTCAC ATGCAGGCCCTGCCGCCTCGG |
| 81 | GEMS core sequence (lead) | CGCTCTTGCTTTCGTCAATGAAACGAGTTGCGTCATTCGAT GAACGTTGT |
| 82 | GEMS core sequence (core) | TCACGAGCAAGCGACCGTTGTTATGTATGCACAAGCAGAT ATGTTAACGATGCTGAATTAGATTTGCGTTACTCGGAACT GTGCGAAATCGCCGACGTAGCGTTCGAGTAGCGCATTACG TACTCAGCTTTCACAATCACTCAAGAAGCACGGTCTAGCA AACTGCTGCCGTCGCACAAGCACAGTCTCGTTAATACAGC ACAAAAGCTTTAGACACAGTAAGACAACGGATCGAGTTTA ACTCACCGAGATGCTCTGCGCGCTGCAACGTTCGTACGCG AGTTCCCGCAATAGAGAGCTTTGACGGCGAAATTATAGTC GTCCGATGCTATTTATTAACGCGTCATAACGTGGAACGTA TCTGCATGTCTAGCGGACAGAGCGAAATCTTCCGTTAATT CTAAAGCAATCGAATCTAAATTTGCAGAATCATGCCTTTA GAATTCAGTACGGAAGTCATATCACGCGCCGTTGTTACAC GCGTACTGTATTGAACTCGCGTTCGACTGTGTTAGCGCGCT GATCTGCGGACTAGCGTCTGCTTACCGCTGACGCGTTATG CTAAATCCACAGTTTGTGTCATCTACGAAGTCGAGATAAA ATGCGGATTTTTGTGCTCAAGCCGCGTCATTGCAAGTAGA CGCGTAACATCAGACGCAAAGCATAACCAGTACGCAAGA TCGGCGTTTTGGTCCGCCCCCGTCGATTGCTTTCTCATCGT ACTGTTGTCTAATTCAATTTTGCTACATCTTGTAATACGGA CATTTGTTACAAGACCGATCTGCGAGCGATTTAGAAATAC CTTATATTATAATATTCAGTAGAAACGGCTTCTTTTAAACA CTCCGAGCGTGACAGCTCGATAGTGATGTATCTTACACGT ACAGCTACGAGTCACGATGTACGGTTCTTCGTGCGCAGTC CGCTGATCGCAGTGCATTCTCAAGTTTGCTCGAGCGAACA ATGACAATAGCGATAACGCGGATGTGCTGTCTCGAACCGC CGATCGTACATAGATCCTGATCATCTACGCATGTCGTTACG TTCGCGAAGCGTTGCGGACTTGCGATGTACATCCGACGCG CACGCAGCTGTATAACTAATCAACTTTCTGCGCGTAACAA CTTCTGAGTTGCGGATCAGCTGCACTAACAAAGAGCACGT CTAGTTCGTTTACAAAGTACTCATTTACTCGTCGTATGATT GTGATCTGAGCGTTCTAGCTTACTACATGTGCGTGTTCCGA ATATGAATCTTTACTCGCGCGTTTACTCGTCGTATGATTGT CATAGCGCACTCTGCGCTTACTACATGTGCGTGTTCCGGA GCAAGCGAAAACGCGAATCCTAGTTTACTCGTCGTATGAT |

TABLE 8-continued

| Sequences | | |
|---|---|---|
| SEQ ID NO | Description | Sequence (5' to 3') |
| | | TGTTCAATACGAGCTAAAGCTTACTACATGTGCGTGTTCG<br>AAAACGCGTGCACTAGCGAGATTCTGCTTTACTCGTCGTA<br>TGATTGTTGCAGTCACGCAGTGTTCTTACTACATGTGCGTG<br>TTCGCAAAGAGCAAACGAAAATTTTATTTACTCGTCGTAT<br>GATTGTGCGATCAACACGTAACCTTACTACATGTGCGTGTT<br>CTGGAGAATCATAAAAGAGCCGCAATTTTTTTACTCGTCG<br>TATGATTGTCGTAACGCTAAGACGCCTTACTACATGTGCGT<br>GTTCGAGACCAACGAACGACAGAGCATATTTTTCGTTTAC<br>TCGTCGTATGATTGTTTCACATAATCGCACTCTTACTACAT<br>GTGCGTGTTCTGAAAGTATTTTACGTTAGCCTTGCACAGAG<br>TGCGACAACTCTGTGCAAGAGTTTGCAAAATTTCCGCACG<br>CGCTTTCGTTACAAAGCGCGTGCGACAAACGATATTTTCG<br>TTTTACGCGAGAGAATGCTCGCGTAAAACATTCAGAAACG<br>AGCGCGCAGTCAGCACTACTGCGTGCTGACTGCGATCTAC<br>TAGTGACGA |
| 83 | GEMS core sequence (tail) | CAGCTTCGCTTTTCGTCGAGATGCTTTACGTAGATGCAATG<br>ACGCACGTA |
| 84 | GEMS | TCACGAGCAAGCGACCGTTGTTATGTATGCACAAGCAGAT<br>ATGTTAACGATGCTGAATTAGATTTGCGTTACTCGGAACT<br>GTGCGAAATCGCCGACGTAGCGTTCGAGTAGCGCATTACG<br>TACTCAGCTTTCACAATCACTCAAGAAGCACGGTCTAGCA<br>AACTGCTGCCGTCGCACAAGCACAGTCTCGTTAATACAGC<br>ACAAAAGCTTTAGACACAGTAAGACAACGGATCGAGTTTA<br>ACTCACCGAGATGCTCTGCGCGCTGCAACGTTCGTACGCG<br>AGTTCCCGCAATAGAGAGCTTTGACGGCGAAATTATAGTC<br>GTCCGATGCTATTTATTAACGCGTCATAACGTGGAACGTA<br>TCTGCATGTCTAGCGGACAGAGCGAAATCTTCCGTTAATT<br>CTAAAGCAATCGAATCTAAATTTGCAGAATCATGCCTTTA<br>GAATTCAGTACGGAAGTCATATCACGCGCCGTTGTTACAC<br>GCGTACTGTATTGAACTCGCGTTCGACTGTGTTAGCGCGCT<br>GATCTGCGGACTAGCGTCTGCTTACCGCTGACGCGTTATG<br>CTAAATCCACAGTTTGTGTCATCTACGAAGTCGAGATAAA<br>ATGCGGATTTTTGTGCTCAAGCCGCGTCATTGCAAGTAGA<br>CGCGTAACATCAGACGCAAAGCATAACCAGTACGCAAGA<br>TCGGCGTTTTGGTCCGCCCCCGTCGATTGCTTTCTCATCGT<br>ACTGTTGTCTAATTCAATTTTGCTACATCTTGTAATACGGA<br>CATTTGTTACAAGACCGATCTGCGAGCGATTTAGAAATAC<br>CTTATATTATAATATTCAGTAGAAACGGCTTCTTTTAAACA<br>CTCCGAGCGTGACAGCTCGATAGTGATGTATCTTACACGT<br>ACAGCTACGAGTCACGATGTACGGTTCTTCGTGCGCAGTC<br>CGCTGATCGCAGTGCATTCTCAAGTTTGCTCGAGCGAACA<br>ATGACAATAGCGATAACGCGGATGTGCTGTCTCGAACCGC<br>CGATCGTACATAGATCCTGATCATCTACGCATGTCGTTACG<br>TTCGCGAAGCGTTGCGGACTTGCGATGTACATCCGACGCG<br>CACGCAGCTGTATAACTAATCAACTTTCTGCGCGTAACAA<br>CTTCTGAGTTGCGGATCAGCTGCACTAACAAAGAGCACGT<br>CTAGTTCGTTTACAAAGTACTCATTTACTCGTCGTATGATT<br>GTGATCTGAGCGTTCTAGCTTACTACATGTGCGTGTTCCGA<br>ATATGAATCTTTACTCGCGCGTTTACTCGTCGTATGATTGT<br>CATAGCGCACTCTGCGCTTACTACATGTGCGTGTTCCGGA<br>GCAAGCGAAAACGCGAATCCTAGTTTACTCGTCGTATGAT<br>TGTTCAATACGAGCTAAAGCTTACTACATGTGCGTGTTCG<br>AAAACGCGTGCACTAGCGAGATTCTGCTTTACTCGTCGTA<br>TGATTGTTGCAGTCACGCAGTGTTCTTACTACATGTGCGTG<br>TTCGCAAAGAGCAAACGAAAATTTTATTTACTCGTCGTAT<br>GATTGTGCGATCAACACGTAACCTTACTACATGTGCGTGTT<br>CTGGAGAATCATAAAAGAGCCGCAATTTTTTTACTCGTCG<br>TATGATTGTCGTAACGCTAAGACGCCTTACTACATGTGCGT<br>GTTCGAGACCAACGAACGACAGAGCATATTTTTCGTTTAC<br>TCGTCGTATGATTGTTTCACATAATCGCACTCTTACTACAT<br>GTGCGTGTTCTGAAAGTATTTTACGTTAGCCTTGCACAGAG<br>TGCGACAACTCTGTGCAAGAGTTTGCAAAATTTCCGCACG<br>CGCTTTCGTTACAAAGCGCGTGCGACAAACGATATTTTCG<br>TTTTACGCGAGAGAATGCTCGCGTAAAACATTCAGAAACG<br>AGCGCGCAGTCAGCACTACTGCGTGCTGACTGCGATCTAC<br>TAGTGACGA |

What is claimed is:

1. An engineered gene editing multi-site (GEMS) polynucleotide construct for insertion into a genome at an insertion site, wherein said engineered GEMS polynucleotide construct comprises:

a GEMS polynucleotide sequence comprising a plurality of nuclease recognition sequences, wherein at least one of said plurality of nuclease recognition sequences comprises the nucleotide sequence of SEQ ID NO: 14.

2. The engineered GEMS polynucleotide construct of claim 1, wherein said plurality of nuclease recognition sequences comprises at least 2, 3, 4, 5, 6, 7, 8, 9, 10, or more nuclease recognition sequences.

3. The engineered GEMS polynucleotide construct of claim 1, wherein each of said plurality of nuclease recognition sequences comprises a unique sequence.

4. The engineered GEMS polynucleotide construct of claim 1, further comprising:

(a) a first flanking insertion sequence homologous to a first genome sequence upstream of said insertion site, said first flanking insertion sequence located upstream of said GEMS polynucleotide sequence; and (b) a second flanking insertion sequence homologous to a second genome sequence downstream of said insertion site, said second flanking insertion sequence located downstream of said GEMS polynucleotide sequence.

5. The engineered GEMS polynucleotide construct of claim 1, wherein each of said plurality of nuclease recognition sequences is separated from an adjacent nuclease recognition sequence by a polynucleotide spacer.

6. A method of producing a host cell comprising a gene editing multi-site (GEMS) polynucleotide sequence, the method comprising:

introducing said engineered GEMS polynucleotide construct of claim 1 into said host cell.

7. An isolated host cell comprising a gene editing multi-site (GEMS) polynucleotide sequence in said host cell's genome, wherein said GEMS polynucleotide sequence comprises a plurality of nuclease recognition sequences, wherein at least one of said plurality of nuclease recognition sequences comprises the nucleotide sequence of SEQ ID NO: 14.

8. The isolated host cell of claim 7, wherein said host cell is a mammalian cell.

9. The isolated host cell of claim 8, wherein said mammalian cell is a stem cell, a T cell, or a NK cell.

10. The isolated host cell of claim 7, further comprising a donor nucleic acid sequence, wherein said donor nucleic acid sequence is inserted within said GEMS polynucleotide sequence.

11. The isolated host cell of claim 10, wherein said donor nucleic acid sequence encodes a therapeutic protein.

12. The isolated host cell of claim 11, wherein said therapeutic protein comprises a chimeric antigen receptor (CAR), a T-cell receptor (TCR), a B-cell receptor (BCR), an $\alpha\beta$ receptor, and a $\gamma\delta$ T-receptor.

13. A method of engineering a GEMS modified cell, the method comprising:

(a) providing said isolated host cell of claim 7; and (b) introducing into said isolated host cell from step (a), (i) a nucleic acid vector comprising a donor nucleic acid sequence; and (ii) a nuclease, wherein said nuclease recognizes one or more nuclease recognition sequence from said plurality of nuclease recognition sequences.

14. The method of claim 13, wherein step (b) further comprises introducing a guide polynucleotide, wherein said nuclease recognizes said one or more nuclease recognition sequences, when bound to said guide polynucleotide.

15. An engineered gene editing multi-site (GEMS) polynucleotide construct, that comprises a GEMS polynucleotide sequence, wherein said GEMS polynucleotide sequence comprises a sequence having at least 80% sequence identity with the nucleotide sequence of SEQ ID NO: 81, or SEQ ID NO: 83.

16. A method of producing a host cell comprising a gene editing multi-site (GEMS) polynucleotide sequence, the method comprising:

introducing said engineered GEMS polynucleotide construct of claim 15 into said host cell.

17. An isolated host cell that comprises a gene editing multi-site (GEMS) polynucleotide sequence in said host cell's genome, wherein said GEMS polynucleotide sequence comprises a sequence having at least 80% sequence identity with the nucleotide sequence of SEQ ID NO: 81, or SEQ ID NO: 83.

18. A method of engineering a GEMS modified cell, the method comprising:

(a) providing said isolated host cell of claim 17; and (b) introducing into said isolated host cell from step (a), (i) a nucleic acid vector comprising a donor nucleic acid sequence; and (ii) a nuclease, wherein said nuclease recognizes one or more nuclease recognition sequence from said plurality of nuclease recognition sequences.

* * * * *

SEQUENCE LISTING

<160> NUMBER OF SEQ ID NOS: 86

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tagggataac agggtaat 18

<210> SEQ ID NO 2
<211> LENGTH: 755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
ccatcgtacg tcggaatacg gatctaatca actttctgcc gtactgtgat acacgcgaca 60
ggaactgtgc gaaatcgcca tagcgattta tcggagcgcc attacgtact cagcttatta 120
ccgatacgat acgaacaggt ctagcaaact gctgcctgac gacggttgcg cgtccgttaa 180
tacagcacaa aagtaatcgg ttgcgccgct cgggggatcg agtttaactc acctacgcta 240
cgctaacggg cgatcgttcg tacgcgagtt ttatttaccc cgcgcgaggt gggcgaaatt 300
atagtcgtcc aagaccgacg tacgatacaa ctctaaattt gcagaatagt attcgagtac 360
gcgtcgatgg aagtcatatc acgcgcccat cgacgcgtac tcgaatactg aactcgcgtt 420
cgacgcgtgc gatcgtaccg tgtacggact agcgtctgct tacctacgct acgctaacgg 480
gcgatcacag tttgtgtcat ccgcatggca atctacgcgc gaggattttt gtgctcaagc 540
cggatcgacc gggtcggttc actaacatca gacgcaaatt cttcgatacg gtacgaatag 600
gcgttttggt ccgcccccgg cgtacgcgtc ccatataaac tgttgtctaa ttcaaagagt 660
ggccgcgata atcgaaggac atttgttaca agacctaccg gttaccgcga ggattaatgt 720
atcttacacg taagagtggg cgcgaatatc gtagg 755

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ttccggagca cttccttct 19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ccgataaaac acatgcgtca 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cacgcggtcg ttatagttca 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cggaggaata tgtcccagat 20

<210> SEQ ID NO 7
<211> LENGTH: 518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
cgtcttcact cgctgggttc ccttttcctt ctccttctgg ggcctgtgcc atctctcgtt 60
tcttaggatg gccttctccg acggatgtct cccttgcgtc ccgcctcccc ttcttgtagg 120
cctgcatcat caccgttttt ctggacaacc ccaaagtacc ccgtctccct ggctttagcc 180
acctctccat cctcttgctt tctttgcctg gacaccccgt tctcctgtgg attcgggtca 240
cctctcactc ctttcatttg ggcagctccc ctaccccct tacctctcta gtctgtgcta 300
gctcttccag ccccctgtca tggcatcttc caggggtccg agagctcagc tagtcttctt 360
cctccaaccc gggcccctat gtccacttca ggacagcatg tttgctgcct ccagggatcc 420
tgtgtccccg agctgggacc accttatatt cccagggccg gttaatgtgg ctctggttct 480
gggtactttt atctgtcccc tccaccccac agtggggc 518

<210> SEQ ID NO 8
<211> LENGTH: 530
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
ggacaggatt ggtgacagaa aagccccatc cttaggcctc ctccttccta gtctcctgat 60
attgggtcta acccccacct cctgttaggc agattcctta tctggtgaca cacccccatt 120
tcctggagcc atctctctcc ttgccagaac ctctaaggtt tgcttacgat ggagccagag 180
aggatcctgg gagggagagc ttggcagggg gtgggaggga aggggggat gcgtgacctg 240 cccggttctc agtggccacc ctgcgctacc ctctcccaga acctgagctg ctctgacgcg 300
gccgtctggt gcgtttcact gatcctggtg ctgcagcttc cttacacttc ccaagaggag 360
aagcagtttg gaaaaacaaa atcagaataa gttggtcctg agttctaact ttggctcttc 420
acctttctag tccccaattt atattgttcc tccgtgcgtc agttttacct gtgagataag 480
gccagtagcc agccccgtcc tggcagggct gtggtgagga ggggggtgtc 530

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
ggggccacta gggacaggat tgg 23

<210> SEQ ID NO 10
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
ggggccacta gggacaggat gttttagagc tagaaatagc aagttaaaat aaggctagtc 60
cgttatcaac ttgaaaaagt ggcaccgagt cggtgctttt tt 102

<210> SEQ ID NO 11
<211> LENGTH: 616
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
acattgatta ttgactagtt attaatagta atcaattacg gggtcattag ttcatagccc 60
atatatggag ttccgcgtta cataacttac ggtaaatggc ccgcctggct gaccgcccaa 120
cgacccccgc ccattgacgt caataatgac gtatgttccc atagtaacgc caatagggac 180
tttccattga cgtcaatggg tggactattt acggtaaact gcccacttgg cagtacatca 240
agtgtatcat atgccaagta cgccccctat tgacgtcaat gacggtaaat ggcccgcctg 300
gcattatgcc cagtacatga ccttatggga ctttcctact tggcagtaca tctacgtatt 360
agtcatcgct attaccatgg tgatgcggtt ttggcagtac atcaatgggc gtggatagcg 420
gtttgactca cggggatttc caagtctcca ccccattgac gtcaatggga gtttgttttg 480
gcaccaaaat caacgggact ttccaaaatg tcgtaacaac tccgccccat tgacgcaaat 540
gggcggtagg cgtgtacggt gggaggtcta tataagcaga gctctctggc taactagaga 600
acccactgct tactgg 616

<210> SEQ ID NO 12
<211> LENGTH: 756
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
atggagagcg acgagagcgg cctgcccgcc atggagatcg agtgccgcat caccggcacc 60
ctgaacggcg tggagttcga gctggtgggc ggcggagagg gcacccccaa gcagggccgc 120
atgaccaaca agatgaagag caccaaaggc gccctgacct tcagccccta cctgctgagc 180
cacgtgatgg gctacggctt ctaccacttc ggcacctacc ccagcggcta cgagaacccc 240
ttcctgcacg ccatcaacaa cggcggctac accaacaccc gcatcgagaa gtacgaggac 300
ggcggcgtgc tgcacgtgag cttcagctac cgctacgagg ccggccgcgt gatcggcgac 360
ttcaaggtgg tgggcaccgg cttccccgag gacagcgtga tcttcaccga caagatcatc 420
cgcagcaacg ccaccgtgga gcacctgcac cccatgggcg ataacgtgct ggtgggcagc 480
ttcgcccgca ccttcagcct gcgcgacggc ggctactaca gcttcgtggt ggacagccac 540
atgcacttca agagcgccat ccaccccagc atcctgcaga acgggggccc catgttcgcc 600
ttccgccgcg tggaggagct gcacagcaac accgagctgg gcatcgtgga gtaccagcac 660
gccttcaaga cccccatcgc cttcgccaga tcccgcgctc agtcgtccaa ttctgccgtg 720
gacggcaccg ccggacccgg ctccaccgga tctcgc 756

<210> SEQ ID NO 13
<211> LENGTH: 597
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atgaccgagt acaagcccac ggtgcgcctc gccacccgcg acgacgtccc cagggccgtc 60
cgcaccctcg ccgccgcgtt cgccgactac cccgccacgc gccacaccgt cgatccggac 120
cgccacatcg agcgggtcac cgagctgcaa gaactcttcc tcacgcgcgt cgggctcgac 180
atcggcaagg tgtgggtcgc ggacgacggc gccgcggtgg cggtctggac cacgccggag 240
agcgtcgaag cgggggcggt gttcgccgag atcggcccgc gcatggccga gttgagcggt 300
tcccggctgg ccgcgcagca acagatggaa ggcctcctgg cgccgcaccg gcccaaggag 360
cccgcgtggt tcctggccac cgtcggcgtc tcgcccgacc accagggcaa gggtctgggc 420
agcgccgtcg tgctccccgg agtggaggcg gccgagcgcg ccggggtgcc cgccttcctg 480
gagacctccg cgccccgcaa cctccccttc tacgagcggc tcggcttcac cgtcaccgcc 540
gacgtcgagg tgcccgaagg accgcgcacc tggtgcatga cccgcaagcc cggtgcc 597

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
tgcttgtgca tacataacaa cgg 23

<210> SEQ ID NO 15
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
tgcttgtgca tacataacaa gttttagagc tagaaatagc aagttaaaat aaggctagtc 60
cgttatcaac ttgaaaaagt ggcaccgagt cggtgc 96

<210> SEQ ID NO 16
<211> LENGTH: 383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
gggacagccc ccccccaaag cccccaggga tgtaattacg tccctccccc gctagggggc 60
agcagcgagc cgcccggggc tccgctccgg tccggcgctc cccccgcatc cccgagccgg 120
cagcgtgcgg ggacagcccg ggcacgggga aggtggcacg ggatcgcttt cctctgaacg 180
cttctcgctg ctctttgagc ctgcagacac ctgggggat acggggaaaa ggcctccaag 240
gccagcttcc cacaataagt tgggtgaatt ttggctcatt cctcctttct ataggattga 300
ggtcagagct ttgtgatggg aattctgtgg aatgtgtgtc agttagggtg tggaaagtcc 360
cgcgatcgct cacgagcaag cga 383

<210> SEQ ID NO 17
<211> LENGTH: 600
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
gatatgttaa cgatgctgaa ttagatttgc gttactcgga actgtgcgaa atcgccgacg 60
tagcgttcga gtagcgcatt acgtactcag ctttcacaat cactcaagaa gcacggtcta 120
gcaaactgct gccgtcgcac aagcacagtc tcgttaatac agcacaaaag ctttagacac 180
agtaagacaa cggatcgagt ttaactcacc gagatgctct gcgcgctgca acgttcgtac 240
gcgagttccc gcaatagaga gctttgacgg cgaaattata gtcgtccgat gctatttatt 300
aacgcgtcat aacgtggaac gtatctgcat gtctagcgga cagagcgaaa tcttccgtta 360
attctaaagc aatcgaatct aaatttgcag aatcatgcct ttagaattca gtacggaagt 420
catatcacgc gccgttgtta cacgcgtact gtattgaact cgcgttcgac tgtgttagcg 480
cgctgatctg cggactagcg tctgcttacc gctgacgcgt tatgctaaat ccacagtttg 540
tgtcatctac gaagtcgaga taaaatgcgg atttttgtgc tcaagccgcg tcattgcaag 600

<210> SEQ ID NO 18
<211> LENGTH: 1184
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggtaa 240
gtgccgtgtg tggttcccgc gggcctggcc tctttacggg ttatggccct tgcgtgcctt 300

```
gaattacttc cacctggctg cagtacgtga ttcttgatcc cgagcttcgg gttggaagtg    360

ggtgggagag ttcgaggcct tgcgcttaag gagccccttc gcctcgtgct tgagttgagg    420

cctggcctgg gcgctggggc cgccgcgtgc gaatctggtg gcaccttcgc gcctgtctcg    480

ctgctttcga taagtctcta gccatttaaa atttttgatg acctgctgcg acgctttttt    540

tctggcaaga tagtcttgta aatgcgggcc aagatctgca cactggtatt tcggtttttg    600

gggccgcggg cggcgacggg gcccgtgcgt cccagcgcac atgttcggcg aggcggggcc    660

tgcgagcgcg gccaccgaga atcggacggg ggtagtctca agctggccgg cctgctctgg    720

tgcctggcct cgcgccgccg tgtatcgccc cgccctgggc ggcaaggctg gcccggtcgg    780

caccagttgc gtgagcggaa agatggccgc ttcccggccc tgctgcaggg agctcaaaat    840

ggaggacgcg gcgctcggga gagcgggcgg gtgagtcacc cacacaaagg aaaagggcct    900

ttccgtcctc agccgtcgct tcatgtgact ccacggagta ccgggcgccg tccaggcacc    960

tcgattagtt ctcgagcttt tggagtacgt cgtctttagg ttgggggag gggttttatg    1020

cgatggagtt tccccacact gagtgggtgg agactgaagt taggccagct tggcacttga   1080

tgtaattctc cttggaattt gcccttttg agtttggatc ttggttcatt ctcaagcctc    1140

agacagtggt tcaaagtttt tttcttccat ttcaggtgtc gtga                    1184
```

```
<210> SEQ ID NO 19
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

atggccaagc ctttgtctca agaagaatcc accctcattg aaagagcaac ggctacaatc     60

aacagcatcc ccatctctga agactacagc gtcgccagcg cagctctctc tagcgacggc    120

cgcatcttca ctggtgtcaa tgtatatcat tttactgggg gaccttgtgc agaactcgtg    180

gtgctgggca ctgctgctgc tgcggcagct ggcaacctga cttgtatcgt cgcgatcgga    240

aatgagaaca ggggcatctt gagcccctgc ggacggtgcc gacaggtgct tctcgatctg    300

catcctggga tcaaagccat agtgaaggac agtgatggac agccgacggc agttgggatt    360

cgtgaattgc tgccctctgg ttatgtgtgg gagggc                              396
```

```
<210> SEQ ID NO 20
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

gaaattgtga tgacccagtc acccgccact cttagccttt cacccggtga gcgcgcaacc     60

ctgtcttgca gagcctccca agacatctca aaatacctta attggtatca acagaagccc    120

ggacaggctc ctcgccttct gatctaccac accagccggc tccattctgg aatccctgcc    180

aggttcagcg gtagcggatc tgggaccgac tacaccctca ctatcagctc actgcagcca    240

gaggacttcg ctgtctattt ctgtcagcaa gggaacaccc tgccctacac ctttggacag    300

ggcaccaagc tcgagattaa aggtggaggt ggcagcggag gaggtgggtc cggcggtgga    360
```

ggaagccagg tccaactcca agaaagcgga ccgggtcttg tgaagccatc agaaactctt 420
tcactgactt gtactgtgag cggagtgtct ctccccgatt acggggtgtc ttggatcaga 480
cagccaccgg ggaagggtct ggaatggatt ggagtgattt ggggctctga gactacttac 540
tacaactcat ccctcaagtc acgcgtcacc atctcaaagg acaactctaa gaatcaggtg 600
tcactgaaac tgtcatctgt gaccgcagcc gacaccgccg tgtactattg cgctaagcat 660
tactattatg gcgggagcta cgcaatggat tactggggac agggtactct ggtcaccgtg 720
tccagc 726

<210> SEQ ID NO 21
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
accactaccc cagcaccgag gccacccacc ccggctccta ccatcgcctc ccagcctctg 60
tccctgcgtc cggaggcatg tagacccgca gctggtgggg ccgtgcatac ccggggtctt 120
gacttcgcct gcgatatcta catttgggcc cctctggctg gtacttgcgg ggtcctgctg 180
ctttcactcg tgatcactct ttactgt 207

<210> SEQ ID NO 22
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
aagcgcggtc ggaagaagct gctgtacatc tttaagcaac ccttcatgag gcctgtgcag 60
actactcaag aggaggacgg ctgttcatgc cggttcccag aggaggagga aggcggctgc 120
gaactg 126

<210> SEQ ID NO 23
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
cgcgtgaaat tcagccgcag cgcagatgct ccagcctaca agcaggggca gaaccagctc 60
tacaacgaac tcaatcttgg tcggagagag gagtacgacg tgctggacaa gcggagagga 120
cgggacccag aaatgggcgg gaagccgcgc agaaagaatc cccaagaggg cctgtacaac 180
gagctccaaa aggataagat ggcagaagcc tatagcgaga ttggtatgaa aggggaacgc 240
agaagaggca aaggccacga cggactgtac cagggactca gcaccgccac caaggacacc 300
tatgacgctc ttcacatgca ggccctgccg cctcgg 336

<210> SEQ ID NO 24
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 24
tgcttgtgca tacataacaa 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cccgcaatag agagctttga 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttgcagcgcg cagagcatct 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttttgctaca tcttgtaata 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atacagtacg cgtgtaacaa 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tacgatgaga aagcaatcga 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
caatgacaat agcgataacg 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
tgaattagat ttgcgttact 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
tgtgttagcg cgctgatctg 20

<210> SEQ ID NO 33
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 33
ugaauuagau uugcguuacu 20

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 34
ucacaaucac ucaagaagca 20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 35
cuuuagacac aguaagacaa 20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 36
cccgcaauag agagcuuuga 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 37
gaacguatcu gcaugucuag 20

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
caugccuuua gaauucagua 20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
uguguuagcg cgcugaucug 20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
uacgaagucg agauaaaaug 20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 41
gcauaaccag uacgcaagau 20

<210> SEQ ID NO 42
<211> LENGTH: 20
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 42
uuuugcuaca ucuuguaaua 20

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
auuauaauau ucaguagaaa 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
cagctacgag ucacgaugua 20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
caaugacaau agcgauaacg 20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
guuacguucg cgaagcguug 20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gcguaacaac uucugaguug 20

<210> SEQ ID NO 48
<211> LENGTH: 20
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 48
aacaauacau acguguucgu 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
ugcatcgcaa gctcaucgcg 20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
agcguguucg ugucagagca 20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ucuacgagac gcgcgacguu 20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uacgauaaau aauugcgcag 20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
aauuaagauu ucguuagcuu 20

<210> SEQ ID NO 54

<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
aacaaugugc gcaugacaua 20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
gacugcgcaa uacgauuuag 20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
gcaguaacgu ucaucugcgc 20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
agcuaacgaa agaguagcau 20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
uagacgcucg cuaaaucuuu 20

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59
ucgcacuguc gagcuaucac 20

<210> SEQ ID NO 60
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60

gacuagcguc acguaagagu                                              20


<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61

agcuagcaug uaucuaggac                                              20


<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62

ugcgcgugcg ucgacauauu                                              20


<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63

auccguauuc cgacguacga                                              20


<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64

cguacuguga uacacgcgac                                              20


<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65

ggcgcuccga uaaaucgcua                                              20


<210> SEQ ID NO 66
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 66
auuaccgaua cgauacgaac 20

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acggacgcgc aaccgucguc 20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uaaucgguug cgccgcucgg 20

<210> SEQ ID NO 69
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uuauuuaccc cgcgcgaggu 20

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
guuguaucgu acgucggucu 20

<210> SEQ ID NO 71
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aguauucgag uacgcgucga 20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
guauucgagu acgcgucgau 20

<210> SEQ ID NO 73
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
gcgugcgauc guaccgugua 20

<210> SEQ ID NO 74
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
cgcauggcaa ucuacgcgcg 20

<210> SEQ ID NO 75
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
gugaaccgac ccggucgauc 20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
uucuucgaua cgguacgaau 20

<210> SEQ ID NO 77
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 77
uuuauauggg acgcguacgc 20

<210> SEQ ID NO 78
<211> LENGTH: 20
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 78
agaguggccg cgauaaucga 20

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
uaauccucgc gguaaccggu 20

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 80
agagugggcg cgaauaucgu 20

<210> SEQ ID NO 81
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
cgctcttgct ttcgtcaatg aaacgagttg cgtcattcga tgaacgttgt 50

<210> SEQ ID NO 82
<211> LENGTH: 1941
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82
tcacgagcaa gcgaccgttg ttatgtatgc acaagcagat atgttaacga tgctgaatta 60
gatttgcgtt actcggaact gtgcgaaatc gccgacgtag cgttcgagta gcgcattacg 120
tactcagctt tcacaatcac tcaagaagca cggtctagca aactgctgcc gtcgcacaag 180
cacagtctcg ttaatacagc acaaaagctt tagacacagt aagacaacgg atcgagttta 240
actcaccgag atgctctgcg cgctgcaacg ttcgtacgcg agttcccgca atagagagct 300
ttgacggcga aattatagtc gtccgatgct atttattaac gcgtcataac gtggaacgta 360
tctgcatgtc tagcggacag agcgaaatct tccgttaatt ctaaagcaat cgaatctaaa 420
tttgcagaat catgccttta gaattcagta cggaagtcat atcacgcgcc gttgttacac 480
gcgtactgta ttgaactcgc gttcgactgt gttagcgcgc tgatctgcgg actagcgtct 540
gcttaccgct gacgcgttat gctaaatcca cagtttgtgt catctacgaa gtcgagataa 600
aatgcggatt tttgtgctca agccgcgtca ttgcaagtag acgcgtaaca tcagacgcaa 660
agcataacca gtacgcaaga tcggcgtttt ggtccgcccc cgtcgattgc tttctcatcg 720
tactgttgtc taattcaatt ttgctacatc ttgtaatacg gacatttgtt acaagaccga 780
tctgcgagcg atttagaaat accttatatt ataatattca gtagaaacgg cttcttttaa 840
acactccgag cgtgacagct cgatagtgat gtatcttaca cgtacagcta cgagtcacga 900
tgtacggttc ttcgtgcgca gtccgctgat cgcagtgcat tctcaagttt gctcgagcga 960
acaatgacaa tagcgataac gcggatgtgc tgtctcgaac cgccgatcgt acatagatcc 1020
tgatcatcta cgcatgtcgt tacgttcgcg aagcgttgcg gacttgcgat gtacatccga 1080
cgcgcacgca gctgtataac taatcaactt tctgcgcgta acaacttctg agttgcggat 1140
cagctgcact aacaaagagc acgtctagtt cgtttacaaa gtactcattt actcgtcgta 1200
tgattgtgat ctgagcgttc tagcttacta catgtgcgtg ttccgaatat gaatctttac 1260
tcgcgcgttt actcgtcgta tgattgtcat agcgcactct gcgcttacta catgtgcgtg 1320
ttccggagca agcgaaaacg cgaatcctag tttactcgtc gtatgattgt tcaatacgag 1380
ctaaagctta ctacatgtgc gtgttcgaaa acgcgtgcac tagcgagatt ctgctttact 1440
cgtcgtatga ttgttgcagt cacgcagtgt tcttactaca tgtgcgtgtt cgcaaagagc 1500
aaacgaaaat tttatttact cgtcgtatga ttgtgcgatc aacacgtaac cttactacat 1560
gtgcgtgttc tggagaatca taaaagagcc gcaatttttt tactcgtcgt atgattgtcg 1620
taacgctaag acgccttact acatgtgcgt gttcgagacc aacgaacgac agagcatatt 1680
tttcgtttac tcgtcgtatg attgtttcac ataatcgcac tcttactaca tgtgcgtgtt 1740
ctgaaagtat tttacgttag ccttgcacag agtgcgacaa ctctgtgcaa gagtttgcaa 1800
aatttccgca cgcgctttcg ttacaaagcg cgtgcgacaa acgatatttt cgttttacgc 1860
gagagaatgc tcgcgtaaaa cattcagaaa cgagcgcgca gtcagcacta ctgcgtgctg 1920
actgcgatct actagtgacg a 1941

<210> SEQ ID NO 83
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
cagcttcgct tttcgtcgag atgctttacg tagatgcaat gacgcacgta 50

<210> SEQ ID NO 84
<211> LENGTH: 1941
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84
tcacgagcaa gcgaccgttg ttatgtatgc acaagcagat atgttaacga tgctgaatta 60
gatttgcgtt actcggaact gtgcgaaatc gccgacgtag cgttcgagta gcgcattacg 120
tactcagctt tcacaatcac tcaagaagca cggtctagca aactgctgcc gtcgcacaag 180
cacagtctcg ttaatacagc acaaaagctt tagacacagt aagacaacgg atcgagttta 240
actcaccgag atgctctgcg cgctgcaacg ttcgtacgcg agttcccgca atagagagct 300
ttgacggcga aattatagtc gtccgatgct atttattaac gcgtcataac gtggaacgta 360

```
tctgcatgtc tagcggacag agcgaaatct tccgttaatt ctaaagcaat cgaatctaaa    420

tttgcagaat catgccttta gaattcagta cggaagtcat atcacgcgcc gttgttacac    480

gcgtactgta ttgaactcgc gttcgactgt gttagcgcgc tgatctgcgg actagcgtct    540

gcttaccgct gacgcgttat gctaaatcca cagtttgtgt catctacgaa gtcgagataa    600

aatgcggatt tttgtgctca agccgcgtca ttgcaagtag acgcgtaaca tcagacgcaa    660

agcataacca gtacgcaaga tcggcgtttt ggtccgcccc cgtcgattgc tttctcatcg    720

tactgttgtc taattcaatt ttgctacatc ttgtaatacg gacatttgtt acaagaccga    780

tctgcgagcg atttagaaat accttatatt ataatattca gtagaaacgg cttcttttaa    840

acactccgag cgtgacagct cgatagtgat gtatcttaca cgtacagcta cgagtcacga    900

tgtacggttc ttcgtgcgca gtccgctgat cgcagtgcat tctcaagttt gctcgagcga    960

acaatgacaa tagcgataac gcggatgtgc tgtctcgaac cgccgatcgt acatagatcc   1020

tgatcatcta cgcatgtcgt tacgttcgcg aagcgttgcg gacttgcgat gtacatccga   1080

cgcgcacgca gctgtataac taatcaactt tctgcgcgta acaacttctg agttgcggat   1140

cagctgcact aacaaagagc acgtctagtt cgtttacaaa gtactcattt actcgtcgta   1200

tgattgtgat ctgagcgttc tagcttacta catgtgcgtg ttccgaatat gaatctttac   1260

tcgcgcgttt actcgtcgta tgattgtcat agcgcactct gcgcttacta catgtgcgtg   1320

ttccggagca agcgaaaacg cgaatcctag tttactcgtc gtatgattgt tcaatacgag   1380

ctaaagctta ctacatgtgc gtgttcgaaa acgcgtgcac tagcgagatt ctgctttact   1440

cgtcgtatga ttgttgcagt cacgcagtgt tcttactaca tgtgcgtgtt cgcaaagagc   1500

aaacgaaaat tttatttact cgtcgtatga ttgtgcgatc aacacgtaac cttactacat   1560

gtgcgtgttc tggagaatca taaaagagcc gcaatttttt tactcgtcgt atgattgtcg   1620

taacgctaag acgccttact acatgtgcgt gttcgagacc aacgaacgac agagcatatt   1680

tttcgtttac tcgtcgtatg attgtttcac ataatcgcac tcttactaca tgtgcgtgtt   1740

ctgaaagtat tttacgttag ccttgcacag agtgcgacaa ctctgtgcaa gagtttgcaa   1800

aatttccgca cgcgctttcg ttacaaagcg cgtgcgacaa acgatatttt cgttttacgc   1860

gagagaatgc tcgcgtaaaa cattcagaaa cgagcgcgca gtcagcacta ctgcgtgctg   1920

actgcgatct actagtgacg a                                             1941
```

<210> SEQ ID NO 85
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 85

```
cuuacuacau gugcguguuc                                                 20
```

-continued

```
<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86

acaaucauac gacgaguaaa                                                  20
```